(12) United States Patent
Bhattacharyya et al.

(10) Patent No.: US 10,045,499 B2
(45) Date of Patent: Aug. 14, 2018

(54) ARABIDOPSIS NONHOST RESISTANCE GENE(S) AND USE THEREOF TO ENGINEER DISEASE RESISTANT PLANTS

(71) Applicant: IOWA STATE UNIVERSITY RESEARCH FOUNDATION, INC., Ames, IA (US)

(72) Inventors: Madan K. Bhattacharyya, Ames, IA (US); Rishi Sumit, Des Moines, IA (US); Binod B. Sahu, Odisha (IN)

(73) Assignee: Iowa State University Research Foundation, Inc., Ames, IA (US)

( * ) Notice: Subject to any disclaimer, the term of this patent is extended or adjusted under 35 U.S.C. 154(b) by 418 days.

(21) Appl. No.: 13/783,682

(22) Filed: Mar. 4, 2013

(65) Prior Publication Data
US 2014/0123334 A1    May 1, 2014

Related U.S. Application Data

(60) Provisional application No. 61/651,149, filed on May 24, 2012.

(51) Int. Cl.
| C12N 15/82 | (2006.01) |
| A01H 5/10 | (2018.01) |
| C07K 14/415 | (2006.01) |

(52) U.S. Cl.
CPC ............. *A01H 5/10* (2013.01); *C07K 14/415* (2013.01); *C12N 15/8282* (2013.01)

(58) Field of Classification Search
None
See application file for complete search history.

(56) References Cited

U.S. PATENT DOCUMENTS

| 6,544,733 B1 * | 4/2003 | Rommens ............ C07K 14/415 435/320.1 |
| 6,583,107 B2 * | 6/2003 | Laby ..................... C07K 14/27 435/411 |
| 6,861,573 B2 * | 3/2005 | Chen ..................... C07H 21/04 435/320.1 |
| 2006/0107345 A1 * | 5/2006 | Alexandrov et al. ......... 800/278 |
| 2012/0222167 A1 * | 8/2012 | Li et al. ...................... 800/281 |

FOREIGN PATENT DOCUMENTS

| DE | 198 28 850 A1 | 12/1999 |
| WO | WO 00/12736 A2 | 3/2000 |
| WO | WO 2012/007916 A2 | 1/2012 |

OTHER PUBLICATIONS

Kuc, Acta Physiologiae Plantarum (1997) vol. 19. No. 4 pp. 551-559.*
Martins et al (Biochimica et Biophysica Acta (2000) 1492: 1-14.*
Hoff et al (BMC Genomics (2009) vol. 10 pp. 1-9.*
Mangeon et al, Plant Signaling & Behavior (2010) 5: 99-104.*
Naqvi et al (1998), Plant Mol. Biol 37(3), 571-576.*
Bedhomme, Marlette et al., "Folate Metabolism in Plants" "An *Arabidopsis* Homolog of the Mammalian Mitochondrial Folate Transporter Mediates Folate Import into Chloroplasts*", The Journal of Biological Chemistry, vol. 280, No. 41, pp. 34823-34831, Oct. 14, 2005.
Bhattacharyya, Madan "Nonhost Resistance for Engineering Disease Resistance", Iowa State University, presentation May 27, 2011,18 pages.
Huitema, Edgar et al., "Active defence responses associated with non-host resistance of *Arabidopsis thaliana* to the oomycete pathogen Phytophthora infestans" Molecular Plant Pathology (2003), 4(6), pp. 487-500.
Kamoun, Sophien, "Nonhost resistance to Phytophthora: novel prospects for a classical problem", Current Opinion in Plant Biology, vol. 4, No. 4, Aug. 2001 pp. 295-300.
Loehrer, Marco et al., "Characterization of Nonhost Resistance of *Arabidopsis* to the Asian Soybean Rust", MPMI vol. 21, No. 11, 2008, pp. 1421-1430.
Sumit et al., "*Arabidopsis* nonhost resistance gene PSS1 confers immunity against an oomycete and a fungal pathogen but not a bacterial pathogen that cause diseases in soybean" BMC Plant Biology, Biomed Central, London, GB, vol. 12, No. 1, Jun. 13, 2012, p. 87.
XP-002707948, "DEAD-box RNA helicase SEQ:121.", Mar. 1, 2012, retrieved from EBI Asscession No. GSP: AZS56794 sequence.
XP-002707950, RecName: Full-Folate transporter 1, chloroplastic; Short=AtFOLT1; Oct. 1, 2003, retrieved from EBI Accession No. UNIPROT:Q7XA87 sequence.
XP002707951, "*A. thaliana* SLD1 Protein.", Apr. 27, 2000, retrieved from EBI Accession No. GSP:AAY51334.
XP002707677, "SubName: Full-Putative uncharacterized protein At3g60310; SubName: Full-Putative uncharacterized protein F27H5_100; SubName: Full-Uncharacterized protein;", Oct. 1, 2000, retrieved from EBI Accession No. UNIPROT:Q9LY34.
XP002707678, "*Arabidopsis thaliana* mRNA for hypothetical protein, complete cds, clone: RAFL09-43-L10", Jul. 27, 2006, retrieved from EBI Accession No. EM_STD:AK226994.
XP002707679, "SubName: Full-Uncharacterized protein;" Jun. 28, 2011, retrieved from EBI Accession No. UNIPROT: F4JD14.
Iowa State University Research Foundation, Inc., PCT/US2013/042431 filed May 23, 2013, "Notification of Transmittal of the International Search Report and the Written Opinion of the International Searching Authority, or the Declaration" dated Aug. 16, 2013.

* cited by examiner

*Primary Examiner* — Medina A Ibrahim
(74) *Attorney, Agent, or Firm* — McKee, Voorhees & Sease, PLC

(57) ABSTRACT

The present invention relates to a method of increasing resistance against plant pathogens, particularly *Phytophthora* and *Fusarium virguliforme* in transgenic plants and/or plant cells, through the use of non host resistance nucleic acid molecules isolated from *Arabidopsis*. In these plants, at least one nonhost *Arabidopsis* resistance protein is introduced in comparison to the wild-type plants to confer resistance to plant pathogens. The invention relates to transgenic plants and/or plant cells having an increased resistance against plant pathogens particularly *Phytophthora* and *Fusarium virguliforme* to expression vectors, transformed plants and plant cells as well as the use of such plants in a plant breeding program.

9 Claims, 35 Drawing Sheets

25827439 G to A
>Ch 5 25825101 gtttggttttgaacaagcaaaagctcgatgtccggaggaggaaagagaccgttgtagatctgtcttcttcatcgaag
ATGGTGAAACACAGAAACTCATCTCGCTCGATAATCTCATATTCTTCTTCAATAGCAAGATTCTTCTCTAGAAAAGC
TATTTCTCTCTACTTGATCTTCGTCTTTGCTTTTACCATCTGGGTTCTCGTCTTCAGCTCCAGAAACATTCAAACCG
ATGATGACCACACCAAACATCAACAACAACATCATCGGGATCTAATCGATTCAGAATCATTTCCGCCACCGTATTTG
CCTCCTAGGAAGgtaaagttgttaatatttcatgggttgtggatttgaatgaagaaatgaggtgacttgatttggtt
tttgatcggaacaattgagaaagcataactttattgagcttcagAATTTGCAGAAACCGTATGAAAATACTCAACTT
TGGACTCCTCCTTTCAGCTTTGGGTTGCATCCATGTGTCAAACCTACTCCGAAATACAAAGgtatgccaaagaagct
cacttccaatttctgatggatctatcttgggttttgtttatgaattcagaactgtgcttttgattgatttcaagttc
gtttcttgcagAATTTTCAGAATCAGATCATTATATAACAGTGAAAAGTAATGGTGGACTAAATCAAATGCGTACTG
GTgtaagtaaaaccatttaagttgttgttttcatgattcttttgtcttgcttagtaccaaagtgattcaataagca
tgttattgtacagATAGCAGATATAGTGGCTGTTGCGCACATCATGAATGCAACTTTAGTCATTCCTGAGCTGGATA
AGCGATCGTTTGGCAAGATTCAAGgtattttgaaacttcaaacaaacaaaaatgcagcttacttaattagtggtt
atgagatttatactatttctaacttacattttcgctatgtctcagTGTTTTTTCAGATATTTTTGACGAGGAACAAT
TCATTAAATCATTGCGAAGAGATGTCAAGGTTATTAAAAAGCTCCCAAAGGAAGTGGAATCTCTACCTAGAGCAAGG
AAGCATTTCACTTCTTGGTCTAGTGTTGGATATTATGAAGAAATGACTCACTTGTGGAAGGAGTACAAGgtcggtct
taagcaacttcttttacattttgcatttgctgtttcattcaactgctgatagaataataacaatgcagGTCATCCAT
GTCGCAAAATCAGATTCTCGCCTTGCAAATAATGACCTGCCTATCGACGTTCAAAGACTGAGATGTCGTGTACTATA
TCGTGGTCTCTGCTTCTCTCCTGCAATTGAAAGCCTTGGACAGgttgggaccctttcctgtcttgtacacaacata
gataggctgtagtaacataaaattcatttcatacacataagatttcaagttaatgttctctttgggtaccgaatagc
tatatagaagtttcaaaaccatcgtttgggtcaacgagttttcattgtcaaatgatagaacttgcaataacatagtt
tatgcatttaagaggtgtgtaatgatagaataggagaatggatacatctttttctatcaaacatagtttatgcattt
aagaggtgtcctatggggattcctgtagactgtgggttctgagcaatcatgacggtgacaccacagAAGCTGGTTGA
GAGACTCAAGTCACGTGCTGGGAGATATATTGCATTGCACCTGAGATATGAGAAAGATATGTTGGCTTTCACTGGTT
GCACCTATGGTCTCACTGATGCTGAATCCGAAGAACTGAGAGTAATGCGgtaattgattactctctgcatctattct
taacaaagcaaacatgcaaaacgtcttcatgggataaaattacagtttcaagctcaatatgttatctgttggtcaca
gGGAAAGTACAAGCCATTGGAAGATCAAAAGTATAAATTCAACAGAGCAGAGAGAGGAAGGCCTTTGTCCATTGACT
CCAAAAGAAGTGGGAATATTTCTGAAAGGTCTCGGATATTCTCAGTCAACAGTCATATATATTGCAGCAGGGGAAAT
CTATGGGGGTGATGATAGACTCTCTGAGCTTAAGTCGCGCTTCCCAAATCTGGTTTTTAAGgtctgttcaaccacct
ctaatctttcatgttactgacaatctaaagatgataaatgtttatgtttcatgtactggattttgtagGAAACGCTT
GCTGGGAACGAAGAGTTAAAAGGTTTCACTGGCCATGCGACTAAAACGGCTGCTCTTGATTACATAATTTCTGTTGA
GAGTGATGTGTTTGTTCCTTCACATTCTGGAAACATGGCAAGAGCAGTTGAAGGTCACCGCAGATTTCTAGGGCATC
GCAGGACTATCACTCCCGACAGgttctatctccttccttctgttaccttaaaaaaaagcattaatcttttagtcatt
ttgttataggccatgacaagtttggtgttgtatgcagGAAAGGACTAGTGAAACTCTTCGTTAAGATGGAGAGAGGA
CAGCTAAAAGAAGGACCAAAGTTGTCCAATTTTGTGAATCAAATGCATAAAGACAGgtagcaaaagagtcatacgtt
tgcttcttaaacaataaacctataaaaaaagcacatctttgatgcgagaagaggatttgtttgatcggttttgcag
ACAAGGTGCACCGAGGAGAAGGAAAGGACCAACGCAGGGGATCAAAGGACGTGCACGGTTTAGAACTGAAGAAGCCT
TTTATGAGAATCCATATCCAGAGTGTATTTGCAGTTCAAAGGAGCACAAAGAACCCTAActaaaattttccaaactt
tttttgttctgtatcattacatctcatttatagtcatcttaattatagttt  25828000

*FIG. 6*

26358667 G to A
>Ch 5  26358201 acattagaacactctcgaattcgaagaaaatacgtagcaaaacccttattttttgaatttcagacgaattccgatttc
ttaatcaaaaatccgataagagctttggatttggcggcgaataagaaaacATGGCGAATTTGGATATGGAGCAACAT
TCATCCGAAAACGAAGAGATTAAGAAGAAGAAGCATAAGAAAAGAGCGAGAGACGAAGCTAAGAAACTAAAGCAGCC
AGCAATGGAAGAAGAACCCGATCATGAAGATGGTGATGCCAAAGAGAACAATGCGTTAATTGACGAAGAACCGAAGA
AGAAGAAGAAGAAGAAAAATAAGAAGCGTGGAGATACTGATGATGGAGAGGACGAAGCGGTAGCAGAAGAAGAGCCG
AAGAAGAAGAAGAAGAAAAATAAAAAGCTACAGCAGCGTGGAGATACTAATGACGAAGAGGACGAAGTGATAGCAGA
AGAAGAAGAGCCGAAGAAGAAGAAGAAGAAACAGAGGAAGGACACGGAAGCGAAGTCTGAAGAAGAAGAAGTAGAAG
ATAAGGAAGAAGAAAAAAAATTGGAAGAAACTAGCATAATGACTAATAAAACGTTTGAGTCATTGTCATTATCTGAT
AACACTTATAAATCTATCAAGGAGATGGGTTTTGCACGCATGACTCAGgtaatgtttttggaattgaagctttatgt
ttttgtatagcaaagattcaaccttttacagtttggaatttggttggatttcaacacttttgcagATACAAGCTAAA
GCAATTCCACCATTGATGATGGGAGAAGATGTACTTGGAGCTGCCAGGACCGGTTCTGGTAAAACCTTAGCTTTTCT
TATTCCTGCTGTTGAGCTTCTTTACCGTGTTAAGTTTACTCCTCGCAATGGAACTGGTGTTCTTGTTATTTGCCCAA
CAAGAGAGCTTGCTATTCAGgttctaattctctcacaatttctatatagtctgtagaatatgctaaaagtgatact
tactatacatcattaatgtttcagTCTTATGGAGTGGCAAAAGAACTTCTTAAGTATCATTCACAGACTGTGGGAAA
AGTTATTGGCGGTGAGAAAAGAAAGACAGAAGCTGAGATTCTTGCGAAAGGTGTTAATTTATTAGTAGCTACCCCTG
GAAGACTTCTCGACCACCTTGAAAATACTAATGGTTTTATTTTCAAGAACTTAAAGgtaaacacaaatttctgattt
cagttttgggtatactggtattgatttaatgcaacatttttattcgttaatttgcagTTTCTTGTAATGGATGAGG
CTGATAGGATATTGGAACAGAACTTTGAAGAAGACCTCAAGAAGATTTTGAACCTTCTACCAAAGtattctcgtgg
cttgcatagtgaagtcacctcaacattctgaatcatagagatgtaaatttcgtttcatgtcaatgtgttgttgataa
tggtaaaccgtcttttttgtattgctgcagACTAGACAGACGTCACTATTTTCAGCCACACAGAGCGCAAAGgtctgc
ttaccaatcagtatagttttcacttaattctttattagtgtcagtttattaaaattactggaacttgattaaaccat
cagGTTGAGGATCTTGCTCGGGTGTCACTTACCTCACCTGTTTATATTGATGTGGATGAAGGACGAAAAGAGtagc
tattaacacaatttctattatctttctcgcaatttactttgtgaccaaaacaggcctttttcaattataagaaaac
tggaaagtgcagGTTACAAATGAAGGCTTGGAGCAAGGTTATTGCGTTGTGCCAAGTGCGATGCGGTTACTTTTTT
ACTTACCTTCTTGAAGAGATTCCAAGGGAAAAGAAAATTATGGTGTTTTTCTCTACATGCAAGTCGACAAAGTTCC
ACGCCGAGCTCTTTCGATATATCAAATTCGATTGCCTTGAAATCCGTGGAGGGATAGACCAGAACAAAAGAACTCCA
ACATTTTTGCAATTCATAAAGGCGGAAACCGGTATTTTGTTGTGTACTAATGTCGCTGCCCGAGGTCTTGATTTTCC
TCATGTGgtatgctttcttaacaactttaatgttttaataatctggattggttggtcttaatcaaattattgtctg
cttgtttagGACTGGATTGTGCAGTATGATCCTCCTGATAACCCAACGgtatgttgcttataatttagggttttttat
gcaaacacgcggaagaataagggataagaaatcactcaaattcttgaatgttacttttgatttagGATTATATTCAT
CGAGTTGGTAGAACAGCTCGTGGTGAAGGAGCAAAAGGAAAGGCTCTGCTTGTCCTAACTCCACAGGAGTTGAAGTT

*FIG. 7A*

TATACAGTATCTCAAGgtaaattattttcattcaataaaaactttgataattttcaaattatagaaattttgataa
aagaatctgtttccaactgtataatttgcagGCGGCGAAAATTCCTGTTGAGGAACATGAATTTGAAGAAAAGAAAT
TGCTCGATGTGAAACCTTTTGTGgtaaaacattcttgctctttcaaataagttttactacactgaagaaacaaaagt
tgagagatttatttaaaatgttattgcagGAGAATTTGATATCTGAAAACTATGCATTGAAGGAGTCAGCAAAAGAA
GCATACAAGACATACATTTCAGGATATGATTCTCACTCTATGAAAGATGTCTTTAATGTTCACCAACTCAATCTCAC
Ggtaaccaaatctgcagcatacatataacaatacgaaacgtcatgaaatcaggaatacaatttgttttgttttctg
caatttaaacgttaaccgaaggtctttgtttatgtgcagGAGGTTGCGACTTCGTTTGGTTTCTCAGATCCTCCCAA
AGTTGCTCTGAAGATAGATCGAGGAGGGTACAGAAGTAAGAGAGAACCGGTTAATAAGTTTAAGAGAGGTCGTGGTG
GTGGTAGACCCGGCGGTAAAAGCAAGTTCGAGAGGTACTAAaaatacagttgcacaaacaacgtcatacttagtagt
atggcacatgccttttaacgaatgttgtatcttattttggattcatttacgattgtgttgtcttaagctgtttcca
gagatatcagacgagataccagttttgtccccgttacttagaa26361500

>Ch 5  26513501 ttttagctgtgatcgtaaaagttagaaccatggaacgcacataaaatatatgtatatcaaagaataattctctagta
ttgggagtgacaagtcaaccgcgtgcgtgttgagtctaagaaataacggtaaaggaagaggaagagtCTAATCTTTT
GTTGTTGGATGCTGTTTTAGCAATTTCAGAACGTTTTCATAGACGATGAATGTGATGGAAGACGCAGGTACATTTTT
CAAAAGATTAGCCGTTAGTCCCCTGTAGAAACCCCTGAGACCTTCATATctgcagagagacccaaaagtgttactca
gtgaaactaaccaaaaagatcatcattccagacataatcgagaccaagaatatgccctgacCTCGCGGTTTCTCTGA
TGACATGTAAGCTGTCTATATATCTTGGGATTCCGTTGGTACTAGGTCGTTGctgaacaagaaaagaaccatgttta
tgaaatcctcatatattgcagaaggtcaaaggtagaaagtaaggaagctcaaggaatttagatttgagctaacaata
ataagactgaagaagacacggtcgataggtacCTGTAATCGTGCTCGTATAACTTGAAATGGATACGTAAGAAGAAC
TGCAGCGACTTTGGAGGAGCCACCAAGTGCAGCATAATCTGCTGAGTTctaaagaaaaattgcaatggagtgtgtta
gaatagtatatatccgtgatgctggaaatagccgtagaattaagattaatgtggctatataacttaagaaccgcaat
gtagcctattcagaagaattactctgtacCAATAGATTGTCAGTGGATTCGGACTTTCTTCTCCTTTCTTTCAAATC
CACAATGATTTTACGGAGTTCCTCATAAGCTGTGAACTGAATAGCACCATGAGAAActgctgaacccaaaatgtaa
accattcaatctgtaaggcctcctctttcgcaactaatagtcatcttttatagttccaaaactgtggatcttgtggt
agttttacgaacgaacgttacaagagatagatcaggatagttactaacCAGTACAAGACCAGGGACAATACCCTTGT
AGAGCGCCCTGGGTCCTTCCTCTTTCACTATGGTTCTAAAGGCATCttaagatcacaaaatacacatttagaatgaa
acactagaaacaatgaaaactgaattttgtgtgtgcagcatattgcaaacCTAATAGCCCTGAGTATGGTTGAGTTT
GATGAAGAGGTGTCTGAAGCTGTAACCTTGTTTTGACAAGCCAAATAGGATTTGTGCATAAACAGACctgaaagcat
cattcccttgatactgagatcgaaaaacataggagaaatgagatgtttatggcgcctgttagactcacCAAGGCCC
CTGCTTCAGCAGCAGAAGCAAGGTGGAGAGCAGGGCTGAGTTTCTCATCGTCCCTGCCTCTAGCGTACCTCTGCTTG
GCTCTTCCATAActacagagagataatatatttgttccagaacatttttaaacaagatccacggctaaaaacattaaa
aaaactaacagaaaactgtttgaatagaaatcatgaagaaagaagatatgtgctaaacgaaagtaacactcacAAAA
AGAAGTATAAGCCCCAGGAAACAGTAGAACCGATAACTGCAGGGAAGAAGCCTGCATAAAGCCCTCTCAAACCctac
agaagatttaaaccaaatgagtcaaccacataacatagagaagataatatggaagatgccagaagagagtttcatct
gggaaaCTCGAGACGGGCAATGGTGAAGACAGCGTGAGCAGTGTTCTTGTACGTCGGCAGACTTGACCCTCTTCCG
TCGTTGActgttgttcaatcaagttagcaacttttaaaagcaaaatcgatgagttaatccaggagtgaaaaaccag
acCTTGGAATCTCGTACGAACAACATCAAGAGAGTGCATAGCAGCTACGGTGGCGAATCCAGCGACGGCGCCGGCGG
TGGCATTTTCCCACTGCCACGACGCCGCCATcaacgaatccttagatgcaatccggactaatcgcgattgtttacag
agctaatctgaagttaaagactcatttgacgcgtataaaaaacgaaaggacagtagatggaagattcgccgtcctcc
ggtacgatctccgactccgagttctgccgtccgttcaagatatgcttccaacacggcgccgtttta ctcggaagcta
aaacccaaatcagaagaggtttcgatagttatttgaggcccaatacgtttagttaattctaaaaacc  26515800

*FIG. 8*

Chromosome 5 = CP002688.1
Chromosome 3 = CP002686.1

At5g64600
Accession number: NM_125856.5

O-fucosyltransferase family protein

```
CDS (SEQ ID NO:1)
   1 ATGGTGAAAC ACAGAAACTC ATCTCGCTCG ATAATCTCAT ATTCTTCTTC
  51 AATAGCAAGA TTCTTCTCTA GAAAAGCTAT TTCTCTCTAC TTGATCTTCG
 101 TCTTTGCTTT TACCATCTGG GTTCTCGTCT TCAGCTCCAG AAACATTCAA
 151 ACCGATGATG ACCACACCAA ACATCAACAA CAACATCATC GGGATCTAAT
 201 CGATTCAGAA TCATTTCCGC CACCGTATTT GCCTCCTAGG AAGAATTTGC
 251 AGAAACCGTA TGAAAATACT CAACTTTGGA CTCCTCCTTT CAGCTTTGGG
 301 TTGCATCCAT GTGTCAAACC TACTCCGAAA TACAAAGAAT TTCAGAATC
 351 AGATCATTAT ATAACAGTGA AAAGTAATGG TGGACTAAAT CAAATGCGTA
 401 CTGGTATAGC AGATATAGTG GCTGTTGCGC ACATCATGAA TGCAACTTTA
 451 GTCATTCCTG AGCTGGATAA GCGATCGTTT TGGCAAGATT CAAGTGTTTT
 501 TTCAGATATT TTTGACGAGG AACAATTCAT TAAATCATTG CGAAGAGATG
 551 TCAAGGTTAT TAAAAAGCTC CCAAAGGAAG TGGAATCTCT ACCTAGAGCA
 601 AGGAAGCATT TCACTTCTTG GTCTAGTGTT GGATATTATG AAGAAATGAC
 651 TCACTTGTGG AAGGAGTACA AGGTCATCCA TGTCGCAAAA TCAGATTCTC
 701 GCCTTGCAAA TAATGACCTG CCTATCGACG TTCAAAGACT GAGATGTCGT
 751 GTACTATATC GTGGTCTCTG CTTCTCTCCT GCAATTGAAA GCCTTGGACA
 801 GAAGCTGGTT GAGAGACTCA AGTCACGTGC TGGGAGATAT ATTGCATTGC
 851 ACCTGAGATA TGAGAAAGAT ATGTTGGCTT TCACTGGTTG CACCTATGGT
 901 CTCACTGATG CTGAATCCGA AGAACTGAGA GTAATGCGGG AAAGTACAAG
 951 CCATTGGAAG ATCAAAAGTA TAAATTCAAC AGAGCAGAGA GAGGAAGGCC
1001 TTTGTCCATT GACTCCAAAA GAAGTGGGAA TATTTCTGAA AGGTCTCGGA
1051 TATTCTCAGT CAACAGTCAT ATATATTGCA GCAGGGGAAA TCTATGGGGG
1101 TGATGATAGA CTCTCTGAGC TTAAGTCGCG CTTCCCAAAT CTGGTTTTTA
1151 AGGAAACGCT TGCTGGGAAC GAAGAGTTAA AAGGTTTCAC TGGCCATGCG
1201 ACTAAAACGG CTGCTCTTGA TTACATAATT TCTGTTGAGA GTGATGTGTT
1251 TGTTCCTTCA CATTCTGGAA ACATGGCAAG AGCAGTTGAA GGTCACCGCA
1301 GATTTCTAGG GCATCGCAGG ACTATCACTC CCGACAGGAA AGGACTAGTG
1351 AAACTCTTCG TTAAGATGGA GAGAGGACAG CTAAAAGAAG GACCAAAGTT
1401 GTCCAATTTT GTGAATCAAA TGCATAAAGA CAGACAAGGT GCACCGAGGA
1451 GAAGGAAAGG ACCAACGCAG GGGATCAAAG GACGTGCACG GTTTAGAACT
1501 GAAGAAGCCT TTTATGAGAA TCCATATCCA GAGTGTATTT GCAGTTCAAA
1551 GGAGCACAAA GAACCCTAA

Genomic (SEQ ID NO:19)
   1 CTTCATCGAA GATGGTGAAA CACAGAAACT CATCTCGCTC GATAATCTCA
  51 TATTCTTCTT CAATAGCAAG ATTCTTCTCT AGAAAAGCTA TTTCTCTCTA
 101 CTTGATCTTC GTCTTTGCTT TTACCATCTG GGTTCTCGTC TTCAGCTCCA
 151 GAAACATTCA AACCGATGAT GACCACACCA AACATCAACA ACAACATCAT
 201 CGGGATCTAA TCGATTCAGA ATCATTTCCG CCACCGTATT TGCCTCCTAG
 251 GAAGGTAAAG TTGTTAATAT TTCATGGGTT GTGGATTTGA ATGAAGAAAT
```

FIG. 9A

```
 301 GAGGTGACTT GATTTGGTTT TTGATCGGAA CAATTGAGAA AGCATAACTT
 351 TATTGAGCTT CAGAATTTGC AGAAACCGTA TGAAAATACT CAACTTTGGA
 401 CTCCTCCTTT CAGCTTTGGG TTGCATCCAT GTGTCAAACC TACTCCGAAA
 451 TACAAAGGTA TGCCAAAGAA GCTCACTTCC AATTTCTGAT GGATCTATCT
 501 TGGGTTTTGT TTATGAATTC AGAACTGTGC TTTTGATTGA TTTCAAGTTC
 551 GTTTCTTGCA GAATTTTCAG AATCAGATCA TTATATAACA GTGAAAAGTA
 601 ATGGTGGACT AAATCAAATG CGTACTGGTG TAAGTAAAAC CATTTAAGTT
 651 GTTGTTTTCA TGATTCTTTT TGTCTTGCTT AGTACCAAAG TGATTCAATA
 701 AGCATGTTAT TGTACAGATA GCAGATATAG TGGCTGTTGC GCACATCATG
 751 AATGCAACTT TAGTCATTCC TGAGCTGGAT AAGCGATCGT TTTGGCAAGA
 801 TTCAAGGTAT TTTGAAACTT CAAACAAACA AAAATGCAG CTTACTTAAT
 851 TAGTGGTTAT GAGATTTATA CTATTTCTAA CTTACATTTT CGCTATGTCT
 901 CAGTGTTTTT TCAGATATTT TTGACGAGGA ACAATTCATT AAATCATTGC
 951 GAAGAGATGT CAAGGTTATT AAAAAGCTCC CAAGGAAGT GGAATCTCTA
1001 CCTAGAGCAA GGAAGCATTT CACTTCTTGG TCTAGTGTTG ATATTATGA
1051 AGAAATGACT CACTTGTGGA AGGAGTACAA GGTCGGTCTT AAGCAACTTC
1101 TTTTACATTT TGCATTTGCT GTTTCATTCA ACTGCTGATA GAATAATAAC
1151 AATGCAGGTC ATCCATGTCG CAAAATCAGA TTCTCGCCTT GCAAATAATG
1201 ACCTGCCTAT CGACGTTCAA AGACTGAGAT GTCGTGTACT ATATCGTGGT
1251 CTCTGCTTCT CTCCTGCAAT TGAAAGCCTT GGACAGGTTG GGACCCTTTT
1301 CCTGTCTTGT ACACAACATA GATAGGCTGT AGTAACATAA AATTCATTTC
1351 ATACACATAA GATTTCAAGT TAATGTTCTC TTTGGGTACC GAATAGCTAT
1401 ATAGAAGTTT CAAACCATC GTTTGGGTCA ACGAGTTTTC ATTGTCAAAT
1451 GATAGAACTT GCAATAACAT AGTTTATGCA TTTAAGAGGT GTGTAATGAT
1501 AGAATAGGAG AATGGATACA TCTTTTTCTA TCAAACATAG TTTATGCATT
1551 TAAGAGGTGT CCTATGGGGA TTCCTGTAGA CTGTGGGTTC TGAGCAATCA
1601 TGACGGTGAC ACCACAGAAG CTGGTTGAGA GACTCAAGTC ACGTGCTGGG
1651 AGATATATTG CATTGCACCT GAGATATGAG AAAGATATGT TGGCTTTCAC
1701 TGGTTGCACC TATGGTCTCA CTGATGCTGA ATCCGAAGAA CTGAGAGTAA
1751 TGCGGTAATT GATTACTCTC TGCATCTATT CTTAACAAAG CAAACATGCA
1801 AAACGTCTTC ATGGGATAAA ATTACAGTTT CAAGCTCAAT ATGTTATCTG
1851 TTGGTCACAG GGAAAGTACA AGCCATTGGA AGATCAAAAG TATAAATTCA
1901 ACAGAGCAGA GAGAGGAAGG CCTTTGTCCA TTGACTCCAA AGAAGTGGG
1951 AATATTTCTG AAAGGTCTCG GATATTCTCA GTCAACAGTC ATATATATTG
2001 CAGCAGGGA AATCTATGGG GGTGATGATA GACTCTCTGA GCTTAAGTCG
2051 CGCTTCCCAA ATCTGGTTTT TAAGGTCTGT TCAACCACCT CTAATCTTTC
2101 ATGTTACTGA CAATCTAAAG ATGATAAATG TTTATGTTTC ATGTACTGGA
2151 TTTTGTAGGA AACGCTTGCT GGGAACGAAG AGTTAAAAGG TTTCACTGGC
2201 CATGCGACTA AAACGGCTGC TCTTGATTAC ATAATTTCTG TTGAGAGTGA
2251 TGTGTTTGTT CCTTCACATT CTGGAAACAT GGCAAGAGCA GTTGAAGGTC
2301 ACCGCAGATT TCTAGGGCAT CGCAGGACTA TCACTCCCGA CAGGTTCTAT
2351 CTCCTTCCTT CTGTTACCTT AAAAAAAGC ATTAATCTTT TAGTCATTTT
2401 GTTATAGGCC ATGACAAGTT TGGTGTTGTA TGCAGGAAAG GACTAGTGAA
2451 ACTCTTCGTT AAGATGGAGA GAGGACAGCT AAAAGAAGGA CCAAAGTTGT
2501 CCAATTTTGT GAATCAAATG CATAAAGACA GGTAGCAAAA GAGTCATACG
2551 TTTGCTTCTT AAACAATAAA CCTATAAAAA AAGCACATC TTTGATGCGA
2601 GAAGAGGATT TGTTTGATCG GTTTGCAGA CAAGGTGCAC CGAGGAGAAG
2651 GAAAGGACCA ACGCAGGGGA TCAAGGACG TGCACGGTTT AGAACTGAAG
2701 AAGCCTTTTA TGAGAATCCA TATCCAGAGT GTATTTGCAG TTCAAAGGAG
2751 CACAAAGAAC CCTAACTAAA ATTTTCCAAA CTTTTTTTGT TCTGTATCAT
2801 TACATCTCAT TTATAGTCAT CTTAATTATA GTTTTCACAT ATCCCTTGAT
2851 ATCTTTTCTG TTTTTGATAT CCGGAGATCT CTAGCCGAAG TAGAAAGCCA
```

*FIG. 9B*

```
2901 GAAATTTTTA ACATTTAGTT ATAAAACTTC TCTTTCGGCA TTTTTTCAAA
2951 TATTCCAAAT TTTAACCAAA CTGTTGTCAA TCAGAATGGA ACAAGAATGA
3001 AACACCAAAG TTACTACTG
```

Amino acid (SEQ ID NO:2)
```
  1 MVKHRNSSRS IISYSSSIAR FFSRKAISLY LIFVFAFTIW VLVFSSRNIQ
 51 TDDDHTKHQQ QHHRDLIDSE SFPPPYLPPR KNLQKPYENT QLWTPFFSFG
101 LHPCVKPTPK YKEFSESDHY ITVKSNGGLN QMRTGIADIV AVAHIMNATL
151 VIPELDKRSF WQDSSVFSDI FDEEQFIKSL RRDVKVIKKL PKEVESLPRA
201 RKHFTSWSSV GYYEEMTHLW KEYKVIHVAK SDSRLANNDL PIDVQRLRCR
251 VLYRGLCFSP AIESLGQKLV ERLKSRAGRY IALHLRYEKD MLAFTGCTYG
301 LTDAESEELR VMRESTSHWK IKSINSTEQR EEGLCPLTPK EVGIFLKGLG
351 YSQSTVIYIA AGEIYGGDDR LSELKSRFPN LVFKETLAGN EELKGFTGHA
401 TKTAALDYII SVESDVFVPS HSGNMARAVE GHRRFLGHRR TITPDRKGLV
451 KLFVKMERGQ LKEGPKLSNF VNQMHKDRQG APRRRKGPTQ GIKGRARFRT
501 EEAFYENPYP ECICSSKEHK EP
```

*FIG. 9C*

At5g65900
DEA(D/H)-box RNA helicase
Accession number NM_125987.2
CDS (SEQ ID NO:3)

```
   1 ATGGCGAATT TGGATATGGA GCAACATTCA TCCGAAAACG AAGAGATTAA
  51 GAAGAAGAAG CATAAGAAAA GAGCGAGAGA CGAAGCTAAG AAACTAAAGC
 101 AGCCAGCAAT GGAAGAAGAA CCCGATCATG AAGATGGTGA TGCCAAAGAG
 151 AACAATGCGT TAATTGACGA AGAACCGAAG AAGAAGAAGA GAAGAAAAA
 201 TAAGAAGCGT GGAGATACTG ATGATGGAGA GGACGAAGCG GTAGCAGAAG
 251 AAGAGCCGAA GAAGAAGAAG AAGAAAAATA AAAGCTACA GCAGCGTGGA
 301 GATACTAATG ACGAAGAGGA CGAAGTGATA GCAGAAGAAG AAGAGCCGAA
 351 GAAGAAGAAG AAGAAACAGA GGAAGGACAC GGAAGCGAAG TCTGAAGAAG
 401 AAGAAGTAGA AGATAAGGAA GAAGAAAAAA AATTGGAAGA AACTAGCATA
 451 ATGACTAATA AAACGTTTGA GTCATTGTCA TTATCTGATA ACACTTATAA
 501 ATCTATCAAG GAGATGGGTT TTGCACGCAT GACTCAGATA CAAGCTAAAG
 551 CAATTCCACC ATTGATGATG GGAGAAGATG TACTTGGAGC TGCCAGGACC
 601 GGTTCTGGTA AAACCTTAGC TTTTCTTATT CCTGCTGTTG AGCTTCTTTA
 651 CCGTGTTAAG TTTACTCCTC GCAATGGAAC TGGTGTTCTT GTTATTTGCC
 701 CAACAAGAGA GCTTGCTATT CAGTCTTATG GAGTGGCAAA AGAACTTCTT
 751 AAGTATCATT CACAGACTGT GGGAAAAGTT ATTGGCGGTG AGAAAAGAAA
 801 GACAGAAGCT GAGATTCTTG CGAAAGGTGT TAATTTATTA GTAGCTACCC
 851 CTGGAAGACT TCTCGACCAC CTTGAAAATA CTAATGGTTT TATTTTCAAG
 901 AACTTAAAGT TTCTTGTAAT GGATGAGGCT GATAGGATAT TGGAACAGAA
 951 CTTTGAAGAA GACCTCAAGA AGATTTTGAA CCTTCTACCA AAGACTAGAC
1001 AGACGTCACT ATTTTCAGCC ACACAGAGCG CAAAGGTTGA GGATCTTGCT
1051 CGGGTGTCAC TTACCTCACC TGTTTATATT GATGTGGATG AAGGACGAAA
1101 AGAGGTTACA AATGAAGGCT GGAGCAAGG TTATTGCGTT GTGCCAAGTG
1151 CGATGCGGTT ACTTTTTTTA CTTACCTTCT TGAAGAGATT CCAAGGGAAA
1201 AAGAAAATTA TGGTGTTTTT CTCTACATGC AAGTCGACAA AGTTCCACGC
1251 CGAGCTCTTT CGATATATCA AATTCGATTG CCTTGAAATC CGTGGAGGGA
1301 TAGACCAGAA CAAAAGAACT CCAACATTTT TGCAATTCAT AAAGGCGGAA
1351 ACCGGTATTT TGTTGTGTAC TAATGTCGCT GCCCGAGGTC TTGATTTTCC
1401 TCATGTGGAC TGGATTGTGC AGTATGATCC TCCTGATAAC CCAACGGATT
1451 ATATTCATCG AGTTGGTAGA ACAGCTCGTG GTGAAGGAGC AAAAGGAAAG
1501 GCTCTGCTTG TCCTAACTCC ACAGGAGTTG AAGTTTATAC AGTATCTCAA
1551 GGCGGCGAAA ATTCCTGTTG AGGAACATGA ATTTGAAGAA AAGAAATTGC
1601 TCGATGTGAA ACCTTTTGTG GAGAATTTGA TATCTGAAAA CTATGCATTG
1651 AAGGAGTCAG CAAAAGAAGC ATACAAGACA TACATTTCAG GATATGATTC
1701 TCACTCTATG AAAGATGTCT TTAATGTTCA CCAACTCAAT CTCACGGAGG
1751 TTGCGACTTC GTTTGGTTTC TCAGATCCTC CCAAAGTTGC TCTGAAGATA
1801 GATCGAGGAG GGTACAGAAG TAAGAGAGAA CCGGTTAATA AGTTTAAGAG
1851 AGGTCGTGGT GGTGGTAGAC CCGGCGGTAA AAGCAAGTTC GAGAGGTACT
1901 AA
```

Genomic (SEQ ID NO:20)

```
   1 AGAACACTCT CGAATTCGAA GAAAATACGT AGCAAAACCC TTATTTTTGA
  51 ATTTCAGACG AATTCCGATT TCTTAATCAA AAATCCGATA AGAGCTTTGG
 101 ATTTGGCGGC GAATAAGAAA ACATGGCGAA TTTGGATATG GAGCAACATT
 151 CATCCGAAAA CGAAGAGATT AAGAAGAAGA AGCATAAGAA AAGAGCGAGA
 201 GACGAAGCTA AGAAACTAAA GCAGCCAGCA ATGGAAGAAG AACCCGATCA
 251 TGAAGATGGT GATGCCAAAG AGAACAATGC GTTAATTGAC GAAGAACCGA
```

*FIG. 9D*

```
 301 AGAAGAAGAA GAAGAAGAAA AATAAGAAGC GTGGAGATAC TGATGATGGA
 351 GAGGACGAAG CGGTAGCAGA AGAAGAGCCG AAGAAGAAGA AGAAGAAAAA
 401 TAAAAAGCTA CAGCAGCGTG GAGATACTAA TGACGAAGAG GACGAAGTGA
 451 TAGCAGAAGA AGAAGAGCCG AAGAAGAAGA AGAAGAAACA GAGGAAGGAC
 501 ACGGAAGCGA AGTCTGAAGA AGAAGAAGTA AAGATAAGG AAGAAGAAAA
 551 AAAATTGGAA GAAACTAGCA TAATGACTAA TAAAACGTTT GAGTCATTGT
 601 CATTATCTGA TAACACTTAT AAATCTATCA AGGAGATGGG TTTTGCACGC
 651 ATGACTCAGG TAATGTTTTT GGAATTGAAG CTTTATGTTT TTGTATAGCA
 701 AAGATTCAAC CTTTTACAGT TTGGAATTTG GTTGGATTTC AACACTTTTG
 751 CAGATACAAG CTAAAGCAAT TCCACCATTG ATGATGGGAG AAGATGTACT
 801 TGGAGCTGCC AGGACCGGTT CTGGTAAAAC CTTAGCTTTT CTTATTCCTG
 851 CTGTTGAGCT TCTTTACCGT GTTAAGTTTA CTCCTCGCAA TGGAACTGGT
 901 GTTCTTGTTA TTTGCCCAAC AAGAGAGCTT GCTATTCAGG TTCTAATTCT
 951 CTCACAATTT TCTATATAGT CTGTAGAATA TGCTAAAAGT GATACTTACT
1001 ATACATCATT AATGTTCAG TCTTATGGAG TGGCAAAAGA ACTTCTTAAG
1051 TATCATTCAC AGACTGTGGG AAAAGTTATT GGCGGTGAGA AAGAAAGAC
1101 AGAAGCTGAG ATTCTTGCGA AGGTGTTAA TTATTAGTA GCTACCCCTG
1151 GAAGACTTCT CGACCACCTT GAAAATACTA ATGGTTTTAT TTCAAGAAC
1201 TTAAAGGTAA ACACAAATTT CTGATTTCAG TTTGGGTAT ACTGGTATTG
1251 ATTTAATGCA ACATTTTTA TTCGTTAATT TGCAGTTTCT TGTAATGGAT
1301 GAGGCTGATA GGATATTGGA ACAGAACTTT GAAGAAGACC TCAAGAAGAT
1351 TTTGAACCTT CTACCAAGG TATTCTCGTG GCTTGCATAG TGAAGTCACC
1401 TCAACATTCT GAATCATAGA GATGTAAATT TCGTTTCATG TCAATGTGTT
1451 GTTGATAATG GTAAACCGTC TTTTTGTATT GCTGCAGACT AGACAGACGT
1501 CACTATTTTC AGCCACACAG AGCGCAAAGG TCTGCTTACC AATCAGTATA
1551 GTTTTCACTT AATTCTTTAT TAGTGTCAGT TTATTAAAAT TACTGGAACT
1601 TGATTAAACC ATCAGGTTGA GGATCTTGCT CGGGTGTCAC TTACCTCACC
1651 TGTTTATATT GATGTGGATG AAGGACGAAA AGAGGTAGCT ATTAACACAA
1701 TTTCTATTAT CTTTTCTCGC AATTTACTTT GTGACCAAAA CAGGCCTTTT
1751 TCAATTATAA GAAAACTGGA AAGTGCAGGT TACAAATGAA GGCTTGGAGC
1801 AAGGTTATTG CGTTGTGCCA AGTGCGATGC GGTTACTTTT TTTACTTACC
1851 TTCTTGAAGA GATTCCAAGG GAAAAGAAA ATTATGGTGT TTTTCTCTAC
1901 ATGCAAGTCG ACAAAGTTCC ACGCCGAGCT CTTTCGATAT ATCAAATTCG
1951 ATTGCCTTGA ATCCGTGGA GGGATAGACC AGAACAAAAG AACTCCAACA
2001 TTTTTGCAAT TCATAAAGGC GGAAACCGGT ATTTGTTGT GTACTAATGT
2051 CGCTGCCCGA GGTCTTGATT TTCCTCATGT GGTATGCTTT CTTAACAACT
2101 TTAATGTTTT AATAATCTGG ATTGGTTGGT CTTTAATCAA ATTATTGTCT
2151 GCTTGTTTAG GACTGGATTG TGCAGTATGA TCCTCCTGAT AACCCAACGG
2201 TATGTTGCTT ATAATTTAGG GTTTTATGC AAACACGCGG AAGAATAAGG
2251 GATAAGAAAT CACTCAAATT CTTGAATGTT ACTTTTGATT TAGGATTATA
2301 TTCATCGAGT TGGTAGAACA GCTCGTGGTG AAGGAGCAAA AGGAAAGGCT
2351 CTGCTTGTCC TAACTCCACA GGAGTTGAAG TTTATACAGT ATCTCAAGGT
2401 AAATTATTTT CATTCAATAA AAACTTTGAT AATTTTTCAA ATTATAGAAA
2451 TTTTGATAAA AGAATCTGTT TCCAACTGTA TAATTTGCAG GCGGCGAAAA
2501 TTCCTGTTGA GGAACATGAA TTTGAAGAAA AGAAATTGCT CGATGTGAAA
2551 CCTTTTGTGG TAAAACATTC TTGCTCTTTC AAATAAGTTT TACTACACTG
2601 AAGAAACAAA AGTTGAGAGA TTTATTTAAA ATGTTATTGC AGGAGAATTT
2651 GATATCTGAA AACTATGCAT TGAAGGAGTC AGCAAAAGAA GCATACAAGA
2701 CATACATTTC AGGATATGAT TCTCACTCTA TGAAAGATGT CTTTAATGTT
2751 CACCAACTCA ATCTCACGGT AACCAAATCT GCAGCATACA TATAACAATA
2801 CGAAACGTCA TGAAATCAGG AATACAATTT GTTTTGTTT TCTGCAATTT
2851 AAACGTTAAC CGAAGGTCTT TGTTTATGTG CAGGAGGTTG CGACTTCGTT
```

*FIG. 9E*

```
2901 TGGTTTCTCA GATCCTCCCA AAGTTGCTCT GAAGATAGAT CGAGGAGGGT
2951 ACAGAAGTAA GAGAGAACCG GTTAATAAGT TTAAGAGAGG TCGTGGTGGT
3001 GGTAGACCCG GCGGTAAAAG CAAGTTCGAG AGGTACTAAA AATACAGTTG
3051 CACAAACAAC GTCATACTTA GTAGTATGGC ACATGCCTTT TAACGAATGT
3101 TGTATCTTAT TTTTGGATTC ATTTACGATT GTGTTGTCTT AAGCTGTTTC
3151 CAGAGATATC AGACGAGATA CCAGTTTTGT CCCCGTTACT TAGAAATATT
3201 GATCATTTTG TTTTGCGAAT AAACTTGGTC TTATATAT

Aa (SEQ ID NO:4)
     1 MANLDMEQHS SENEEIKKKK HKKRARDEAK KLKQPAMEEE PDHEDGDAKE
    51 NNALIDEEPK KKKKKKNKKR GDTDDGEDEA VAEEEPKKKK KKNKKLQQRG
   101 DTNDEEDEVI AEEEEPKKKK KKQRKDTEAK SEEEEVEDKE EEKKLEETSI
   151 MTNKTFESLS LSDNTYKSIK EMGFARMTQI QAKAIPPLMM GEDVLGAART
   201 GSGKTLAFLI PAVELLYRVK FTPRNGTGVL VICPTRELAI QSYGVAKELL
   251 KYHSQTVGKV IGGEKRKTEA EILAKGVNLL VATPGRLLDH LENTNGFIFK
   301 NLKFLVMDEA DRILEQNFEE DLKKILNLLP KTRQTSLFSA TQSAKVEDLA
   351 RVSLTSPVYI DVDEGRKEVT NEGLEQGYCV VPSAMRLLFL LTFLKRFQGK
   401 KKIMVFFSTC KSTKFHAELF RYIKFDCLEI RGGIDQNKRT PTFLQFIKAE
   451 TGILLCTNVA ARGLDFPHVD WIVQYDPPDN PTDYIHRVGR TARGEGAKGK
   501 ALLVLTPQEL KFIQYLKAAK IPVEEHEFEE KKLLDVKPFV ENLISENYAL
   551 KESAKEAYKT YISGYDSHSM KDVFNVHQLN LTEVATSFGF SDPPKVALKI
   601 DRGGYRSKRE PVNKFKRGRG GGRPGGKSKF ERY
```

*FIG. 9F*

At5g66380
 ATFOLT1    FOLATE TRANSPORTER 1
 FOLT1      FOLATE TRANSPORTER 1
            NCBI Accession number: BT010139.1

CDS (SEQ ID NO:5)
   1 ATGGCGGCGT CGTGGCAGTG GGAAAATGCC ACCGCCGGCG CCGTCGCTGG
  51 ATTCGCCACC GTAGCTGCTA TGCACTCTCT TGATGTTGTT CGTACGAGAT
 101 TCCAAGTCAA CGACGGAAGA GGGTCAAGTC TGCCGACGTA CAAGAACACT
 151 GCTCACGCTG TCTTCACCAT TGCCCGTCTC GAGGGTTTGA GAGGGCTTTA
 201 TGCAGGCTTC TTCCCTGCAG TTATCGGTTC TACTGTTTCC TGGGGCTTAT
 251 ACTTCTTTTT TTATGGAAGA GCCAAGCAGA GGTACGCTAG AGGCAGGGAC
 301 GATGAGAAAC TCAGCCCTGC TCTCCACCTT GCTTCTGCTG CTGAAGCAGG
 351 GGCCTTGGTC TGTTTATGCA CAAATCCTAT TGGCTTGTCA AAACAAGGT
 401 TACAGCTTCA GACACCTCTT CATCAAACTC AACCATACTC AGGGCTATTA
 451 GATGCCTTTA GAACCATAGT GAAAGAGGAA GGACCCAGGG CGCTCTACAA
 501 GGGTATTGTC CCTGGTCTTG TACTGGTTTC TCATGGTGCT ATTCAGTTCA
 551 CAGCTTATGA GGAACTCCGT AAAATCATTG TGGATTTGAA AGAAAGGAGA
 601 AGAAAGTCCG AATCCACTGA CAATCTATTG AACTCAGCAG ATTATGCTGC
 651 ACTTGGTGGC TCCTCCAAAG TCGCTGCAGT TCTTCTTACG TATCCATTTC
 701 AAGTTATACG AGCACGATTA CAGCAACGAC CTAGTACCAA CGGAATCCCA
 751 AGATATATAG ACAGCTTACA TGTCATCAGA GAAACCGCGA GATATGAAGG
 801 TCTCAGGGGT TTCTACAGGG GACTAACGGC TAATCTTTTG AAAAATGTAC
 851 CTGCGTCTTC CATCACATTC ATCGTCTATG AAAACGTTCT GAATTGCTA
 901 AAACAGCATC AACAACAAA AGATTAG

Genomic (SEQ ID NO:21)
   1 CTTGAACGGA CGGCAGAACT CGGAGTCGGA GATCGTACCG GAGGACGGCG
  51 AATCTTCCAT CTACTGTCCT TTCGTTTTTT ATACGCGTCA ATGAGTCTT
 101 TAACTTCAGA TTAGCTCTGT AAACAATCGC GATTAGTCCG GATTGCATCT
 151 AAGGATTCGT TGATGGCGGC GTCGTGGCAG TGGGAAAATG CCACCGCCGG
 201 CGCCGTCGCT GGATTCGCCA CCGTAGCTGC TATGCACTCT CTTGATGTTG
 251 TTCGTACGAG ATTCCAAGGT CTGGTTTTTC ACTCCTGGAT TAACTCATCG
 301 ATTTTGCTTT TAAAAAGTTG CTAACTTGAT TGAACAACAG TCAACGACGG
 351 AAGAGGGTCA AGTCTGCCGA CGTACAAGAA CACTGCTCAC GCTGTCTTCA
 401 CCATTGCCCG TCTCGAGGTT TCCCAGATGA AACTCTCTTC TGGCATCTTC
 451 CATATTATCT CTCTATGTT ATGTGGTTGA CTCATTTGGT TTAAATCTTC
 501 TGTAGGGTTT GAGAGGGCTT TATGCAGGCT TCTTCCCTGC AGTTATCGGT
 551 TCTACTGTTT CCTGGGGCTT ATACTTCTTT TTGTGAGTGT ACTTTCGTT
 601 TAGCACATAT CTTCTTTCTT CATGATTTCT ATTCAAACAG TTTTCTGTTA
 651 GTTTTTTTAA TGTTTTTAGC CGTGGATCTT GTTTAAAATG TTCTGGAACA
 701 AATATATTAT CTCTCTGTAG TTATGGAAGA GCCAAGCAGA GGTACGCTAG
 751 AGGCAGGGAC GATGAGAAAC TCAGCCCTGC TCTCCACCTT GCTTCTGCTG
 801 CTGAAGCAGG GGCCTTGGTG AGTCTAACAG GCGCCATAAA CATCTCATTT
 851 CTCCTATGTT TTTTCGATCT CAGTATCAAG GGAATGATGC TTTCAGGTCT
 901 GTTTATGCAC AAATCCTATT TGGCTTGTCA AAACAAGGTT ACAGCTTCAG
 951 ACACCTCTTC ATCAAACTCA ACCATACTCA GGGCTATTAG TTTGCAATA
1001 TGCTGCACAC ACAAAATTCA GTTTTCATTG TTTCTAGTGT TTCATTCTAA
1051 ATGTGTATTT TGTGATCTTA AGATGCCTTT AGAACCATAG TGAAAGAGGA
1101 AGGACCCAGG GCGCTCTACA AGGGTATTGT CCCTGGTCTT GTACTGGTTA
1151 GTAACTATCC TGATCTATCT CTTGTAACGT TCGTTCGTAA AACTACCACA
1201 AGATCCACAG TTTTGGAACT ATAAAGATG ACTATTAGTT GCGAAAGAGG

FIG. 9G

```
1251 AGGCCTTACA GATTGAATGG TTTACATTTT GGGTTCAGCA GGTTTCTCAT
1301 GGTGCTATTC AGTTCACAGC TTATGAGGAA CTCCGTAAAA TCATTGTGGA
1351 TTTGAAAGAA AGGAGAAGAA AGTCCGAATC CACTGACAAT CTATTGGTAC
1401 AGAGTAATTC TTCTGAATAG GCTACATTGC GGTTCTTAAG TTATATAGCC
1451 ACATTAATCT TAATTCTACG GCTATTTCCA GCATCACGGA TATATACTAT
1501 TCTAACACAC TCCATTGCAA TTTTTCTTTA GAACTCAGCA GATTATGCTG
1551 CACTTGGTGG CTCCTCCAAA GTCGCTGCAG TTCTTCTTAC GTATCCATTT
1601 CAAGTTATAC GAGCACGATT ACAGGTACCT ATCGACCGTG TCTTCTTCAG
1651 TCTTATTATT GTTAGCTCAA ATCTAAATTC CTTGAGCTTC CTTACTTTCT
1701 ACCTTTGACC TTCTGCAATA TATGAGGATT TCATAAACAT GGTTCTTTTC
1751 TTGTTCAGCA ACGACCTAGT ACCAACGGAA TCCCAAGATA TATAGACAGC
1801 TTACATGTCA TCAGAGAAAC CGCGAGGTCA GGGCATATTC TTGGTCTCGA
1851 TTATGTCTGG AATGATGATC TTTTTGGTTA GTTTCACTGA GTAACACTTT
1901 TGGGTCTCTC TGCAGATATG AAGGTCTCAG GGGTTTCTAC AGGGGACTAA
1951 CGGCTAATCT TTTGAAAAAT GTACCTGCGT CTTCCATCAC ATTCATCGTC
2001 TATGAAAACG TTCTGAAATT GCTAAACAG CATCCAACAA CAAAAGATTA
2051 GACTCTTCCT CTTCCTTTAC CGTTATTTCT TAGACTCAAC ACGCACGCGG
2101 TTGACTTGTC ACTCCCAATA CTAGAGAATT ATTCTTTGAT ATACATATAT
2151 TTTATGTGCG TTCCATGGTT CT

Aa (SEQ ID NO:6)
   1 MAASWQWENA TAGAVAGFAT VAAMHSLDVV RTRFQVNDGR GSSLPTYKNT
  51 AHAVFTIARL EGLRGLYAGF FPAVIGSTVS WGLYFFFYGR AKQRYARGRD
 101 DEKLSPALHL ASAAEAGALV CLCTNPIWLV KTRLQLQTPL HQTQPYSGLL
 151 DAFRTIVKEE GPRALYKGIV PGLVLVSHGA IQFTAYEELR KIIVDLKERR
 201 RKSESTDNLL NSADYAALGG SSKVAAVLLT YPFQVIRARL QQRPSTNGIP
 251 RYIDSLHVIR ETARYEGLRG FYRGLTANLL KNVPASSITF IVYENVLKLL
 301 KQHPTTKD
```

*FIG. 9H*

At3g59640 glycine-rich protein
NCBI Accession number NM_001084845.1

CDS (SEQ ID NO:7)
```
   1 ATGAGCTCTA CGCAGGCTAA TCTATGCAGA CCATCCTTGT TCTGTGCAAG
  51 GACAACGCAA ACAAGACATG TCTCTAGTGC ACCTTTTATG TCGTCATTAC
 101 GCTTTGATTA TCGACCACTC CCCAAATTAG CTATTCGGGC ATCTGCATCA
 151 TCATCGATGT CTTCTCAGTT TTCGCCTCTA CAGAATCATC GCTGCCGGAA
 201 TCAGAGGCAA GGTCCTGTTG TGTGTTTACT TGGTGGGAAG GATAAGTCTA
 251 ACGGTAGTAA TGAGCTATCA TCAACATGGG AAGCTATTGA GAAAGCAATG
 301 GGGAAGAAAT CAGTTGAAGA TATGTTGCGT GAGCAGATAC AAAAGAAAGA
 351 CACTGGCGGC ATTCCTCCAC GAGGACGAGG AGGAGGGGGT GGCGGTAGAA
 401 ATGGTGGGAA TAATGGGTCT GGAGGCTCAT CAGGGGAAGA TGGTGGTCTT
 451 GCTAGTTTTG GGGATGAAAC TCTGCAAGTG GTATTAGCAA CCTTAGGCTT
 501 CATCTTTCTG TACTTCTACA TCATCAATGG GGAGGAGTTG TTCCGTCTTG
 551 CAAGAGATTA CATTAGGTAC CTTATAGGAA GACCCAAGAG TGTTAGGCTG
 601 ACCCGAGTTA TGGAAGGTTG GAGTAGATTC TTCGAGAAGA TGTCGAGGAA
 651 AAAAGTGTAT AACGAGTACT GGCTAAAGAT TAAGCGATCA TCAACAAGTC
 701 TACCTGGTCT GGTAACCCGG GCAAATACAA ACGCATCTTG A
```

Genomic (SEQ ID NO:22)
```
   1 ACACAAACAA GAAAACGCAA AACTAATCCT CTCTCGAATT AGGGTTTCGT
  51 CAAGGTATTA CATTATTTCA CACCCTTATC ATCATCTTCT GATTTCTGGT
 101 AATCTTCTTT TGATTAGATC TTCCTATCGA TTGGTTCAGT CCTTTCTTAT
 151 TTTCGAATTC TTGATTGGTT TACCGTGGTT GCTACGATTT AAACCTTTAA
 201 CATACCTAAA AGAACGTTTT TGTTTTTGCT TTTTGTTGTT ATTGAAGTTT
 251 TTTTTTTTTT TTATTGTTGT TGATGAAGAT CCTGGAGTTG ATGTATTGAG
 301 AGAAGCCATT GAGATAAGAG ATGAGCTCTA CGCAGGCTAA TCTATGCAGA
 351 CCATCCTTGT TCTGTGCAAG GACAACGCAA ACAAGACATG TCTCTAGTGC
 401 ACCTTTTATG TCGTCATTAC GCTTTGATTA TCGACCACTC CCCAAATTAG
 451 CTATTCGGGC ATCTGCATCA TCATCGATGT CTTCTCAGTT TTCGCCTCTA
 501 CAGAATCATC GCTGCCGGAA TCAGAGGCAA GGTCCTGTTG TGTGTTTACT
 551 TGGTGGGAAG GATAAGTCTA ACGGTAGTAA TGAGGTGAGA TGCTTCGTCT
 601 TCATTCTAAG ATGTCTTTGC TTATTAGATC ATATAAAGAT GATGCTTAAT
 651 CTTTAAATGT TCCAATTGA TCTTTTTGTG TGTGTGTGCG TGTAAGAAGT
 701 TCGGCACAGA GTTGAGTTAT GTTCTGATT ATAAGTAGTA TTGATATGAT
 751 TCTTTTCTGT TTTATACTTA CTTGGTCGAA AGGATAAATC TGATAGTAGT
 801 TATGAGATCA GATGATTTCT CTTCATTCTA TAGATGTTCT TGCTGAGATT
 851 TGAATATTAA ATCTTGCAAA AGTGATCTTT TTGTCTGTGT TTGTAAGTTA
 901 AGGCACAGAA CTTTAGTGCG TCTGATATTA ATACGCTCAG TGATGATGTT
 951 TTATCATCAG CTATCATCAA CATGGGAAGC TATTGAGAAA GCAATGGGGA
1001 GAAATCAGT TGAAGATATG TTGCGTGAGC AGATACAAAA GAAAGACACT
1051 GGCGGCATTC CTCCACGAGG ACGAGGAGGA GGGGGTGGCG GTAGAAATGG
1101 TGGGAATAAT GGGTCTGGAG GCTCATCAGG GAAGATGGT GGTCTTGCTA
1151 GTTTTGGGGA TGAAACTCTG CAAGTGGTAT TAGCAACCTT AGGCTTCATC
1201 TTTCTGGTAA GGACAAGATC ACAAGCCCGC ACAAGTTATC TTTGAATTAT
1251 AGTATCTTTA GCTTTGATCA TTGTTTCTTT TTTTGCAGT ACTTCTACAT
1301 CATCAATGGG GAGGAGTTGT TCCGTCTTGC AAGAGATTAC ATTAGGTACC
1351 TTATAGGAAG ACCCAAGAGT GTTAGGCTGA CCCGAGTTAT GGAAGGTTGG
1401 AGTAGATTCT TCGAGAAGAT GTCGAGGAAA AAAGTGTATA ACGAGTACTG
```

*FIG. 9I*

```
1451 GCTAAAGATT AAGCGATCAT CAACAAGTCT ACCTGGTCTG GTAACCCGGG
1501 CAAATACAAA CGCATCTTGA GATCTTATGT TGATTCAAAT GAAATGAAGA
1551 TAGTGATCGG TTTTCTTACT GGTTTAAGTA GTTTCCCTTA GACCCTTACC
1601 CGTGTTTTTG TTTTTGTTTA AGTTACTTTT GCCAGTAGTA AATATTGATG
1651 CTCATCGTCA CAAGT
```

Amino acid (SEQ ID NO:8)

```
  1 MSSTQANLCR PSLFCARTTQ TRHVSSAPFM SSLRFDYRPL PKLAIRASAS
 51 SSMSSQFSPL QNHRCRNQRQ GPVVCLLGGK DKSNGSNELS STWEAIEKAM
101 GKKSVEDMLP EQIQKKDTGG IPPRGRGGGG GGRNGGNNGS GGSSGEDGGL
151 ASFGDETLQV VLATLGFIFL YFYIINGEEL FRLARDYIRY LIGRPKSVRL
201 TRVMEGWSRF FEKMSPKKVY NEYWLKIKRC STSLPGLVTR ANTNAS
```

FIG. 9J

At3G59650
mitochondrial ribosomal protein L51/S25/CI-B8 family protein
NCBI Accession number NM_001203208.1

```
Cds (SEQ ID NO:9)
   1 ATGGCGCTTA GAGGAGTTTG GCAGCTCAAG AAACTCGTTG TGAGCTACTG
  51 TAATTGGGGT GGTAGCAGTA GAGGCATCAG AGCCTTTATG GAATCAGAAT
 101 TGCCTGCTCT AAAGGAGAAA AACCCGCAGC TCGAAGTAAT TACCGAGCTT
 151 TCACGGGGAC AACATCCTTA TTTGAAGGGC ATTTACAGGA ATAGAAATGA
 201 AAGGGTAGTG TGTGTGAAGA ACATGGATCC TGAAGAAGTG CTTTTGAATG
 251 CAACGAGGCT GAGGAACTCG CTTGGACGGA AAGTGGTTAA ACTGAGGACC
 301 AGACATGTCA CCAAACACCC CAGTGTTCAA GGCACCTGGA CAACTGCTGT
 351 CAAATTCTGA

Genomic (SEQ ID NO:23)
   1 ATCACGTGAT CATCTTCTTT CTTCCTTTTT TCTTGTCATC TGTTACACAT
  51 CGGTTAGGGT TTTAGTTTCT CTTACCGAGA TTCAAATGGC GCTTAGAGGA
 101 GTTTGGCAGC TCAAGAAACT CGTTGTGAGC TACTGTAATT GGGGTGGTAG
 151 CAGTAGAGGC ATCAGGTAAT TTTGTTTACC TATAATTTGA TTTCGCAATC
 201 TATGAGCCGT ATTTTTTCAT TTATCATCGA TCTACCATTT TTCCTGTAAT
 251 TCACTTTGGA ACTGAGACT ATCTATACGA ATCTATGAGT CTGTACTTGG
 301 TATTTGTGAA GCAAATTAAC TTTTCATGTC AATGTGGGTT TAGAAATGTG
 351 AAGCAAAATG ATTTAGTAAT GAATCGTTAC CATTTCATCC TAGTTTGGTA
 401 CTACGCATTT TCTTATGATG TGTTGTTAAA CATACAGAGC CTTTATGGAA
 451 TCAGAATTGC CTGCTCTAAA GGAGAAAAAC CCGCAGCTCG AAGTAATTAC
 501 CGAGCTTTCA CGGGGACAAC ATCCTTATTT GAAGGGCATT TACAGTATGT
 551 ATATTTCTCC TCTATTGAAT ACAATCCTGA TTCAACGGTT GTTGATATTA
 601 GCAATTTCAC TTGCACAATT CATAGGGAAT AGAAATGAAA GGGTAGTGTG
 651 TGTGAAGAAC ATGGATCCTG AAGAAGTGCT TTTGAATGCA ACGAGGCTGA
 701 GGAACTCGCT TGGACGGAAA GTGGTTAAAC TGAGGACCAG ACATGTCACC
 751 AAACACCCCA GTGTTCAAGG CACCTGGACA ACTGCTGTCA AATTCTGAGA
 801 CTTTCCTGCT AAATTGTTTG CAGGTTTTCA TCTTCTAGCT GTTAAATCGA
 851 ATGTTGCAAG TATCAGGATT GGTCGTTTAT CTGTATTGCA ACCCCAAGTT
 901 GTTTGTACCG TCTGTGACTT GGGACAAAGA TGTAGTCTTC AAATGTTTTG
 951 CAGTTTTTGC AATGTTTGAA TTTTGTCTTG TCCTTCTGGT TGAGTCTATA
1001 ATAAGATTAC ACAAGGGTTT AAGGTTA Amino acid (SEQ ID NO:10)
   1 MALRGVWQLK KLVVSYCNWG GSSRGIRAFM ESELPALKEK NPQLEVITEL
  51 SRGQHPYLKG IYRNRNERVV CVKNMDPEEV LLNATRLRNS LGRKVVKLRT
 101 RHVTKHPSVQ GTWTTAVKF
```

FIG. 9K

At3g60310
Unknown protein
NCBI Accession number NM_115895.3

CDS (SEQ ID NO:11)
```
   1 ATGCCCTCTC CGTCTGCAGT CGCCGATCTC TTGGCCGCTC TTGCTTACAG
  51 GCTTCAGAAC GGAGATGAAT TATTCGAAGA AGAAGAAGAA GCGGAAGAGT
 101 CTACTTCTTC TATGGGACTA GCTATCTCGG AGCTTAACCG ATCTCTGACT
 151 CTGGATATCG GCTGCGAGGA TTCTGGGGTC AGGGTTGTGG ACGCAGCGTT
 201 ATCTATAATG TGCTTCAAGG CACCTCAGGT TTTTGATTCG CAATTGAGT
 251 TTATGGTACG AACAATTGTT TGCGCCTTAT CATCTTCAAG CAATTGTAAG
 301 GTAATTAGGT ATCGAAACGA GGAAACATTA CAGTTTGGGA GCTCCAATTT
 351 ACCTGGCTGC TCTGAAGAAT TGATCGAAAT CTCTAAGGAT ATTATTGAGA
 401 AACTGTGGGG AAATGGAAGA TTGGCTACAT TGTTATTCGA AGCTGTTGTA
 451 AGGTCAGCAG CCTCAACATG TAAGATCAGC AGTTTCAACG CGCATGGAAA
 501 GCTTATGGAT GGAAGAAATA GGGCTGTCTC GAAGCTTCTT GCTTACTTAC
 551 CGGGAGAATC ATCTATAGAG AACCACAAGA TACCTCTGAG GATTCTTTTC
 601 TGGTATCGAG ATCCATTGTC TTTGAAGGTA GATGTTTCCA GAATCTTGAA
 651 AGAGGTGGTG GAAAGGCCTT TCCTTTGTGT AAAAAGGGAG CTTTTCGAGA
 701 GGGGGGAGTG GCGCGATATT GTCATCTGCC TAGCGATATC TCCTACTATG
 751 TTTATCAACA CTAGATCACT CTTACATAAA TGGCTTTTGC TTACGGGACT
 801 TGCTTCTGTT TTTGAAGTAC TTGCTGGTTT GGCCTCTGCA ATAATGGATA
 851 CAATTTCAAG GCCATCGTTG TGGGGTATAC AATGGAACT AGCTTCCATG
 901 TTGCCATTTT CTGATACATA CTTTCCTTTC CAGTGTCAAT TCTGAGAAT
 951 CTTGGCGGGT CCTCTCAGTT CCAAGTCCCT CCTAATGTTA GCTCATACTG
1001 TCAGTAAAGC GTCTGCTGTC CCTGGGCAAC AACAACGGGA TACTAATTGT
1051 AAGCCTACTC CAATAAAAGT TCAAGCATTA GATGACAAAA CCGAATGGGC
1101 TTTGGCTATT AACTTCCCAG ATTGGTTCTA TTTTGCATCT GCTATGCTCT
1151 TCTCAGAAGG AAAGTCGTTT GAAAATATCC ACCATATATG CGCTTCAAAA
1201 GTGGCTGACT GTAGACAAGT ATGTGATGTA AAGATCTCT CCATTGCTGC
1251 GGCTACATAC ATTTCTTGGA TTCTAAACCC TGGAAGTGGA ACCATTCAAG
1301 AGTCAGTAAG TAAGTCTCTC ATTAGAGTCT CAGAGATATG TATCAGTAAA
1351 AGTTGCGGCT CAGAAGCATA TCGTACTGAG ACTATAACTG GCAAGAGAAA
1401 GAAACCAGAT AGGCTCGTTT CTGGCAAAAT AAATGCTTCC AGTATTGTGG
1451 AAGACCTATT GAGAGAATTT GAAAACAATA TCACCAATTC AGTTTCTTAT
1501 GATTTGGATT CTCGGAAAAC GCATCCATCT TTCAGCTCTG CCTCCAAAA
1551 CAATTTGTTG GTAAGAAGAG TTGTGGTTGG CGTTCTGTTT GGTTCTCCAT
1601 ATTCAGTAAC AGATGAGGAG TATGAACTGG TATTACACTA TGCAGCAACT
1651 GGGAAAATTC TTGACTTTAA GAAATCACGG AGTACCGGAT TCAAACAAGG
1701 AAAGAAATTC TCTAGAATAT CTGCTTTACT GTCGAATGAA ATTACCAAGG
1751 AGGAGGCTAC AGAAGGCACA CTTCTTGTTT TCAACTTAAC TGACACTTTG
1801 GAGAGTATGT GTGTATCAAG TTTTGAGGCC AAAGAGGACG CAGAGAAGTT
1851 TATTAACCAT TTTAAGCTGA GATCCAGCAA GTACTTGGTC AAATGCATAG
1901 ATCGCCTGAT ACAACTTCAC TGTACACAAG ATGGAGATCC AATACTAAGT
1951 GACATTAATA TCAGACTGCT GCAATGGACA GTAAAAGGAC TAGAAGATCC
2001 ACATTTTAAC AAAGTTCTTG ATGATATCGC TGCTAAGTTG GCCTGCATAT
2051 TCTCGCGCGT GTAA
```

Genomic (SEQ ID NO:24)
```
   1 TCTGAGTGGG CATTACAAAT ATTTGGCTTA ACCGGTTCCG AGCCATTTGT
  51 AATTTCCGAG TATCTACATC GCCGGCGATT GATTCTGCTC ATCTTTTCGA
 101 TGCCCTCTCC GTCTGCAGTC GCCGATCTCT TGGCCGCTCT TGCTTACAGG
```

FIG. 9L

```
 151 CTTCAGAACG GAGATGAATT ATTCGAAGAA GAAGAAGAAG CGGAAGAGTC
 201 TACTTCTTCT ATGGGACTAG CTATCTCGGA GCTTAACCGA TCTCTGACTC
 251 TGGATATCGG CTGCGAGGAT TCTGGGGTCA GGGTTGTGGA CGCAGCGTTA
 301 TCTATAATGT GCTTCAAGGC ACCTCAGGTT AGTATCATAT CTATCCTGGA
 351 CTTGCATTGT TTCTACGTAG CTGAGTTCTT ACTTGTGAGT GATTTTCTTA
 401 TTAAAATTCA GGTTTTTGAT TCGGCAATTG AGTTTATGGT ACGAACAATT
 451 GTTTGCGCCT TATCATCTTC AAGCAATTGT AAGGTAATTA GGTATCGAAA
 501 CGAGGAAACA TTACAGTTTG GGAGCTCCAA TTTACCTGGC TGCTCTGAAG
 551 AATTGATCGA AATCTCTAAG GATATTATTG AGAAACTGTG GGGAAATGGT
 601 GCGTTTGATT TAGCTTATCC TAGAGTTATC TGAAGATTTT AACTTTTGTT
 651 TGTTCTCTCA TATTTTTCTG ACTTGGAAAT GTTCATAGGA AGATTGGCTA
 701 CATTGTTATT CGAAGCTGTT GTAAGGTCAG CAGCCTCAAC ATGTAAGATC
 751 AGCAGTTTCA ACGCGCATGG AAAGCTTATG GATGGAAGAA ATAGGGCTGT
 801 CTCGAAGCTT CTTGCTTACT TACCGGGAGA ATCATCTATA GAGAACCACA
 851 AGATACCTCT GAGGTTTGAC CTCTTGTACT GTTTCTGTTC CAAGCTATGT
 901 TAGTCTGCAT TTTCCATATT ACTCAAGAAG CCACAGCTTC GAGATGTTT
 951 GCTCTCTTGT TTCAGAAAAA GGTAGACCGG TCTGACACTT TTTGATGATC
1001 AGGATTCTTT TCTGGTATCG AGATCCATTG TCTTTGAAGG TAGATGTTTC
1051 CAGAATCTTG AAAGAGGTGG TGGAAAGGCC TTTCCTTTGT GTAAAAGGG
1101 AGCTTTTCGA GAGGGGGGAG TGGCGCGATA TTGTCATCTG CCTAGCGATA
1151 TCTCCTACTA TGTTTATCAA CACTAGATCA CTCTTACATA AATGGCTTTT
1201 GCTTACGTGA GTTCCTATCC AATTGGTGTC ATGTAAATCT ACAATAATAG
1251 ACATGTGTAA TCTTATGCGT TGTGATCTCT AGTTTCCAT CTTTCTTGCT
1301 TTCTGATGCA ATTTCTTTCT TTACGCCAGG GGACTTGCTT CTGTTTTTGA
1351 AGTACTTGCT GGTTTGGCCT CTGCAATAAT GGATACAATT TCAAGGCCAT
1401 CGTTGTGGGG TATACCAATG GAACTAGCTT CCATGTTGCC ATTTTCTGAT
1451 ACATACTTTC CTTTCCAGTG TCAATTTCTG AGAATCTTGG CGGGTCCTCT
1501 CAGTTCCAAG TCCCTCCTAA TGTTAGCTCA TACTGTCAGT AAAGCGTCTG
1551 CTGTCCCTGG GCAACAACAA CGGGATACTA ATTGTAAGCC TACTCCAATA
1601 AAAGTTCAAG CATTAGATGA CAAAACCGAA TGGTAACTTT ACATAAAATG
1651 CAAATTGATA CCCTCAGATT TGATCTATTT ATATATACGT GCGTGTGAGT
1701 GGTTTTTGAA TGATGTTGTA TCTTCTGGCA GGGCTTTGGC TATTAACTTC
1751 CCAGATTGGT TCTATTTTGC ATCTGCTATG CTCTTCTCAG AAGGAAAGTC
1801 GTTTGAAAAT ATCCACCATA TATGCGCTTC AAAAGTGGCT GACTGTAGAC
1851 AAGTATGTGA TGTAGAAGAT CTCTCCATTG CTGCGGCTAC ATACATTTCT
1901 TGGATTCTAA ACCCTGGAAG TGGAACCATT CAAGAGTCAG TAAGTAAGTC
1951 TCTCATTAGA GTCTCAGAGA TATGTATCAG TAAAAGTTGC GGCTCAGAAG
2001 CATATCGTAC TGAGACTATA ACTGGCAAGA GAAAGAAACC AGATAGGCTC
2051 GTTTCTGGCA AAATAAATGC TTCCAGTATT GTGGAAGACC TATTGAGAGA
2101 ATTTGAAAAC AATATCACCA ATTCAGTTTC TTATGATTTG GATTCTCGGA
2151 AAACGCATCC ATCTTTCAGC TCTGGCCTCC AAAACAATTT GTTGGTAAGA
2201 AGAGTTGTGG TTGGCGTTCT GTTTGGTTCT CCATATTCAG TAACAGATGA
2251 GGAGTATGAA CTGGTATTAC ACTATGCAGC AACTGGGAAA ATTCTTGACT
2301 TTAAGAAATC ACGGAGTACC GGATTCAAAC AAGGAAGAA ATTCTCTAGA
2351 ATATCTGCTT TACTGTCGAA TGAAATTACC AAGGAGGAGG CTACAGAAGG
2401 CACACTTCTT GTTTTCAACT TAACTGACAC TTTGGAGAGT ATGTGTGTAT
2451 CAAGTTTTGA GGCCAAAGAG GACGCAGAGA AGTTTATTAA CCATTTTAAG
2501 CTGAGATCCA GCAAGTACTT GGTCAAATGC ATAGATCGCC TGATACAACT
2551 TCACTGTACA AAGATGGAG ATCCAATACT AAGTGACATT AATATCAGAC
2601 TGCTGCAATG GACAGTAAAA GGACTAGAAG ATCCACATTT TAACAAAGTT
2651 CTTGATGATA TCGCTGCTAA GTTGGCCTGC ATATTCTCGC GCGTGTAACT
2701 GTCACCATAT AGCCTGACTT GTGTCATATT TGGTGGTACA CTAATTTTG
```

*FIG. 9M*

```
2751 GGAAAATGGT GATCAAATGT GAACTGTTCA AAGCACTCGC ACGACTGGTA
2801 TGAGGATATA ACTGGTGTAC AGGTAATTGT AATTGATTGG TCTAATTTCT
2851 AATACAGTAA CACAATCATA AGTGATAAGC CGGTTTAGTC GTCAAAGTAG
2901 CAACATTCTT GGCTAAATTT GAGTTGGATG TCTGAATGTC TTTGGTATCA
2951 GTGTAATGGT TATCTATAAT ATGTTGCCAC CGCTAAATAT GATCTAGTAC
3001 ACTAGTTTGT TTAGAGCCTA AAGTTTTTTA TGTTGGTGGC TATCATATGT
3051 TATCATCAAG GGAGCTTTAT GTTAATATA TTACTCTACA TGGGTGATGA
3101 GACATTTGAC CTGCATTTTT TTTTCATAAT ACTGTTAAAT TTTTTGTGAT
3151 CATAATAACA TATTACCTTC ATCCTTTCTA TTTCAGCTCC ACAACTGAAA
3201 TTATTTGATC TGCCTGGACT GGACCAGAGA ATTGTGGACA ATTCAATGGT
3251 GAGCCTTGAA AGCACTTGAT GCCTTATTCA ATGGTGAGCC TTGGAACCAC
3301 TTGATGCCTT TGCCATGCTC TCTTAATTCC ACTTGATAAC CACAAAACAA
3351 TAACCGGATT TCCTGCTGAA AAGGGTAATG TAGATTCATT ATCATGATTT
3401 GCTCTCTATG TTCAAATAGT CATTTGTTTC TTAGATCTCT TGGCTAATTA
3451 TGCGCAAAAA CACAATTAGC CAGGGCATCT GAGTTTCGTC ATCCCAAGCC
3501 CCTGAGAGTT GCAAAAGGAG TATGATCCAG AGAAGTGAGT TATTGTGAGT
3551 ACATGTACTT GGGTTTTGCC TTTTAGGCTT TTAATCATGT TGTTAAATAT
3601 TTCTTATTGA ATCAGTTGGT TTCAGAC

Amino acid (SEQ ID NO:12)
  1 MPSPSAVADL LAALAYRLQN GDELFEEEEE AEESTSSMGL AISELNRSLT
 51 LDIGCEDSGV RVVDAALSIM CFKAPQVFDS AIEFMVRTIV CALSSSSNCK
101 VIRYRNEETL QFGSSNLPGC SEELIEISKD IIEKLWGNGR LATLLFEAVV
151 RSAASTCKIS SFNAHGKLMD GRNRAVSKLL AYLPGESSIE NHKIPLRILF
201 WYRDPLSLKV DVSRILKEVV ERPFLCVKRE LFERGEWRDI VICLAISPTM
251 FINTRSLLHK WLLLTGLASV FEVLAGLASA IMDTISRPSL WGIPMELASM
301 LPFSDTYFPF QCQFLRILAG PLSSKSLLML AHTVSKASAV PGQQQRDTNC
351 KPTPIKVQAL DDKTEWALAI NFPDWFYFAS AMLFSEGKSF ENIHHICASK
401 VADCRQVCDV EDLSIAAATY ISWILNPGSG TIQESVSKSL IRVSEICISK
451 SCGSEAYRTE TITGKRKKPD RLVSGKINAS SIVEDLLREF ENNITNSVSY
501 DLDSRKTHPS FSSGLQNNLL VRRVVVGVLF GSPYSVTDEE YELVLHYAAT
551 GKILDFKKSR STGFKQGKKF SRISALLSNE ITKEEATEGT LLVFNLTDTL
601 ESMCVSSFEA KEDAEKFINH FKLRSSKYLV KCIDRLIQLH CTQDGDPILS
651 DINIRLLQWT VKGLEDPHFN KVLDDIAAKL ACIFSRV
```

FIG. 9N

At3G60840
                    MAP65-4              MICROTUBULE-ASSOCIATED PROTEIN 65-4
    NCBI Accession number NM_115948.1

Cds (SEQ ID NO:13)
    1 ATGGGAGAGA CTGAGGATGA AAAAGATGCT TCTTTGGCTG ATATCGAGAA
   51 GGAGTGTCTC TCGGTTTATA AGCGAAAGGT CGAGGAGGCT AGTCGGGGTA
  101 AAGCGAATTT GCTGAAAGAA ATCGCTGTTG GCAGAGCAGA AATTGCAGCT
  151 ATTGGCTCTT CTATGGGTGG ACAAGAGATT CATTCTAACA GCAGGTTAGG
  201 AGAAAACTTG AAAGAGGAGC TTGAGAATGT TAATGTGCAA TTGGATGGAC
  251 TGCGCAAAAG GAAAGCTGAG AGAATGATTC GGTTTAATGA AGTTATCGAT
  301 CAGTTACTGA AGTTGTCACT GCAACTTGGA AATCCAACAG ATTATCTGAA
  351 GAAGTTTGCT GCTGAAGAGA CCGATCTTTC GCTTCAGAGG TTGGAGGAAT
  401 TGCGTAGCCA GTTGGGTGAG CTCCAAAATG AAAAGAGCAA AGATTGGAA
  451 GAGGTAGAGT GTTTGCTGAA AACGCTTAAC TCGTTGTGCT CGGTTCTTGG
  501 TGAAGATTTC AAAGGCATGA TAAGAGGGAT ACATTCATCT CTGGTTGATT
  551 CCAACACTAG GGATGTGAGC AGAAGTACTC TTGATAAGTT GGATATGATG
  601 ATTGTGAATT TACGAGAGGC CAAGTTACAG CGAATGCAGA AGGTTCAAGA
  651 TCTTGCAGTG TCCTTGTTGG AGCTCTGGAA TCTGCTGGAC ACGCCTGCGG
  701 AAGAGCAAAA GATATTTCAC AATGTCACAT GTAGCATCGC TTTGACTGAG
  751 TCTGAAATAA CTGAGGCCAA CATACTTTCT GTTGCTTCCA TTAAACGCGT
  801 TGAGGATGAA GTCATTAGGC TTAGCAAGAT CAAAATAACT AAGATCAAAG
  851 AGGTGATACT GAGGAAGAGG CTTGAGCTTG AGGAAATATC AAGGAAGATG
  901 CACATGGCCA CCGAAGTTCT TAAATCAGAA AACTTTCAG TTGAAGCTAT
  951 AGAATCTGGT GTCAAGGATC CTGAGCAGTT GTTAGAGCAA ATTGATTCCG
 1001 AGATTGCAAA GGTCAAAGAG GAAGCTTCAA GCAGGAAGGA GATTCTTGAA
 1051 AAAGTGGAGA ATGGATGTC AGCTTGTGAA GAAGAGTCTT GGCTGGAAGA
 1101 GTACAATCGG GATGATAACC GGTACAACGC TGGAAGAGGA GCTCATCTTA
 1151 CATTGAAGCG TGCAGAAAAA GCCCGTTTAC TTGTCAATAA ACTTCCTGGG
 1201 ATGGTGGAAG CTTTGACCGC CAAAGTCACT GCTTGGGAGA ATGAAAGAGG
 1251 AAATGAATTC TTATATGATG GGGTCCGAGT CTTATCGATG CTTGGTCAGT
 1301 ACAAGACTGT ATGGGAAGAG AAAGAGCATG AAAAACAGAG ACAGAGAGAT
 1351 ATGAAGAAAC TTCATGGACA ACTCATAACA GAGCAAGAAG CTCTTTATGG
 1401 GTCTAAACCA AGCCCAAATA AAGCGGAAA GAAACCACTG AGAACACCAG
 1451 TAAATGCTGC CATGAACAGA AAACTCTCCC TTGGTGGTGC CATGCTTCAT
 1501 CAAAGCTTAA AGCATGAGAA GGCAACACTC AATAGCAAAA GGACGAAGTA
 1551 CTATGACCAG AACGCTACTA GTAGAAGAGA TTCAGCTCTT CCAACTCTTT
 1601 CAGGGAGGAG AAACTCAGAG CTTCCTGGTC GTATCAGATC AAAGAACGTT
 1651 CCGGTTGCAG GAAAAGCTGC GAGATCTCCA ATGCTTAGGA AGCCTCTTTC
 1701 ACCTGTCACT TCCAATATCT TGAATTCCCC AGAAGATCAT CACAAGGATG
 1751 CTTACACAAC AAAGGAGAGA ATCTTGACAC CTAAAACCAA CGAAGAAAAG
 1801 AAAAGAGCTG TTCCAACAAC TCCTGCAGCT TCAGTCGCTA TGACAGAGGC
 1851 AACAACGCCG TTCACTCCTG CTGTGGAGAA GAGAATGGAT GAGGAAGACG
 1901 TTATTGTTGA GTATTCGTTT GAAGAGGTTA GGGCCGGTTT TTGCTAA

Genomic (SEQ ID NO:25)

1 ATGGGAGAGA CTGAGGATGA AAAAGATGCT TCTTTGGCTG ATATCGAGAA
   51 GGAGTGTCTC TCGGTTTATA AGCGAAAGGT CGAGGAGGCT AGTCGGGGTA
  101 AAGCGAATTT GCTGAAAGAA ATCGCTGTTG GCAGAGCAGA AATTGCAGCT

*FIG. 90*

```
151  ATTGGCTCTT CTATGGGTGG ACAAGAGATT CATGTAAGTG TATTCAAGAC
201  TTCAGTTTTG ATATATTTGG TTTTTGTCTG CTGGAGTTAT GGCAAGTAAT
251  GGTGCATTTT CTTCTTACAG TCTAACAGCA GGTTAGGAGA AAACTTGAAA
301  GAGGAGCTTG AGAATGTTAA TGTGCAATTG GATGGACTGC GCAAAAGGAA
351  AGCTGAGAGA ATGATTCGGT TTAATGAAGT TATCGATCAG TTACTGAAGT
401  TGTCACTGCA ACTTGGAAAT CCAACAGATT ATCTGAAGAA GTTTGCTGCT
451  GAAGAGACCG ATCTTTCGCT TCAGAGGTTG GAGGAATTGC GTAGCCAGTT
501  GGGTGAGCTC CAAAATGAAA AGGTTGGTTT TGCTGTTAGA TCTCATGATA
551  TGGGACTTAT ATTACAAGAG CATGTGCACC TGTTTTCCTT ATGTTAACTT
601  TGAATTCTTT TCAAAATGTA GAGCAAAAGA TTGGAAGAGG TAGAGTGTTT
651  GCTGAAAACG CTTAACTCGT TGTGCTCGGT TCTTGGTGAA GATTTCAAAG
701  GCATGATAAG AGGGATACAT TCATCTCTGG TTGATTCCAA CACTAGGGAT
751  GTGAGCAGAA GTACTCTTGA TAAGTTGGAT ATGATGATTG TGAATTTACG
801  AGAGGCCAAG TTACAGCGAA TGCAGAAGGT TACAAGTCTG AGCTCTTCTT
851  TGTAATGTAG TGCAAGTTTT TCTGCGTGAT TATGGTTTCT GACTCTCATC
901  ACTTTGTTTT TCTAGGTTCA AGATCTTGCA GTGTCCTTGT TGGAGCTCTG
951  GAATCTGCTG GACACGCCTG CGGAAGAGCA AAAGATATTT CACAATGTCA
1001 CATGTAGCAT CGCTTTGACT GAGTCTGAAA TAACTGAGGC CAACATACTT
1051 TCTGTTGCTT CCATTAAACG CGTGAGTGCA CAGGACCAAA CCTTTCTGTG
1101 TTTTCTCCCT GTATTGTTTA GTCTATCCGT TTATAATAGT ATAGGAACAA
1151 TCTTTTTTAT AATGTGAGTT TGTTTTACAG GTTGAGGATG AAGTCATTAG
1201 GCTTAGCAAG ATCAAAATAA CTAAGATCAA AGAGGTGATA CTGAGGAAGA
1251 GGCTTGAGCT TGAGGAAATA TCAAGGAAGA TGCACATGGC CACCGAAGTT
1301 CTTAAATCAG AAAACTTTTC AGTTGAAGCT ATAGAATCTG GTAAACCATT
1351 ATTAGGAACA GCTTATCTT TACATAATAT GATGTGCACA AACTCCAGAA
1401 ATGTTATGCT CATTATACTG GTAGATAACA TGAACATGCT AATAATAACA
1451 TGTTTCCACT CATCTTTTAG GTGTCAAGGA TCCTGAGCAG TTGTTAGAGC
1501 AAATTGATTC CGAGATTGCA AAGGTCAAAG AGGAAGCTTC AAGCAGGAAG
1551 GAGATTCTTG AAAAAGTGGA GAAATGGATG TCAGCTTGTG AAGAAGAGTC
1601 TTGGCTGGAA GAGTACAATC GGGTTAGACA TTTAAATCTA AATCTATTCC
1651 TTTGCCTCAA TCTTTTTTTT GTTTTGTTCT CACATCGTTG GCTTCGCAGG
1701 ATGATAACCG GTACAACGCT GGAAGAGGAG CTCATCTTAC ATTGAAGCGT
1751 GCAGAAAAAG CCCGTTTACT TGTCAATAAA CTTCCTGGTA ACATTCTTGC
1801 TCTTTAGATT ATATTACAAA AACCTACAAA CTCATAACTT ATGATCTTTT
1851 TTGTCTATTG CTTTCTGCTG CTATTGATGC AGGGATGGTG GAAGCTTTGA
1901 CCGCCAAAGT CACTGCTTGG GAGAATGAAA GAGGAAATGA ATTCTTATAT
1951 GATGGGGTAA GTGGTTTTTT ACTGATCAAT GATCTGTTCT ACACAATTAT
2001 CAAATCAGCA TCTTTACACA AAAGCACGTA ATATTTCAG GTCCGAGTCT
2051 TATCGATGCT TGGTCAGTAC AAGACTGTAT GGGAAGAGAA AGAGCATGAA
2101 AAACAGAGAC AGAGAGTAAG GAAAACTGTT TTTTACTAGG AACCAAGGTC
2151 ACTATGAGCC AAAAGCATCA TTGGCAATTT GACATTGTTA CTTTCATCTC
2201 AGGATATGAA GAAACTTCAT GGACAACTCA TAACAGAGCA AGAAGCTCTT
2251 TATGGGTCTA AACCAAGCCC AAATAAAAGC GGAAAGAAAC CACTGAGAAC
2301 ACCAGTAAAT GCTGCCATGA ACAGAAAACT CTCCCTTGGT GGTGCCATGC
2351 TTCATCAAAG CTTAAAGCAT GAGAAGGCAA CACTCAATAG CAAAAGGACG
2401 AAGTACTATG ACCAGAACGC TACTAGTAGA AGAGATTCAG CTCTTCCAAC
2451 TCTTTCAGGT ACATAATAAT AACACAAGAT TTGGTTTAC ACTTAACAGA
2501 GACCAAGAGA GAGATTTGTG TTAAGAGAAT TATGTCAATA TGTGTAGGGA
2551 GGAGAAACTC AGAGCTTCCT GGTCGTATCA GATCAAAGAA CGTTCCGGTT
2601 GCAGGAAAAG CTGCGAGATC TCCAATGCTT AGGAAGCCTC TTTCACCTGT
2651 CACTTCCAAT ATCTTGAATT CCCCAGAAGA TCATCACAAG GATGCTTACA
2701 CAACAAAGGA GAGAATCTTG ACACCTAAAA CCAACGAAGA AAAGAAAAGA
```

*FIG. 9P*

```
2751 GCTGTTCCAA CAACTCCTGC AGCTTCAGTC GCTATGACAG AGGCAACAAC
2801 GCCGTTCACT CCTGCTGTGG AGAAGAGAAT GGATGAGGAA GACGTTATTG
2851 TTGAGTATTC GTTTGAAGAG GTTAGGGCCG GTTTTTGCTA A
```

Amino acid (SEQ ID NO:14)

```
  1 MGETEDEKDA SLADIEKECL SVYKRKVEEA SRGKANLLKE IAVGRAEIAA
 51 IGSSMGGQEI HSNSRLGENL KEELENVNVQ LDGLRKRKAE RMIRFNEVID
101 QLLKLSLQLG NPTDYLKFA  AEETDLSLQR LEELRSQLGE LQNEKSKRLE
151 EVECLLKTLN SLCSVLGEDF KGMIRGIHSS LVDSNTRDVS RSTLDKLDMM
201 IVNLREAKLQ RMQKVQDLAV SLLELWNLLD TPAEEQKIFH NVTCSIALTE
251 SEITEANILS VASIKRVEDE VIRLSKIKIT KIKEVILRKR LELEEISRKM
301 HMATEVLKSE NFSVEAIESG VKDPEQLLEQ IDSEIAKVKE EASSRKEILE
351 KVEKWMSACE EESWLEEYNR DDNRYNAGRG AHLTLKRAEK ARLLVNKLPG
401 MVEALTAKVT AWENERGNEF LYDGVRVLSM LGQYKTVWEE KEHEKQRQRD
451 MKKLHGQLIT EQEALYGSKP SPNKSGKKPL RTPVNAAMNR KLSLGGAMLH
501 QSLKHEKATL NSKRTKYYDQ NATSRRDSAL PTLSGRRNSE LPGRIRSKNV
551 PVAGKAARSP MLRKPLSPVT SNILNSPEDH HKDAYTTKER ILTPKTNEEK
601 KRAVPTTPAA SVAMTEATTP FTPAVEKRMD EEDVIVEYSF EEVRAGFC
```

*FIG. 9Q*

At3g60920
CONTAINS InterPro DOMAIN/s: Beige/BEACH (InterPro:IPR000409); BEST Arabidopsis thaliana protein match is:
WD-40 repeat family protein / beige-related (TAIR:AT2G46540.1);
NCBI Accession number NM_115956.3

Genomic (SEQ ID NO:26)

```
   1 ATGAATGGAA AGGAATCAAG AGGACCTGCG TGTAGCTTTG AGTTTGTTGG
  51 TGAAAGCTCA GGTTTACTTG GTCCAGGAGA AAGTCGCTGG CCTTTTACCA
 101 ATGGCTATGC ATTTGCGACT TGGATTTATA TTGAATCATT TGCTGACACA
 151 TTAGATGCTT CAACCGCGGC AGCTGCAATT GCTGCTGCTT CAGCGGCAAA
 201 ATCAGGAAAA ATATCTAATG CAGCGCCTGC GAATGTACAC ACTGGTGAGG
 251 GTACTGCTCA TATGCCTCGT CTGTTCAGCT TTTTGACCCC TGATAATCAG
 301 GGAATTGAAG CTTATTTCTA TGCACAATTT TTGGTGGTTG AGAGTGGCAG
 351 TGGGAAAGGA AGTAAAACTT CACTTCATTT CACTCATGCA TTTAAGCCTC
 401 AGTGTTGGTA CTTTATTGGC CTTGAGCATA CCTGCAATCA GGGACTTTTA
 451 GGGAATTCAG ATAGTGAATT ACGGCTATAT ATTGACGGGT CGTTGTATGA
 501 AACTCGACCA TTTGACTATC CTCGGATATC CAAACCGCTT TCTTTCTGTT
 551 GCATTGGGTC AAATCCTCCT TCTACAACTG CTGGTCTACA ACGTCGTCGA
 601 CGTCAGTGTG CTTTGTTTGC TGAGATGGGA CCAGTTTATA TATTTAAAGA
 651 ACCGATTGGT CCTGAAAGAA TGACACGATT GGCAACTAGA GGTGGGGATG
 701 TTTTGCCTTG TTTTGGCAAT GGGGCAGGTC TTCCATGGTT AGCTACAAAT
 751 GACCATGTCC GTAATGTGGC AGAGGAAAGT AGTCTTTCGG ATGCAGAGCT
 801 TGGAGGATAC ATTCACCTAC TTTACCACCC ATGTCTACTA GTGGGCGGT
 851 TCTGTCCAGA TGCTTCTCTT TCTGGAGCAG CAGGTGCTTA TATTATACTC
 901 TTGATTTTTA ATATATCTGA GAAGGCTCTA CAAGTCTGAA AAATATTCCC
 951 TAGTATGATG TGTTTTATTA GTACTTGTTT TCAGATGCTC ATTTGGTTGA
1001 GTTTGTTGTA TACTTTTATC TGTTCTTGTG CTATCTATAT CGCTTTCACT
1051 CGGTCTCACT ATTCTCCATT TCATATGAA CTTTGTTTTT ATTTATCTTG
1101 TGTCTTAGGA GATGAGAAAA CACCATATTC TTTTTCTGCT GTAGTTTTCG
1151 CACTTTGTTA TTTGGTTTTC CCTTACTTTG GAAGTTCGTT ATTTTTTCTT
1201 GATTAAGGCA CTCAAAGACG ACCAGCTGAG GTAATTGGAC AAGTCCATGT
1251 TGCAACGAGA ATGAAGTCTG GAGTCCTTCT GGGCCTTAGC TTATGGAGGA
1301 CCCATGTCTT TGCTTCCTCT AACCGTAAGC AGTGTGCACA AGATAATCT
1351 AGAGCCATGT TCTAGAAATG TTCCATCTTC TTTGACAACA TATTCTCTGG
1401 CTGCACCTAT TTTTAGAATG ATCTCATTTG CTATTAAACA TCCTGGGAAC
1451 AATGAAGAGT TATCTCGTAC TAGGGGCCT GAAATTCTGG CCACAGTTCT
1501 CGGTTACCTT CTTCATTCAC TTGCATCCTT TGATATCAAG CACGATAGAG
1551 TAGGAGATGA GGAGCTAGTT GCTGCTATTG TTTCTCTTTG CCAATCTCAA
1601 AAGATCAATC ATGCTCTTAA AGTGCAGCTC TTCTGTACAC TATTGTTGGA
1651 TCTGAAGATA TGGAGTGTGT GCAGTTACAG ACTCCAAAAG AAGCTGTTGT
1701 CATCTCTTCA AGATATGGTT TTCACCGAAG CAACAGCTAT GAGGAATGCT
1751 GATGCCATTC AGGTACTTCT GGATGGATGT CGAAGATATT CTGGACAAT
1801 TCAAGAGAAA GACTCCGTGA ACACGTTTTC TCTAGATGGG GATGCACGTC
1851 AAGTGGGGGA AGTTAATGCA TTGGTTGATG AACTTTTGGT GATTATTGAA
1901 CTTCTAATGG GAGCAGCATC TCCTTCGTTT GCTGCTGATG ACCTCCATCG
1951 ATTACTTGGC TTTATAATTG AGAGTCCACA ACCAAATCAG GTAACACGTT
2001 TCTTAGTGAT ATTTCATAAT TGTTAAACAT GTGTCATTTC TCAGATCTTT
2051 TAATATTTTT TCTCTGACAT CATTCAGTTG TTACCTCTAT TTAGGTTGCA
2101 AGGGTATTGC ATCTCATGTT TAGGTTGGTT GTACAGCCAA ATGCTGCAAA
2151 GGCTCAGACA TTTGCAGAGG CATTTATCAC ATCTGGTGGG ATAGAAACAC
2201 TTCTTGTTCT CATAGCAAAC AGAGTCAACA CAATGGGCCT GGTTTGTTAA
```

FIG. 9R

```
2251 AGTTGGATTC AGTTCCACAA GATAATGAGG GTGACCCTCA TGCTCATGAT
2301 GATAATGTAG GATCTTTGAA GGAAACAGAG TCATTTCAAC AAGTAAAAGT
2351 GCATGGATCC GAAACTGTCA TTTGTGAGAC TGGCTCAGTT ACCCTCTCCA
2401 GTTCCGTGAA TGCTGACAGA ATATCCTCTG TTTCTGAAAC TCCATTCAAT
2451 AATAATGCAA GAAACAATGT TGACGATAGA GATCGTGTCA TGGTTGGGAT
2501 CATCAGATTG ATTGGTGCGT TGATTTCAAA AGGGCACTTA AAATTTCCG
2551 TTGGTGCCAA ATCTGATGTA ATGAGTAACC TCATGGGTAG TGAGTTTCGT
2601 GAAAATGGTG GAACAATGTT TGATTATAAA GTCGCATTGC TTCTATTTGC
2651 TCTGCTGAAA GCATTTCAAG CAGCTCCAAA CAGATTGATG ACCGACAATG
2701 TCTACACAAC TTTGCTTGGG GCTTCGGTAT GACATGTCTT AATATATCTT
2751 TCATTTGTTT GATCTATCTT TAAGCGTAGC TGGTTTAATG TCAAGAATTT
2801 GGTGGAAAAA GAGAGTCTCT GAGGTGCAAC TTTTTTTTAG TAAGATTTAT
2851 ATGTATACCT GGTTTAATGT CAAGGATCTT TCTTGCAGGT TAATGCTTCA
2901 TCAACTGAGG ATGGCCTGAA CTTTTGTGAT TTAGGTCATC GATTTGAACA
2951 TCCTCAACTT CTGTTAATCC TCCTGCGTTC TCTACCATTT GCATCTAAGG
3001 CACTACAAAA TCGAGCACTT CAGGTATAAA TGTCATAGTT AAAGACACTT
3051 TTGTGCACCA AATGCACTTG TGAAAGTGCT CTACAAACTT CTACTTGTCC
3101 GGTCTCTACA ATGTCTCCTT CTGAACTCAC TTTTTCTACG TCAGGATATT
3151 CTATTTTTGG CTTGTACCCA TCCAGAAAAA AGGAGTAGTC TGACCAAAAT
3201 GGAAGAGTGG CCTGAGTGGA TCTTGGAGAT TTTAATCTCT AACTACGAGG
3251 TATAACTCAA ACGTTAAAAA TTTTAAAGTT CGCCTCCATG ATTATTGTAT
3301 CAGTAATGAG CCAAGTTGGC TATATTTACA CTAGTGTGAT AAGGCGAGTT
3351 ACATTTTTTA TCTGGCAAGT CTCTTAAGCA TGTACCATAA AACTTTAAAA
3401 ATGCTGACTA TTCTGCGTAC ACACAGAAAG ATGCAGGGAA ACAATCTGCT
3451 TCACCCGGTT CTGCTGAAGA GGAGGATCTG ATTCATAACT TCTTGATCAT
3501 AATGTTGGAA CATTCAATGC GCCAGAAGGA TGGCTGGAAG GTAAATTTGT
3551 TTGTTTCAGC GGTCTACCAG ATTAATTCCC TTTCACGTTT TTTCCAAGCT
3601 CATTTGTGTT TATTTATATT TTTCGCTACA TCTGATTCCT TTTACAGGAT
3651 ATTGAGGCTA CAATTCATTG TGCAGAGTGG CTTACTTTTG TTGGTGGGTC
3701 TAGCACTGGG GAGAAACGAA TTAGGTATTT TCATGCACTA CTGCGCCACA
3751 TTTTACGCGT GCCTTTGGG ATGCCAATAA CATTTTGAGT GTCATCTGTT
3801 TTTCTTGTCA CATTGTTAGT TTGTGAAGGT ATCTTTTGGA TCATATTGTT
3851 GTTGCACTGT AGTGCTTCTT CCATGTATTT TGAGATAAGC ATGTTTCTGT
3901 TCAATTATAT TTACACTTTT TTCCTAATAC TTTTTTCAAA GGCGTGAGGA
3951 ATCACTGCCA ATTTTCAAAC GAAGACTTTT AGGTGGATTG CTAGACTTTG
4001 CTGCCAGTGA ACTGCAAGCT CAGGTATAGC TCCTGTTTTA TCTTTGACTT
4051 ATATGGTTAG TTATACAATT CCTTGCTAGA GAAACACGAA GTTCGTCTTA
4101 CACATGCATT GTATAGTTGA CATTGGTCGT ACTCTCACAA GAAAATATTG
4151 TCAGATCTTT TTTTATTTGC TCTATATTAG CTATAATATT GTTAAAGACA
4201 GTAAGCTTTC AAGCCTTGTT CTGTTATGTT GGTCGACTGC TATAATTTAA
4251 CCTACACATT AAACTTTCCC CAAACAGACT CAAGTTATAG CTGCAGCATC
4301 TGCTGGTTTC GCGGCAGAGA GTCTAACACC AAAAGATGCA AAAGCGGGAG
4351 TAGAAAATGC TGCACTGCTT TCAGTGTTTC TAGTGGAAAA TACAGTTGTG
4401 ATTTTGATGC TTGTCGAAGA TCATTTGCGA CTACAAAGCA AGCAAAATTG
4451 TGCTGCAAGC GCAGTTGATG TCTCTCCATC TCCTCTTTCA CTTGTTTATC
4501 CTCCCAACTA CCGTTCACAC ACATTGCCAA CGGTCGGAGA ATCATCAGAG
4551 GTTTCTAGTA GCTGTGCTTC AGTGTCCAGT GATTCAGGAG GGGTCCATTT
4601 AGATGTAAGT GGAAATTACT CTCAATTTCT TTCTTCCGGA TCAATATCTC
4651 CCCTTATTTA TTGGCTTTTT TCCTTTTTGT TTTTATAACA TCATTTAAGA
4701 AAGATAGTTC TGATCATCTG ATTAACTTTC TGCTATTTTC CTGCTTTTAC
4751 TTTTTCTTCA GATACTTGCT TCAATGGCCG ATGCAAGTGG CCAGATATCT
4801 ACAGCCGTAA TGGAGCGTCT TGCTGCTGCT GCTGCAGCTG AGCCCTATGA
```

FIG. 9S

```
4851 ATCTGTTTCT TGCGCTTTTG TTTCATATGG AAGTTGTACC AGGGATTTGG
4901 CTGATGCTTG GAAGTACAGA AGTCGATTGT GGTACGGTGT TGGACTACCT
4951 TCTAAAACTA GTTGTTTTGG TGGTGGTGGA AGTGGTTGGG ACTCTTGGAA
5001 GCATGCTCTA CAAAAAGATG CTCAGGGTAA CTGGATCGAA CTTCCTTTGG
5051 TTAAAAAATC AGTATCCATG CTTCAAGCCT TGCTGCTAGA TGAGTCTGGA
5101 CTTGGAGGTG GCCTAGGAAT TGGTGGAGGA TCTGGTACCG GGATGGGAGG
5151 GATGTCAGGC CTCTACCAGT TGCTAGATAG TGATCAGCCT TTCTTATGCA
5201 TGCTTCGAAT GGTACTCTTG TCTTTGAGGG AAGAAGACCA TGGTGAAGAT
5251 AGTCTGTTGA TGAAAAATTT AAGTTCTGAA GATGGTATAA CTGGTGGACT
5301 CCAGTGCCCC TTAGGAAATT CTGCCTCAGT AGATATCAGT TCTCAGTTGT
5351 CTATGCGACA GTCACCATCA GCTTTATTGT GGAGGTAAAG TAATAACATG
5401 TTTTTTCTTA CTTCCCTATG TGACTTTGCG AATTATAAAC CCATCTGCAT
5451 TGATACGATT TTGTCCAAAG TATGTTGTCG CTCACTCAAG ATTATGACCA
5501 CATGCCTTAA GCATTTTTAG ACTAGACTTT GTCACAAAAT TAGAATACAA
5551 GGGCATATTT GGCATCTTTT GGACGCCTGA CTTGACGTTG CATGCCTTCT
5601 AAATGGTTGT TTGCTCATAG AGAATTTAAT GTGACTGTTT TTTTTTATCT
5651 CCAGTGTGCT CTCTCCCGTT CTAAACATGC CAATCTCTGA TTCTAAGAGG
5701 CAGAGGGTAT TGGTTACTAC ATGTGTTCTA TATTCTGAGG TTAGTTCTCC
5751 CCTAATTAAG GTTCCATACT TCAATTAATT ATGGTCTGGT CTCACATTTT
5801 CATGTTGAGT TTTTGGAGAA CGATAATGGA AATTGCTCCC CTAGTCTTCT
5851 TTGTGAACTT AATAATGCTC ACTTTGTTTT ATTTTATGGT TTTTCGATTT
5901 TTTGATTCAA AATCTGTTGC AGGTATGGAA TGCTGTTAGC AAAGATAAAA
5951 GACCACTACG TAAGCAGTAT CTAGAGGCTA TTTTACCACC ATTTGTTGCA
6001 ATTCTCCGAA GATGGAGGCC TCTTTTGGCT GGTATTCATG AACTTTCCAC
6051 TGGTGATGGT GTGAATCCCC TTGTCGTTGA TACTCGTGCT TTGGCTGCTG
6101 ATGCACTTCC CATTGAGGTT CCACAAATCT GTTCACATAC CCTGTAGTTT
6151 CTATCACATA TATTTATAGC TTCTGACAGT GCTGCTTCAT CCCTTAGCCT
6201 AAGGTATTAA ACTGTTACTT TTTATTCTAG GCGGCTCTCT CTATGATTTC
6251 TCCGGAGTGG GCAGCTGCTT TTGCATCGCC TCCTTCTGCA ATGGCACTGG
6301 CAATGATAGC TGCAGGGGCA GCTGGTTGGG AAGCGCCGGC ACATCCAGCA
6351 CCTCCAGCGC CTCCACCTCT TAGGCGAGAC AGTTCATTAC TTGAGCGTAA
6401 GAGTACCAAA CTTCAGACCT TTTCAAGCTT CCAGAAACCC TTGGAGGCTC
6451 CAAATGATGA TACACCAGGT CGAGCAAGAG ATAAGGCTGC TGCAAATATT
6501 GATTCACATT TATTGATTCA ACCGCTCACC AGATTGACAG GCGTATGCAA
6551 AATGATAAAA TAGTGAAAAA TCGCTTATGC ATGGGAATCC GTGGTTGGCG
6601 CAAACTCGTT CGTTACTTGG TGGACATGAG ATGCTTCTTT GGACCCTTCG
6651 GAGACCATTT ATGCAGTCCC AAACACGTAA GCTACGTTGT TCTGGGGTAA
6701 ATTTAAAACA TGTTGAGAAC ATTTCCAGTG ATGTAACATC ATCACATATG
6751 CAGGTTTTCT GGAAACTGGA TTCTATGGAA AGTTCTTCGA GGATGAGACA
6801 ATGTTTAAGG AGGAATTATT CTGGCACTGG TCATCTTGAG ACAACAAGAA
6851 ACTATGGGGA TCAGACATAC TTGATGAATA ATCACGACTC ACCTGTTCTT
6901 GCTGTTGAAG CAATATCAAA GGAAATAATG TATGAAGATG ATGAACATGG
6951 AGATGCCGAT GATCTTGAAA TAGAGGGTAA TGTTGGAGAA CGCAAGGGGG
7001 AAAACGAAGA GAGAAGGTCT GGCTCACTTG AGGATGCAAT AACACTGTCA
7051 ACTGGAATCA ACGATCATCG ACCTTTGAGT GAACAGAATA TGGTTCAAAA
7101 TTCTACAGAA GTAAAAGATC TCAGTGAACT TAAAGAAGG ATTGTTCTTG
7151 AAATTTCCTC TACTATGGTC CGACCACTAG GGGTTGTGAA AGGAACCTTT
7201 CAAGTATGCT CTCACTAACA CTACCTATTT ATCTTTTGAA CAAATAGCTG
7251 ACACAAATGA GTATTCCATT GATGACCAAG AAATAAAACA GAGCATAAGT
7301 GACCAGATTT TGTAATGTTT GTTTTCTGTC TTTCTCAGAT CACAACACGG
7351 AGAATAAATT TTATTGTTGA CATCAGAGAA GACCAACATT TGGATGAAAA
7401 GTCAGACGGT TCAAAATCAA GAGACGAAGA AAGAGATCGA AGTTGGCTGA
```

*FIG. 9T*

```
7451 TGTCTTCTCT TCATCAGATT TATAGCCGAC GGTAAAGTTC ATCATTAATG
7501 TTGTCTCTAG CTCACTATTT CCTCCGCATT ATCATGTAAA TAGATGGAGA
7551 CCTATATCTT TGTTAATATT TTTCTTTCAC AGATATCTAC TGAAGAAGAG
7601 TGCTCTTGAA CTATTTATGG TGGATCGCTC AAACTTCTTC TTTGATTTTG
7651 GGGTATCTAA AAAACTCTCT CTGTTACATT ACATTATTTG ATCTCTTTCG
7701 TTGGAAATTT CAAGTTTCTA GCTCCTCTCA CTATATGATG TTTGATGAAA
7751 ACTATAGAAC ACCGAGGGAC GAAGAAATGC TTGTCGGGCT ATTGTTCAAG
7801 CAAGGCCTCC TCATTTGAAA AATATTTACT CGGCAACTCA GGTTTTTTTT
7851 TTTCCCTCCG TTTGCCCATT CTTTAGTGCA TGGTGGACAA AGCTAGGAAT
7901 CAAGCTGAGT AAATTTTTCT CAATGCTGCA AAACTTACAT AAAACGTTTC
7951 CTTTTTAGAA GCCAGAACAA GTTCGAGAA GAACACAGTT AATGGAGCGT
8001 TGGGCTAGAT GGGAGGTAAC CAGAGAATAT CCTTTATCTC CATCATGCAA
8051 TTTCATTTTG TTCCCTTGAA TAACATCTGG CAGTAACTCT CGCTGGATAC
8101 TTTGCATCTT TTCTGCAGAT CAGCAATTTT GAGTACTTAA TGCAGCTCAA
8151 CACATTGGCT GGGCGTAGTT ATAATGACAT CACTCAGGTA AATCTCGTGC
8201 TAGTTAAAAT GTTTTTTCTT ATAATCTTTG ATATCATTTT CTCTTTGGTT
8251 ATCTTGATCT ATTTTTCATA TCTTTGCAGT ATCCTATTTT CCCATGGATT
8301 TTATGCGACT ATGTATCAGA AATTTTGGAC CTATCAAATC CATCTAATTA
8351 CAGGGATCTT TCCAAGGTGG TATTATTAGT AATTTATTAT TAGTAGTTTT
8401 TCGCTTTATG CTTGCCTATA GTTATCCATA AACCTATAAA ACTGGTTGTA
8451 ATGTGGATCC GTATATGTTC AGCCAATTGG TGCACTGAAC CCGGAGCGGC
8501 TGAAAAAGTT TCAAGAAAAA CACTCTAGCT TTGAAGATCC AGTCATCCCC
8551 AAATTTCATT ATGGTTCACA TTACTCAAGT GCTGGAGCAG TAAGTTATCT
8601 TCTCTATGAT ATCTGCCATA GTTTTATCA TTTCTTCTCT TACATTTTCT
8651 TCGTTTTAAA ACTCTGTTCC TCCTATCACC AAAGAAAGAC AATAATTAGT
8701 ATTTTGATTT GCAAGAGGAT AGAGTTTTCA CTAAATACTA ATGATGGTCT
8751 AATAATTTGT TATTTCTTGT GTGTAGGTGT TGCATTATCT AGCTAGAGTC
8801 GAACCTTTTA CAACCCTTTC GATTCAACTG CAAGGTAGAA AGTTTGATCG
8851 TGCAGACCAA ATATTTTCAG ACATTGCAGC CACTTGGAAA GGAGTTCTCC
8901 AAGATATGAA TAATGTGAAG GAGTTGGTAA GACTTGGTTC CTCCCAAAAA
8951 CATTCAAACG AGTATCCATA ATCGCCGTCC TTTGCTTTGC AAGTGAAGAG
9001 CCTAGCCATA TTTATTTTGC TTCCTCATTT TCGTATATTA TACGACCATC
9051 TATCTTTAGG GTTTATGAAC TTACGGACAA ACCCGGAATT GTTCAAAAGT
9101 TTCAGGAAAA TTTATTGCAA ATGGTAAATT CAGTTTGTCT TTGGCGTTTT
9151 AGTTACATTC GTTTTTCATG GTATCAACAT TAATGTGATT TTTTTTATTT
9201 ACAGAACACA ACTGATCCAA ACACTCACAT GGTCTCAAGC TTTTCAAACC
9251 CAACTACCAG CGAGGTTTGC TACTGAATAA GCATTAGATA GACAACAAAT
9301 TTCATTTAGG GATAAGTAAT TATTTTGGTG ATATCTTTTT TAGACTGAAC
9351 CTGATTCAGA CATGAACATT GTCTCTACCC CTTCAAATGC AACTACAAAT
9401 CAGGTAATAA CTCTAACGTT CCATTACATT TAATTTTCAA GTGCTTATGT
9451 ATTTTAAAAT TTTGAATTTT ATTTTTGTTT AGATTGACAC TGAATCTTCC
9501 GAGGCGGCTA ACTATGAAAA CAGCAACTCG TCTATCAAGA CTTCTAAGAA
9551 CACTTCAAAG ATCACTAAAT TGACCCCGAC GTCAAAACGA TCACTAACTT
9601 CATCGAAAGA TAATGCAGCT CAAAAGTCAT CTACAAAGCC TAAATTGTTG
9651 TCCAAGGCTG AGATAATAAA GGTTGATGTT TATTCGTATA TTATGAGTTT
9701 ATAG

Cds (SEQ ID NO:15)
       1 ATGAATGGAA AGGAATCAAG AGGACCTGCG TGTAGCTTTG AGTTTGTTGG
      51 TGAAAGCTCA GGTTTACTTG GTCCAGGAGA AAGTCGCTGG CCTTTTACCA
     101 ATGGCTATGC ATTTGCGACT TGGATTTATA TTGAATCATT TGCTGACACA
     151 TTAGATGCTT CAACCGCGGC AGCTGCAATT GCTGCTGCTT CAGCGGCAAA
```

FIG. 9U

```
 201 ATCAGGAAAA ATATCTAATG CAGCGCCTGC GAATGTACAC ACTGGTGAGG
 251 GTACTGCTCA TATGCCTCGT CTGTTCAGCT TTTTGACCCC TGATAATCAG
 301 GGAATTGAAG CTTATTTCTA TGCACAATTT TTGGTGGTTG AGAGTGGCAG
 351 TGGGAAAGGA AGTAAAACTT CACTTCATTT CACTCATGCA TTTAAGCCTC
 401 AGTGTTGGTA CTTTATTGGC CTTGAGCATA CCTGCAATCA GGGACTTTTA
 451 GGGAATTCAG ATAGTGAATT ACGGCTATAT ATTGACGGGT CGTTGTATGA
 501 AACTCGACCA TTTGACTATC CTCGGATATC CAAACCGCTT TCTTTCTGTT
 551 GCATTGGGTC AAATCCTCCT TCTACAACTG CTGGTCTACA ACGTCGTCGA
 601 CGTCAGTGTG CTTTGTTTGC TGAGATGGGA CCAGTTTATA TATTTAAAGA
 651 ACCGATTGGT CCTGAAAGAA TGACACGATT GGCAACTAGA GGTGGGGATG
 701 TTTTGCCTTG TTTTGGCAAT GGGGCAGGTC TTCCATGGTT AGCTACAAAT
 751 GACCATGTCC GTAATGTGGC AGAGGAAAGT AGTCTTTCGG ATGCAGAGCT
 801 TGGAGGATAC ATTCACCTAC TTTACCACCC ATGTCTACTA GTGGGCGGT
 851 TCTGTCCAGA TGCTTCTCTT TCTGGAGCAG CAGGAGATGA GAAAACACCA
 901 TATTCTTTTT CTGCTGTAGT TTTCGCACTT TGTTATTTGG TTTTCCCTTA
 951 CTTTGGAAGA CCCATGTCTT TGCTTCCTCT AACCGTAAGC AGTGTGCACA
1001 AAGATAATCT AGAGCCATGT TCTAGAAATG TTCCATCTTC TTTGACAACA
1051 TATTCTCTGG CTGCACCTAT TTTTAGAATG ATCTCATTTG CTATTAAACA
1101 TCCTGGGAAC AATGAAGAGT TATCTCGTAC TAGGGGGCCT GAAATTCTGG
1151 CCACAGTTCT CGGTTACCTT CTTCATTCAC TTGCATCCTT TGATATCAAG
1201 CACGATAGAG TAGGAGATGA GGAGCTAGTT GCTGCTATTG TTTCTCTTTG
1251 CCAATCTCAA AAGATCAATC ATGCTCTTAA AGTGCAGCTC TTCTGTACAC
1301 TATTGTTGGA TCTGAAGATA TGGAGTGTGT GCAGTTACAG ACTCCAAAAG
1351 AAGCTGTTGT CATCTCTTCA AGATATGGTT TTCACCGAAG CAACAGCTAT
1401 GAGGAATGCT GATGCCATTC AGGTACTTCT GGATGGATGT CGAAGATATT
1451 TCTGGACAAT TCAAGAGAAA GACTCCGTGA ACACGTTTTC TCTAGATGGG
1501 GATGCACGTC AAGTGGGGGA AGTTAATGCA TTGGTTGATG AACTTTTGGT
1551 GATTATTGAA CTTCTAATGG GAGCAGCATC TCCTTCGTTT GCTGCTGATG
1601 ACCTCCATCG ATTACTTGGC TTTATAATTG AGAGTCCACA ACCAAATCAG
1651 GTTGCAAGGG TATTGCATCT CATGTTTAGG TTGGTTGTAC AGCCAAATGC
1701 TGCAAAGGCT CAGACATTTG CAGAGGCATT TATCACATCT GGTGGGATAG
1751 AAACACTTCT TGTTCTCATA GCAAACAGAG TCAACACAAT GGGCCTGGAA
1801 ACAGAGTCAT TCAACAAGT AAAAGTGCAT GGATCCGAAA CTGTCATTTG
1851 TGAGACTGGC TCAGTTACCC TCTCCAGTTC CGTGAATGCT GACAGAATAT
1901 CCTCTGTTTC TGAAACTCCA TTCAATAATA ATGCAAGAAA CAATGTTGAC
1951 GATAGAGATC GTGTCATGGT TGGGATCATC AGATTGATTG GTGCGTTGAT
2001 TTCAAAAGGG CACTTAAAAT TTTCCGTTGG TGCCAAATCT GATGTAATGA
2051 GTAACCTCAT GGGTAGTGAG TTTCGTGAAA ATGGTGGAAC AATGTTTGAT
2101 TATAAAGTCG CATTGCTTCT ATTTGCTCTG CTGAAAGCAT TCAAGCAGC
2151 TCCAAACAGA TTGATGACCG ACAATGTCTA CACAACTTTG CTTGGGGCTT
2201 CGGTTAATGC TTCATCAACT GAGGATGGCC TGAACTTTTG TGATTTAGGT
2251 CATCGATTTG AACATCCTCA ACTTCTGTTA ATCCTCCTGC GTTCTCTACC
2301 ATTTGCATCT AAGGCACTAC AAAATCGAGC ACTTCAGGAT ATTCTATTTT
2351 TGGCTTGTAC CCATCCAGAA AAAGGAGTA GTCTGACCAA AATGGAAGAG
2401 TGGCCTGAGT GGATCTTGGA GATTTAATC TCTAACTACG AGAAAGATGC
2451 AGGGAAACAA TCTGCTTCAC CCGGTTCTGC TGAAGAGGAG GATCTGATTC
2501 ATAACTTCTT GATCATAATG TTGGAACATT CAATGCGCCA GAAGGATGGC
2551 TGGAAGGATA TTGAGGCTAC AATTCATTGT GCAGAGTGGC TTACTTTTGT
2601 TGGTGGGTCT AGCACTGGGG AGAAACGAAT TAGGCGTGAG GAATCACTGC
2651 CAATTTTCAA ACGAAGACTT TTAGGTGGAT TGCTAGACTT TGCTGCCAGT
2701 GAACTGCAAG CTCAGACTCA AGTTATAGCT GCAGCATCTG CTGGTTTCGC
2751 GGCAGAGAGT CTAACACCAA AAGATGCAAA AGCGGGAGTA GAAAATGCTG
```

FIG. 9V

```
2801 CACTGCTTTC AGTGTTTCTA GTGGAAAATA CAGTTGTGAT TTTGATGCTT
2851 GTCGAAGATC ATTTGCGACT ACAAAGCAAG CAAAATTGTG CTGCAAGCGC
2901 AGTTGATGTC TCTCCATCTC CTCTTTCACT TGTTTATCCT CCCAACTACC
2951 GTTCACACAC ATTGCCAACG GTCGGAGAAT CATCAGAGGT TTCTAGTAGC
3001 TGTGCTTCAG TGTCCAGTGA TTCAGGAGGG GTCCATTTAG ATATACTTGC
3051 TTCAATGGCC GATGCAAGTG GCCAGATATC TACAGCCGTA ATGGAGCGTC
3101 TTGCTGCTGC TGCTGCAGCT GAGCCCTATG AATCTGTTTC TTGCGCTTTT
3151 GTTTCATATG GAAGTTGTAC CAGGGATTTG GCTGATGCTT GGAAGTACAG
3201 AAGTCGATTG TGGTACGGTG TTGGACTACC TTCTAAAACT AGTTGTTTTG
3251 GTGGTGGTGG AAGTGGTTGG GACTCTTGGA AGCATGCTCT ACAAAAGAT
3301 GCTCAGGGTA ACTGGATCGA ACTTCCTTTG GTTAAAAAT CAGTATCCAT
3351 GCTTCAAGCC TTGCTGCTAG ATGAGTCTGG ACTTGGAGGT GGCCTAGGAA
3401 TTGGTGGAGG ATCTGGTACC GGGATGGGAG GGATGTCAGG CCTCTACCAG
3451 TTGCTAGATA GTGATCAGCC TTTCTTATGC ATGCTTCGAA TGGTACTCTT
3501 GTCTTTGAGG GAAGAAGACC ATGGTGAAGA TAGTCTGTTG ATGAAAAATT
3551 TAAGTTCTGA AGATGGTATA ACTGGTGGAC TCCAGTGCCC CTTAGGAAAT
3601 TCTGCCTCAG TAGATATCAG TTCTCAGTTG TCTATGCGAC AGTCACCATC
3651 AGCTTTATTG TGGAGTGTGC TCTCTCCCGT TCTAAACATG CCAATCTCTG
3701 ATTCTAAGAG GCAGAGGGTA TTGGTTACTA CATGTGTTCT ATATTCTGAG
3751 GTATGGAATG CTGTTAGCAA AGATAAAAGA CCACTACGTA AGCAGTATCT
3801 AGAGGCTATT TTACCACCAT TTGTTGCAAT TCTCCGAAGA TGGAGGCCTC
3851 TTTTGGCTGG TATTCATGAA CTTTCCACTG GTGATGGTGT GAATCCCCTT
3901 GTCGTTGATA CTCGTGCTTT GGCTGCTGAT GCACTTCCCA TTGAGGCGGC
3951 TCTCTCTATG ATTTCTCCGG AGTGGGCAGC TGCTTTTGCA TCGCCTCCTT
4001 CTGCAATGGC ACTGGCAATG ATAGCTGCAG GGCAGCTGG TTGGGAAGCG
4051 CCGGCACATC CAGCACCTCC AGCGCCTCCA CCTCTTAGGC GAGACAGTTC
4101 ATTACTTGAG CGTAAGAGTA CCAAACTTCA GACCTTTTCA AGCTTCCAGA
4151 AACCCTTGGA GGCTCCAAAT GATGATACAC CAGGTCGAGC AAGAGATAAG
4201 GCTGCTGCAA ATATTGATTC ACATTATTG ATTCAACCGC TCACCAGATT
4251 GACAGGCGTT TTCTGGAAAC TGGATTCTAT GGAAAGTTCT TCAGGATGA
4301 GACAATGTTT AAGGAGGAAT TATTCTGGCA CTGGTCATCT TGAGACAACA
4351 AGAAACTATG GGGATCAGAC ATACTTGATG AATAATCACG ACTCACCTGT
4401 TCTTGCTGTT GAAGCAATAT CAAAGGAAAT AATGTATGAA GATGATGAAC
4451 ATGGAGATGC CGATGATCTT GAAATAGAGG GTAATGTTGG AGAACGCAAA
4501 GGGGAAAACG AAGAGAGAAG GTCTGGCTCA CTTGAGGATG CAATAACACT
4551 GTCAACTGGA ATCAACGATC ATCGACCTTT GAGTGAACAG AATATGGTTC
4601 AAAATTCTAC AGAAGTAAAA GATCTCAGTG AACTTAAAGA AAGGATTGTT
4651 CTTGAAATTT CCTCTACTAT GGTCCGACCA CTAGGGGTTG TGAAAGGAAC
4701 CTTTCAAATC ACAACACGGA GAATAAATTT TATTGTTGAC ATCAGAGAAG
4751 ACCAACATTT GGATGAAAAG TCAGACGGTT CAAAATCAAG AGACGAAGAA
4801 AGAGATCGAA GTTGGCTGAT GTCTTCTCTT CATCAGATTT ATAGCCGACG
4851 ATATCTACTG AAGAAGAGTG CTCTTGAACT ATTTATGGTG GATCGCTCAA
4901 ACTTCTTCTT TGATTTTGGG AACACCGAGG GACGAAGAAA TGCTTGTCGG
4951 GCTATTGTTC AAGCAAGGCC TCCTCATTTG AAAAATATTT ACTCGGCAAC
5001 TCAGCCAGAA CAAGTTTCGA GAAGAACACA GTTAATGGAG CGTTGGGCTA
5051 GATGGGAGAT CAGCAATTTT GAGTACTTAA TGCAGCTCAA CACATTGGCT
5101 GGGCGTAGTT ATAATGACAT CACTCAGTAT CCTATTTTCC CATGGATTTT
5151 ATGCGACTAT GTATCAGAAA TTTTGGACCT ATCAAATCCA TCTAATTACA
5201 GGGATCTTTC CAAGGTGCCA ATTGGTGCAC TGAACCCGGA GCGGCTGAAA
5251 AAGTTTCAAG AAAAACACTC TAGCTTTGAA GATCCAGTCA TCCCCAAATT
5301 TCATTATGGT TCACATTACT CAAGTGCTGG AGCAGTGTTG CATTATCTAG
5351 CTAGAGTCGA ACCTTTTACA ACCCTTTCGA TTCAACTGCA AGGTAGAAAG
```

*FIG. 9W*

```
5401 TTTGATCGTG CAGACCAAAT ATTTTCAGAC ATTGCAGCCA CTTGGAAAGG
5451 AGTTCTCCAA GATATGAATA ATGTGAAGGA GTTAACACA ACTGATCCAA
5501 ACACTCACAT GGTCTCAAGC TTTTCAAACC CAACTACCAG CGAGACTGAA
5551 CCTGATTCAG ACATGAACAT TGTCTCTACC CCTTCAAATG CAACTACAAA
5601 TCAGATTGAC ACTGAATCTT CCGAGGCGGC TAACTATGAA ACAGCAACT
5651 CGTCTATCAA GACTTCTAAG AACACTTCAA AGATCACTAA ATTGACCCCG
5701 ACGTCAAAAC GATCACTAAC TTCATCGAAA GATAATGCAG CTCAAAAGTC
5751 ATCTACAAAG CCTAAATTGT TGTCCAAGGC TGAGATAATA AAGGTTGATG
5801 TTTATTCGTA TATTATGAGT TTATAG

Amino acid (SEQ ID NO:16)

1 MNGKESRGPA CSFEFVGESS GLLGPGESRW PFTNGYAFAT WIYIESFADT
  51 LDASTAAAAI AAASAAKSGK ISNAAPANVH TGEGTAHMPR LFSFLTPDNQ
 101 GIEAYFYAQF LVVESGSGKG SKTSLHFTHA FKPQCWYFIG LEHTCNQGLL
 151 GNSDSELRLY IDGSLYETRP FDYPRISKPL SFCCIGSNPP STTAGLQRRR
 201 RQCALFAEMG PVYIFKEPIG PERMTRLATR GGDVLPCFGN GAGLPWLATN
 251 DHVRNVAEES SLSDAELGGY IHLLYHPCLL SGRFCPDASL SGAAGDEKTP
 301 YSFSAVVFAL CYLVFPYFGR PMSLLPLTVS SVHKDNLEPC SRNVPSSLTT
 351 YSLAAPIFRM ISFAIKHPGN NEELSRTRGP EILATVLGYL LHSLASFDIK
 401 HDRVGDEELV AAIVSLCQSQ KINHALKVQL FCTLLLDLKI WSVCSYRLQK
 451 KLLSSLQDMV FTEATAMRNA DAIQVLLDGC RRYFWTIQEK DSVNTFSLDG
 501 DARQVGEVNA LVDELLVIIE LLMGAASPSF AADDLHRLLG FIIESPQPNQ
 551 VARVLHLMFR LVVQPNAAKA QTFAEAFITS GGIETLLVLI ANRVNTMGLE
 601 TESFQQVKVH GSETVICETG SVTLSSSVNA DRISSVSETP FNNNARNNVD
 651 DRDRVMVGII RLIGALISKG HLKFSVGAKS DVMSNLMGSE FRENGGTMFD
 701 YKVALLLFAL LKAFQAAPNR LMTDNVYTTL LGASVNASST EDGLNFCDLG
 751 HRFEHPQLLL ILLRSLPFAS KALQNRALQD ILFLACTHPE KRSSLTKMEE
 801 WPEWILEILI SNYEKDAGKQ SASPGSAEEE DLIHNFLIIM LEHSMRQKDG
 851 WKDIEATIHC AEWLTFVGGS STGEKRIRRE ESLPIFKRRL LGGLLDFAAS
 901 ELQAQTQVIA AASAGFAAES LTPKDAKAGV ENAALLSVFL VENTVVILML
 951 VEDHLRLQSK QNCAASAVDV SPSPLSLVYP PNYRSHTLPT VGESSEVSSS
1001 CASVSSDSGG VHLDILASMA DASGQISTAV MERLAAAAAA EPYESVSCAF
1051 VSYGSCTRDL ADAWKYRSRL WYGVGLPSKT SCFGGGGSGW DSWKHALQKD
1101 AQGNWIELPL VKKSVSMLQA LLLDESGLGG GLGIGGGSGT GMGGMSGLYQ
1151 LLDSDQPFLC MLRMVLLSLR EEDHGEDSLL MKNLSSEDGI TGGLQCPLGN
1201 SASVDISSQL SMRQSPSALL WSVLSPVLNM PISDSKRQRV LVTTCVLYSE
1251 VWNAVSKDKR PLRKQYLEAI LPPFVAILRR WRPLLAGIHE LSTGDGVNPL
1301 VVDTRALAAD ALPIEAALSM ISPEWAAAFA SPPSAMALAM IAAGAAGWEA
1351 PAHPAPPAPP PLRRDSSLLE RKSTKLQTFS SFQKPLEAPN DDTPGRARDK
1401 AAANIDSHLL IQPLTRLTGV FWKLDSMESS SRMRQCLRRN YSGTGHLETT
1451 RNYGDQTYLM NNHDSPVLAV EAISKEIMYE DDEHGDADDL EIEGNVGERK
1501 GENEERRSGS LEDAITLSTG INDHRPLSEQ NMVQNSTEVK DLSELKERIV
1551 LEISSTMVRP LGVVKGTFQI TTRRINFIVD IREDQHLDEK SDGSKSRDEE
1601 RDRSWLMSSL HQIYSRRYLL KKSALELFMV DRSNFFFDFG NTEGRRNACR
1651 AIVQARPPHL KNIYSATQPE QVSRRTQLME RWARWEISNF EYLMQLNTLA
1701 GRSYNDITQY PIFPWILCDY VSEILDLSNP SNYRDLSKVP IGALNPERLK
1751 KFQEKHSSFE DPVIPKFHYG SHYSSAGAVL HYLARVEPFT TLSIQLQGRK
1801 FDRADQIFSD IAATWKGVLQ DMNNVKELNT TDPNTHMVSS FSNPTTSETE
1851 PDSDMNIVST PSNATTNQID TESSEAANYE NSNSSIKTSK NTSKITKLTP
1901 TSKRSLTSSK DNAAQKSSTK PKLLSKAEII KVDVYSYIMS L
```

SLD1    SPHINGOID LCB DESATURASE 1

ATSLD1
NCBI Accession number NM_115922.2

CDS (SEQ ID NO:17)
```
   1 ATGGCGGAAG AGACGGAGAA AAAGTACATT ACGAACGAAG ATCTTAAAAA
  51 ACACAACAAA TCTGGAGATC TATGGATCGC GATTCAAGGC AAGGTCTACA
 101 ACGTCTCCGA TTGGATTAAA ACTCATCCCG GAGGCGACAC GGTGATTCTC
 151 AATCTCGTTG GTCAAGACGT CACCGATGCT TTCATCGCAT TCATCCCGG
 201 AACCGCTTGG CACCATCTCG ACCATCTCTT CACCGGTTAC ACATCAGAG
 251 ATTTCCAAGT CTCCGAAGTC TCACGCGATT ACCGTCGTAT GGCTGCCGAG
 301 TTTCGTAAAC TCGGTCTCTT CGAAAACAAA GGTCACGTTA CTCTCTACAC
 351 TCTAGCCTTC GTCGCCGCCA TGTTCCTCGG AGTTCTCTAC GGTGTTTTGG
 401 CTTGTACCTC CGTCTTCGCT CACCAAATCG CCGCCGCGCT TCTCGGTCTC
 451 CTCTGGATCC AGAGCGCTTA CATAGGTCAC GATTCTGGTC ATTACGTTAT
 501 CATGTCGAAC AAATCTTATA ACAGATTCGC TCAGCTTCTC TCCGGTAACT
 551 GTCTCACCGG AATCTCAATC GCGTGGTGGA ATGGACTCA CAATGCTCAT
 601 CATCTAGCTT GTAACAGCCT CGATTACGAT CCAGATCTAC AACACATCCC
 651 TGTCTTCGCC GTCTCCACCA AATTCTTCTC CTCATTGACC TCGAGATTCT
 701 ACGATCGGAA ACTCACGTTT GATCCAGTCG CGAGATTCTT AGTCAGCTAT
 751 CAACACTTTA CTTATTATCC AGTTATGTGC TTTGGAAGAA TCAATCTCTT
 801 CATTCAAACG TTTCTCTTGC TCTTCTCCAA ACGTGAAGTA CCAGATCGTG
 851 CTTTAAACTT CGCCGGAATC TTAGTCTTCT GGACTTGGTT CCCACTCTTA
 901 GTCTCATGTC TACCAAACTG GCCTGAGAGA TTCTTCTTCG TCTTCACAAG
 951 CTTCACCGTC ACGGCGCTTC AACACATTCA ATTCACGCTT AACCATTTCG
1001 CTGCTGATGT CTACGTTGGT CCACCCACCG GTAGCGACTG GTTCGAGAAG
1051 CAAGCGGCGG GAACAATCGA TATCTCTTGT AGATCATACA TGGATTGGTT
1101 CTTTGGTGGA TTACAGTTTC AGCTTGAGCA TCATTGTTC CCTCGCTTAC
1151 CTCGTTGCCA TCTCCGGAAA GTTTCTCCGG TGGTTCAAGA GCTTTGCAAG
1201 AAGCATAATC TTCCGTATAG GAGTATGTCG TGGTTTGAAG CAAATGTGTT
1251 GACCATTAAC ACTTTGAAGA CAGCAGCTTA TCAAGCTAGA GACGTGGCTA
1301 ATCCGGTGGT TAAGAACTTG GTTTGGGAAG CTTTGAATAC TCATGGCTAA
```

Genomic (SEQ ID NO:27)
```
   1 AAGGAAGGAG TCGAAGATAA GCGGAGAGAG AGAGAGAGAC AGAGAGAGAT
  51 TCAAAAATCC GATTCCAGAT CCATTCCTGG GCAAACAAAG GTTGGTGTTT
 101 CTCTAATCTC AAAGCTTTTT TCAAATTCGG AAAAAGCAAA TCGTGGGAAG
 151 AGATTCATCT TCTCTCTGTG CGTTCATCGG ATCTCGGAGC TTTTGGTTCG
 201 TCGTCAATGG CGGAAGAGAC GGAGAAAAAG TACATTACGA ACGAAGATCT
 251 TAAAAACAC AACAAATCTG GAGATCTATG GATCGCGATT CAAGGCAAGG
 301 TCTACAACGT CTCCGATTGG ATTAAAACTC ATCCCGGAGG CGACACGGTG
 351 ATTCTCAATC TCGTTGGTCA AGACGTCACC GATGCTTTCA TCGCATTTCA
 401 TCCCGGAACC GCTTGGCACC ATCTCGACCA TCTCTTCACC GGTTACCACA
 451 TCAGAGATTT CCAAGTCTCC GAAGTCTCAC GCGATTACCG TCGTATGGCT
 501 GCCGAGTTTC GTAAACTCGG TCTCTTCGAA AACAAAGGTC ACGTTACTCT
 551 CTACACTCTA GCCTTCGTCG CCGCCATGTT CCTCGGAGTT CTCTACGGTG
 601 TTTTGGCTTG TACCTCCGTC TTCGCTCACC AAATCGCCGC CGCTTCTC
 651 GGTCTCCTCT GGATCCAGAG CGCTTACATA GGTCACGATT CTGGTCATTA
 701 CGTTATCATG TCGAACAAAT CTTATAACAG ATTCGCTCAG CTTCTCTCCG
 751 GTAACTGTCT CACCGGAATC TCAATCGCGT GGTGGAAATG GACTCACAAT
```

FIG. 9Y

```
 801 GCTCATCATC TAGCTTGTAA CAGCCTCGAT TACGATCCAG ATCTACAACA
 851 CATCCCTGTC TTCGCCGTCT CCACCAAATT CTTCTCCTCA TTGACCTCGA
 901 GATTCTACGA TCGGAAACTC ACGTTTGATC CAGTCGCGAG ATTCTTAGTC
 951 AGCTATCAAC ACTTTACTTA TTATCCAGTT ATGTGCTTTG AAGAATCAA
1001 TCTCTTCATT CAAACGTTTC TCTTGCTCTT CTCCAAACGT GAAGTACCAG
1051 ATCGTGCTTT AAACTTCGCC GGAATCTTAG TCTTCTGGAC TTGGTTCCCA
1101 CTCTTAGTCT CATGTCTACC AAACTGGCCT GAGAGATTCT TCTTCGTCTT
1151 CACAAGCTTC ACCGTCACGG CGCTTCAACA CATTCAATTC ACGCTTAACC
1201 ATTTCGCTGC TGATGTCTAC GTTGGTCCAC CCACCGGTAG CGACTGGTTC
1251 GAGAAGCAAG CGGCGGGAAC AATCGATATC TCTTGTAGAT CATACATGGA
1301 TTGGTTCTTT GGTGGATTAC AGTTTCAGCT TGAGCATCAT TTGTTCCCTC
1351 GCTTACCTCG TTGCCATCTC CGGAAAGTTT CTCCGGTGGT TCAAGAGCTT
1401 TGCAAGAAGC ATAATCTTCC GTATAGGAGT ATGTCGTGGT TTGAAGCAAA
1451 TGTGTTGACC ATTAACACTT TGAAGACAGC AGCTTATCAA GCTAGAGACG
1501 TGGCTAATCC GGTGGTTAAG AACTTGGTTT GGGAAGCTTT GAATACTCAT
1551 GGCTAAATGA TTTTAATCAA AACAAAATAT GCTTTTGTTT GGGTTAAATT
1601 TGATGTGTTG TTTTTATGCT TTATTGAATC TTTGAATTTC GTTTTGTTAC
1651 TTACTTACAT GGAAGAGATG TTTTAGATCG AAATTGAATC GAGATTTGAT
1701 TTTTTTATTA GACAACTCTT CGTATCGTAA TGATTTATTA ATAATATTAT
1751 TTTGAATTTA ATTTGTTTTT TTATATAAGT TTTTGTTTCA CATGGCTCTT
1801 TTTTGTTGCC TGTGACTTAC TTTGTGGTTT TGCGGCTTTT GGCCTTTTCA
1851 ATGTTTTGTC GTGTTACATT AAAATACGTG TGTGGATGCT ATTTGAGATC
1901 CTCTATATGT AAGGTTTTAA CAGATC

Amino acid (SEQ ID NO:18)
   1 MAEETEKKYI TNEDLKKHNK SGDLWIAIQG KVYNVSDWIK THPGGDTVIL
  51 NLVGQDVTDA FIAFHPGTAW HHLDHLFTGY HIRDFQVSEV SRDYRRMAAE
 101 FRKLGLFENK GHVTLYTLAF VAAMFLGVLY GVLACTSVFA HQIAAALLGL
 151 LWIQSAYIGH DSGHYVIMSN KSYNRFAQLL SGNCLTGISI AWWKWTHNAH
 201 HLACNSLDYD PDLQHIPVFA VSTKFFSSLT SRFYDRKLTF DPVARFLVSY
 251 QHFTYYPVMC FGRINLFIQT FLLLFSKREV PDRALNFAGI LVFWTWFPLL
 301 VSCLPNWPER FFFVFTSFTV TALQHIQFTL NHFAADVYVG PPTGSDWFEK
 351 QAAGTIDISC RSYMDWFFGG LQFQLEHHLF PRLPRCHLRK VSPVVQELCK
 401 KHNLPYRSMS WFEANVLTIN TLKTAAYQAR DVANPVVKNL VWEALNTHG
```

FIG. 9Z

*Phytophthora sojae* isolates

SEQUENCE LISTING

<160> NUMBER OF SEQ ID NOS: 27

<210> SEQ ID NO 1
<211> LENGTH: 1569
<212> TYPE: DNA
<213> ORGANISM: Arabidopsis thaliana

<400> SEQUENCE: 1

```
atggtgaaac acagaaactc atctcgctcg ataatctcat attcttcttc aatagcaaga      60
ttcttctcta gaaaagctat ttctctctac ttgatcttcg tctttgcttt taccatctgg     120
gttctcgtct tcagctccag aaacattcaa accgatgatg accacaccaa acatcaacaa     180
caacatcatc gggatctaat cgattcagaa tcatttccgc accgtatttt gcctcctagg     240
aagaatttgc agaaaccgta tgaaaatact caactttgga ctcctccttt cagctttggg     300
ttgcatccat gtgtcaaacc tactccgaaa tacaaagaat tttcagaatc agatcattat     360
ataacagtga aaagtaatgg tggactaaat caaatgcgta ctggtatagc agatatagtg     420
gctgttgcgc acatcatgaa tgcaaacttta gtcattcctg agctggataa gcgatcgttt     480
tggcaagatt caagtgtttt ttcagatatt tttgacgagg aacaattcat taaatcattg     540
cgaagagatg tcaaggttat taaaaagctc ccaaggaag tggaatctct acctagagca     600
aggaagcatt tcacttcttg gtctagtgtt ggatattatg aagaaatgac tcacttgtgg     660
aaggagtaca aggtcatcca tgtcgcaaaa tcagattctc gccttgcaaa taatgacctg     720
cctatcgacg ttcaaagact gagatgtcgt gtactatatc gtggtctctg cttctctcct     780
gcaattgaaa gccttggaca gaagctggtt gagagactca agtcacgtgc tgggagatat     840
attgcattgc acctgagata tgagaaagat atgttggctt tcactggttg cacctatggt     900
ctcactgatg ctgaatccga agaactgaga gtaatgcggg aaagtacaag ccattggaag     960
atcaaaagta taaattcaac agagcagaga gaggaaggcc tttgtccatt gactccaaaa    1020
gaagtgggaa tatttctgaa aggtctcgga tattctcagt caacagtcat atatattgca    1080
gcaggggaaa tctatggggg tgatgataga ctctctgagc ttaagtcgcg cttcccaaat    1140
ctggttttta aggaaacgct tgctgggaac gaagagttaa aaggtttcac tggccatgcg    1200
actaaaacgg ctgctcttga ttacataatt tctgttgaga gtgatgtgtt tgttccttca    1260
```
cattctggaa acatggcaag agcagttgaa ggtcaccgca gatttctagg gcatcgcagg    1320
actatcactc ccgacaggaa aggactagtg aaactcttcg ttaagatgga gagaggacag    1380 ctaaagaag gaccaaagtt gtccaattttt gtgaatcaaa tgcataaaga cagacaaggt    1440
gcaccgagga gaaggaaagg accaacgcag gggatcaaag gacgtgcacg gtttagaact    1500
gaagaagcct tttatgagaa tccatatcca gagtgtattt gcagttcaaa ggagcacaaa    1560
gaaccctaa                                                             1569

<210> SEQ ID NO 2
<211> LENGTH: 522
<212> TYPE: PRT
<213> ORGANISM: Arabidopsis thaliana

<400> SEQUENCE: 2

Met Val Lys His Arg Asn Ser Ser Arg Ser Ile Ile Ser Tyr Ser Ser
1               5                   10                  15

Ser Ile Ala Arg Phe Phe Ser Arg Lys Ala Ile Ser Leu Tyr Leu Ile
            20                  25                  30

Phe Val Phe Ala Phe Thr Ile Trp Val Leu Val Phe Ser Ser Arg Asn
        35                  40                  45

Ile Gln Thr Asp Asp His Thr Lys His Gln Gln His His Arg
    50                  55                  60

Asp Leu Ile Asp Ser Glu Ser Phe Pro Pro Tyr Leu Pro Pro Arg
65              70                  75                  80

Lys Asn Leu Gln Lys Pro Tyr Glu Asn Thr Gln Leu Trp Thr Pro Pro
                85                  90                  95

Phe Ser Phe Gly Leu His Pro Cys Val Lys Pro Thr Pro Lys Tyr Lys
            100                 105                 110

Glu Phe Ser Glu Ser Asp His Tyr Ile Thr Val Lys Ser Asn Gly Gly
        115                 120                 125

Leu Asn Gln Met Arg Thr Gly Ile Ala Asp Ile Val Ala Val Ala His
    130                 135                 140

Ile Met Asn Ala Thr Leu Val Ile Pro Glu Leu Asp Lys Arg Ser Phe
145                 150                 155                 160

Trp Gln Asp Ser Ser Val Phe Ser Asp Ile Phe Asp Glu Glu Gln Phe
                165                 170                 175

Ile Lys Ser Leu Arg Arg Asp Val Lys Val Ile Lys Lys Leu Pro Lys
            180                 185                 190

Glu Val Glu Ser Leu Pro Arg Ala Arg Lys His Phe Thr Ser Trp Ser
        195                 200                 205

Ser Val Gly Tyr Tyr Glu Glu Met Thr His Leu Trp Lys Glu Tyr Lys
    210                 215                 220

Val Ile His Val Ala Lys Ser Asp Ser Arg Leu Ala Asn Asn Asp Leu
225                 230                 235                 240

Pro Ile Asp Val Gln Arg Leu Arg Cys Arg Val Leu Tyr Arg Gly Leu
                245                 250                 255

Cys Phe Ser Pro Ala Ile Glu Ser Leu Gly Gln Lys Leu Val Glu Arg
            260                 265                 270

Leu Lys Ser Arg Ala Gly Arg Tyr Ile Ala Leu His Leu Arg Tyr Glu
        275                 280                 285

Lys Asp Met Leu Ala Phe Thr Gly Cys Thr Tyr Gly Leu Thr Asp Ala
    290                 295                 300

Glu Ser Glu Glu Leu Arg Val Met Arg Glu Ser Thr Ser His Trp Lys

```
       305                 310                 315                 320
Ile Lys Ser Ile Asn Ser Thr Glu Gln Arg Glu Glu Gly Leu Cys Pro
                    325                 330                 335
Leu Thr Pro Lys Glu Val Gly Ile Phe Leu Lys Gly Leu Gly Tyr Ser
                    340                 345                 350
Gln Ser Thr Val Ile Tyr Ile Ala Ala Gly Glu Ile Tyr Gly Gly Asp
                    355                 360                 365
Asp Arg Leu Ser Glu Leu Lys Ser Arg Phe Pro Asn Leu Val Phe Lys
            370                 375                 380
Glu Thr Leu Ala Gly Asn Glu Glu Leu Lys Gly Phe Thr Gly His Ala
385                 390                 395                 400
Thr Lys Thr Ala Ala Leu Asp Tyr Ile Ile Ser Val Glu Ser Asp Val
                    405                 410                 415
Phe Val Pro Ser His Ser Gly Asn Met Ala Arg Ala Val Glu Gly His
                    420                 425                 430
Arg Arg Phe Leu Gly His Arg Arg Thr Ile Thr Pro Asp Arg Lys Gly
                    435                 440                 445
Leu Val Lys Leu Phe Val Lys Met Glu Arg Gly Gln Leu Lys Glu Gly
                    450                 455                 460
Pro Lys Leu Ser Asn Phe Val Asn Gln Met His Lys Asp Arg Gln Gly
465                 470                 475                 480
Ala Pro Arg Arg Lys Gly Pro Thr Gln Gly Ile Lys Gly Arg Ala
                    485                 490                 495
Arg Phe Arg Thr Glu Glu Ala Phe Tyr Glu Asn Pro Tyr Pro Glu Cys
                    500                 505                 510
Ile Cys Ser Ser Lys Glu His Lys Glu Pro
                    515                 520

<210> SEQ ID NO 3
<211> LENGTH: 1902
<212> TYPE: DNA
<213> ORGANISM: Arabidopsis thaliana

<400> SEQUENCE: 3
atggcgaatt tggatatgga gcaacattca tccgaaaacg aagagattaa gaagaagaag     60
cataagaaaa gagcgagaga cgaagctaag aaactaaagc agccagcaat ggaagaagaa    120
cccgatcatg aagatggtga tgccaaagag aacaatgcgt taattgacga gaaccgaag    180 aagaagaaga agaagaaaaa taagaagcgt ggagatactg atgatggaga ggacgaagcg    240
gtagcagaag aagagccgaa gaagaagaag aagaaaaata aaaagctaca gcagcgtgga    300
gatactaatg acgaagagga cgaagtgata gcagaagaag aagagccgaa gaagaagaag    360
aagaaacaga ggaaggacac ggaagcgaag tctgaagaag aagaagtaga agataaggaa    420
gaagaaaaaa aattggaaga aactagcata atgactaata aaacgtttga gtcattgtca    480
ttatctgata acacttataa atctatcaag gagatggggt ttgcacgcat gactcagata    540
caagctaaag caattccacc attgatgatg ggagaagatg tacttggagc tgccaggacc    600
ggttctggta aaaccttagc ttttctattt cctgctgttg agcttcttta ccgtgttaag    660
tttactcctc gcaatggaac tggtgttctt gttatttgcc caacaagaga gcttgctatt    720
cagtcttatg gagtggcaaa agaacttctt aagtatcatt cacagactgt gggaaaagtt    780
attggcggtg agaaaagaaa gacagaagct gagattcttg cgaaaggtgt taatttatta    840
gtagctaccc ctggaagact tctcgaccac cttgaaaata ctaatggttt tattttcaag    900
```

```
aacttaaagt tcttgtaat ggatgaggct gataggatat tggaacagaa ctttgaagaa    960
gacctcaaga agattttgaa ccttctacca aagactagac agacgtcact attttcagcc   1020
acacagagcg caaaggttga ggatcttgct cgggtgtcac ttacctcacc tgtttatatt   1080
gatgtggatg aaggacgaaa agaggttaca aatgaaggct tggagcaagg ttattgcgtt   1140
gtgccaagtg cgatgcggtt actttttta cttaccttct tgaagagatt ccaagggaaa    1200
aagaaaatta tggtgttttt ctctacatgc aagtcgacaa agttccacgc cgagctcttt   1260
cgatatatca aattcgattg cctttgaaatc cgtggaggga tagaccagaa caaaagaact   1320
ccaacatttt tgcaattcat aaaggcggaa accggtattt tgttgtgtac taatgtcgct   1380
gcccgaggtc ttgatttcc tcatgtggac tggattgtgc agtatgatcc tcctgataac    1440
ccaacggatt atattcatcg agttggtaga acagctcgtg gtgaaggagc aaaaggaaag   1500
gctctgcttg tcctaactcc acaggagttg aagtttatac agtatctcaa ggcggcgaaa   1560
attcctgttg aggaacatga atttgaagaa aagaaattgc tcgatgtgaa acctttgtg    1620 gagaatttga tatctgaaaa ctatgcattg aaggagtcag caaaagaagc atacaagaca   1680
tacatttcag gatatgattc tcactctatg aaagatgtct ttaatgttca ccaactcaat   1740
ctcacggagg ttgcgacttc gtttggtttc tcagatcctc ccaaagttgc tctgaagata   1800
gatcgaggag ggtacagaag taagagagaa ccggttaata agtttaagag aggtcgtggt   1860
ggtggtagac ccggcggtaa aagcaagttc gagaggtact aa                      1902
```

<210> SEQ ID NO 4
<211> LENGTH: 633
<212> TYPE: PRT
<213> ORGANISM: Arabidopsis thaliana

<400> SEQUENCE: 4

```
Met Ala Asn Leu Asp Met Glu Gln His Ser Glu Asn Glu Glu Ile
1               5                   10                  15

Lys Lys Lys Lys His Lys Lys Arg Ala Arg Asp Glu Ala Lys Lys Leu
            20                  25                  30

Lys Gln Pro Ala Met Glu Glu Glu Pro Asp His Glu Asp Gly Asp Ala
        35                  40                  45

Lys Glu Asn Asn Ala Leu Ile Asp Glu Glu Pro Lys Lys Lys Lys Lys
    50                  55                  60

Lys Lys Asn Lys Lys Arg Gly Asp Thr Asp Asp Gly Glu Asp Glu Ala
65                  70                  75                  80

Val Ala Glu Glu Glu Pro Lys Lys Lys Lys Lys Asn Lys Lys Leu
                85                  90                  95

Gln Gln Arg Gly Asp Thr Asn Asp Glu Glu Asp Glu Val Ile Ala Glu
            100                 105                 110

Glu Glu Pro Lys Lys Lys Lys Lys Gln Arg Lys Asp Thr Glu
        115                 120                 125

Ala Lys Ser Glu Glu Glu Val Glu Asp Lys Glu Glu Lys Lys
    130                 135                 140

Leu Glu Glu Thr Ser Ile Met Thr Asn Lys Thr Phe Glu Ser Leu Ser
145                 150                 155                 160

Leu Ser Asp Asn Thr Tyr Lys Ser Ile Lys Glu Met Gly Phe Ala Arg
                165                 170                 175

Met Thr Gln Ile Gln Ala Lys Ala Ile Pro Pro Leu Met Met Gly Glu
            180                 185                 190

Asp Val Leu Gly Ala Ala Arg Thr Gly Ser Gly Lys Thr Leu Ala Phe
```

-continued

```
            195                 200                 205
Leu Ile Pro Ala Val Glu Leu Leu Tyr Arg Val Lys Phe Thr Pro Arg
    210                 215                 220
Asn Gly Thr Gly Val Leu Val Ile Cys Pro Thr Arg Glu Leu Ala Ile
225                 230                 235                 240
Gln Ser Tyr Gly Val Ala Lys Glu Leu Leu Lys Tyr His Ser Gln Thr
                245                 250                 255
Val Gly Lys Val Ile Gly Gly Glu Lys Arg Lys Thr Glu Ala Glu Ile
                260                 265                 270
Leu Ala Lys Gly Val Asn Leu Leu Val Ala Thr Pro Gly Arg Leu Leu
            275                 280                 285
Asp His Leu Glu Asn Thr Asn Gly Phe Ile Phe Lys Asn Leu Lys Phe
        290                 295                 300
Leu Val Met Asp Glu Ala Asp Arg Ile Leu Gln Asn Phe Glu Glu
305                 310                 315                 320
Asp Leu Lys Lys Ile Leu Asn Leu Leu Pro Lys Thr Arg Gln Thr Ser
                325                 330                 335
Leu Phe Ser Ala Thr Gln Ser Ala Lys Val Glu Asp Leu Ala Arg Val
                340                 345                 350
Ser Leu Thr Ser Pro Val Tyr Ile Asp Val Asp Glu Gly Arg Lys Glu
            355                 360                 365
Val Thr Asn Glu Gly Leu Glu Gln Gly Tyr Cys Val Val Pro Ser Ala
        370                 375                 380
Met Arg Leu Leu Phe Leu Leu Thr Phe Leu Lys Arg Phe Gln Gly Lys
385                 390                 395                 400
Lys Lys Ile Met Val Phe Ser Thr Cys Lys Ser Thr Lys Phe His
                405                 410                 415
Ala Glu Leu Phe Arg Tyr Ile Lys Phe Asp Cys Leu Glu Ile Arg Gly
                420                 425                 430
Gly Ile Asp Gln Asn Lys Arg Thr Pro Thr Phe Leu Gln Phe Ile Lys
            435                 440                 445
Ala Glu Thr Gly Ile Leu Leu Cys Thr Asn Val Ala Ala Arg Gly Leu
        450                 455                 460
Asp Phe Pro His Val Asp Trp Ile Val Gln Tyr Asp Pro Pro Asp Asn
465                 470                 475                 480
Pro Thr Asp Tyr Ile His Arg Val Gly Arg Thr Ala Arg Gly Glu Gly
                485                 490                 495
Ala Lys Gly Lys Ala Leu Leu Val Leu Thr Pro Gln Glu Leu Lys Phe
                500                 505                 510
Ile Gln Tyr Leu Lys Ala Ala Lys Ile Pro Val Glu Glu His Glu Phe
            515                 520                 525
Glu Glu Lys Lys Leu Leu Asp Val Lys Pro Phe Val Glu Asn Leu Ile
        530                 535                 540
Ser Glu Asn Tyr Ala Leu Lys Glu Ser Ala Lys Glu Ala Tyr Lys Thr
545                 550                 555                 560
Tyr Ile Ser Gly Tyr Asp Ser His Ser Met Lys Asp Val Phe Asn Val
                565                 570                 575
His Gln Leu Asn Leu Thr Glu Val Ala Thr Ser Phe Gly Phe Ser Asp
            580                 585                 590
Pro Pro Lys Val Ala Leu Lys Ile Asp Arg Gly Gly Tyr Arg Ser Lys
            595                 600                 605
Arg Glu Pro Val Asn Lys Phe Lys Arg Gly Arg Gly Gly Arg Pro
        610                 615                 620
```

Gly Gly Lys Ser Lys Phe Glu Arg Tyr
625                 630

<210> SEQ ID NO 5
<211> LENGTH: 927
<212> TYPE: DNA
<213> ORGANISM: Arabidopsis thaliana

<400> SEQUENCE: 5

| | | |
|---|---|---|
| atggcggcgt cgtggcagtg ggaaaatgcc accgccggcg ccgtcgctgg attcgccacc | 60 |
| gtagctgcta tgcactctct tgatgttgtt cgtacgagat ccaagtcaa cgacggaaga | 120 |
| gggtcaagtc tgccgacgta caagaacact gctcacgctg tcttcaccat tgcccgtctc | 180 |
| gagggtttga gagggcttta tgcaggcttc ttccctgcag ttatcggttc tactgtttcc | 240 |
| tggggcttat acttcttttt ttatggaaga gccaagcaga ggtacgctag aggcagggac | 300 |
| gatgagaaac tcagccctgc tctccacctt gcttctgctg ctgaagcagg ggccttggtc | 360 |
| tgtttatgca caaatcctat ttggcttgtc aaaacaaggt tacagcttca gacacctctt | 420 |
| catcaaactc aaccatactc agggctatta gatgccttta gaaccatagt gaaagaggaa | 480 |
| ggacccaggg cgctctacaa gggtattgtc cctggtcttg tactggtttc tcatggtgct | 540 |
| attcagttca cagcttatga ggaactccgt aaaatcattg tggatttgaa gaaaaggaga | 600 |
| agaaagtccg aatccactga caatctattg aactcagcag attatgctgc acttggtggc | 660 |
| tcctccaaag tcgctgcagt tcttcttacg tatccatttc aagttatacg agcacgatta | 720 |
| cagcaacgac ctagtaccaa cggaatccca agatatatag acagcttaca tgtcatcaga | 780 |
| gaaaccgcga gatatgaagg tctcaggggt ttctacaggg gactaacggc taatctttg | 840 |
| aaaaatgtac ctgcgtcttc catcacattc atcgtctatg aaaacgttct gaaattgcta | 900 |
| aaacagcatc aacaacaaa agattag | 927 |

<210> SEQ ID NO 6
<211> LENGTH: 308
<212> TYPE: PRT
<213> ORGANISM: Arabidopsis thaliana

<400> SEQUENCE: 6

Met Ala Ala Ser Trp Gln Trp Glu Asn Ala Thr Ala Gly Ala Val Ala
1               5                   10                  15

Gly Phe Ala Thr Val Ala Ala Met His Ser Leu Asp Val Val Arg Thr
            20                  25                  30

Arg Phe Gln Val Asn Asp Gly Arg Gly Ser Ser Leu Pro Thr Tyr Lys
        35                  40                  45

Asn Thr Ala His Ala Val Phe Thr Ile Ala Arg Leu Glu Gly Leu Arg
    50                  55                  60

Gly Leu Tyr Ala Gly Phe Phe Pro Ala Val Ile Gly Ser Thr Val Ser
65                  70                  75                  80

Trp Gly Leu Tyr Phe Phe Phe Tyr Gly Arg Ala Lys Gln Arg Tyr Ala
                85                  90                  95

Arg Gly Arg Asp Asp Glu Lys Leu Ser Pro Ala Leu His Leu Ala Ser
            100                 105                 110

Ala Ala Glu Ala Gly Ala Leu Val Cys Leu Cys Thr Asn Pro Ile Trp
        115                 120                 125

Leu Val Lys Thr Arg Leu Gln Leu Gln Thr Pro Leu His Gln Thr Gln
    130                 135                 140

```
Pro Tyr Ser Gly Leu Leu Asp Ala Phe Arg Thr Ile Val Lys Glu Glu
145                 150                 155                 160

Gly Pro Arg Ala Leu Tyr Lys Gly Ile Val Pro Gly Leu Val Leu Val
                165                 170                 175

Ser His Gly Ala Ile Gln Phe Thr Ala Tyr Glu Glu Leu Arg Lys Ile
            180                 185                 190

Ile Val Asp Leu Lys Glu Arg Arg Lys Ser Glu Ser Thr Asp Asn
        195                 200                 205

Leu Leu Asn Ser Ala Asp Tyr Ala Ala Leu Gly Gly Ser Ser Lys Val
    210                 215                 220

Ala Ala Val Leu Leu Thr Tyr Pro Phe Gln Val Ile Arg Ala Arg Leu
225                 230                 235                 240

Gln Gln Arg Pro Ser Thr Asn Gly Ile Pro Arg Tyr Ile Asp Ser Leu
                245                 250                 255

His Val Ile Arg Glu Thr Ala Arg Tyr Glu Gly Leu Arg Gly Phe Tyr
            260                 265                 270

Arg Gly Leu Thr Ala Asn Leu Leu Lys Asn Val Pro Ala Ser Ser Ile
                275                 280                 285

Thr Phe Ile Val Tyr Glu Asn Val Leu Lys Leu Leu Lys Gln His Pro
    290                 295                 300

Thr Thr Lys Asp
305

<210> SEQ ID NO 7
<211> LENGTH: 741
<212> TYPE: DNA
<213> ORGANISM: Arabidopsis thaliana

<400> SEQUENCE: 7
atgagctcta cgcaggctaa tctatgcaga ccatccttgt tctgtgcaag acaacgcaa      60 acaagacatg tctctagtgc accttttatg tcgtcattac gctttgatta tcgaccactc    120
cccaaattag ctattcgggc atctgcatca tcatcgatgt cttctcagtt ttcgcctcta    180
cagaatcatc gctgccggaa tcagaggcaa ggtcctgttg tgtgtttact tggtgggaag    240
gataagtcta cggtagtaa tgagctatca tcaacatggg aagctattga aaagcaatg     300 gggaagaaat cagttgaaga tatgttgcgt gagcagatac aaaagaaaga cactggcggc    360
attcctccac gaggacgagg aggaggggt ggcggtagaa atggtgggaa taatgggtct     420
ggaggctcat caggggaaga tggtggtctt gctagttttg gggatgaaac tctgcaagtg    480
gtattagcaa cctaggctt catctttctg tacttctaca tcatcaatgg ggaggagttg     540
ttccgtcttg caagagatta cattaggtac cttataggaa gacccaagag tgttaggctg    600
acccgagtta tggaaggttg gagtagattc ttcgagaaga tgtcgaggaa aaaagtgtat    660
aacgagtact ggctaaagat taagcgatca tcaacaagtc tacctggtct ggtaacccgg    720
gcaaatacaa acgcatcttg a                                              741

<210> SEQ ID NO 8
<211> LENGTH: 246
<212> TYPE: PRT
<213> ORGANISM: Arabidopsis thaliana

<400> SEQUENCE: 8

Met Ser Ser Thr Gln Ala Asn Leu Cys Arg Pro Ser Leu Phe Cys Ala
1               5                   10                  15

Arg Thr Thr Gln Thr Arg His Val Ser Ser Ala Pro Phe Met Ser Ser
```

```
                20                  25                  30
Leu Arg Phe Asp Tyr Arg Pro Leu Pro Lys Leu Ala Ile Arg Ala Ser
            35                  40                  45
Ala Ser Ser Ser Met Ser Ser Gln Phe Ser Pro Leu Gln Asn His Arg
        50                  55                  60
Cys Arg Asn Gln Arg Gln Gly Pro Val Val Cys Leu Leu Gly Gly Lys
65                  70                  75                  80
Asp Lys Ser Asn Gly Ser Asn Glu Leu Ser Ser Thr Trp Glu Ala Ile
                85                  90                  95
Glu Lys Ala Met Gly Lys Lys Ser Val Glu Asp Met Leu Arg Glu Gln
            100                 105                 110
Ile Gln Lys Lys Asp Thr Gly Ile Pro Pro Arg Gly Arg Gly Gly
        115                 120                 125
Gly Gly Gly Gly Arg Asn Gly Gly Asn Asn Gly Ser Gly Gly Ser Ser
        130                 135                 140
Gly Glu Asp Gly Gly Leu Ala Ser Phe Gly Asp Glu Thr Leu Gln Val
145                 150                 155                 160
Val Leu Ala Thr Leu Gly Phe Ile Phe Leu Tyr Phe Tyr Ile Ile Asn
                165                 170                 175
Gly Glu Glu Leu Phe Arg Leu Ala Arg Asp Tyr Ile Arg Tyr Leu Ile
            180                 185                 190
Gly Arg Pro Lys Ser Val Arg Leu Thr Arg Val Met Glu Gly Trp Ser
        195                 200                 205
Arg Phe Phe Glu Lys Met Ser Arg Lys Lys Val Tyr Asn Glu Tyr Trp
        210                 215                 220
Leu Lys Ile Lys Arg Ser Ser Thr Ser Leu Pro Gly Leu Val Thr Arg
225                 230                 235                 240

Ala Asn Thr Asn Ala Ser
                245

<210> SEQ ID NO 9
<211> LENGTH: 360
<212> TYPE: DNA
<213> ORGANISM: Arabidopsis thaliana

<400> SEQUENCE: 9
atggcgctta gaggagtttg gcagctcaag aaactcgttg tgagctactg taattggggt      60
ggtagcagta gaggcatcag agcctttatg gaatcagaat tgcctgctct aaaggagaaa    120
aacccgcagc tcgaagtaat taccgagctt tcacggggac aacatcctta tttgaagggc    180
atttacagga atagaaatga aagggtagtg tgtgtgaaga acatggatcc tgaagaagtg    240
cttttgaatg caacgaggct gaggaactcg cttggacgga agtggttaa actgaggacc     300 agacatgtca ccaaacaccc cagtgttcaa ggcacctgga caactgctgt caaattctga    360

<210> SEQ ID NO 10
<211> LENGTH: 119
<212> TYPE: PRT
<213> ORGANISM: Arabidopsis thaliana

<400> SEQUENCE: 10

Met Ala Leu Arg Gly Val Trp Gln Leu Lys Lys Leu Val Val Ser Tyr
1               5                   10                  15
Cys Asn Trp Gly Gly Ser Ser Arg Gly Ile Arg Ala Phe Met Glu Ser
            20                  25                  30
Glu Leu Pro Ala Leu Lys Glu Lys Asn Pro Gln Leu Glu Val Ile Thr
```

```
                35                  40                  45
Glu Leu Ser Arg Gly Gln His Pro Tyr Leu Lys Gly Ile Tyr Arg Asn
        50                  55                  60

Arg Asn Glu Arg Val Val Cys Val Lys Asn Met Asp Pro Glu Glu Val
 65                  70                  75                  80

Leu Leu Asn Ala Thr Arg Leu Arg Asn Ser Leu Gly Arg Lys Val Val
                85                  90                  95

Lys Leu Arg Thr Arg His Val Thr Lys His Pro Ser Val Gln Gly Thr
            100                 105                 110

Trp Thr Thr Ala Val Lys Phe
        115

<210> SEQ ID NO 11
<211> LENGTH: 2064
<212> TYPE: DNA
<213> ORGANISM: Arabidopsis thaliana

<400> SEQUENCE: 11
atgccctctc cgtctgcagt cgccgatctc ttggccgctc ttgcttacag gcttcagaac      60
ggagatgaat tattcgaaga agaagaagaa gcggaagagt ctacttcttc tatgggacta     120
gctatctcgg agcttaaccg atctctgact ctggatatcg gctgcgagga ttctggggtc     180
agggttgtgg acgcagcgtt atctataatg tgcttcaagg cacctcaggt ttttgattcg     240
gcaattgagt ttatggtacg aacaattgtt tgcgccttat catcttcaag caattgtaag     300
gtaattaggt atcgaaacga ggaaacatta cagtttggga gctccaattt acctggctgc     360
tctgaagaat tgatcgaaat ctctaaggat attattgaga aactgtgggg aaatggaaga     420
ttggctacat tgttattcga agctgttgta aggtcagcag cctcaacatg taagatcagc     480
agtttcaacg cgcatggaaa gcttatggat ggaagaaata gggctgtctc gaagcttctt     540
gcttacttac cgggagaatc atctatagag aaccacaaga tacctctgag gattcttttc     600
tggtatcgag atccattgtc tttgaaggta gatgtttcca gaatcttgaa agaggtggtg     660
gaaaggcctt tcctttgtgt aaaaaggggag cttttcgaga gggggagtg gcgcgatatt     720 gtcatctgcc tagcgatatc tcctactatg tttatcaaca ctagatcact cttacataaa     780 tggctttgc ttacgggact tgcttctgtt tttgaagtac ttgctggttt ggcctctgca     840
ataatggata caatttcaag gccatcgttg tggggtatac aatggaact agcttccatg     900 ttgccatttt ctgatacata cttttccttc cagtgtcaat tctgagaat cttggcgggt     960 cctctcagtt ccaagtccct cctaatgtta gctcatactg tcagtaaagc gtctgctgtc    1020
cctgggcaac aacaacggga tactaattgt aagcctactc caataaaagt tcaagcatta    1080
gatgacaaaa ccgaatgggc tttggctatt aacttcccag attggttcta ttttgcatct    1140
gctatgctct tctcagaagg aaagtcgttt gaaaatatcc accatatatg cgcttcaaaa    1200
gtggctgact gtagacaagt atgtgatgta gaagatctct ccattgctgc ggctacatac    1260
atttcttgga ttctaaaccc tggaagtgga accattcaag agtcagtaag taagtctctc    1320
attagagtct cagagatatg tatcagtaaa agttgcggct cagaagcata tcgtactgag    1380
actataactg gcaagagaaa gaaaccagat aggctcgttt ctggcaaaat aaatgcttcc    1440
agtattgtgg aagacctatt gagagaattt gaaaacaata tcaccaattc agtttcttat    1500
gatttggatt ctcggaaaac gcatccatct ttcagctctg gcctccaaaa caatttgttg    1560
gtaagaagag ttgtggttgg cgttctgttt ggttctccat attcagtaac agatgaggag    1620
```

```
tatgaactgg tattacacta tgcagcaact gggaaaattc ttgactttaa gaaatcacgg   1680
agtaccggat tcaaacaagg aaagaaattc tctagaatat ctgctttact gtcgaatgaa   1740
attaccaagg aggaggctac agaaggcaca cttcttgttt tcaacttaac tgacactttg   1800
gagagtatgt gtgtatcaag ttttgaggcc aaagaggacg cagagaagtt tattaaccat   1860
tttaagctga gatccagcaa gtacttggtc aaatgcatag atcgcctgat acaacttcac   1920
tgtacacaag atggagatcc aatactaagt gacattaata tcagactgct gcaatggaca   1980
gtaaaaggac tagaagatcc acattttaac aaagttcttg atgatatcgc tgctaagttg   2040
gcctgcatat tctcgcgcgt gtaa                                           2064

<210> SEQ ID NO 12
<211> LENGTH: 687
<212> TYPE: PRT
<213> ORGANISM: Arabidopsis thaliana

<400> SEQUENCE: 12

Met Pro Ser Pro Ser Ala Val Ala Asp Leu Leu Ala Ala Leu Ala Tyr
1               5                   10                  15

Arg Leu Gln Asn Gly Asp Glu Leu Phe Glu Glu Glu Glu Ala Glu
            20                  25                  30

Glu Ser Thr Ser Ser Met Gly Leu Ala Ile Ser Glu Leu Asn Arg Ser
        35                  40                  45

Leu Thr Leu Asp Ile Gly Cys Glu Asp Ser Gly Val Arg Val Val Asp
    50                  55                  60

Ala Ala Leu Ser Ile Met Cys Phe Lys Ala Pro Gln Val Phe Asp Ser
65                  70                  75                  80

Ala Ile Glu Phe Met Val Arg Thr Ile Val Cys Ala Leu Ser Ser Ser
                85                  90                  95

Ser Asn Cys Lys Val Ile Arg Tyr Arg Asn Glu Glu Thr Leu Gln Phe
            100                 105                 110

Gly Ser Ser Asn Leu Pro Gly Cys Ser Glu Glu Leu Ile Glu Ile Ser
        115                 120                 125

Lys Asp Ile Ile Glu Lys Leu Trp Gly Asn Gly Arg Leu Ala Thr Leu
    130                 135                 140

Leu Phe Glu Ala Val Arg Ser Ala Ala Ser Thr Cys Lys Ile Ser
145                 150                 155                 160

Ser Phe Asn Ala His Gly Lys Leu Met Asp Gly Arg Asn Arg Ala Val
                165                 170                 175

Ser Lys Leu Leu Ala Tyr Leu Pro Gly Glu Ser Ile Glu Asn His
            180                 185                 190

Lys Ile Pro Leu Arg Ile Leu Phe Trp Tyr Arg Asp Pro Leu Ser Leu
        195                 200                 205

Lys Val Asp Val Ser Arg Ile Leu Lys Glu Val Val Glu Arg Pro Phe
    210                 215                 220

Leu Cys Val Lys Arg Glu Leu Phe Glu Arg Gly Glu Trp Arg Asp Ile
225                 230                 235                 240

Val Ile Cys Leu Ala Ile Ser Pro Thr Met Phe Ile Asn Thr Arg Ser
                245                 250                 255

Leu Leu His Lys Trp Leu Leu Leu Thr Gly Leu Ala Ser Val Phe Glu
            260                 265                 270

Val Leu Ala Gly Leu Ala Ser Ala Ile Met Asp Thr Ile Ser Arg Pro
        275                 280                 285

Ser Leu Trp Gly Ile Pro Met Glu Leu Ala Ser Met Leu Pro Phe Ser
```

```
                290                 295                 300
Asp Thr Tyr Phe Pro Phe Gln Cys Gln Phe Leu Arg Ile Leu Ala Gly
305                 310                 315                 320

Pro Leu Ser Ser Lys Ser Leu Leu Met Leu Ala His Thr Val Ser Lys
                325                 330                 335

Ala Ser Ala Val Pro Gly Gln Gln Arg Asp Thr Asn Cys Lys Pro
            340                 345                 350

Thr Pro Ile Lys Val Gln Ala Leu Asp Asp Lys Thr Glu Trp Ala Leu
                355                 360                 365

Ala Ile Asn Phe Pro Asp Trp Phe Tyr Phe Ala Ser Ala Met Leu Phe
370                 375                 380

Ser Glu Gly Lys Ser Phe Glu Asn Ile His His Ile Cys Ala Ser Lys
385                 390                 395                 400

Val Ala Asp Cys Arg Gln Val Cys Asp Val Glu Asp Leu Ser Ile Ala
                405                 410                 415

Ala Ala Thr Tyr Ile Ser Trp Ile Leu Asn Pro Gly Ser Gly Thr Ile
            420                 425                 430

Gln Glu Ser Val Ser Lys Ser Leu Ile Arg Val Ser Glu Ile Cys Ile
            435                 440                 445

Ser Lys Ser Cys Gly Ser Glu Ala Tyr Arg Thr Glu Thr Ile Thr Gly
    450                 455                 460

Lys Arg Lys Lys Pro Asp Arg Leu Val Ser Gly Lys Ile Asn Ala Ser
465                 470                 475                 480

Ser Ile Val Glu Asp Leu Leu Arg Glu Phe Glu Asn Asn Ile Thr Asn
                485                 490                 495

Ser Val Ser Tyr Asp Leu Asp Ser Arg Lys Thr His Pro Ser Phe Ser
            500                 505                 510

Ser Gly Leu Gln Asn Asn Leu Leu Val Arg Arg Val Val Gly Val
            515                 520                 525

Leu Phe Gly Ser Pro Tyr Ser Val Thr Asp Glu Glu Tyr Glu Leu Val
    530                 535                 540

Leu His Tyr Ala Ala Thr Gly Lys Ile Leu Asp Phe Lys Lys Ser Arg
545                 550                 555                 560

Ser Thr Gly Phe Lys Gln Gly Lys Lys Phe Ser Arg Ile Ser Ala Leu
                565                 570                 575

Leu Ser Asn Glu Ile Thr Lys Glu Glu Ala Thr Glu Gly Thr Leu Leu
            580                 585                 590

Val Phe Asn Leu Thr Asp Thr Leu Glu Ser Met Cys Val Ser Ser Phe
            595                 600                 605

Glu Ala Lys Glu Asp Ala Glu Lys Phe Ile Asn His Phe Lys Leu Arg
    610                 615                 620

Ser Ser Lys Tyr Leu Val Lys Cys Ile Asp Arg Leu Ile Gln Leu His
625                 630                 635                 640

Cys Thr Gln Asp Gly Asp Pro Ile Leu Ser Asp Ile Asn Ile Arg Leu
                645                 650                 655

Leu Gln Trp Thr Val Lys Gly Leu Glu Asp Pro His Phe Asn Lys Val
            660                 665                 670

Leu Asp Asp Ile Ala Ala Lys Leu Ala Cys Ile Phe Ser Arg Val
            675                 680                 685

<210> SEQ ID NO 13
<211> LENGTH: 1947
<212> TYPE: DNA
<213> ORGANISM: Arabidopsis thaliana
```

<400> SEQUENCE: 13

```
atgggagaga ctgaggatga aaaagatgct tctttggctg atatcgagaa ggagtgtctc     60
tcggtttata agcgaaaggt cgaggaggct agtcggggta aagcgaattt gctgaaagaa    120
atcgctgttg gcagagcaga aattgcagct attggctctt ctatgggtgg acaagagatt    180
cattctaaca gcaggttagg agaaaacttg aagaggagc ttgagaatgt taatgtgcaa     240
ttggatggac tgcgcaaaag gaaagctgag agaatgattc ggtttaatga agttatcgat    300
cagttactga agttgtcact gcaacttgga atccaacag attatctgaa gaagtttgct     360
gctgaagaga ccgatctttc gcttcagagg ttggaggaat gcgtagcca gttgggtgag    420
ctccaaaatg aaaagagcaa agattggaa gaggtagagt gtttgctgaa aacgcttaac     480
tcgttgtgct cggttcttgg tgaagatttc aaaggcatga taagagggat acattcatct    540
ctggttgatt ccaacactag ggatgtgagc agaagtactc ttgataagtt ggatatgatg    600
attgtgaatt tacgagaggc caagttacag cgaatgcaga aggttcaaga tcttgcagtg    660
tccttgttgg agctctggaa tctgctggac acgcctgcgg aagagcaaaa gatatttcac    720
aatgtcacat gtagcatcgc tttgactgag tctgaaataa ctgaggccaa catactttct    780
gttgcttcca ttaaacgcgt tgaggatgaa gtcattaggc ttagcaagat caaaataact    840
aagatcaaag aggtgatact gaggaagagg cttgagcttg aggaaatatc aaggaagatg    900
cacatggcca ccgaagttct taaatcagaa acttttcag ttgaagctat agaatctggt     960
gtcaaggatc ctgagcagtt gttagagcaa attgattccg agattgcaaa ggtcaaagag   1020
gaagcttcaa gcaggaagga gattcttgaa aaagtggaga atggatgtc agcttgtgaa    1080
gaagagtctt ggctgaaaga gtacaatcgg gatgataacc ggtacaacgc tggaagagga   1140
gctcatctta cattgaagcg tgcagaaaaa gcccgtttac ttgtcaataa acttcctggg   1200
atggtggaag cttttgaccgc caaagtcact gcttgggaga tgaaagagg aaatgaattc   1260
ttatatgatg gggtccgagt cttatcgatg cttggtcagt acaagactgt atgggaagag   1320
aaagagcatg aaaaacagag acagagagat atgaagaaac ttcatggaca actcataaca   1380
gagcaagaag ctctttatgg gtctaaacca agcccaaata aaagcggaaa gaaaccactg   1440
agaacaccag taaatgctgc catgaacaga aaactctccc ttggtggtgc catgcttcat   1500
caaagcttaa agcatgagaa ggcaacactc aatagcaaaa ggacgaagta ctatgaccag   1560
aacgctacta gtagaagaga ttcagctctt ccaactcttt cagggaggag aaactcagag   1620
cttcctggtc gtatcagatc aaagaacgtt ccggttgcag aaaagctgc gagatctcca   1680
atgcttagga agcctctttc acctgtcact tccaatatct tgaattcccc agaagatcat   1740
cacaaggatg cttacacaac aaaggagaga atcttgacac ctaaaaccaa cgaagaaaag   1800
aaaagagctg ttccaacaac tcctgcagct tcagtcgcta tgacagaggc aacaacgccg   1860
ttcactcctg ctgtggagaa gagaatggat gaggaagacg ttattgttga gtattcgttt   1920
gaagaggtta gggccggttt ttgctaa                                       1947
```

<210> SEQ ID NO 14
<211> LENGTH: 648
<212> TYPE: PRT
<213> ORGANISM: Arabidopsis thaliana

<400> SEQUENCE: 14

```
Met Gly Glu Thr Glu Asp Glu Lys Asp Ala Ser Leu Ala Asp Ile Glu
1               5                   10                  15
```

-continued

```
Lys Glu Cys Leu Ser Val Tyr Lys Arg Lys Val Glu Ala Ser Arg
         20                  25                  30

Gly Lys Ala Asn Leu Leu Lys Glu Ile Ala Val Gly Arg Ala Glu Ile
         35                  40                  45

Ala Ala Ile Gly Ser Ser Met Gly Gly Gln Glu Ile His Ser Asn Ser
         50                  55                  60

Arg Leu Gly Glu Asn Leu Lys Glu Glu Leu Glu Asn Val Asn Val Gln
65                   70                  75                  80

Leu Asp Gly Leu Arg Lys Arg Lys Ala Glu Arg Met Ile Arg Phe Asn
                 85                  90                  95

Glu Val Ile Asp Gln Leu Leu Lys Leu Ser Leu Gln Leu Gly Asn Pro
                100                 105                 110

Thr Asp Tyr Leu Lys Lys Phe Ala Ala Glu Glu Thr Asp Leu Ser Leu
                115                 120                 125

Gln Arg Leu Glu Glu Leu Arg Ser Gln Leu Gly Glu Leu Gln Asn Glu
                130                 135                 140

Lys Ser Lys Arg Leu Glu Glu Val Glu Cys Leu Leu Lys Thr Leu Asn
145                 150                 155                 160

Ser Leu Cys Ser Val Leu Gly Glu Asp Phe Lys Gly Met Ile Arg Gly
                165                 170                 175

Ile His Ser Ser Leu Val Asp Ser Asn Thr Arg Asp Val Ser Arg Ser
                180                 185                 190

Thr Leu Asp Lys Leu Asp Met Met Ile Val Asn Leu Arg Glu Ala Lys
                195                 200                 205

Leu Gln Arg Met Gln Lys Val Gln Asp Leu Ala Val Ser Leu Leu Glu
                210                 215                 220

Leu Trp Asn Leu Leu Asp Thr Pro Ala Glu Glu Gln Lys Ile Phe His
225                 230                 235                 240

Asn Val Thr Cys Ser Ile Ala Leu Thr Glu Ser Glu Ile Thr Glu Ala
                245                 250                 255

Asn Ile Leu Ser Val Ala Ser Ile Lys Arg Val Glu Asp Glu Val Ile
                260                 265                 270

Arg Leu Ser Lys Ile Lys Ile Thr Lys Ile Lys Glu Val Ile Leu Arg
                275                 280                 285

Lys Arg Leu Glu Leu Glu Glu Ile Ser Arg Lys Met His Met Ala Thr
290                 295                 300

Glu Val Leu Lys Ser Glu Asn Phe Ser Val Glu Ala Ile Glu Ser Gly
305                 310                 315                 320

Val Lys Asp Pro Glu Gln Leu Leu Glu Gln Ile Asp Ser Glu Ile Ala
                325                 330                 335

Lys Val Lys Glu Glu Ala Ser Arg Lys Glu Ile Leu Glu Lys Val
                340                 345                 350

Glu Lys Trp Met Ser Ala Cys Glu Glu Glu Ser Trp Leu Glu Glu Tyr
                355                 360                 365

Asn Arg Asp Asp Asn Arg Tyr Asn Ala Gly Arg Gly Ala His Leu Thr
                370                 375                 380

Leu Lys Arg Ala Glu Lys Ala Arg Leu Leu Val Asn Lys Leu Pro Gly
385                 390                 395                 400

Met Val Glu Ala Leu Thr Ala Lys Val Thr Ala Trp Glu Asn Glu Arg
                405                 410                 415

Gly Asn Glu Phe Leu Tyr Asp Gly Val Arg Val Leu Ser Met Leu Gly
                420                 425                 430
```

```
Gln Tyr Lys Thr Val Trp Glu Glu Lys Glu His Glu Lys Gln Arg Gln
            435                 440                 445

Arg Asp Met Lys Lys Leu His Gly Gln Leu Ile Thr Glu Gln Glu Ala
450                 455                 460

Leu Tyr Gly Ser Lys Pro Ser Pro Asn Lys Ser Gly Lys Lys Pro Leu
465                 470                 475                 480

Arg Thr Pro Val Asn Ala Ala Met Asn Arg Lys Leu Ser Leu Gly Gly
                485                 490                 495

Ala Met Leu His Gln Ser Leu Lys His Glu Lys Ala Thr Leu Asn Ser
            500                 505                 510

Lys Arg Thr Lys Tyr Tyr Asp Gln Asn Ala Thr Ser Arg Arg Asp Ser
        515                 520                 525

Ala Leu Pro Thr Leu Ser Gly Arg Arg Asn Ser Glu Leu Pro Gly Arg
530                 535                 540

Ile Arg Ser Lys Asn Val Pro Val Ala Gly Lys Ala Ala Arg Ser Pro
545                 550                 555                 560

Met Leu Arg Lys Pro Leu Ser Pro Val Thr Ser Asn Ile Leu Asn Ser
                565                 570                 575

Pro Glu Asp His His Lys Asp Ala Tyr Thr Thr Lys Glu Arg Ile Leu
            580                 585                 590

Thr Pro Lys Thr Asn Glu Glu Lys Lys Arg Ala Val Pro Thr Thr Pro
        595                 600                 605

Ala Ala Ser Val Ala Met Thr Glu Ala Thr Thr Pro Phe Thr Pro Ala
610                 615                 620

Val Glu Lys Arg Met Asp Glu Glu Asp Val Ile Val Glu Tyr Ser Phe
625                 630                 635                 640

Glu Glu Val Arg Ala Gly Phe Cys
                645

<210> SEQ ID NO 15
<211> LENGTH: 5826
<212> TYPE: DNA
<213> ORGANISM: Arabidopsis thaliana

<400> SEQUENCE: 15
atgaatggaa aggaatcaag aggacctgcg tgtagctttg agtttgttgg tgaaagctca      60
ggtttacttg gtccaggaga aagtcgctgg cctttttacca atggctatgc atttgcgact    120 tggattttata ttgaatcatt tgctgacaca ttagatgctt caaccgcggc agctgcaatt    180
gctgctgctt cagcggcaaa atcaggaaaa atatctaatg cagcgcctgc gaatgtacac    240
actggtgagg gtactgctca tatgcctcgt ctgttcagct ttttgacccc tgataatcag    300
ggaattgaag cttatttcta tgcacaattt ttggtggttg agagtggcag tgggaaagga    360
agtaaaactt cacttcattt cactcatgca tttaagcctc agtgttggta ctttattggc    420
cttgagcata cctgcaatca gggacttta gggaattcag atagtgaatt acggctatat    480
attgacgggt cgttgtatga aactcgacca tttgactatc ctcggatatc caaaccgctt   540
tctttctgtt gcattgggtc aaatcctcct tctacaactg ctggtctaca acgtcgtcga    600
cgtcagtgtg ctttgtttgc tgagatggga ccagtttata tatttaaaga accgattggt    660
cctgaaagaa tgacacgatt ggcaactaga ggtggggatg ttttgccttg ttttggcaat    720
ggggcaggtc ttccatggtt agctacaaat gaccatgtcc gtaatgtggc agaggaaagt    780
agtctttcgg atgcagagct tggaggatac attcacctac tttaccaccc atgtctacta    840
agtgggcggt tctgtccaga tgcttctctt tctggagcag caggagatga gaaaacacca    900
```

```
tattcttttt ctgctgtagt tttcgcactt tgttatttgg ttttcccttta ctttggaaga    960 cccatgtctt tgcttcctct aaccgtaagc agtgtgcaca aagataatct agagccatgt   1020
tctagaaatg ttccatcttc tttgacaaca tattctctgg ctgcacctat ttttagaatg   1080
atctcatttg ctattaaaca tcctgggaac aatgaagagt tatctcgtac taggggggcct  1140 gaaattctgg ccacagttct cggttacctt cttcattcac ttgcatcctt tgatatcaag   1200
cacgatagag taggagatga ggagctagtt gctgctattg tttctctttg ccaatctcaa   1260
aagatcaatc atgctcttaa agtgcagctc ttctgtacac tattgttgga tctgaagata   1320
tggagtgtgt gcagttacag actccaaaag aagctgttgt catctcttca agatatggtt   1380
ttcaccgaag caacagctat gaggaatgct gatgccattc aggtacttct ggatggatgt   1440
cgaagatatt tctggacaat tcaagagaaa gactccgtga acacgttttc tctagatggg   1500
gatgcacgtc aagtggggga agttaatgca ttggttgatg aacttttggt gattattgaa   1560
cttctaatgg gagcagcatc tccttcgttt gctgctgatg acctccatcg attacttggc   1620
tttataattg agagtccaca accaaatcag gttgcaaggg tattgcatct catgtttagg   1680
ttggttgtac agccaaatgc tgcaaaggct cagacatttg cagaggcatt tatcacatct   1740
ggtgggatag aaacacttct tgttctcata gcaaacagag tcaacacaat gggcctggaa   1800
acagagtcat ttcaacaagt aaaagtgcat ggatccgaaa ctgtcatttg tgagactggc   1860
tcagttaccc ctctccagttc cgtgaatgct gacagaatat cctctgtttc tgaaactcca   1920
ttcaataata atgcaagaaa caatgttgac gatagagatc gtgtcatggt tgggatcatc   1980
agattgattg gtgcgttgat ttcaaaaggg cacttaaaat tttccgttgg tgccaaatct   2040
gatgtaatga gtaacctcat gggtagtgag tttcgtgaaa atggtggaac aatgtttgat   2100
tataaagtcg cattgcttct atttgctctg ctgaaagcat ttcaagcagc tccaaacaga   2160
ttgatgaccg acaatgtcta cacactttg cttggggctt cggttaatgc ttcatcaact   2220
gaggatggcc tgaacttttg tgatttaggt catcgatttg aacatcctca acttctgtta   2280
atcctcctgc gttctctacc atttgcatct aaggcactac aaaatcgagc acttcaggat   2340
attctatttt tggcttgtac ccatccagaa aaaggagta gtctgaccaa aatggaagag   2400
tggcctgagt ggatcttgga gattttaatc tctaactacg agaaagatgc agggaaacaa   2460
tctgcttcac ccggttctgc tgaagaggag gatctgattc ataacttctt gatcataatg   2520
ttggaacatt caatgcgcca gaaggatggc tggaaggata ttgaggctac aattcattgt   2580
gcagagtggc ttacttttgt tggtgggtct agcactgggg agaaacgaat taggcgtgag   2640
gaatcactgc caattttcaa acgaagactt ttaggtggat tgctagactt tgctgccagt   2700
gaactgcaag ctcagactca agttatagct gcagcatctg ctggtttcgc ggcagagagt   2760
ctaacaccaa aagatgcaaa agcgggagta gaaaatgctg cactgctttc agtgtttcta   2820
gtggaaaata cagttgtgat tttgatgctt gtcgaagatc atttgcgact acaaagcaag   2880
caaaattgtg ctgcaagcgc agttgatgtc tctccatctc ctctttcact tgtttatcct   2940
cccaactacc gttcacacac attgccaacg gtcggagaat catcagaggt ttctagtagc   3000
tgtgcttcag tgtccagtga ttcaggaggg gtccatttag atatacttgc ttcaatggcc   3060
gatgcaagtg gccagatatc tacagccgta atggagcgtc ttgctgctgc tgctgcagct   3120
gagccctatg aatctgtttc ttgcgctttt gtttcatatg gaagttgtac cagggatttg   3180
gctgatgctt ggaagtacag aagtcgattg tggtacggtg ttggactacc ttctaaaact   3240
```

```
agttgttttg gtggtggtgg aagtggttgg gactcttgga agcatgctct acaaaaagat    3300
gctcagggta actggatcga acttcctttg gttaaaaaat cagtatccat gcttcaagcc    3360
ttgctgctag atgagtctgg acttggaggt ggcctaggaa ttggtggagg atctggtacc    3420
gggatgggag ggatgtcagg cctctaccag ttgctagata gtgatcagcc tttcttatgc    3480
atgcttcgaa tggtactctt gtctttgagg gaagaagacc atggtgaaga tagtctgttg    3540
atgaaaaatt taagttctga agatggtata actggtggac tccagtgccc cttaggaaat    3600
tctgcctcag tagatatcag ttctcagttg tctatgcgac agtcaccatc agctttattg    3660
tggagtgtgc tctctcccgt tctaaacatg ccaatctctg attctaagag gcagagggta    3720
ttggttacta catgtgttct atattctgag gtatggaatg ctgttagcaa agataaaaga    3780
ccactacgta agcagtatct agaggctatt ttaccaccat tgttgcaat tctccgaaga     3840
tggaggcctc ttttggctgg tattcatgaa cttttccactg gtgatggtgt gaatcccctt   3900
gtcgttgata ctcgtgcttt ggctgctgat gcacttccca ttgaggcggc tctctctatg    3960
atttctccgg agtgggcagc tgcttttgca tcgcctcctt ctgcaatggc actggcaatg    4020
atagctgcag gggcagctgg ttgggaagcg ccggcacatc cagcacctcc agcgcctcca    4080
cctcttaggc gagacagttc attacttgag cgtaagagta ccaaacttca gaccttttca    4140
agcttccaga aacccttgga ggctccaaat gatgatacac caggtcgagc aagagataag    4200
gctgctgcaa atattgattc acatttattg attcaaccgc tcaccagatt gacaggcgtt    4260
ttctggaaac tggattctat ggaaagttct cgaggatga  gacaatgttt aaggaggaat    4320
tattctggca ctggtcatct tgagacaaca agaaactatg gggatcagac atacttgatg    4380
aataatcacg actcacctgt tcttgctgtt gaagcaatat caaaggaaat aatgtatgaa    4440
gatgatgaac atggagatgc cgatgatctt gaaatagagg gtaatgttgg agaacgcaaa    4500
ggggaaaacg aagagagaag gtctggctca cttgaggatg caataacact gtcaactgga    4560
atcaacgatc atcgaccttt gagtgaacag aatatggttc aaaattctac agaagtaaaa    4620
gatctcagtg aacttaaaga aaggattgtt cttgaaattt cctctactat ggtccgacca    4680
ctaggggttg tgaaaggaac cttcaaatc acaacacgga gaataaattt tattgttgac     4740
atcagagaag accaacattt ggatgaaaag tcagacggtt caaaatcaag agacgaagaa    4800
agagatcgaa gttggctgat gtcttctctt catcagattt atagccgacg atatctactg    4860
aagaagagtg ctcttgaact atttatggtg gatcgctcaa acttcttctt tgattttggg    4920
aacaccgagg gacgaagaaa tgcttgtcgg gctattgttc aagcaaggcc tcctcatttg    4980
aaaaatattt actcggcaac tcagccagaa caagtttcga gaagaacaca gttaatggag    5040
cgttgggcta gatgggagat cagcaatttt gagtacttaa tgcagctcaa cacattggct    5100
gggcgtagtt ataatgacat cactcagtat cctattttcc catggatttt atgcgactat    5160
gtatcagaaa ttttgaccct atcaaatcca tctaattaca gggatctttc caaggtgcca    5220
attggtgcac tgaacccgga gcggctgaaa aagtttcaag aaaaacactc tagctttgaa    5280
gatccagtca tccccaaatt tcattatggt tcacattact caagtgctgg agcagtgttg    5340
cattatctag ctagagtcga accttttaca acctttcga ttcaactgca aggtagaaag     5400
tttgatcgtg cagaccaaat attttcagac attgcagcca cttggaaagg agttctccaa    5460
gatatgaata atgtgaagga gttgaacaca actgatccaa acactcacat ggtctcaagc    5520
ttttcaaacc caactaccag cgagactgaa cctgattcag acatgaacat tgtctctacc    5580
ccttcaaatg caactacaaa tcagattgac actgaatctt ccgaggcggc taactatgaa    5640
```

```
aacagcaact cgtctatcaa gacttctaag aacacttcaa agatcactaa attgaccccg    5700
acgtcaaaac gatcactaac ttcatcgaaa gataatgcag ctcaaaagtc atctacaaag    5760
cctaaattgt tgtccaaggc tgagataata aaggttgatg tttattcgta tattatgagt    5820
ttatag                                                               5826
```

<210> SEQ ID NO 16
<211> LENGTH: 1941
<212> TYPE: PRT
<213> ORGANISM: Arabidopsis thaliana

<400> SEQUENCE: 16

```
Met Asn Gly Lys Glu Ser Arg Gly Pro Ala Cys Ser Phe Glu Phe Val
1               5                   10                  15

Gly Glu Ser Ser Gly Leu Leu Gly Pro Gly Ser Arg Trp Pro Phe
            20                  25                  30

Thr Asn Gly Tyr Ala Phe Ala Thr Trp Ile Tyr Ile Glu Ser Phe Ala
            35                  40                  45

Asp Thr Leu Asp Ala Ser Thr Ala Ala Ala Ile Ala Ala Ala Ser
    50                  55                  60

Ala Ala Lys Ser Gly Lys Ile Ser Asn Ala Ala Pro Ala Asn Val His
65                  70                  75                  80

Thr Gly Glu Gly Thr Ala His Met Pro Arg Leu Phe Ser Phe Leu Thr
                85                  90                  95

Pro Asp Asn Gln Gly Ile Glu Ala Tyr Phe Tyr Ala Gln Phe Leu Val
            100                 105                 110

Val Glu Ser Gly Ser Gly Lys Gly Ser Lys Thr Ser Leu His Phe Thr
        115                 120                 125

His Ala Phe Lys Pro Gln Cys Trp Tyr Phe Ile Gly Leu Glu His Thr
    130                 135                 140

Cys Asn Gln Gly Leu Leu Gly Asn Ser Asp Ser Glu Leu Arg Leu Tyr
145                 150                 155                 160

Ile Asp Gly Ser Leu Tyr Glu Thr Arg Pro Phe Asp Tyr Pro Arg Ile
                165                 170                 175

Ser Lys Pro Leu Ser Phe Cys Cys Ile Gly Ser Asn Pro Pro Ser Thr
            180                 185                 190

Thr Ala Gly Leu Gln Arg Arg Arg Gln Cys Ala Leu Phe Ala Glu
        195                 200                 205

Met Gly Pro Val Tyr Ile Phe Lys Glu Pro Ile Gly Pro Glu Arg Met
    210                 215                 220

Thr Arg Leu Ala Thr Arg Gly Asp Val Leu Pro Cys Phe Gly Asn
225                 230                 235                 240

Gly Ala Gly Leu Pro Trp Leu Ala Thr Asn Asp His Val Arg Asn Val
                245                 250                 255

Ala Glu Glu Ser Ser Leu Ser Asp Ala Glu Leu Gly Gly Tyr Ile His
            260                 265                 270

Leu Leu Tyr His Pro Cys Leu Leu Ser Gly Arg Phe Cys Pro Asp Ala
        275                 280                 285

Ser Leu Ser Gly Ala Ala Gly Asp Glu Lys Thr Pro Tyr Ser Phe Ser
    290                 295                 300

Ala Val Val Phe Ala Leu Cys Tyr Leu Val Phe Pro Tyr Phe Gly Arg
305                 310                 315                 320

Pro Met Ser Leu Leu Pro Leu Thr Val Ser Ser Val His Lys Asp Asn
                325                 330                 335
```

```
Leu Glu Pro Cys Ser Arg Asn Val Pro Ser Ser Leu Thr Thr Tyr Ser
            340                 345                 350

Leu Ala Ala Pro Ile Phe Arg Met Ile Ser Phe Ala Ile Lys His Pro
            355                 360                 365

Gly Asn Asn Glu Glu Leu Ser Arg Thr Arg Gly Pro Glu Ile Leu Ala
            370                 375                 380

Thr Val Leu Gly Tyr Leu Leu His Ser Leu Ala Ser Phe Asp Ile Lys
385                 390                 395                 400

His Asp Arg Val Gly Asp Glu Leu Val Ala Ala Ile Val Ser Leu
                405                 410                 415

Cys Gln Ser Gln Lys Ile Asn His Ala Leu Lys Val Gln Leu Phe Cys
            420                 425                 430

Thr Leu Leu Leu Asp Leu Lys Ile Trp Ser Val Cys Ser Tyr Arg Leu
            435                 440                 445

Gln Lys Lys Leu Leu Ser Ser Leu Gln Asp Met Val Phe Thr Glu Ala
            450                 455                 460

Thr Ala Met Arg Asn Ala Asp Ala Ile Gln Val Leu Leu Asp Gly Cys
465                 470                 475                 480

Arg Arg Tyr Phe Trp Thr Ile Gln Glu Lys Asp Ser Val Asn Thr Phe
                485                 490                 495

Ser Leu Asp Gly Asp Ala Arg Gln Val Gly Glu Val Asn Ala Leu Val
            500                 505                 510

Asp Glu Leu Leu Val Ile Ile Glu Leu Leu Met Gly Ala Ala Ser Pro
            515                 520                 525

Ser Phe Ala Ala Asp Asp Leu His Arg Leu Leu Gly Phe Ile Ile Glu
            530                 535                 540

Ser Pro Gln Pro Asn Gln Val Ala Arg Val Leu His Leu Met Phe Arg
545                 550                 555                 560

Leu Val Val Gln Pro Asn Ala Ala Lys Ala Gln Thr Phe Ala Glu Ala
                565                 570                 575

Phe Ile Thr Ser Gly Gly Ile Glu Thr Leu Leu Val Leu Ile Ala Asn
            580                 585                 590

Arg Val Asn Thr Met Gly Leu Glu Thr Glu Ser Phe Gln Gln Val Lys
            595                 600                 605

Val His Gly Ser Glu Thr Val Ile Cys Glu Thr Gly Ser Val Thr Leu
            610                 615                 620

Ser Ser Ser Val Asn Ala Asp Arg Ile Ser Ser Val Ser Glu Thr Pro
625                 630                 635                 640

Phe Asn Asn Asn Ala Arg Asn Asn Val Asp Asp Arg Asp Arg Val Met
                645                 650                 655

Val Gly Ile Ile Arg Leu Ile Gly Ala Leu Ile Ser Lys Gly His Leu
            660                 665                 670

Lys Phe Ser Val Gly Ala Lys Ser Asp Val Met Ser Asn Leu Met Gly
            675                 680                 685

Ser Glu Phe Arg Glu Asn Gly Gly Thr Met Phe Asp Tyr Lys Val Ala
            690                 695                 700

Leu Leu Leu Phe Ala Leu Leu Lys Ala Phe Gln Ala Ala Pro Asn Arg
705                 710                 715                 720

Leu Met Thr Asp Asn Val Tyr Thr Leu Leu Gly Ala Ser Val Asn
                725                 730                 735

Ala Ser Ser Thr Glu Asp Gly Leu Asn Phe Cys Asp Leu Gly His Arg
            740                 745                 750
```

```
Phe Glu His Pro Gln Leu Leu Leu Ile Leu Leu Arg Ser Leu Pro Phe
        755                 760                 765

Ala Ser Lys Ala Leu Gln Asn Arg Ala Leu Gln Asp Ile Leu Phe Leu
770                 775                 780

Ala Cys Thr His Pro Glu Lys Arg Ser Ser Leu Thr Lys Met Glu Glu
785                 790                 795                 800

Trp Pro Glu Trp Ile Leu Glu Ile Leu Ile Ser Asn Tyr Glu Lys Asp
                805                 810                 815

Ala Gly Lys Gln Ser Ala Ser Pro Gly Ser Ala Glu Glu Asp Leu
        820                 825                 830

Ile His Asn Phe Leu Ile Ile Met Leu Glu His Ser Met Arg Gln Lys
        835                 840                 845

Asp Gly Trp Lys Asp Ile Glu Ala Thr Ile His Cys Ala Glu Trp Leu
850                 855                 860

Thr Phe Val Gly Gly Ser Ser Thr Gly Glu Lys Arg Ile Arg Arg Glu
865                 870                 875                 880

Glu Ser Leu Pro Ile Phe Lys Arg Arg Leu Leu Gly Gly Leu Leu Asp
                885                 890                 895

Phe Ala Ala Ser Glu Leu Gln Ala Gln Thr Gln Val Ile Ala Ala Ala
        900                 905                 910

Ser Ala Gly Phe Ala Ala Glu Ser Leu Thr Pro Lys Asp Ala Lys Ala
        915                 920                 925

Gly Val Glu Asn Ala Ala Leu Leu Ser Val Phe Leu Val Glu Asn Thr
        930                 935                 940

Val Val Ile Leu Met Leu Val Glu Asp His Leu Arg Leu Gln Ser Lys
945                 950                 955                 960

Gln Asn Cys Ala Ala Ser Ala Val Asp Val Ser Pro Ser Pro Leu Ser
                965                 970                 975

Leu Val Tyr Pro Pro Asn Tyr Arg Ser His Thr Leu Pro Thr Val Gly
            980                 985                 990

Glu Ser Ser Glu Val Ser Ser Ser Cys Ala Ser Val Ser Ser Asp Ser
        995                 1000                1005

Gly Gly Val His Leu Asp Ile Leu Ala Ser Met Ala Asp Ala Ser
1010                1015                1020

Gly Gln Ile Ser Thr Ala Val Met Glu Arg Leu Ala Ala Ala Ala
1025                1030                1035

Ala Ala Glu Pro Tyr Glu Ser Val Ser Cys Ala Phe Val Ser Tyr
1040                1045                1050

Gly Ser Cys Thr Arg Asp Leu Ala Asp Ala Trp Lys Tyr Arg Ser
1055                1060                1065

Arg Leu Trp Tyr Gly Val Gly Leu Pro Ser Lys Thr Ser Cys Phe
1070                1075                1080

Gly Gly Gly Gly Ser Gly Trp Asp Ser Trp Lys His Ala Leu Gln
1085                1090                1095

Lys Asp Ala Gln Gly Asn Trp Ile Glu Leu Pro Leu Val Lys Lys
1100                1105                1110

Ser Val Ser Met Leu Gln Ala Leu Leu Leu Asp Glu Ser Gly Leu
1115                1120                1125

Gly Gly Gly Leu Gly Ile Gly Gly Gly Ser Gly Thr Gly Met Gly
1130                1135                1140

Gly Met Ser Gly Leu Tyr Gln Leu Leu Asp Ser Asp Gln Pro Phe
1145                1150                1155

Leu Cys Met Leu Arg Met Val Leu Leu Ser Leu Arg Glu Glu Asp
```

|  | 1160 |  |  |  | 1165 |  |  |  | 1170 |  |  |
|---|---|---|---|---|---|---|---|---|---|---|---|
| His | Gly | Glu | Asp | Ser | Leu | Leu | Met | Lys | Asn | Leu | Ser | Ser | Glu | Asp |
| 1175 | | | | | 1180 | | | | | 1185 |
| Gly | Ile | Thr | Gly | Gly | Leu | Gln | Cys | Pro | Leu | Gly | Asn | Ser | Ala | Ser |
| 1190 | | | | | 1195 | | | | | 1200 |
| Val | Asp | Ile | Ser | Ser | Gln | Leu | Ser | Met | Arg | Gln | Ser | Pro | Ser | Ala |
| 1205 | | | | | 1210 | | | | | 1215 |
| Leu | Leu | Trp | Ser | Val | Leu | Ser | Pro | Val | Leu | Asn | Met | Pro | Ile | Ser |
| 1220 | | | | | 1225 | | | | | 1230 |
| Asp | Ser | Lys | Arg | Gln | Arg | Val | Leu | Val | Thr | Thr | Cys | Val | Leu | Tyr |
| 1235 | | | | | 1240 | | | | | 1245 |
| Ser | Glu | Val | Trp | Asn | Ala | Val | Ser | Lys | Asp | Lys | Arg | Pro | Leu | Arg |
| 1250 | | | | | 1255 | | | | | 1260 |
| Lys | Gln | Tyr | Leu | Glu | Ala | Ile | Leu | Pro | Pro | Phe | Val | Ala | Ile | Leu |
| 1265 | | | | | 1270 | | | | | 1275 |
| Arg | Arg | Trp | Arg | Pro | Leu | Leu | Ala | Gly | Ile | His | Glu | Leu | Ser | Thr |
| 1280 | | | | | 1285 | | | | | 1290 |
| Gly | Asp | Gly | Val | Asn | Pro | Leu | Val | Val | Asp | Thr | Arg | Ala | Leu | Ala |
| 1295 | | | | | 1300 | | | | | 1305 |
| Ala | Asp | Ala | Leu | Pro | Ile | Glu | Ala | Ala | Leu | Ser | Met | Ile | Ser | Pro |
| 1310 | | | | | 1315 | | | | | 1320 |
| Glu | Trp | Ala | Ala | Ala | Phe | Ala | Ser | Pro | Pro | Ser | Ala | Met | Ala | Leu |
| 1325 | | | | | 1330 | | | | | 1335 |
| Ala | Met | Ile | Ala | Ala | Gly | Ala | Ala | Gly | Trp | Glu | Ala | Pro | Ala | His |
| 1340 | | | | | 1345 | | | | | 1350 |
| Pro | Ala | Pro | Pro | Ala | Pro | Pro | Leu | Arg | Arg | Asp | Ser | Ser | Leu |
| 1355 | | | | | 1360 | | | | | 1365 |
| Leu | Glu | Arg | Lys | Ser | Thr | Lys | Leu | Gln | Thr | Phe | Ser | Ser | Phe | Gln |
| 1370 | | | | | 1375 | | | | | 1380 |
| Lys | Pro | Leu | Glu | Ala | Pro | Asn | Asp | Asp | Thr | Pro | Gly | Arg | Ala | Arg |
| 1385 | | | | | 1390 | | | | | 1395 |
| Asp | Lys | Ala | Ala | Ala | Asn | Ile | Asp | Ser | His | Leu | Leu | Ile | Gln | Pro |
| 1400 | | | | | 1405 | | | | | 1410 |
| Leu | Thr | Arg | Leu | Thr | Gly | Val | Phe | Trp | Lys | Leu | Asp | Ser | Met | Glu |
| 1415 | | | | | 1420 | | | | | 1425 |
| Ser | Ser | Ser | Arg | Met | Arg | Gln | Cys | Leu | Arg | Arg | Asn | Tyr | Ser | Gly |
| 1430 | | | | | 1435 | | | | | 1440 |
| Thr | Gly | His | Leu | Glu | Thr | Thr | Arg | Asn | Tyr | Gly | Asp | Gln | Thr | Tyr |
| 1445 | | | | | 1450 | | | | | 1455 |
| Leu | Met | Asn | Asn | His | Asp | Ser | Pro | Val | Leu | Ala | Val | Glu | Ala | Ile |
| 1460 | | | | | 1465 | | | | | 1470 |
| Ser | Lys | Glu | Ile | Met | Tyr | Glu | Asp | Asp | Glu | His | Gly | Asp | Ala | Asp |
| 1475 | | | | | 1480 | | | | | 1485 |
| Asp | Leu | Glu | Ile | Glu | Gly | Asn | Val | Gly | Glu | Arg | Lys | Gly | Glu | Asn |
| 1490 | | | | | 1495 | | | | | 1500 |
| Glu | Glu | Arg | Arg | Ser | Gly | Ser | Leu | Glu | Asp | Ala | Ile | Thr | Leu | Ser |
| 1505 | | | | | 1510 | | | | | 1515 |
| Thr | Gly | Ile | Asn | Asp | His | Arg | Pro | Leu | Ser | Glu | Gln | Asn | Met | Val |
| 1520 | | | | | 1525 | | | | | 1530 |
| Gln | Asn | Ser | Thr | Glu | Val | Lys | Asp | Leu | Ser | Glu | Leu | Lys | Glu | Arg |
| 1535 | | | | | 1540 | | | | | 1545 |
| Ile | Val | Leu | Glu | Ile | Ser | Ser | Thr | Met | Val | Arg | Pro | Leu | Gly | Val |
| 1550 | | | | | 1555 | | | | | 1560 |

```
Val Lys Gly Thr Phe Gln Ile Thr Thr Arg Arg Ile Asn Phe Ile
    1565            1570            1575

Val Asp Ile Arg Glu Asp Gln His Leu Asp Glu Lys Ser Asp Gly
    1580            1585            1590

Ser Lys Ser Arg Asp Glu Glu Arg Asp Arg Ser Trp Leu Met Ser
    1595            1600            1605

Ser Leu His Gln Ile Tyr Ser Arg Arg Tyr Leu Leu Lys Lys Ser
    1610            1615            1620

Ala Leu Glu Leu Phe Met Val Asp Arg Ser Asn Phe Phe Phe Asp
    1625            1630            1635

Phe Gly Asn Thr Glu Gly Arg Arg Asn Ala Cys Arg Ala Ile Val
    1640            1645            1650

Gln Ala Arg Pro Pro His Leu Lys Asn Ile Tyr Ser Ala Thr Gln
    1655            1660            1665

Pro Glu Gln Val Ser Arg Arg Thr Gln Leu Met Glu Arg Trp Ala
    1670            1675            1680

Arg Trp Glu Ile Ser Asn Phe Glu Tyr Leu Met Gln Leu Asn Thr
    1685            1690            1695

Leu Ala Gly Arg Ser Tyr Asn Asp Ile Thr Gln Tyr Pro Ile Phe
    1700            1705            1710

Pro Trp Ile Leu Cys Asp Tyr Val Ser Glu Ile Leu Asp Leu Ser
    1715            1720            1725

Asn Pro Ser Asn Tyr Arg Asp Leu Ser Lys Val Pro Ile Gly Ala
    1730            1735            1740

Leu Asn Pro Glu Arg Leu Lys Lys Phe Gln Glu Lys His Ser Ser
    1745            1750            1755

Phe Glu Asp Pro Val Ile Pro Lys Phe His Tyr Gly Ser His Tyr
    1760            1765            1770

Ser Ser Ala Gly Ala Val Leu His Tyr Leu Ala Arg Val Glu Pro
    1775            1780            1785

Phe Thr Thr Leu Ser Ile Gln Leu Gln Gly Arg Lys Phe Asp Arg
    1790            1795            1800

Ala Asp Gln Ile Phe Ser Asp Ile Ala Ala Thr Trp Lys Gly Val
    1805            1810            1815

Leu Gln Asp Met Asn Asn Val Lys Glu Leu Asn Thr Thr Asp Pro
    1820            1825            1830

Asn Thr His Met Val Ser Ser Phe Ser Asn Pro Thr Thr Ser Glu
    1835            1840            1845

Thr Glu Pro Asp Ser Asp Met Asn Ile Val Ser Thr Pro Ser Asn
    1850            1855            1860

Ala Thr Thr Asn Gln Ile Asp Thr Glu Ser Ser Glu Ala Ala Asn
    1865            1870            1875

Tyr Glu Asn Ser Asn Ser Ser Ile Lys Thr Ser Lys Asn Thr Ser
    1880            1885            1890

Lys Ile Thr Lys Leu Thr Pro Thr Ser Lys Arg Ser Leu Thr Ser
    1895            1900            1905

Ser Lys Asp Asn Ala Ala Gln Lys Ser Ser Thr Lys Pro Lys Leu
    1910            1915            1920

Leu Ser Lys Ala Glu Ile Ile Lys Val Asp Val Tyr Ser Tyr Ile
    1925            1930            1935

Met Ser Leu
    1940
```

<210> SEQ ID NO 17
<211> LENGTH: 1350
<212> TYPE: DNA
<213> ORGANISM: Arabidopsis thaliana

<400> SEQUENCE: 17

| | | |
|---|---|---|
| atggcggaag agacggagaa aaagtacatt acgaacgaag atcttaaaaa acacaacaaa | 60 | |
| tctggagatc tatggatcgc gattcaaggc aaggtctaca acgtctccga ttggattaaa | 120 | |
| actcatcccg gaggcgacac ggtgattctc aatctcgttg gtcaagacgt caccgatgct | 180 | |
| ttcatcgcat tcatcccgg aaccgcttgg caccatctcg accatctctt caccggttac | 240 | |
| cacatcagag atttccaagt ctccgaagtc tcacgcgatt accgtcgtat ggctgccgag | 300 | |
| tttcgtaaac tcggtctctt cgaaaacaaa ggtcacgtta ctctctacac tctagccttc | 360 | |
| gtcgccgcca tgttcctcgg agttctctac ggtgttttgg cttgtacctc cgtcttcgct | 420 | |
| caccaaatcg ccgccgcgct ctcggtctc ctctggatcc agagcgctta cataggtcac | 480 | |
| gattctggtc attacgttat catgtcgaac aaatcttata acagattcgc tcagcttctc | 540 | |
| tccggtaact gtctcaccgg aatctcaatc gcgtggtgga atggactca caatgctcat | 600 | |
| catctagctt gtaacagcct cgattacgat ccagatctac aacacatccc tgtcttcgcc | 660 | |
| gtctccacca aattcttctc ctcattgacc tcgagattct acgatcggaa actcacgttt | 720 | |
| gatccagtcg cgagattctt agtcagctat caacacttta cttattatcc agttatgtgc | 780 | |
| tttggaagaa tcaatctctt cattcaaacg tttctcttgc tcttctccaa acgtgaagta | 840 | |
| ccagatcgtg ctttaaactt cgccggaatc ttagtcttct ggacttggtt cccactctta | 900 | |
| gtctcatgtc taccaaactg gcctgagaga ttcttcttcg tcttcacaag cttcaccgtc | 960 | |
| acggcgcttc aacacattca attcacgctt aaccatttcg ctgctgatgt ctacgttggt | 1020 | |
| ccacccaccg gtagcgactg gttcgagaag caagcggcgg aacaatcga tatctcttgt | 1080 | |
| agatcataca tggattggtt ctttggtgga ttacagtttc agcttgagca tcatttgttc | 1140 | |
| cctcgcttac ctcgttgcca tctccggaaa gtttctccgg tggttcaaga gctttgcaag | 1200 | |
| aagcataatc ttccgtatag gagtatgtcg tggtttgaag caaatgtgtt gaccattaac | 1260 | |
| actttgaaga cagcagctta tcaagctaga gacgtggcta atccggtggt taagaacttg | 1320 | |
| gtttgggaag ctttgaatac tcatggctaa | 1350 | |

<210> SEQ ID NO 18
<211> LENGTH: 449
<212> TYPE: PRT
<213> ORGANISM: Arabidopsis thaliana

<400> SEQUENCE: 18

Met Ala Glu Glu Thr Glu Lys Lys Tyr Ile Thr Asn Glu Asp Leu Lys
1               5                   10                  15

Lys His Asn Lys Ser Gly Asp Leu Trp Ile Ala Ile Gln Gly Lys Val
            20                  25                  30

Tyr Asn Val Ser Asp Trp Ile Lys Thr His Pro Gly Gly Asp Thr Val
        35                  40                  45

Ile Leu Asn Leu Val Gly Gln Asp Val Thr Asp Ala Phe Ile Ala Phe
    50                  55                  60

His Pro Gly Thr Ala Trp His His Leu Asp His Leu Phe Thr Gly Tyr
65                  70                  75                  80

His Ile Arg Asp Phe Gln Val Ser Glu Val Ser Arg Asp Tyr Arg Arg
                85                  90                  95

Met Ala Ala Glu Phe Arg Lys Leu Gly Leu Phe Glu Asn Lys Gly His
            100                 105                 110

Val Thr Leu Tyr Thr Leu Ala Phe Val Ala Ala Met Phe Leu Gly Val
            115                 120                 125

Leu Tyr Gly Val Leu Ala Cys Thr Ser Val Phe Ala His Gln Ile Ala
        130                 135                 140

Ala Ala Leu Leu Gly Leu Leu Trp Ile Gln Ser Ala Tyr Ile Gly His
145                 150                 155                 160

Asp Ser Gly His Tyr Val Ile Met Ser Asn Lys Ser Tyr Asn Arg Phe
                165                 170                 175

Ala Gln Leu Leu Ser Gly Asn Cys Leu Thr Gly Ile Ser Ile Ala Trp
            180                 185                 190

Trp Lys Trp Thr His Asn Ala His His Leu Ala Cys Asn Ser Leu Asp
        195                 200                 205

Tyr Asp Pro Asp Leu Gln His Ile Pro Val Phe Ala Val Ser Thr Lys
210                 215                 220

Phe Phe Ser Ser Leu Thr Ser Arg Phe Tyr Asp Arg Lys Leu Thr Phe
225                 230                 235                 240

Asp Pro Val Ala Arg Phe Leu Val Ser Tyr Gln His Phe Thr Tyr Tyr
                245                 250                 255

Pro Val Met Cys Phe Gly Arg Ile Asn Leu Phe Ile Gln Thr Phe Leu
            260                 265                 270

Leu Leu Phe Ser Lys Arg Glu Val Pro Asp Arg Ala Leu Asn Phe Ala
        275                 280                 285

Gly Ile Leu Val Phe Trp Thr Trp Phe Pro Leu Leu Val Ser Cys Leu
290                 295                 300

Pro Asn Trp Pro Glu Arg Phe Phe Val Phe Thr Ser Phe Thr Val
305                 310                 315                 320

Thr Ala Leu Gln His Ile Gln Phe Thr Leu Asn His Phe Ala Ala Asp
            325                 330                 335

Val Tyr Val Gly Pro Pro Thr Gly Ser Asp Trp Phe Glu Lys Gln Ala
        340                 345                 350

Ala Gly Thr Ile Asp Ile Ser Cys Arg Ser Tyr Met Asp Trp Phe Phe
        355                 360                 365

Gly Gly Leu Gln Phe Gln Leu Glu His His Leu Phe Pro Arg Leu Pro
    370                 375                 380

Arg Cys His Leu Arg Lys Val Ser Pro Val Val Gln Glu Leu Cys Lys
385                 390                 395                 400

Lys His Asn Leu Pro Tyr Arg Ser Met Ser Trp Phe Glu Ala Asn Val
                405                 410                 415

Leu Thr Ile Asn Thr Leu Lys Thr Ala Ala Tyr Gln Ala Arg Asp Val
            420                 425                 430

Ala Asn Pro Val Val Lys Asn Leu Val Trp Glu Ala Leu Asn Thr His
        435                 440                 445

Gly

<210> SEQ ID NO 19
<211> LENGTH: 3019
<212> TYPE: DNA
<213> ORGANISM: Arabidopsis thaliana

<400> SEQUENCE: 19
cttcatcgaa gatggtgaaa cacagaaact catctcgctc gataatctca tattcttctt    60

| | |
|---|---|
| caatagcaag attcttctct agaaaagcta tttctctcta cttgatcttc gtctttgctt | 120 |
| ttaccatctg ggttctcgtc ttcagctcca gaaacattca aaccgatgat gaccacacca | 180 |
| aacatcaaca acaacatcat cgggatctaa tcgattcaga atcatttccg ccaccgtatt | 240 |
| tgcctcctag gaaggtaaag ttgttaatat ttcatgggtt gtggatttga atgaagaaat | 300 |
| gaggtgactt gatttggttt ttgatcggaa caattgagaa agcataactt tattgagctt | 360 |
| cagaatttgc agaaaccgta tgaaaatact caactttgga ctcctccttt cagctttggg | 420 |
| ttgcatccat gtgtcaaacc tactccgaaa tacaaggta tgccaaagaa gctcacttcc | 480 |
| aatttctgat ggatctatct tgggttttgt ttatgaattc agaactgtgc ttttgattga | 540 |
| tttcaagttc gtttcttgca gaattttcag aatcagatca ttatataaca gtgaaaagta | 600 |
| atggtggact aaatcaaatg cgtactggtg taagtaaaac catttaagtt gttgttttca | 660 |
| tgattctttt tgtcttgctt agtaccaaag tgattcaata agcatgttat tgtacagata | 720 |
| gcagatatag tggctgttgc gcacatcatg aatgcaactt tagtcattcc tgagctggat | 780 |
| aagcgatcgt tttggcaaga ttcaaggtat tttgaaactt caaacaaaca aaaaatgcag | 840 |
| cttacttaat tagtggttat gagatttata ctatttctaa cttacatttt cgctatgtct | 900 |
| cagtgttttt tcagatattt ttgacgagga acaattcatt aaatcattgc gaagagatgt | 960 |
| caaggttatt aaaaagctcc caaggaagt ggaatctcta cctagagcaa ggaagcattt | 1020 |
| cacttcttgg tctagtgttg atattatga agaaatgact cacttgtgga aggagtacaa | 1080 |
| ggtcggtctt aagcaacttc ttttacattt tgcatttgct gtttcattca actgctgata | 1140 |
| gaataataac aatgcaggtc atccatgtcg caaaatcaga ttctcgcctt gcaaataatg | 1200 |
| acctgcctat cgacgttcaa agactgagat gtcgtgtact atatcgtggt ctctgcttct | 1260 |
| ctcctgcaat gaaagccctt ggacaggttg ggacccttt cctgtcttgt acacaacata | 1320 |
| gataggctgt agtaacataa aattcatttc atacacataa gatttcaagt taatgttctc | 1380 |
| tttgggtacc gaatagctat atagaagttt caaaaccatc gtttgggtca acgagttttc | 1440 |
| attgtcaaat gatagaactt gcaataacat agtttatgca tttaagaggt gtgtaatgat | 1500 |
| agaataggag aatggataca tctttttcta tcaaacatag tttatgcatt taagaggtgt | 1560 |
| cctatgggga ttcctgtaga ctgtgggttc tgagcaatca tgacggtgac accacagaag | 1620 |
| ctggttgaga gactcaagtc acgtgctggg agatatattg cattgcacct gagatatgag | 1680 |
| aaagatatgt tggctttcac tggttgcacc tatggtctca ctgatgctga atccgaagaa | 1740 |
| ctgagagtaa tgcggtaatt gattactctc tgcatctatt cttaacaaag caaacatgca | 1800 |
| aaacgtcttc atgggataaa attacagttt caagctcaat atgttatctg ttggtcacag | 1860 |
| ggaaagtaca agccattgga agatcaaaag tataaattca acagagcaga gagaggaagg | 1920 |
| cctttgtcca ttgactccaa aagaagtggg aatatttctg aaaggtctcg gatattctca | 1980 |
| gtcaacagtc atatatattg cagcagggga atctatggg ggtgatgata gactctctga | 2040 |
| gcttaagtcg cgcttcccaa atctggtttt taaggtctgt tcaaccacct ctaatctttc | 2100 |
| atgttactga caatctaaag atgataaatg tttatgtttc atgtactgga ttttgtagga | 2160 |
| aacgcttgct gggaacgaag agttaaaagg tttcactggc catgcgacta aaacggctgc | 2220 |
| tcttgattac ataatttctg ttgagagtga tgtgtttgtt ccttcacatt ctggaaacat | 2280 |
| ggcaagagca gttgaaggtc accgcagatt tctagggcat cgcaggacta tcactcccga | 2340 |
| caggttctat ctccttcctt ctgttacctt aaaaaaaagc attaatcttt tagtcatttt | 2400 |
| gttataggcc atgacaagtt tggtgttgta tgcaggaaag gactagtgaa actcttcgtt | 2460 |

-continued

| | |
|---|---|
| aagatggaga gaggacagct aaaagaagga ccaaagttgt ccaattttgt gaatcaaatg | 2520 |
| cataaagaca ggtagcaaaa gagtcatacg tttgcttctt aaacaataaa cctataaaaa | 2580 |
| aaagcacatc tttgatgcga agaggatt tgtttgatcg ttttgcaga caaggtgcac | 2640 |
| cgaggagaag gaaaggacca acgcagggga tcaaggacg tgcacggttt agaactgaag | 2700 |
| aagccttta tgagaatcca tatccagagt gtatttgcag ttcaaggag cacaagaac | 2760 |
| cctaactaaa atttccaaa cttttttgt tctgtatcat tacatctcat ttatagtcat | 2820 |
| cttaattata gttttcacat atcccttgat atcttttctg ttttgatat ccggagatct | 2880 |
| ctagccgaag tagaaagcca gaaatttta acatttagtt ataaaacttc tctttcggca | 2940 |
| ttttttcaaa tattccaaat tttaaccaaa ctgttgtcaa tcagaatgga acaagaatga | 3000 |
| aacaccaaag ttactactg | 3019 |

<210> SEQ ID NO 20
<211> LENGTH: 3238
<212> TYPE: DNA
<213> ORGANISM: Arabidopsis thaliana

<400> SEQUENCE: 20

| | |
|---|---|
| agaacactct cgaattcgaa gaaaatacgt agcaaaaccc ttatttttga atttcagacg | 60 |
| aattccgatt tcttaatcaa aaatccgata agagctttgg atttggcggc gaataagaaa | 120 |
| acatggcgaa tttggatatg gagcaacatt catccgaaaa cgaagagatt aagaagaaga | 180 |
| agcataagaa aagagcgaga gacgaagcta agaaactaaa gcagccagca atggaagaag | 240 |
| aacccgatca tgaagatggt gatgccaaag agaacaatgc gttaattgac gaagaaccga | 300 |
| agaagaagaa gaagaagaaa aataagaagc gtggagatac tgatgatgga gaggacgaag | 360 |
| cggtagcaga agaagagccg aagaagaaga agaagaaaaa taaaaagcta cagcagcgtg | 420 |
| gagatactaa tgacgaagag gacgaagtga tagcagaaga agaagagccg aagaagaaga | 480 |
| agaagaaaca gaggaaggac acggaagcga agtctgaaga agaagaagta gaagataagg | 540 |
| aagaagaaaa aaaattggaa gaaactagca taatgactaa taaaacgttt gagtcattgt | 600 |
| cattatctga taacacttat aaatctatca aggagatggg ttttgcacgc atgactcagg | 660 |
| taatgttttt ggaattgaag ctttatgttt ttgtatagca agattcaac cttttacagt | 720 |
| ttggaatttg gttggatttc aacactttg cagatacaag ctaaagcaat tccaccattg | 780 |
| atgatgggag aagatgtact tggagctgcc aggaccggtt ctggtaaaac cttagctttt | 840 |
| cttattcctg ctgttgagct tctttaccgt gttaagttta ctcctcgcaa tggaactggt | 900 |
| gttcttgtta tttgcccaac aagagagctt gctattcagg ttctaattct ctcacaattt | 960 |
| tctatatagt ctgtagaata tgctaaaagt gatacttact atacatcatt aatgtttcag | 1020 |
| tcttatggag tggcaaaaga acttcttaag tatcattcac agactgtggg aaaagttatt | 1080 |
| ggcggtgaga aaagaaagac agaagctgag attcttgcga aggtgttaa tttattagta | 1140 |
| gctaccctg gaagacttct cgaccacctt gaaaatacta atggttttat tttcaagaac | 1200 |
| ttaaaggtaa acacaaattt ctgatttcag ttttgggtat actggtattg atttaatgca | 1260 |
| acattttta ttcgttaatt tgcagttct tgtaatggat gaggctgata ggatattgga | 1320 |
| acagaacttt gaagaagacc tcaagaagat tttgaacctt ctaccaaagg tattctcgtg | 1380 |
| gcttgcatag tgaagtcacc tcaacattct gaatcataga gatgtaaatt tcgtttcatg | 1440 |
| tcaatgtgtt gttgataatg gtaaaccgtc tttttgtatt gctgcagact agacagacgt | 1500 |

```
cactattttc agccacacag agcgcaaagg tctgcttacc aatcagtata gttttcactt      1560
aattctttat tagtgtcagt ttattaaaat tactggaact tgattaaacc atcaggttga      1620
ggatcttgct cgggtgtcac ttacctcacc tgtttatatt gatgtggatg aaggacgaaa      1680
agaggtagct attaacacaa tttctattat cttttctcgc aatttacttt gtgaccaaaa      1740
caggcctttt tcaattataa gaaaactgga aagtgcaggt tacaaatgaa ggcttggagc      1800
aaggttattg cgttgtgcca agtgcgatgc ggttactttt tttacttacc ttcttgaaga      1860
gattccaagg gaaaagaaa attatggtgt ttttctctac atgcaagtcg acaaagttcc       1920
acgccgagct ctttcgatat atcaaattcg attgccttga atccgtgga gggatagacc       1980 agaacaaaag aactccaaca tttttgcaat tcataaaggc ggaaaccggt attttgttgt      2040
gtactaatgt cgctgcccga ggtcttgatt ttcctcatgt ggtatgcttt cttaacaact      2100
ttaatgtttt aataatctgg attggttggt ctttaatcaa attattgtct gcttgtttag      2160
gactggattg tgcagtatga tcctcctgat aacccaacgg tatgttgctt ataatttagg      2220 gttttatgc aaacacgcgg aagaataagg ataagaaat cactcaaatt cttgaatgtt        2280
acttttgatt taggattata ttcatcgagt tggtagaaca gctcgtggtg aaggagcaaa      2340
aggaaaggct ctgcttgtcc taactccaca ggagttgaag tttatacagt atctcaaggt      2400
aaattatttt cattcaataa aaactttgat aattttcaa attatagaaa ttttgataaa       2460
agaatctgtt tccaactgta taatttgcag gcggcgaaaa ttcctgttga ggaacatgaa      2520
tttgaagaaa agaaattgct cgatgtgaaa ccttttgtgg taaaacattc ttgctctttc      2580
aaataagttt tactacactg aagaaacaaa agttgagaga tttatttaaa atgttattgc      2640
aggagaattt gatatctgaa aactatgcat tgaaggagtc agcaaaagaa gcatacaaga     2700
catacatttc aggatatgat tctcactcta tgaaagatgt ctttaatgtt caccaactca      2760
atctcacggt aaccaaatct gcagcataca tataacaata cgaaacgtca tgaaatcagg      2820
aatacaattt gttttgttt tctgcaattt aaacgttaac cgaaggtctt tgtttatgtg       2880
caggaggttg cgacttcgtt tggtttctca gatcctccca aagttgctct gaagatagat      2940
cgaggagggt acagaagtaa gagagaaccg gttaataagt ttaagagagg tcgtggtggt     3000
ggtagacccg gcggtaaaag caagttcgag aggtactaaa aatacagttg cacaaacaac     3060
gtcatactta gtagtatggc acatgccttt taacgaatgt tgtatcttat ttttggattc     3120
atttacgatt gtgttgtctt aagctgtttc cagagatatc agacgagata ccagttttgt     3180 cccgttact tagaaatatt gatcattttg ttttgcgaat aaacttggtc ttatatat        3238
```

<210> SEQ ID NO 21
<211> LENGTH: 2172
<212> TYPE: DNA
<213> ORGANISM: Arabidopsis thaliana

<400> SEQUENCE: 21

```
cttgaacgga cggcagaact cggagtcgga gatcgtaccg gaggacggcg aatcttccat        60
ctactgtcct ttcgtttttt atacgcgtca aatgagtctt aacttcaga ttagctctgt        120 aaacaatcgc gattagtccg gattgcatct aaggattcgt tgatggcggc gtcgtggcag       180
tgggaaaatg ccaccgccgg cgccgtcgct ggattcgcca ccgtagctgc tatgcactct       240
cttgatgttg ttcgtacgag attccaaggt ctggtttttc actcctggat taactcatcg       300
attttgcttt taaaaagttg ctaacttgat tgaacaacag tcaacgacgg aagagggtca       360
agtctgccga cgtacaagaa cactgctcac gctgtcttca ccattgcccg tctcgaggtt       420
```

```
tcccagatga aactctcttc tggcatcttc catattatct tctctatgtt atgtggttga    480
ctcatttggt ttaaatcttc tgtagggttt gagagggctt tatgcaggct tcttccctgc    540
agttatcggt tctactgttt cctggggctt atacttcttt ttgtgagtgt tactttcgtt    600
tagcacatat cttctttctt catgatttct attcaaacag ttttctgtta gttttttaa     660 tgttttagc cgtggatctt gtttaaaatg ttctggaaca atatattat ctctctgtag      720 ttatggaaga gccaagcaga ggtacgctag aggcagggac gatgagaaac tcagccctgc    780
tctccacctt gcttctgctg ctgaagcagg ggccttggtg agtctaacag gcgccataaa    840
catctcattt ctcctatgtt ttttcgatct cagtatcaag ggaatgatgc tttcaggtct    900
gtttatgcac aaatcctatt tggcttgtca aaacaaggtt acagcttcag acacctcttc    960
atcaaactca accatactca gggctattag gtttgcaata tgctgcacac acaaaattca   1020
gttttcattg tttctagtgt ttcattctaa atgtgtattt tgtgatctta agatgccttt    1080
agaaccatag tgaaagagga aggacccagg gcgctctaca agggtattgt ccctggtctt   1140
gtactggtta gtaactatcc tgatctatct cttgtaacgt tcgttcgtaa aactaccaca   1200
agatccacag ttttggaact ataaaagatg actattagtt gcgaaagagg aggccttaca   1260
gattgaatgg tttacatttt gggttcagca ggtttctcat ggtgctattc agttcacagc   1320
ttatgaggaa ctccgtaaaa tcattgtgga tttgaaagaa aggagaagaa agtccgaatc   1380
cactgacaat ctattggtac agagtaattc ttctgaatag gctacattgc ggttcttaag   1440
ttatatagcc acattaatct taattctacg gctatttcca gcatcacgga tatatactat   1500
tctaacacac tccattgcaa ttttttcttta gaactcagca gattatgctg cacttggtgg   1560
ctcctccaaa gtcgctgcag ttcttcttac gtatccattt caagttatac gagcacgatt   1620
acaggtacct atcgaccgtg tcttcttcag tcttattatt gttagctcaa atctaaattc   1680
cttgagcttc cttactttct acctttgacc ttctgcaata tatgaggatt tcataaacat   1740
ggttcttttc ttgttcagca acgacctagt accaacggaa tcccaagata tatagacagc   1800
ttacatgtca tcagagaaac cgcgaggtca gggcatattc ttggtctcga ttatgtctgg   1860
aatgatgatc ttttttggtta gtttcactga gtaacacttt tgggtctctc tgcagatatg   1920
aaggtctcag gggttctac aggggactaa cggctaatct tttgaaaaat gtacctgcgt    1980
cttccatcac attcatcgtc tatgaaaacg ttctgaaatt gctaaaacag catccaacaa   2040
caaaagatta gactcttcct cttcctttac cgttatttct tagactcaac acgcacgcgg   2100
ttgacttgtc actcccaata ctagagaatt attctttgat atacatatat tttatgtgcg   2160
ttccatggtt ct                                                        2172
```

<210> SEQ ID NO 22
<211> LENGTH: 1665
<212> TYPE: DNA
<213> ORGANISM: Arabidopsis thaliana

<400> SEQUENCE: 22

```
acacaaacaa gaaaacgcaa aactaatcct ctctcgaatt agggtttcgt caaggtatta     60
cattatttca caccctttatc atcatcttct gatttctggt aatcttctttt tgattagatc   120 ttcctatcga ttggttcagt cctttcttat tttcgaattc ttgattggtt taccgtggtt    180
gctacgattt aaaccctttaa catacctaaa agaacgtttt tgttttgct ttttgttgtt    240 attgaagttt ttttttttttt ttattgttgt tgatgaagat cctggagttg atgtattgag    300
```

```
agaagccatt gagataagag atgagctcta cgcaggctaa tctatgcaga ccatccttgt    360
tctgtgcaag gacaacgcaa acaagacatg tctctagtgc accttttatg tcgtcattac    420
gctttgatta tcgaccactc cccaaattag ctattcgggc atctgcatca tcatcgatgt    480
cttctcagtt ttcgcctcta cagaatcatc gctgccggaa tcagaggcaa ggtcctgttg    540
tgtgtttact tggtgggaag gataagtcta acggtagtaa tgaggtgaga tgcttcgtct    600
tcattctaag atgtctttgc ttattagatc atataaagat gatgcttaat ctttaaatgt    660
tccaaattga tcttttgtg tgtgtgtgcg tgtaagaagt tcggcacaga gttgagttat     720
gtttctgatt ataagtagta ttgatatgat tcttttctgt tttatactta cttggtcgaa    780
aggataaatc tgatagtagt tatgagatca gatgatttct cttcattcta tagatgttct    840
tgctgagatt tgaatattaa atcttgcaaa agtgatcttt ttgtctgtgt ttgtaagtta    900
aggcacagaa ctttagtgcg tctgatatta atacgctcag tgatgatgtt ttatcatcag    960
ctatcatcaa catgggaagc tattgagaaa gcaatgggga agaaatcagt tgaagatatg   1020
ttgcgtgagc agatacaaaa gaaagacact ggcggcattc ctccacgagg acgaggagga   1080
gggggtggcg gtagaaatgg tgggaataat gggtctggag gctcatcagg gaagatggt    1140
ggtcttgcta gttttgggga tgaaactctg caagtggtat tagcaacctt aggcttcatc   1200
tttctggtaa ggacaagatc acaagcccgc acaagttatc tttgaattat agtatcttta   1260
gctttgatca ttgtttcttt tttttgcagt acttctacat catcaatggg gaggagttgt   1320
tccgtcttgc aagagattac attaggtacc ttataggaag acccaagagt gttaggctga   1380
cccgagttat ggaaggttgg agtagattct tcgagaagat gtcgaggaaa aaagtgtata   1440
acgagtactg gctaaagatt aagcgatcat caacaagtct acctggtctg gtaacccggg   1500
caaatacaaa cgcatcttga gatcttatgt tgattcaaat gaaatgaaga tagtgatcgg   1560
ttttcttact ggtttaagta gtttcccttta gacccttacc cgtgttttg ttttgttta    1620
agttactttt gccagtagta aatattgatg ctcatcgtca caagt                  1665

<210> SEQ ID NO 23
<211> LENGTH: 1027
<212> TYPE: DNA
<213> ORGANISM: Arabidopsis thaliana

<400> SEQUENCE: 23
atcacgtgat catcttcttt cttccttttt tcttgtcatc tgttacacat cggttagggt     60
tttagtttct cttaccgaga ttcaaatggc gcttagagga gtttggcagc tcaagaaact    120
cgttgtgagc tactgtaatt gggtggtag cagtagaggc atcaggtaat tttgtttacc     180
tataatttga tttcgcaatc tatgagccgt attttttcat ttatcatcga tctaccattt    240
ttcctgtaat tcactttgga acttgagact atctatacga atctatgagt ctgtacttgg    300
tatttgtgaa gcaaattaac ttttcatgtc aatgtgggtt tagaaatgtg aagcaaaatg    360
atttagtaat gaatcgttac catttcatcc tagtttggta ctacgcattt tcttatgatg    420
tgttgttaaa catacagagc ctttatggaa tcagaattgc ctgctctaaa ggagaaaaac    480
ccgcagctcg aagtaattac cgagctttca cggggacaac atccttattt gaagggcatt    540
tacagtatgt atatttctcc tctattgaat acaatcctga ttcaacggtt gttgatatta    600
gcaatttcac ttgcacaatt catagggaat agaaatgaaa gggtagtgtg tgtgaagaac    660
atggatcctg aagaagtgct tttgaatgca acgaggctga ggaactcgct tggacgaaa    720
gtggttaaac tgaggaccag acatgtcacc aaacaccca gtgttcaagg cacctggaca    780
```

```
actgctgtca aattctgaga ctttcctgct aaattgtttg caggttttca tcttctagct    840
gttaaatcga atgttgcaag tatcaggatt ggtcgtttat ctgtattgca accccaagtt    900
gtttgtaccg tctgtgactt gggacaaaga tgtagtcttc aaatgttttg cagttttgc     960 aatgtttgaa ttttgtcttg tccttctggt tgagtctata ataagattac acaagggttt   1020
aaggtta                                                              1027
```

<210> SEQ ID NO 24
<211> LENGTH: 3627
<212> TYPE: DNA
<213> ORGANISM: Arabidopsis thaliana

<400> SEQUENCE: 24

```
tctgagtggg cattacaaat atttggctta accggttccg agccatttgt aatttccgag     60
tatctacatc gccggcgatt gattctgctc atcttttcga tgccctctcc gtctgcagtc    120
gccgatctct tggccgctct tgcttacagg cttcagaacg agatgaatt attcgaagaa     180 gaagaagaag cggaagagtc tacttcttct atgggactag ctatctcgga gcttaaccga    240
tctctgactc tggatatcgg ctgcgaggat tctggggtca gggttgtgga cgcagcgtta    300
tctataatgt gcttcaaggc acctcaggtt agtatcatat ctatcctgga cttgcattgt    360
ttctacgtag ctgagttctt acttgtgagt gattttctta ttaaaattca ggttttgat     420 tcggcaattg agtttatggt acgaacaatt gtttgcgcct tatcatcttc aagcaattgt    480
aaggtaatta ggtatcgaaa cgaggaaaca ttacagtttg ggagctccaa tttacctggc    540
tgctctgaag aattgatcga atctctaag gatattattg agaaactgtg gggaaatggt    600
gcgtttgatt tagcttatcc tagagttatc tgaagatttt aacttttgtt tgttctctca   660
tatttttctg acttggaaat gttcatagga agattggcta cattgttatt cgaagctgtt   720
gtaaggtcag cagcctcaac atgtaagatc agcagtttca acgcgcatgg aaagcttatg    780
gatggaagaa atagggctgt ctcgaagctt cttgcttact taccgggaga atcatctata    840
gagaaccaca agatacctct gaggtttgac ctcttgtact gtttctgttc caagctatgt    900
tagtctgcat tttccatatt actcaagaag ccacagcttc tgagatgttt gctctcttgt    960
ttcagaaaaa ggtagaccgg tctgacactt tttgatgatc aggattcttt tctggtatcg   1020
agatccattg tctttgaagg tagatgtttc cagaatcttg aaagaggtgg tggaaaggcc   1080
tttcctttgt gtaaaaaggg agcttttcga gagggggag tggcgcgata ttgtcatctg    1140
cctagcgata tctcctacta tgtttatcaa cactagatca ctcttacata aatggctttt   1200
gcttacgtga gttcctatcc aattggtgtc atgtaaatct acaataatag acatgtgtaa   1260
tcttatgcgt tgtgatctct agttttccat ctttcttgct ttctgatgca atttcttct    1320 ttacgccagg ggacttgctt ctgtttttga agtacttgct ggtttggcct ctgcaataat   1380
ggatacaatt tcaaggccat cgttgtgggg tataccaatg gaactagctt ccatgttgcc    1440
attttctgat acatactttc ctttccagtg tcaatttctg agaatcttgg cgggtcctct   1500
cagttccaag tccctcctaa tgttagctca tactgtcagt aaagcgtctg ctgtccctgg   1560
gcaacaacaa cgggatacta attgtaagcc tactccaata aaagttcaag cattagatga    1620
caaaaccgaa tggtaacttt acataaaatg caaattgata ccctcagatt tgatctattt   1680
atatatacgt gcgtgtgagt ggttttgaa tgatgttgta tcttctggca gggctttggc    1740
tattaacttc ccagattggt tctatttgc atctgctatg ctcttctcag aaggaaagtc    1800
```

| | |
|---|---|
| gtttgaaaat atccaccata tatgcgcttc aaaagtggct gactgtagac aagtatgtga | 1860 |
| tgtagaagat ctctccattg ctgcggctac atacatttct tggattctaa accctggaag | 1920 |
| tggaaccatt caagagtcag taagtaagtc tctcattaga gtctcagaga tatgtatcag | 1980 |
| taaaagttgc ggctcagaag catatcgtac tgagactata actggcaaga gaaagaaacc | 2040 |
| agataggctc gtttctggca aaataaatgc ttccagtatt gtggaagacc tattgagaga | 2100 |
| atttgaaaac aatatcacca attcagtttc ttatgatttg gattctcgga aaacgcatcc | 2160 |
| atctttcagc tctgcctcc aaaacaattt gttggtaaga agagttgtgg ttggcgttct | 2220 |
| gtttggttct ccatattcag taacagatga ggagtatgaa ctggtattac actatgcagc | 2280 |
| aactgggaaa attcttgact ttaagaaatc acggagtacc ggattcaaac aaggaaagaa | 2340 |
| attctctaga atatctgctt tactgtcgaa tgaaattacc aaggaggagg ctacagaagg | 2400 |
| cacacttctt gttttcaact taactgacac tttggagagt atgtgtgtat caagttttga | 2460 |
| ggccaaagag gacgcagaga agtttattaa ccattttaag ctgagatcca gcaagtactt | 2520 |
| ggtcaaatgc atagatcgcc tgatacaact tcactgtaca caagatggag atccaatact | 2580 |
| aagtgacatt aatatcagac tgctgcaatg gacagtaaaa ggactagaag atccacattt | 2640 |
| taacaaagtt cttgatgata tcgctgctaa gttggcctgc atattctcgc gcgtgtaact | 2700 |
| gtcaccatat agcctgactt gtgtcatatt tggtggtaca ctaattttg ggaaaatggt | 2760 |
| gatcaaatgt gaactgttca agcactcgc acgactggta tgaggatata actggtgtac | 2820 |
| aggtaattgt aattgattgg tctaatttct aatacagtaa cacaatcata agtgataagc | 2880 |
| cggtttagtc gtcaaagtag caacattctt ggctaaattt gagttggatg tctgaatgtc | 2940 |
| tttggtatca gtgtaatggt tatctataat atgttgccac cgctaaatat gatctagtac | 3000 |
| actagtttgt ttagagccta agttttttta tgttggtggc tatcatatgt tatcatcaag | 3060 |
| ggagctttat gtttaatata ttactctaca tgggtgatga gacatttgac ctgcattttt | 3120 |
| ttttcataat actgttaaat tttttgtgat cataataaca tattaccttc atcctttcta | 3180 |
| tttcagctcc acaactgaaa ttatttgatc tgcctggact ggaccagaga attgtggaca | 3240 |
| attcaatggt gagccttgaa agcacttgat gccttattca atggtgagcc ttggaaccac | 3300 |
| ttgatgcctt tgccatgctc tcttaattcc acttgataac cacaaaacaa taaccggatt | 3360 |
| tcctgctgaa aagggtaatg tagattcatt atcatgattt gctctctatg ttcaaatagt | 3420 |
| catttgtttc ttagatctct tggctaatta tgcgcaaaaa cacaattagc cagggcatct | 3480 |
| gagtttcgtc atcccaagcc cctgagagtt gcaaaaggag tatgatccag agaagtgagt | 3540 |
| tattgtgagt acatgtactt gggttttgcc ttttaggctt ttaatcatgt tgttaaatat | 3600 |
| ttcttattga atcagttggt ttcagac | 3627 |

<210> SEQ ID NO 25
<211> LENGTH: 2891
<212> TYPE: DNA
<213> ORGANISM: Arabidopsis thaliana

<400> SEQUENCE: 25

| | |
|---|---|
| atgggagaga ctgaggatga aaaagatgct tctttggctg atatcgagaa ggagtgtctc | 60 |
| tcggtttata agcgaaaggt cgaggaggct agtcggggta aagcgaattt gctgaaagaa | 120 |
| atcgctgttg gcagagcaga aattgcagct attggctctt ctatgggtgg acaagagatt | 180 |
| catgtaagtg tattcaagac ttcagttttg atatatttgg ttttttgtctg ctggagttat | 240 |
| ggcaagtaat ggtgcatttt cttcttacag tctaacagca ggttaggaga aaacttgaaa | 300 |

```
gaggagcttg agaatgttaa tgtgcaattg gatggactgc gcaaaaggaa agctgagaga    360
atgattcggt ttaatgaagt tatcgatcag ttactgaagt tgtcactgca acttggaaat    420
ccaacagatt atctgaagaa gtttgctgct gaagagaccg atctttcgct tcagaggttg    480
gaggaattgc gtagccagtt gggtgagctc caaaatgaaa aggttggttt tgctgttaga    540
tctcatgata tgggacttat attacaagag catgtgcacc tgttttcctt atgttaactt    600
tgaattcttt tcaaaatgta gagcaaaaga ttggaagagg tagagtgttt gctgaaaacg    660
cttaactcgt tgtgctcggt tcttggtgaa gatttcaaag gcatgataag agggatacat    720
tcatctctgg ttgattccaa cactagggat gtgagcagaa gtactcttga taagttggat    780
atgatgattg tgaatttacg agaggccaag ttacagcgaa tgcagaaggt tacaagtctg    840
agctcttctt tgtaatgtag tgcaagtttt tctgcgtgat tatggtttct gactctcatc    900
actttgtttt tctaggttca agatcttgca gtgtccttgt tggagctctg aatctgctg     960 gacacgcctg cggaagagca aaagatattt cacaatgtca catgtagcat cgctttgact   1020
gagtctgaaa taactgaggc caacatactt tctgttgctt ccattaaacg cgtgagtgca   1080
caggaccaaa cctttctgtg ttttctccct gtattgttta gtctatccgt ttataatagt   1140
ataggaacaa tctttttat aatgtgagtt tgttttacag gttgaggatg aagtcattag    1200
gcttagcaag atcaaaataa ctaagatcaa agaggtgata ctgaggaaga ggcttgagct   1260
tgaggaaata tcaaggaaga tgcacatggc caccgaagtt cttaaatcag aaaacttttc   1320
agttgaagct atagaatctg gtaaaccatt attaggaaca gcttattctt tacataatat   1380
gatgtgcaca aactccagaa atgttatgct cattatactg gtagataaca tgaacatgct   1440
aataataaca tgtttccact catcttttag gtgtcaagga tcctgagcag ttgttagagc   1500
aaattgattc cgagattgca aggtcaaag aggaagcttc aagcaggaag agattcttg     1560 aaaaagtgga gaaatggatg tcagcttgtg aagaagagtc ttggctggaa gagtacaatc   1620
gggttagaca tttaaatcta atctattcc tttgcctcaa tctttttttt gttttgttct    1680
cacatcgttg gcttcgcagg atgataaccg gtacaacgct ggaagaggag ctcatcttac   1740
attgaagcgt gcagaaaaag cccgtttact tgtcaataaa cttcctggta acattcttgc   1800
tctttagatt atattacaaa aacctacaaa ctcataactt atgatctttt ttgtctattg   1860 cttttctgctg ctattgatgc agggatggtg gaagctttga ccgccaaagt cactgcttgg   1920
gagaatgaaa gaggaaatga attcttatat gatggggtaa gtggtttttt actgatcaat   1980
gatctgttct acacaattat caaatcagca tctttacaca aaagcacgta aatatttcag   2040
gtccgagtct tatcgatgct tggtcagtac aagactgtat gggaagagaa agagcatgaa   2100
aaacagagac agagagtaag gaaaactgtt ttttactagg aaccaaggtc actatgagcc   2160
aaaagcatca ttggcaattt gacattgtta ctttcatctc aggatatgaa gaaacttcat   2220
ggacaactca taacagagca agaagctctt tatgggtcta aaccaagccc aaataaaagc   2280
ggaaagaaac cactgagaac accagtaaat gctgccatga acagaaaact ctcccttggt   2340
ggtgccatgc ttcatcaaag cttaaagcat gagaaggcaa cactcaatag caaaaggacg   2400
aagtactatg accagaacgc tactagtaga agagattcag ctcttccaac tctttcaggt   2460
acataataat aacacaagat tttggtttac acttaacaga gaccaagaga gagatttgtg   2520
ttaagagaat tatgtcaata tgtgtaggga ggagaaactc agagcttcct ggtcgtatca   2580
gatcaaagaa cgttccggtt gcaggaaaag ctgcgagatc tccaatgctt aggaagcctc   2640
```

-continued

```
tttcacctgt cacttccaat atcttgaatt ccccagaaga tcatcacaag gatgcttaca      2700
caacaaagga gagaatcttg acacctaaaa ccaacgaaga aaagaaaaga gctgttccaa      2760
caactcctgc agcttcagtc gctatgacag aggcaacaac gccgttcact cctgctgtgg      2820
agaagagaat ggatgaggaa gacgttattg ttgagtattc gtttgaagag gttagggccg      2880
gtttttgcta a                                                           2891
```

<210> SEQ ID NO 26
<211> LENGTH: 9704
<212> TYPE: DNA
<213> ORGANISM: Arabidopsis thaliana

<400> SEQUENCE: 26

```
atgaatggaa aggaatcaag aggacctgcg tgtagctttg agtttgttgg tgaaagctca        60
ggtttacttg gtccaggaga aagtcgctgg ccttttacca atggctatgc atttgcgact       120
tggatttata ttgaatcatt tgctgacaca ttagatgctt caaccgcggc agctgcaatt       180
gctgctgctt cagcggcaaa atcaggaaaa atatctaatg cagcgcctgc gaatgtacac       240
actggtgagg gtactgctca tatgcctcgt ctgttcagct ttttgacccc tgataatcag       300
ggaattgaag cttatttcta tgcacaattt tggtggttg agagtggcag tgggaaagga       360
agtaaaactt cacttcattt cactcatgca tttaagcctc agtgttggta ctttattggc      420
cttgagcata cctgcaatca gggacttta gggaattcag atagtgaatt acggctatat       480
attgacgggt cgttgtatga aactcgacca tttgactatc ctcggatatc caaaccgctt       540
tctttctgtt gcattgggtc aaatcctcct tctacaactg ctggtctaca acgtcgtcga       600
cgtcagtgtg ctttgtttgc tgagatggga ccagtttata tatttaaaga accgattggt       660
cctgaaagaa tgcacgcattg gcaactaga ggtgggatg ttttgccttg ttttggcaat       720
ggggcaggtc ttccatggtt agctacaaat gaccatgtcc gtaatgtggc agaggaaagt       780
agtctttcgg atgcagagct tggaggatac attcacctac tttaccaccc atgtctacta      840
agtgggcggt tctgtccaga tgcttctctt tctggagcag caggtgctta tattatactc       900
ttgattttta atatatctga gaaggctcta caagtctgaa aaatattccc tagtatgatg       960
tgttttatta gtacttgttt tcagatgctc atttggttga gtttgttgta acttttatc       1020 tgttcttgtg ctatctatat cgctttcact cggtctcact attctccatt tcatatgaa       1080 ctttgttttt atttatcttg tgtcttagga gatgagaaaa caccatattc ttttttctgct      1140 gtagttttcg cactttgtta tttggttttc ccttactttg gaagttcgtt attttttctt      1200
gattaaggca ctcaaagacg accagctgag gtaattggac aagtccatgt tgcaacgaga      1260
atgaagtctg gagtccttct gggcttagc ttatggagga cccatgtctt tgcttcctct      1320
aaccgtaagc agtgtgcaca agataatcct agagccatgt tctagaaatg ttccatcttc      1380
tttgacaaca tattctctgg ctgcacctat ttttagaatg atctcatttg ctattaaaca      1440
tcctgggaac aatgaagagt tatctcgtac taggggcct gaaattctgg ccacagttct      1500
cggttacctt cttcattcac ttgcatcctt tgatatcaag cacgatagag taggagatga      1560
ggagctagtt gctgctattg tttctctttg ccaatctcaa aagatcaatc atgctcttaa      1620
agtgcagctc ttctgtacac tattgttgga tctgaagata tggagtgtgt gcagttacag      1680
actccaaaag aagctgttgt catctcttca agatatggtt ttcaccgaag caacagctat      1740
gaggaatgct gatgccattc aggtactct ggatggatgt cgaagatatt tctgacaat       1800 tcaagagaaa gactccgtga acacgttttc tctagatggg gatgcacgtc aagtggggga      1860
```

```
agttaatgca ttggttgatg aacttttggt gattattgaa cttctaatgg gagcagcatc   1920
tccttcgttt gctgctgatg acctccatcg attacttggc tttataattg agagtccaca   1980
accaaatcag gtaacacgtt tcttagtgat atttcataat tgttaaacat gtgtcatttc   2040
tcagatcttt taatatttt tctctgacat cattcagttg ttacctctat ttaggttgca    2100
agggtattgc atctcatgtt taggttggtt gtacagccaa atgctgcaaa ggctcagaca   2160
tttgcagagg catttatcac atctggtggg atagaaacac ttcttgttct catagcaaac   2220
agagtcaaca caatgggcct ggtttgttaa agttggattc agttccacaa gataatgagg   2280
gtgaccctca tgctcatgat gataatgtag gatctttgaa ggaaacagag tcatttcaac   2340
aagtaaaagt gcatggatcc gaaactgtca tttgtgagac tggctcagtt accctctcca   2400
gttccgtgaa tgctgacaga atatcctctg tttctgaaac tccattcaat aataatgcaa   2460
gaaacaatgt tgacgataga gatcgtgtca tggttgggat catcagattg attggtgcgt   2520
tgatttcaaa agggcactta aaattttccg ttggtgccaa atctgatgta atgagtaacc   2580
tcatgggtag tgagtttcgt gaaaatggtg gaacaatgtt tgattataaa gtcgcattgc   2640
ttctatttgc tctgctgaaa gcatttcaag cagctccaaa cagattgatg accgacaatg   2700
tctacacaac tttgcttggg gcttcggtat gacatgtctt aatatatctt tcatttgttt   2760
gatctatctt taagcgtagc tggtttaatg tcaagaattt ggtggaaaaa gagagtctct   2820
gaggtgcaac tttttttag taagatttat atgtataccct ggtttaatgt caaggatctt   2880
tcttgcaggt taatgcttca tcaactgagg atggcctgaa cttttgtgat ttaggtcatc   2940
gatttgaaca tcctcaactt ctgttaatcc tcctgcgttc tctaccatt gcatctaagg    3000
cactacaaaa tcgagcactt caggtataaa tgtcatagtt aaagacactt ttgtgcacca   3060
aatgcacttg tgaaagtgct ctacaaactt ctacttgtcc ggtctctaca atgtctcctt   3120
ctgaactcac tttttctacg tcaggatatt ctatttttgg cttgtaccca tccagaaaaa   3180
aggagtagtc tgaccaaaat ggaagagtgg cctgagtgga tcttggagat tttaatctct   3240
aactacgagg tataactcaa acgttaaaaa ttttaaagtt cgcctccatg attattgtat   3300
cagtaatgag ccaagttggc tatatttaca ctagtgtgat aaggcgagtt acatttttta   3360
tctggcaagt ctcttaagca tgtaccataa aactttaaaa atgctgacta ttctgcgtac   3420
acacagaaag atgcagggaa acaatctgct tcacccggtt ctgctgaaga ggaggatctg   3480
attcataact tcttgatcat aatgttggaa cattcaatgc gccagaagga tggctggaag   3540
gtaaatttgt ttgtttcagc ggtctaccag attaattccc tttcacgttt tttccaagct   3600
catttgtgtt tatttatatt tttcgctaca tctgattcct tttacaggat attgaggcta   3660
caattcattg tgcagagtgg cttacttttg ttggtgggtc tagcactggg gagaaacgaa   3720
ttaggtattt tcatgcacta ctgcgccaca ttttacgcgt gccttttggg atgccaataa   3780
cattttgagt gtcatctgtt tttcttgtca cattgttagt ttgtgaaggt atcttttgga   3840
tcatattgtt gttgcactgt agtgcttctt ccatgtattt tgagataagc atgtttctgt   3900
tcaattatat ttacactttt ttcctaatac tttttcaaa ggcgtgagga atcactgcca    3960
attttcaaac gaagactttt aggtggattg ctagactttg ctgccagtga actgcaagct   4020
caggtatagc tcctgtttta tctttgactt atatggttag ttatacaatt ccttgctaga   4080
gaaacacgaa gttcgtctta cacatgcatt gtatagttga cattggtcgt actctcacaa   4140
gaaaatattg tcagatcttt ttttatttgc tctatattag ctataatatt gttaaagaca   4200
```

```
gtaagctttc aagccttgtt ctgttatgtt ggtcgactgc tataatttaa cctacacatt    4260
aaactttccc caaacagact caagttatag ctgcagcatc tgctggtttc gcggcagaga    4320
gtctaacacc aaaagatgca aaagcgggag tagaaaatgc tgcactgctt tcagtgtttc    4380
tagtggaaaa tacagttgtg attttgatgc ttgtcgaaga tcatttgcga ctacaaagca    4440
agcaaaattg tgctgcaagc gcagttgatg tctctccatc tcctctttca cttgtttatc    4500
ctcccaacta ccgttcacac acattgccaa cggtcggaga atcatcagag gtttctagta    4560
gctgtgcttc agtgtccagt gattcaggag gggtccattt agatgtaagt ggaaattact    4620
ctcaatttct ttcttccgga tcaatatctc cccttattta ttggcttttt tccttttgt     4680 ttttataaca tcatttaaga aagatagttc tgatcatctg attaactttc tgctattttc    4740
ctgcttttac ttttcttca gatacttgct tcaatggccg atgcaagtgg ccagatatct     4800
acagccgtaa tggagcgtct tgctgctgct gctgcagctg agccctatga atctgtttct    4860
tgcgcttttg tttcatatgg aagttgtacc agggatttgg ctgatgcttg gaagtacaga    4920
agtcgattgt ggtacggtgt tggactacct tctaaaacta gttgttttgg tggtggtgga    4980
agtggttggg actcttggaa gcatgctcta caaaagatg ctcagggtaa ctggatcgaa      5040
cttcctttgg ttaaaaaatc agtatccatg cttcaagcct tgctgctaga tgagtctgga    5100
cttggaggtg gcctaggaat tggtggagga tctggtaccg ggatgggagg gatgtcaggc    5160
ctctaccagt tgctagatag tgatcagcct ttccttatgca tgcttcgaat ggtactcttg   5220
tctttgaggg aagaagacca tggtgaagat agtctgttga tgaaaatttt aagttctgaa    5280
gatggtataa ctggtggact ccagtgcccc ttaggaaatt ctgcctcagt agatatcagt    5340
tctcagttgt ctatgcgaca gtcaccatca gctttattgt ggaggtaaag taataacatg    5400 tttttttctta cttccctatg tgactttgcg aattataaac ccatctgcat tgatacgatt    5460
ttgtccaaag tatgttgtcg ctcactcaag attatgacca catgccttaa gcattttag     5520 actagacttt gtcacaaaat tagaatacaa gggcatattt ggcatctttt ggacgcctga    5580
cttgacgttg catgccttct aaatggttgt ttgctcatag agaatttaat gtgactgttt    5640
ttttttatct ccagtgtgct ctctcccgtt ctaaacatgc caatctctga ttctaagagg    5700
cagagggtat tggttactac atgtgttcta tattctgagg ttagttctcc cctaattaag    5760
gttccatact tcaattaatt atggtctggt ctcacatttt catgttgagt ttttggagaa    5820
cgataatgga aattgctccc ctagtcttct ttgtgaactt aataatgctc actttgtttt    5880 atttttatggt ttttcgattt tttgattcaa aatctgttgc aggtatggaa tgctgttagc    5940
aaagataaaa gaccactacg taagcagtat ctagaggcta ttttaccacc atttgttgca    6000
attctccgaa gatggaggcc tcttttggct ggtattcatg aacttccac tggtgatggt     6060 gtgaatcccc ttgtcgttga tactcgtgct ttggctgctg atgcacttcc cattgaggtt    6120
ccacaaatct gttcacatac cctgtagttt ctatcacata tatttatagc ttctgacagt    6180
gctgcttcat cccttagcct aaggtattaa actgttactt tttattctag gcggctctct    6240
ctatgatttc tccggagtgg gcagctgctt ttgcatcgcc tccttctgca atggcactgg    6300
caatgatagc tgcaggggca gctggttggg aagcgccggc acatccagca cctccagcgc    6360
ctccacctct taggcgagac agttcattac ttgagcgtaa gagtaccaaa cttcagacct    6420
tttcaagctt ccagaaaccc ttggaggctc caaatgatga tacaccaggt cgagcaagag    6480
ataaggctgc tgcaaatatt gattcacatt tattgattca accgctcacc agattgacag    6540
gcgtatgcaa aatgataaaa tagtgaaaaa tcgcttatgc atgggaatcc gtggttggcg    6600
```

```
caaactcgtt cgttacttgg tggacatgag atgcttcttt ggacccttcg gagaccattt    6660
atgcagtccc aaacacgtaa gctacgttgt tctggggtaa atttaaaaca tgttgagaac    6720
atttccagtg atgtaacatc atcacatatg caggttttct ggaaactgga ttctatggaa    6780
agttcttcga ggatgagaca atgtttaagg aggaattatt ctggcactgg tcatcttgag    6840
acaacaagaa actatgggga tcagacatac ttgatgaata atcacgactc acctgttctt    6900
gctgttgaag caatatcaaa ggaaataatg tatgaagatg atgaacatgg agatgccgat    6960
gatcttgaaa tagagggtaa tgttggagaa cgcaaagggg aaaacgaaga gagaaggtct    7020
ggctcacttg aggatgcaat aacactgtca actggaatca acgatcatcg acctttgagt    7080
gaacagaata tggttcaaaa ttctacagaa gtaaaagatc tcagtgaact taagaaaagg    7140
attgttcttg aaatttcctc tactatggtc cgaccactag gggttgtgaa aggaaccttt    7200
caagtatgct ctcactaaca ctacctattt atcttttgaa caaatagctg acacaaatga    7260
gtattccatt gatgaccaag aaataaaaca gagcataagt gaccagattt tgtaatgttt    7320
gttttctgtc tttctcagat cacaacacgg agaataaatt ttattgttga catcagagaa    7380
gaccaacatt tggatgaaaa gtcagacggt tcaaaatcaa gagacgaaga aagagatcga    7440
agttggctga tgtcttctct tcatcagatt tatagccgac ggtaaagttc atcattaatg    7500
ttgtctctag ctcactattt cctccgcatt atcatgtaaa tagatggaga cctatatctt    7560
tgttaatatt tttctttcac agatatctac tgaagaagag tgctcttgaa ctatttatgg    7620
tggatcgctc aaacttcttc tttgattttg gggtatctaa aaaactctct ctgttacatt    7680
acattatttg atctctttcg ttggaaattt caagtttcta gctcctctca ctatatgatg    7740
tttgatgaaa actatagaac accgagggac gaagaaatgc ttgtcgggct attgttcaag    7800
caaggcctcc tcatttgaaa aatatttact cggcaactca ggttttttt tttccctccg    7860 tttgcccatt ctttagtgca tggtggacaa agctaggaat caagctgagt aaattttct    7920 caatgctgca aaacttacat aaaacgtttc cttttagaa gccagaacaa gtttcgagaa    7980
gaacacagtt aatggagcgt tgggctagat gggaggtaac cagagaatat cctttatctc    8040
catcatgcaa tttcattttg ttcccttgaa taacatctgg cagtaactct cgctggatac    8100
tttgcatctt ttctgcagat cagcaatttt gagtacttaa tgcagctcaa cacattggct    8160
gggcgtagtt ataatgacat cactcaggta atctcgtgc tagttaaaat gttttttctt    8220
ataatctttg atatcatttt ctctttggtt atcttgatct attttcata tctttgcagt    8280 atcctatttt cccatggatt ttatgcgact atgtatcaga aattttggac ctatcaaatc    8340
catctaatta cagggatctt tccaaggtgg tattattagt aatttattat tagtagtttt    8400
tcgctttatg cttgcctata gttatccata aacctataaa actggttgta atgtggatcc    8460
gtatatgttc agccaattgg tgcactgaac ccggagcggc tgaaaaagtt tcaagaaaaa    8520
cactctagct tgaagatcc agtcatcccc aaatttcatt atggttcaca ttactcaagt    8580
gctggagcag taagttatct tctctatgat atctgccata gttttatca tttcttctct    8640 tacattttct tcgtttaaa actctgttcc tcctatcacc aaagaaagac aataattagt    8700
attttgattt gcaagaggat agagttttca ctaaatacta atgatggtct ataaatttgt    8760
tatttcttgt gtgtaggtgt tgcattatct agctagagtc gaaccttta caacccttc    8820 gattcaactg caaggtagaa agtttgatcg tgcagaccaa atattttcag acattgcagc    8880
cacttggaaa ggagttctcc aagatatgaa taatgtgaag gagttggtaa gacttggttc    8940
```

| | |
|---|---:|
| ctcccaaaaa cattcaaacg agtatccata atcgccgtcc tttgctttgc aagtgaagag | 9000 |
| cctagccata tttattttgc ttcctcattt tcgtatatta tacgaccatc tatctttagg | 9060 |
| gtttatgaac ttacggacaa acccggaatt gttcaaaagt ttcaggaaaa tttattgcaa | 9120 |
| atggtaaatt cagtttgtct ttggcgtttt agttacattc gttttttcatg gtatcaacat | 9180 |
| taatgtgatt ttttttattt acagaacaca actgatccaa acactcacat ggtctcaagc | 9240 |
| ttttcaaacc caactaccag cgaggtttgc tactgaataa gcattagata dacaacaaat | 9300 |
| ttcatttagg gataagtaat tatttttggtg atatcttttt tagactgaac ctgattcaga | 9360 |
| catgaacatt gtctctaccc cttcaaatgc aactacaaat caggtaataa ctctaacgtt | 9420 |
| ccattacatt taattttcaa gtgcttatgt attttaaaat tttgaatttt attttttgttt | 9480 |
| agattgacac tgaatcttcc gaggcggcta actatgaaaa cagcaactcg tctatcaaga | 9540 |
| cttctaagaa cacttcaaag atcactaaat tgaccccgac gtcaaaacga tcactaactt | 9600 |
| catcgaaaga taatgcagct caaaagtcat ctacaaagcc taaattgttg tccaaggctg | 9660 |
| agataataaa ggttgatgtt tattcgtata ttatgagttt atag | 9704 |

<210> SEQ ID NO 27
<211> LENGTH: 1926
<212> TYPE: DNA
<213> ORGANISM: Arabidopsis thaliana

<400> SEQUENCE: 27

| | |
|---|---:|
| aaggaaggag tcgaagataa gcggagagag agagagagac agagagagat tcaaaaatcc | 60 |
| gattccagat ccattcctgg gcaaacaaag gttggtgttt ctctaatctc aaagcttttt | 120 |
| tcaaattcgg aaaaagcaaa tcgtgggaag agattcatct tctctctgtg cgttcatcgg | 180 |
| atctcggagc ttttggttcg tcgtcaatgg cggaagagac ggagaaaaag tacattacga | 240 |
| acgaagatct taaaaaacac aacaaatctg gagatctatg gatcgcgatt caaggcaagg | 300 |
| tctacaacgt ctccgattgg attaaaaactc atcccggagg cgacacggtg attctcaatc | 360 |
| tcgttggtca agacgtcacc gatgctttca tcgcatttca tcccggaacc gcttggcacc | 420 |
| atctcgacca tctcttcacc ggttaccaca tcagagattt ccaagtctcc gaagtctcac | 480 |
| gcgattaccg tcgtatggct gccgagtttc gtaaaactcgg tctcttcgaa aacaaaggtc | 540 |
| acgttactct ctacactcta gccttcgtcg ccgccatgtt cctcggagtt ctctacggtg | 600 |
| ttttggcttg tacctccgtc ttcgctcacc aaatcgccgc cgcgcttctc ggtctcctct | 660 |
| ggatccagag cgcttacata ggtcacgatt ctggtcatta cgttatcatg tcgaacaaat | 720 |
| cttataacag attcgctcag cttctctccg gtaactgtct caccggaatc tcaatcgcgt | 780 |
| ggtggaaatg gactcacaat gctcatcatc tagcttgtaa cagcctcgat tacgatccag | 840 |
| atctacaaca catccctgtc ttcgccgtct ccaccaaatt cttctcctca ttgacctcga | 900 |
| gattctacga tcggaaactc acgtttgatc cagtcgcgag attcttagtc agctatcaac | 960 |
| actttactta ttatccagtt atgtgctttg gaagaatcaa tctcttcatt caaacgtttc | 1020 |
| tcttgctctt ctccaaacgt gaagtaccag atcgtgcttt aaacttcgcc ggaatcttag | 1080 |
| tcttctggac ttggttccca ctcttagtct catgtctacc aaactggcct gagagattct | 1140 |
| tcttcgtctt cacaagcttc accgtcacgg cgcttcaaca cattcaattc acgcttaacc | 1200 |
| atttcgctgc tgatgtctac gttggtccac ccaccggtag cgactggttc gagaagcaag | 1260 |
| cggcgggaac aatcgatatc tcttgtagat catacatgga ttggttcttt ggtggattac | 1320 |
| agtttcagct tgagcatcat ttgttccctc gcttacctcg ttgccatctc cggaaagttt | 1380 |

```
ctccggtggt tcaagagctt tgcaagaagc ataatcttcc gtataggagt atgtcgtggt    1440
ttgaagcaaa tgtgttgacc attaacactt tgaagacagc agcttatcaa gctagagacg    1500
tggctaatcc ggtggttaag aacttggttt gggaagcttt gaatactcat ggctaaatga    1560
ttttaatcaa aacaaaatat gcttttgttt gggttaaatt tgatgtgttg tttttatgct    1620
ttattgaatc tttgaatttc gttttgttac ttacttacat ggaagagatg ttttagatcg    1680
aaattgaatc gagatttgat tttttatta gacaactctt cgtatcgtaa tgatttatta    1740
ataatattat tttgaattta atttgttttt ttatataagt ttttgtttca catggctctt    1800
ttttgttgcc tgtgacttac tttgtggttt tgcggctttt ggccttttca atgttttgtc    1860
gtgttacatt aaaatacgtg tgtggatgct atttgagatc ctctatatgt aaggttttaa    1920
cagatc                                                                1926
```

ARABIDOPSIS NONHOST RESISTANCE GENE(S) AND USE THEREOF TO ENGINEER DISEASE RESISTANT PLANTS

CROSS-REFERENCE TO RELATED APPLICATIONS

This application claims priority under 35 U.S.C. § 119 to provisional application Ser. No. 61/651,149 filed May 24, 2012, herein incorporated by reference in its entirety.

GRANT REFERENCE

This invention was made with government support under Grant No. DE-FG36-02GO12026 awarded by DOE. The government has certain rights in the invention.

FIELD OF THE INVENTION

The present invention is in the field of plant genetics. More specifically, the invention relates to nucleic acid molecules from regions of the *Arabidopsis* genome which are associated with nonhost pathogen resistance, particularly to *Phytophthora* spp. and *Fusarium virguliforme*. The invention also relates to proteins encoded by such nucleic acid molecules as well as nucleic acid markers which are associated with *Phytophthora* resistance. Moreover, the invention relates to uses of such molecules, including, transforming *Phytophthora* and *Fusarium* susceptible plants with constructs containing the nucleic acid molecules to create transgenic plants with *Phytophthora* and *Fusarium* resistance and the use of such molecules, transformed cells, plants and plant parts in a plant breeding program.

BACKGROUND OF THE INVENTION

Soybean [*Glycine max* L. (Merrill)] is a major oil seed crop and is grown throughout much of the world. The United States alone produces over half of the world output. Soybean seed typically contains 40% protein and 20% oil and is used primarily for livestock feed and industrial purposes, in addition to human consumption. In North America, soybean suffers yield loss from the root and stem rot disease caused by oomycete pathogen *Phytophthora sojae*. *Phytophthora sojae* (Kauffman & Gerdemann) is an oomycete pathogen which causes extensive damage to roots and stems of soybean plants (*Glycine max*) (Zhang et al., MPMI, 19:1302-1310 (2006)). Symptoms of *Phytophthora* Root Rot (PRR) caused by *P. sojae* include yellowing and wilting of leaves and browning of lower stems and branches (Demirbas et al., Crop Sci. 41:1220-1227 (2001)). In the United States the annual crop losses from this disease were valued to about 0.2-0.3 billion dollars (Wrather et al. 2001) Annual worldwide soybean crop losses amount to $1 to $2 billion (Zhang et al., MPMI, 19: 1302-1310 (2006)). Plant resistance to this and other sort of pathogens present a major problem to soybean growers.

Resistance generally means the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host dies off. An incompatible interaction occurs on the other hand when the pathogen infects the plant but is inhibited in its growth before or after weak development of symptoms. In the latter case, the plant is resistant to the respective pathogen (Schopfer and Brennick, vide supra). In both compatible and incompatible interactions a defensive and specific reaction of the host to the pathogen occurs.

In nature, however, this host resistance is often overcome because of the rapid evolutionary development of pathogens (Neu et al. (2003) American Cytopathol. Society, MPMI 16 No. 7: 626-633). In contrast, non-host resistance offers strong, broad, and permanent protection from phytopathogens. Non-host resistance relates to the phenomenon where a pathogen can induce a disease in a certain plant species, but not in other plant species (Heath (2002) Can. J. Plant Pathol. 24: 259-264).

Despite this interesting characteristic, the genetic and molecular biological basis for nonhost resistance have up to now only been poorly understood. There are indications that non-host resistance is induced by unspecific agents, and also that individual pathogen proteins induce the non-host resistance reaction (Heath (1981) Phytopathology 71: 1121-1123; Heath (2001) Physiol. Mol. Plant. Pathol. 58: 53-54; Kamoun et al. (1998) Plant Cell 10: 1413-1425; Lauge et al. (2000) Plant J. 23: 735-745; Whalen et al. (1988) Proc. Natl. Acad. Sci. USA 85: 6743-6747). The phenomenon of non-host resistance might also be based on structural or chemical properties of the plant species, such as the thickness of the cuticle or the presence of inhibitory substances.

It is an object of the present invention to use non-host resistance in *Arabidopsis* to engineer resistance to susceptible host plants against *Phytophthora* and *Fusarium*.

Other objects will become apparent from the description of the invention which follows.

SUMMARY OF THE INVENTION

In one aspect, this invention relates to nucleic acid isolated from *Arabidopsis thaliana* which are associated with its non-host resistance to *Phytophthora*. Also according to the invention, protein sequences are disclosed which are encoded by the same. These sequences alone, or in combination with other sequences, can be used to improve the resistance in susceptible plant species such as soybean to *Phytophthora*. In another aspect of the present invention, expression cassettes and transformation vectors comprising the isolated nucleotide sequences are disclosed. The transformation vectors can be used to transform plants and express these pathogen non host resistance genes in the transformed cells. Transformed cells as well as regenerated transgenic plants and seeds containing and expressing the isolated DNA sequences and protein products are also provided.

Therefore, in one aspect, the present invention relates to an isolated nucleic acid comprising an isolated polynucleotide sequence encoding a non-host resistance gene product isolated from Arabeopsis that confers its non-host resistance. Several non-host resistance genes have been identified according to the invention, including At5g64600 (O-fucosyltrasnferase protein) (SEQ ID NOS: 1, 2, and 19); At5g65900 (DEAD-box ATP-dependent RNA helicase 27)

(SEQ ID NOS 3, 4, and 20); At5g66380 (folate transporter 1, or FOLT1) (SEQ ID NOS: 3, 4, and 21); At3g59640 (glycine-rich protein) (SEQ ID NOS 7, 8, and 22); At3g59650 (mitochondrial ribosomal protein L51/S25/Cl-B8 protein) (SEQ ID NOS 9, 10, and 23); At3g60310 (protein of unknown function) (SEQ ID NOS 11. 12. And 24); At3g60840 (MAP65-4, microtubule-associated protein 65-4) (SEQ ID NOs:13, 14, and 25; At3g60920 (protein of unknown function) (SEQ ID NOS:15, 16, and 26); At3g61580 (fatty acid/spingolipid desaturase) (SEQ ID NOS:17, 18 and 27). Sequences reported above are non-limiting examples of potential coding sequences of these genes recited herein and are reported as CDS, amino acid, and genomic respectively.

In a further aspect, the present invention includes a nucleic acid selected from: (a) an isolated polynucleotide encoding a polypeptide of the present invention; (b) a polynucleotide having at least 90% or 95% identity to a polynucleotide of the present invention; (c) a polynucleotide comprising at least 50 or more nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (e). The present invention includes and provides a method of investigating an haplotype of a plant comprising: (A) isolating nucleic acid molecules from the plant; (B) determining the nucleic acid sequence of a nonhost resistance gene; and, (C) comparing the nucleic acid sequence of the allele or part thereof to a reference nucleic acid sequence. The present invention includes and provides a method of introgressing *Phytophthora* resistance or partial *Phytophthora* resistance into a susceptible plant comprising: performing marker assisted selection of the plant with a nucleic acid marker, wherein the nucleic acid marker specifically hybridizes with a nucleic acid molecule encoding a non host resistance gene reported herein and, selecting the plant based on the marker assisted selection.

The present invention includes and provides a method of investigating a nonhost *Phytoptora* and *Fusarium* resistance haplotype of a plant comprising: (A) isolating nucleic acid molecules from the plant; (B) determining the nucleic acid sequence of an nonhost resistance allele or part thereof; and (C) comparing the nucleic acid sequence of the allele or part thereof to a reference nucleic acid sequence.

In another aspect, the present invention relates to a recombinant expression cassette comprising a nucleic acid as described, supra. Additionally, the present invention relates to a vector containing the recombinant expression cassette. Further, the vector containing the recombinant expression cassette can facilitate the transcription and translation of the nucleic acid in a host cell. The present invention also relates to host cells able to express the polynucleotide of the present invention. A number of host cells could be used, such as but not limited to, microbial, mammalian, plant, or insect. Thus the invention is also directed to transgenic cells, containing the nucleic acids of the present invention as well as cells, plants, tissue cultures and ultimately lines derived therefrom. The invention also relates to vectors and cassettes designed to introduce the expression of nonhost resistance proteins for modulation of the *Phytophthora* interaction, or for delineation of information about the regulatory pathways involving the same.

This invention also provides an isolated polypeptide comprising (a) a polypeptide comprising at least 90% or 95% sequence identity to a polypeptide of the present invention (b) a polypeptide encoded by a nucleic acid of the present invention; and (c) a polypeptide comprising a nonhost resistance activity and comprising conserved structural domain motifs of the same.

Another embodiment of the subject invention comprises methods for engineering broad-spectrum pathogen resistance in soybean or other *Phytophthora* susceptible crop plants by introducing nonhost resistance protein encoding sequences to said plants. Plants' tolerance to *Phytophthora* and other soybean pathogens may be improved by elucidating the pathways that regulate gene transcription involved in enhancing accumulation of products shown to be associated with expression of other pathogen resistance, methods for providing for increased nonspecific resistance to particularly virulent races or strains of pathogenic agents including *P. sojae*, *Pseudomonas syringae* pv. *glycenia* (*Psg*), soybean cyst nematode (SCN), *Fusarium virguliforme* or soybean mosaic virus.

Nucleotide sequences isolated from the nonhost resistance genes which may be introduced to plants can be used in developing perfect molecular markers that can be routinely used in breeding programs for incorporating *Phytophthora* resistance into new cultivars.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989)).

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN AUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, the term "nonhost resistance protein" shall include any amino acid sequence which retain one or more of the properties of proteins listed herein in general. They also must be capable of interacting with *Phytophthora* infection in that loss of function mutations can render an *Arabidopsis* plant susceptible to *Phytophthora* infection. Such proteins may include At5g64600 (O-fucosyltrasnferase protein) (SEQ ID NOS: 1, 2, and 19); At5g65900 (DEAD-box ATP-dependant RNA helicase 27) (SEQ ID NOS 3, 4, and 20); At5g66380 (folate transporter 1, or FOLT1) (SEQ ID NOS: 3, 4, and 21); At3g59640 (glycine-rich protein) (SEQ ID NOS:7, 8, and 22); At3g59650 (mitochondrial ribosomal protein L51/S25/Cl-B8 protein) (SEQ ID NOS:9, 10, and 23); At3g60310 (protein of unknown function) (SEQ ID NOS: 11, 12, and 24); At3g60840 (MAP65-4, microtubule-associated protein 65-4) (SEQ ID NOS:13, 14, and 25; At3g60920 (protein of unknown function) (SEQ ID NOS: 15, 16, and 26); At3g61580 (fatty acid/spingolipid desaturase) (SEQ ID NOS:17, 18 and 27) and any conservatively modified variants, fragments, and homologs or full length sequences incorporating the same which retain the *Phyphthora* infection related activity described herein. Nonhost resistance proteins are capable of suppressing, controlling, and/or preventing invasion by the pathogenic organism. A non host resistance protein will reduce the disease symptoms resulting from pathogen challenge in a previously susceptible plant by at least about 2%, including but not limited to, about 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater. In particular embodiments, the disease symptoms resulting from pathogen challenge are reduced by non host resistance protein by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. Resistance may vary from a slight increase in tolerance to the effects of the pathogen (e.g., partial inhibition) to total resistance such that the plant is unaffected by the presence of the pathogen. An increased level of resistance against a particular pathogen or against a wider spectrum of pathogens may both constitute complete resistance or improved resistance.

"Pathogen resistance", "disease resistance" or "*Phytophthora* resistance" is intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an non host resistance polypeptide shows a decrease in tissue necrosis (i.e., lesion diameter) or a decrease in plant death following pathogen challenge when compared to a control plant that was not engineered to express the nonhost resistance protein.

Alternatively, antipathogenic activity can be measured by a decrease in pathogen biomass. For example, a plant expressing non host resistance protein is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) Plant Biology 95:15107-15111, herein incorporated by reference. According to the invention, the term "increased resistance" (against *Phytophthora* sp.) is understood to mean that the transgenic plants, or plant cells, according to the invention are less vigorously, and/or less frequently, affected by *Phytophthora* than non-transformed wild type plants, or plant cells, which were otherwise treated in the same way (such as climate and cultivation conditions, pathogen type, etc.). According to the invention, the term "wild type" is to be understood as the respective non genetically modified parent organism. The penetration efficiency as well as the rate of papillae formation offer a possibility to quantify the reaction of the plant to the pathogen infestation (see examples). The term "increased resistance" also comprises what is known as transient pathogen resistance, i.e. the transgenic plants, or plant cells, according to the invention have an increased pathogen resistance as compared to the respective wild type only for a limited period of time.

By "nucleic acid library" is meant a collection of isolated DNA or cDNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, $2^{nd}$ ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley, and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C. for 20 minutes.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995). In general a high stringency wash is 2×15 min in 0.5×SSC containing 0.1% SDS at 65° C.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information World Wide Web at ncbi.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) The terms "substantial Identity" in the context of a peptide indicates that a peptide comprises a sequence with at least 70% sequence identity to a reference sequence, preferably 80%, or preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DESCRIPTION OF THE FIGURES

FIG. 6 shows the sequence of 2582739.
FIG. 7 (A-B) shows the sequence of 2638667.
FIG. 8 shows the sequence of 26514954 and 26515178.
FIG. 9 (A-Z) shows the sequences from At5g64600.

Transgenic plants from two separate transformation events, ST154-13 and ST154-21, were inoculated with *P. sojae* zoospores ($10^5$ spores/mL) from three different *P. sojae* isolates, CC5C, R1005 and R25. Two unifoliate leaves from 12-day old seedlings were inoculated with a 15 µl zoospores drop/isolate/leaf and lesion lengths were recorded 3-day post inoculation (dpi) and 4 dpi. Plants from both transgenic events showed significantly reduced disease lesion against all three *P. sojae* isolates as compared to the wild type, Williams 82 plants. The experiment was conducted two times with similar results. Error bars indicate SE.

Figure 13:
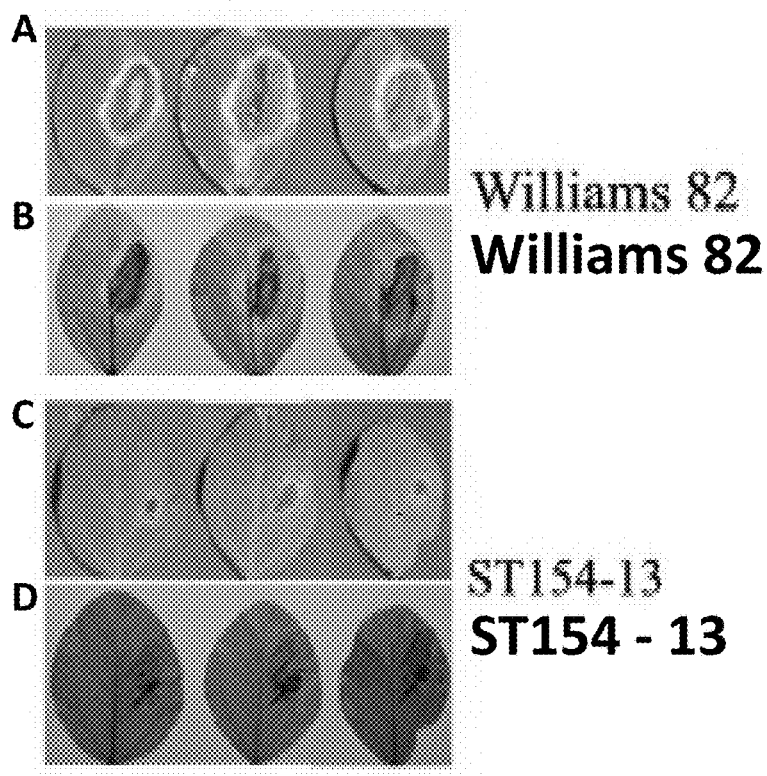

FIG. 13 (A-D) shows leaves of transgenic soybean Williams 82 plants carrying the GRP1 gene showed resistance to *F. virguliforme*. The central leaflet of the trifoliate ($3^{rd}$ from top opened leaf) of 26-day old soybean plants were wounded with carborundum powder and then inoculated with the conidial spores of *Fusarium virguliforme* (15 µl from $10^7$ spores/mL) that causes sudden death syndrome in soybean. Bleaching of the leaves was performed by dipping the infected leaf in 80% ethanol at 50° C. for 2 days. A shows leaves of the nontransgenic soybean cultivar, Williams 82 were susceptible to the pathogen. B shows leaves shown in A following bleaching with 80% alcohol. Note that the white area at the advancing region of the lesions was the chlorotic (yellow hallow) caused presumably by pathogen toxins. C shows the transgenic soybean leaves carrying the *Arabidopsis* GRP1 gene provides resistance against the pathogen. D shows leaves of C following bleaching with 80% alcohol show necrotic lesions of the resistant response. Images shown are representatives of inoculated leaves from three biological replications.

Figure 14:
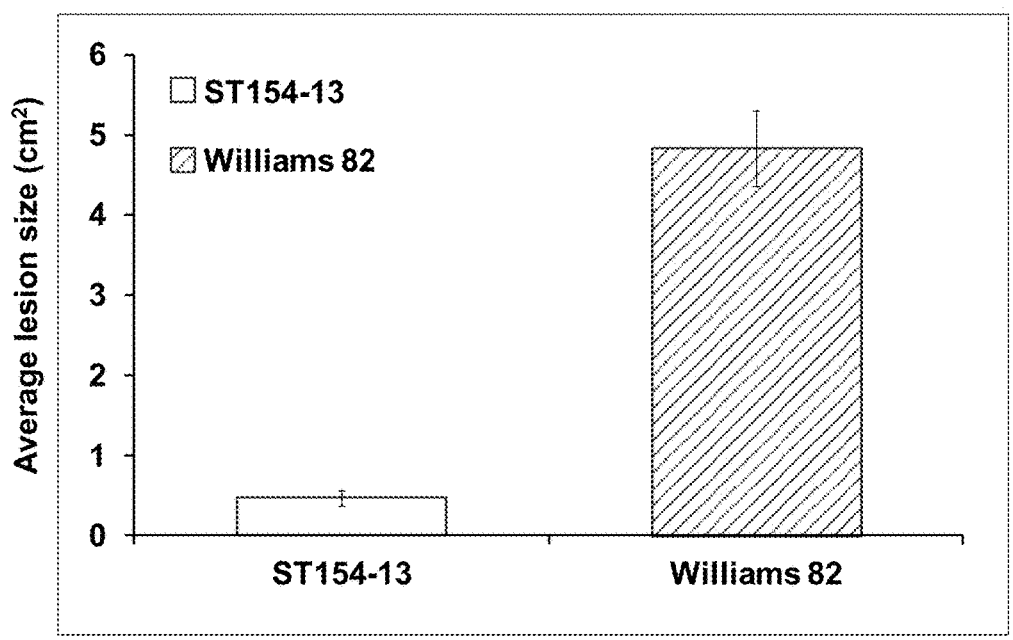

FIG. 14 shows *Arabidopsis* GRP1 suppressed the lesion development in *F. virguliforme*-infected leaves of the transgenic soybean lines. The central leaflet of the unifoliate ($3^{rd}$ from top opened leaf) of 26-day old soybean plants were wounded with carborundum powder and infected with the *Fusarium virguliforme* conidial spores (15 µl from $10^7$ spores/mL). Data presented are the average area of the disease spread at the wounded sites. Williams 82, the non-transgenic Williams 82 was used as the negative control. ST154-13, the soybean transgenic line carries *Arabidopsis* GRP1.

DETAILED DESCRIPTION OF THE INVENTION

The present invention provides, inter alia, compositions and methods for promoting pathogen resistance in plants, more particularly for improving *Phytophthora* resistance of susceptible plants. The compositions of the invention relate to the nonhost resistance gens identified from *Arabidopsis* which when mutated resulted in an increase in *Phytophthora* sojae susceptibility. Thus, these genes confer nonhost pathogen resistance of *Arabidopsis* and as such may be used to confer resistance in susceptible plant species such as soybean. Thus the genes and proteins identified here introduced or modulated to confer improved *Phytophthora* resistance in plants. These compositions can be transferred into plants to confer or improve *Phytophthora* resistance, modified to engineer gene sequences for broad based nonspecific resistance in plants, or to isolate and identify alternate gene forms and markers which may be used in breeding regimes. By "confer or improve *Phytophthora* or other such pathogen resistance" is intended that the proteins or sequences, either alone or in combination with other proteins or sequences, enhance resistance of a plant to *Phytophthora* and *Phytophthora*-caused damage or to other pathogens which cause a similar plant reaction. In this manner, resistance to these fungal pathogens and other pathogens such as *Pseudomonas syringae* pv. *glycinea* (Psg), soybean cyst nematode (SCN), or soybean mosaic virus (SMV), *Fusarium virguliforme* can be enhanced or improved in the transformed plant or its progeny when at least one of the sequences of the invention is introduced to a susceptible plant or otherwise modulated according to the invention.

The compositions include nucleic acid molecules comprising sequences of plant genes and the polypeptides encoded thereby which are associated with nonhost disease resistance against *Phytophthora* in *Arabidopsis* have been identified. Particularly, the nucleotide and amino acid sequences for At5g64600 (O-fucosyltrasnferase protein) (SEQ ID NOS: 1, 2, and 19); At5g65900 (DEAD-box ATP-dependant RNA helicase 27) (SEQ ID NOS 3, 4, and 20); At5g66380 (folate transporter 1, or FOLT1) (SEQ ID NOS: 3, 4, and 21); At3g59640 (glycine-rich protein) (SEQ ID NOS 7, 8, and 22); At3g59650 (mitochondrial ribosomal protein L51/S25/Cl-B8 protein) (SEQ ID NOS 9, 10, and 23); At3g60310 (protein of unknown function) (SEQ ID NOS 11. 12. And 24); At3g60840 (MAP65-4, microtubule-associated protein 65-4) (SEQ ID NOs:13, 14, and 25; At3g60920 (protein of unknown function) (SEQ ID NOS: 15, 16, and 26); At3g61580 (fatty acid/spingolipid desaturase) (SEQ ID NOS:17, 18 and 27) and any conservatively modified variants, fragments, and homologs or full length sequences incorporating the same which retain the *Phytophthora* infection related activity described herein are part of the invention.

As discussed in more detail below, the sequences of the invention are presumably involved in many basic biochemical pathways that regulate plant pathogen resistance. Thus, methods are provided for the introduction or modulation of these sequences in a susceptible host plant to improve plant defense responses. Some of the methods involve stably transforming a plant with a nucleotide sequence of the invention operably linked with a promoter capable of driving expression of a gene in a plant cell other methods may involve inhibition of the same sequences to confer improved pathogen resistance in a particular plant.

Promoter and other regulatory elements which are natively associated with these genes can be easily isolated using the sequences and methods described herein with no more than routine experimentation. These sequences can also be used to identify promoter, enhancer or other signaling sequences in the regulatory regions of non host resistance genes. Such regulatory elements or promoters would provide for temporal and spatial expression of operably linked sequences with pathogen infection in a plant. Nucleotide sequences operably linked to such promoter sequences are transformed into a plant cell. Exposure of the transformed plant to a stimulus such as pathogen infection could induce transcriptional activation of the nucleotide sequences operably linked to these promoter regulatory sequences.

Transformed plants can be obtained having altered or enhanced responses to *Phytophthora* attack; hence, the methods and compositions may find uses in altering the response of plants to similar stresses as well. Thus, the sequences of the invention find use in engineering broad-spectrum disease and pest resistance in a variety of plants. It is within the skill in the art to assay protein activities obtained from various sources to determine whether the properties of the proteins are the same. In so doing, one of skill in the art may employ any of a wide array of known assays including, for example, biochemical and/or pathological assays. For example, one of skill in the art could readily produce a plant transformed with a non host resistance protein variant and assay a property of the native protein in that plant material to determine whether a particular property was retained by the variant.

The compositions and methods of the invention are presumably involved in biochemical pathways and as such may also find use in the activation or modulation of expression of other genes, including those involved in other aspects of pathogen defense and response.

By "modulating" or "modulation" is intended that the level of expression of a gene may be increased or decreased relative to genes driven by other promoters or relative to the normal or uninduced level of the gene in question.

The present invention provides for isolated nucleic acid molecules comprising nucleotide sequences encoding the amino acid sequence herein: At5g64600 (O-fucosyltrasnferase protein) (SEQ ID NOS: 1, 2, and 19); At5g65900 (DEAD-box ATP-dependant RNA helicase 27) (SEQ ID NOS 3, 4, and 20); At5g66380 (folate transporter 1, or FOLT1) (SEQ ID NOS: 3, 4, and 21); At3g59640 (glycine-rich protein) (SEQ ID NOS 7, 8, and 22); At3g59650 (mitochondrial ribosomal protein L51/S25/Cl-B8 protein) (SEQ ID NOS 9, 10, and 23); At3g60310 (protein of unknown function) (SEQ ID NOS 11. 12. And 24); At3g60840 (MAP65-4, microtubule-associated protein 65-4) (SEQ ID NOs:13, 14, and 25; At3g60920 (protein of unknown function) (SEQ ID NOS:15, 16, and 26); At3g61580 (fatty acid/spingolipid desaturase) (SEQ ID NOS:17, 18 and 27) and any conservatively modified variants, fragments, and homologs or full length sequences incorporating the same which retain the *Phyphthora* infection related activity described herein. Further provided are polypeptides having an amino acid sequence encoded by a nucleic acid molecule described herein, for example those polypeptides comprising the sequences set forth in the herein, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In some embodiments, an "isolated" nucleic acid is free of sequences (such as other protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.4 kb, 0.3 kb, 0.2 kb, or 0.1 kb, or 50, 40, 30, 20, or 10 nucleotides that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, culture medium may represent less than about 30%, 20%, 10%, or 5% (by dry weight) of chemical precursors or non-protein-of-interest chemicals.

Fragments and variants of the disclosed nucleotide sequences are encompassed by the present invention. Fragments and variants of proteins encoded by the disclosed nucleotide sequences are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect development, developmental pathways, stress responses, and/or disease resistance by retaining Non host resistance-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a non host resistance nucleotide sequence that encodes a biologically active portion of a non host resistance protein of the invention will encode at least 12, 25, 30, 50, 75, etc. contiguous amino acids, or up to the total number of amino acids present in a full-length non host resistance protein of the invention.

Fragments of a non host resistance nucleotide sequence that are useful as hybridization probes or PCR primers generally may or may not encode a biologically active portion of a protein. Thus, a fragment of a non host resistance protein nucleotide sequence may encode a biologically active portion of a non host resistance protein, or it may be used as a hybridization probe or PCR primer using methods disclosed below. A biologically active portion of a non host resistance protein can be prepared by isolating a portion of the Non host resistance nucleotide sequences of the invention, expressing the encoded portion of the Non host resistance protein (e.g., by recombinant expression in vitro), and assessing the activity of the encoded portion of the Non host resistance protein. Nucleic acid molecules that are fragments of a Non host resistance nucleotide sequence comprise at least 16, 20, 25, 30, 40, 50, 60, 70, 80, 90, 100, 125, 150, 175, 200, etc. nucleotides, or up to the number of nucleotides present in a full-length Non host resistance nucleotide sequences disclosed herein.

The proteins of the invention may be altered in various ways including amino acid substitutions, deletions, truncations, and insertions. Methods for such manipulations are generally known in the art. For example, amino acid sequence variants of the Non host resistance proteins can be prepared by mutations in the DNA. Methods for mutagenesis and nucleotide sequence alterations are well known in the art. See, for example, Kunkel (1985) *Proc. Nat. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

It is recognized that having identified the nucleotide sequences disclosed herein, it is within the state of the art to isolate and identify regulatory elements in the 5' untranslated region upstream from regions defined herein. Thus for example, the promoter regions of the gene sequences disclosed herein may further comprise upstream regulatory elements that confer tissue-preferred expression of heterologous nucleotide sequences operably linked to the disclosed promoter sequence. See particularly, Australian Patent No. AU-A-77751/94 and U.S. Pat. Nos. 5,466,785 and 5,635, 618. It is also recognized by those of skill in the art that regulatory elements may be found in transcribed regions of a gene, for example in the region between transcription start and translation start as well as 3' to the end of translation; such elements may be found in the sequences set forth herein.

The nucleotide sequences of the invention can be used to isolate corresponding sequences from other organisms, particularly other plants, more particularly other crop plants. In this manner, methods such as PCR, hybridization, and the like can be used to identify such sequences based on their sequence homology to the sequences set forth herein. Sequences isolated based on their sequence identity to the nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have Non host resistance-like activity or and which hybridize under stringent conditions to the Non host resistance sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present it a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the disease-resistant sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire sequence disclosed herein, or one or more portions thereof, may be used as a probe capable of specifically hybridizing to corresponding *Phytophthora*-response sequences, including promoters and messenger RNAs. To achieve specific hybridization under a variety of conditions, such probes include sequences that are unique among *Phytophthora*-response sequences and may be at least about 10 or 15 or 17 nucleotides in length or at least about 20 or 22 or 25 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Assays that measure antipathogenic activity induced by the signal pathway from the sequences herein are commonly known in the art, as are methods to quantitate disease resistance in plants following pathogen infection. See, for example, U.S. Pat. No. 5,614,395, herein incorporated by reference. These assays may be used to measure the activity of the polypeptides of the invention. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic proteins to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference).

Pathogens of the invention include, but are not limited to, fungal and viral pathogens for primarily soybeans which include: *Phytophthora sojae, Macrophomina phaseolina, Rhizoctonia solani, Sclerotinia sclerotiorum, Fusarium virguliformae, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassfcola, Septoria glycines, Phyllosticta sojicola, Alternaria alternate, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus,

*Phakopsora pachyrhizi, Pythium aphanidermatum, Pythium ultimum, Pythium debaryanum,* Tomato spotted wilt virus, *Heterodera glycines.*

It is understood in the art that plant DNA viruses and fungal pathogens remodel the control of the host replication and gene expression machinery to accomplish their own replication and effective infection. The plant response to stress, such as stress caused by *Phytophthora* attack, is known to involve many basic biochemical pathways and cellular functions. Hence, the sequences of the invention may find use in altering the defense mechanisms of a host plant to provide broad-based resistance to disease or insect pests. Additionally, the present invention may be useful in preventing corruption of the cell machinery by viruses and other plant pathogens.

The compositions and methods of the invention function to inhibit or prevent plant diseases. The gene products may accomplish their anti-pathogenic effects by suppressing, controlling, and/or killing the invading pathogenic organism in non host plants and these sequence may then be used to engineer resistance in susceptible plants.

The cells that have been transformed may be grown into plants in accordance with conventional ways. See, for example, McCormick et al. (1986) *Plant Cell Reports* 5:8184. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The invention in one aspect comprises expression constructs comprising a DNA sequence which encodes upon expression an Non host resistance nucleic acid sequence operably linked to a promoter to direct expression of the protein. These constructs are then introduced into plant cells using standard molecular biology techniques. The invention can be also be used for hybrid plant or seed production, once transgenic inbred parental lines have been established.

The methods of the invention described herein may be applicable to any species of plant.

Production of a genetically modified plant tissue either expressing or inhibiting expression of a structural gene combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural gene selection are other parameters which may be optimized to achieve desired plant expression or inhibition as is known to those of skill in the art and taught herein.

The following is a non-limiting general overview of Molecular biology techniques which may be used in performing the methods of the invention.

Promoters

The constructs, promoters or control systems used in the methods of the invention may include a tissue specific promoter, an inducible promoter or a constitutive promoter.

A large number of suitable promoter systems are available. For example one constitutive promoter useful for the invention is the cauliflower mosaic virus (CaMV) 35S. It has been shown to be highly active in many plant organs and during many stages of development when integrated into the genome of transgenic plants and has been shown to confer expression in protoplasts of both dicots and monocots.

Organ-specific promoters are also well known. For example, the E8 promoter is only transcriptionally activated during tomato fruit ripening, and can be used to target gene expression in ripening tomato fruit (Deikman and Fischer, *EMBO J.* (1988) 7:3315; Giovannoni et al., *The Plant Cell* (1989) 1:53). The activity of the E8 promoter is not limited to tomato fruit, but is thought to be compatible with any system wherein ethylene activates biological processes. Similarly the Lipoxegenase ("the LOX gene") is a fruit specific promoter.

Other fruit specific promoters are the 1.45 promoter fragment disclosed in Bird, et al., *Plant Mol. Bio.*, pp 651-663 (1988) and the polygalacturonase promoter from tomato disclosed in U.S. Pat. No. 5,413,937 to Bridges et al.

Leaf specific promoters include as the AS-1 promoter disclosed in U.S. Pat. No. 5,256,558 to Coruzzi and the RBCS-3A promoter isolated from pea the RBCS-3A gene disclosed in U.S. Pat. No. 5,023,179 to Lam et al.

And finally root specific promoters include the CamV 35S promoter disclosed in U.S. Pat. No. 391,725 to Coruzzi et al; the RB7 promoter disclosed in U.S. Pat. No. 5,459,252 to Conking et al and the promoter isolated from *Brassica napus* disclosed in U.S. Pat. No. 5,401,836 to Bazczynski et al. which give root specific expression.

Other examples of promoters include maternal tissue promoters such as seed coat, pericarp and ovule. Promoters highly expressed early in endosperm development are most effective in this application. Of particular interest is the promoter from the a' subunit of the soybean β-conglycinin gene [Walling et al., *Proc. Natl. Acad. Sci. USA* 83:2123-2127 (1986)] which is expressed early in seed development in the endosperm and the embryo.

Further seed specific promoters include the Napin promoter described in U.S. Pat. No. 5,110,728 to Calgene, which describes and discloses the use of the napin promoter in directing the expression to seed tissue of an acyl carrier protein to enhance seed oil production; the DC3 promoter from carrots which is early to mid embryo specific and is disclosed at *Plant Physiology*, October 1992 100(2) p. 576-581, "Hormonal and Environmental Regulation of the Carrot Lea-class Gene Dc 3, and *Plant Mol. Biol.*, April 1992, 18(6) p. 1049-1063, "Transcriptional Regulation of a Seed Specific Carrot Gene, DC 8": the phaseolin promoter described in U.S. Pat. No. 5,504,200 to Mycogen which discloses the gene sequence and regulatory regions for phaseolin, a protein isolated from *P. vulgaris* which is expressed only while the seed is developing within the pod, and only in tissues involved in seed generation.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, Trans. R. Soc. London (1986) B314-343. mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

Another very important method that can be used to identify cell type specific promoters that allow even to identification of genes expressed in a single cell is enhancer detection (O'Kane, C., and Gehring, W. J. (1987), "Detection in situ of genomic regulatory elements in *Drosophila*", *Proc. Natl. Acad. Sci. USA*, 84, 9123-9127). This method was first developed in *Drosophila* and rapidly adapted to mice and plants (Wilson, C., Pearson, R. K., Bellen, H. J., O'Kane, C. J., Grossniklaus, U., and Gehring, W. J. (1989), "P-element-mediated enhancer detection: an efficient method for isolating and characterizing developmentally regulated genes in *Drosophila*", *Genes & Dev.*, 3, 1301-1313; Skarnes, W. C. (1990), "Entrapment vectors: a new tool for mammalian genetics", *Biotechnology*, 8, 827-831; Topping, J. F., Wei, W., and Lindsey, K. (1991), "Functional tagging of regulatory elements in the plant genome", *Development*, 112, 1009-1019; Sundaresan, V., Springer, P. S., Volpe, T., Haward, S., Jones, J. D. G., Dean, C., Ma, H., and Martienssen, R. A., (1995), "Patterns of gene action in plant development revealed by enhancer trap and gene trap transposable elements", *Genes & Dev.*, 9, 1797-1810).

The promoter used in the method of the invention may be an inducible promoter. An inducible promoter is a promoter that is capable of directly or indirectly activating transcription of a DNA sequence in response to an inducer. In the absence of an inducer, the DNA sequence will not be transcribed. Typically, the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 kd heat shock promoter of *D. melanogaster* (Freeling, M., Bennet, D. C., Maize ADN 1, *Ann. Rev. of Genetics*, 19:297-323) and the alcohol dehydrogenase promoter which is induced by ethanol (Nagao, R. T., et al., Miflin, B. J., Ed. Oxford Surveys of Plant Molecular and Cell Biology, Vol. 3, p. 384-438, Oxford University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecule(s).

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl-=2-chloro-4-(trifluoromethyl)-5-thiazolecarboxylate (common name: flurazole). In addition, a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

The preferred promoters may be used in conjunction with naturally occurring flanking coding or transcribed sequences of the feronia regulatory genes or with any other coding or transcribed sequence that is critical to pollin tube formation and/or fertilization.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to female gametophyte development and/or function.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements.

Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium* octopine synthase signal (Gielen et al., *EMBO J.* (1984) 3:835-846) or the nopaline synthase signal (Depicker et al., *Mol. and Appl. Genet.* (1982) 1:561-573).

Marker Genes

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8: 238 (1989). See also, U.S. Pat. No. 5,563,055, (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 m. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559-563 (1988), Sanford, J. C., *Physiol Plant* 79: 206 (1990), Klein et al., *Biotechnology* 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.*, 4: 2731 (1985), Christou et al., *Proc Natl. Acad. Sci. U.S.A.* 84: 3962 (1987). Direct uptake of DNA into protoplasts using $CaCl_2$ precipitation, polyvinyl alcohol or poly-L-ornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495-1505 (1992) and Spencer et al., *Plant Mol. Biol.* 24: 51-61 (1994).

Following transformation of target tissues, expression of the above-described selectable marker genes allows for preferential selection of transformed cells, tissues and/or plants, using regeneration and selection methods now well known in the art.

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

The transformed cells may then be regenerated into a transgenic plant. The regenerated plants are transferred to standard soil conditions and cultivated in a conventional manner.

After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species this is accomplished rather easily by the use of another culture or isolated microspore culture. This is especially true for the oil seed crop *Brassica napus* (Keller and Armstrong, Z. flanzenzucht 80:100-108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

Molecular Markers

The present invention provides a method of genotyping a plant comprising a heterologous polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Clark, Ed., Plant Molecular Biology: A Laboratory Manual. Berlin, Springer Verlag, 1997. Chapter 7. For molecular marker methods, see generally, "The DNA Revolution" in: Paterson, A. H., Genome Mapping in Plants (Austin, Tex., Academic Press/R. G. Landis Company, 1996) pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed.

Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention.

Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5'UTR) of the RNA. Positive sequence motifs include translational initiation consensus sequences (Kozak, Nucleic Acids Res. 15: 8125 (1987)) and the 7-methylguanosine cap structure (Drummond et al., *Nucleic Acids Res.* 13: 7375 (1985)). Negative elements include stable intramolecular 5'UTR stem-loop structures (Muesing et al., Cell 48: 691 (1987)) and AUG sequences or short open reading frames preceded by an appropriate AUG in the 5'UTR (Kozak, supra, Rao et al., Mol. and Cell. Biol. 8: 284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., Nucleic Acids Res. 12: 387-395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.-H., et al. Proc. Natl. Acad. Sci. USA 94: 4504-4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased Km and/or increased KCat over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms.

Alternatively, a polynucleotide having a consensus sequence generated from orthologous genes can be used to identify or isolate orthologs of other taxa. Typically, a polynucleotide having a consensus sequence will be at least 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of Current Protocols in Molecular Biology, F. M. Ausubel et al., Eds., Current Protocols, a joint venture between Greene Publishing Associates, Inc. and John Wiley & Sons, Inc. (Supplement 30).

A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Use in Breeding Methods

The transformed plants of the invention may be used in a plant breeding program. The goal of plant breeding is to combine, in a single variety or hybrid, various desirable traits. For field crops, these traits may include, for example, resistance to diseases and insects, tolerance to heat and drought, reduced time to crop maturity, greater yield, and better agronomic quality. With mechanical harvesting of many crops, uniformity of plant characteristics such as germination and stand establishment, growth rate, maturity, and plant height is desirable. Traditional plant breeding is an important tool in developing new and improved commercial crops. This invention encompasses methods for producing a plant by crossing a first parent plant with a second parent plant wherein one or both of the parent plants is a transformed plant according to the invention displaying *Phytophthora* resistance as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids, and transformation. Often combinations of these techniques are used.

The development of hybrids in a plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation, then the transgenic plants could be crossed to a different inbred in order to produce a transgenic hybrid plant. As used herein, "crossing" can refer to a simple X by Y cross, or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly uniform; and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are offered by way of illustration and not by way of limitation.

Example 1

Five *Arabidopsis* Homozygous Mutants that are Infected by *P. Sojae*

We observed that single cells of the *Arabidopsis* mutant, pen1-1, but not that of its progenitor ecotype, Columbia, are penetrated by *P. sojae*. This observation suggested that the first line of defense in *Arabidopsis* against the pathogen is lost in this mutant. We used the chemical mutagen, ethyl methane sulfonate (EMS), to generate 3,556 EMS-induced mutant plants in pen1-1. Then we have screened over 3,000 $M_2$ families developed from these mutants for possible loss of *Phytophthora* resistance in 24-well microtiter plates as follows. Seedling were grown in water for 10 days and then inoculated with *P. sojae* zoospores for 48 hours in wells of microtiter plates. Thereafter, dead cells of inoculated seedlings were stained with trypan blue dye (Koch and Slusarenko 1990) and identified by conducting light microscopy. We identified 30 putative *P. sojae* susceptible mutants. We tentatively named these putative mutants (putants) pss1 (*Phytophthora* sojae susceptible) through pss30.

We selected Niederzenz to cross with pss mutants to generate materials that segregate for the Pss genes, because this ecotype is immune to *P. sojae*. We generated a global map of SSLP and CAPS markers that are polymorphic between Columbia and Niederzenz. We sequenced the Niederzenz genome by applying high through-put Solexa (Illumina, Inc., San Diego) sequencing technology and developed a sequence-based polymorphic (SBP) markers technology to fill out the marker-poor regions of the genome developed earlier using SSLP and CAPS markers (Sahu et al. 2012). We developed SBP markers for saturating the Pss1 region with molecular markers.

We investigated map locations of three additional putative Pss genes, Pss6, Pss26 and Pss30. By conducting bulk-segregant analysis (Michelmore et al. 1991) we have shown that none of the putative Pss6, Pss26 and Pss30 genes mapped to the Pss1 locus. Pss30 was mapped to the south arm of Chromosome 5.

Pss6 is tentatively mapped to the Chromosome 4. Additional SBP markers are being generated to map this gene.

Pss1 mutant is susceptible to a second soybean pathogen, *Fusarium virguliforme*. We inoculated all available 26 pss mutants and discovered that pss21 is also infected by *F. virguliforme*. Earlier we have shown through T-DNA tagged mutant analyses that the GRP1 gene encoding a glycine-rich protein is the Pss1 gene. We investigated if Pss21 is the Pss1 gene. We sequence the GRP1 gene from the pss21 mutant and observed that it did not contain any mutation. Therefore, we concluded that Pss21 is most likely different from Pss1 and there are most likely at least two mechanisms conferring immunity of *Arabidopsis* against the fungal pathogen, *F. virguliforme* that causes sudden death syndrome in soybean. pss6 and pss30 mutants are immune to *F. virguliforme*. Therefore, Pss21 is most unlikely mapped to either of Pss6 and Pss30 loci. Thus, we have so far identified four genetic loci that are involved in immunity of *Arabidopsis* against *P. sojae*; they are: Pss1, Pss6, Pss21 and Pss30.

High-Resolution and High-Density Molecular Maps of Two *Arabidopsis* Genes that Confer Nonhost Resistance Against *Phytophthora sojae*.

We have developed a high density map of the Pss1 region. We have also mapped the Pss30 region, where Pss30 was localized to a 1.5 Mb region close to the south telomere of Chromosome 5. We analyzed 273 $F_{2:3}$ families for markers of the Pss30 region. *P. sojae* susceptible families were applied in mapping the Pss30 gene to a 1 Mb DNA region located between SBP markers, SBP5_25.52 and SBP5_26.52. We isolated genomic DNA of five homozygous susceptible $F_{2:3}$ families to sequence the pss30 genome at the Iowa State University DNA sequencing facility.

We compared the sequence of the Pss30 region of the pss30 allele with that of the ecotype Col-0 with the aid of the SHORE program (Ossowski et al. 2010) and identified three mutations at the Pss30 region. We therefore concluded that mapping of the Pss30 region was completed. We have finished mapping two *Arabidopsis* Pss genes, Pss1 and Pss30; and therefore, have completed this research objective.

One *Arabidopsis* Gene that Confers Nonhost Resistance Against *P. Sojae*.

We sequenced a DNA sample of seven pss1pss1 homozygous families by applying the Solexa sequencing technology. By comparing sequences of the Pss1 region of the bulked susceptible $F_{2:3}$ families homozygous for the pss1 allele with that of the ecotype Col-0 with the aid of the SHORE program (Ossowski et al. 2010), we identified nine mutations that are located in the Pss1 region. Three of the nine mutations were originated from the pen1-1 mutant background used to generate the pss1 mutant. Therefore, they are not candidate Pss1 genes and were not considered for further investigation. The remaining six genes carrying point mutations are listed in Table 1.

TABLE 1

Candidate Pss1 genes carrying mutations in their exonic sequences.

| SNP Location (bp) | Locus | Gene name | Base change | Amino acid Change |
|---|---|---|---|---|
| 22029832 | AT3G59640 | Glycine-rich protein | G-A | Gly/Asp |
| 22033274 | AT3G59650 | Mitochondrial ribosomal protein | G-A | Gly/Asp |
| 22290347 | AT3G60310 | Unknown protein | G-A | Ala/Thr |
| 22477739 | AT3G60840 | Microtubule associated protein 65-4 | G-A | Pro/Leu |
| 22504152 | AT3G60920 | Contains inter-pro domain | G-A | Ala/Asp |
| 22786292 | AT3G61580 | Fatty acid/Sphingolipid desaturase | G-A | Asp/Asn |

We investigated if any of the candidate Pss1 genes are present in the soybean genome by conducting BLAST search at the NCBI website. The results are presented in Table 2. We observed that none of the six candidate Pss1 genes are conserved in soybean. Thus, it is possible that orthologous Pss1 sequence is missing in soybean and transfer of Pss1 to soybean may result in enhanced *Phytophthora* resistance in soybean. In order to identify the mutant genotypes carrying T-DNA insertion mutations in homozygous condition, PCR was performed using the T-DNA left border-specific primer and the gene specific “Forward” and “Reverse” primers. Twenty-eight T-DNA mutants with insertion in five candidate Pss1 genes were collected from ABRC and analyzed for T-DNA insertion and the disease phenotypes following *P. sojae* infection. CS850460, SALK_148857C and SALK_090245C lines carrying T-DNA insertion mutations in the At3g59640 gene encoding a glycine rich protein were consistently infected by *P. sojae*. We termed the At3g59640 gene tentatively as GRP1. The homozygous T-DNA mutants in the GRP1 gene identified from CS850460, SALK_148857C and SALK_090245C lines were termed grp1-1, grp1-2 and grp1-3, respectively (FIG. 1). The lines carrying T-DNA insertion mutations for remaining four candidate Pss1 genes segregated for the T-DNA insertions, but were resistant to *P. sojae* (data not presented) and therefore these four genes cannot be candidate Pss1 genes. GK-476F03 line was obtained from NASC. It contains a T-DNA insertion in the sixth candidate Pss1 gene, AT3G59650. The mutant was resistant to *P. sojae*; therefore, AT3G59650 is not a candidate Pss1 gene.

TABLE 2

Soybean homologues of the Pss1 candidate genes.

| Gene ID | Arabidopsis Protein ID | Amino Acid | Soybean Homologue | Identity (%) | E-value |
|---|---|---|---|---|---|
| AT3G59640 | Glycine-rich protein | 246 | Unknown Protein | 38 (89/235) | 1.00E−34 |
| AT3G59650 | Mitochondrial ribosomal protein | 119 | Unknown Protein | 27 (22/83) | 6.00E−04 |

TABLE 2-continued Soybean homologues of the Pss1 candidate genes.

| Gene ID | Arabidopsis Protein ID | Amino Acid | Soybean Homologue | Identity (%) | E-value |
| --- | --- | --- | --- | --- | --- |
| AT3G60310 | Unknown protein | 687 | Unknown Protein | 27 (29/106) | 0.049 |
| AT3G60840 | Microtubule assoc. protein 65-4 | 648 | Unknown Protein | 24 (19/78) | 0.023 |
| AT3G60920 | Contains inter-pro domain | 1941 | Unknown Protein | 32 (18/56) | 0.01 |
| AT3G61580 | Fatty acid/sphingolipid desaturase | 449 | Unknown Protein | 38 (28/73) | 6.00E−15 |

Figure 1:
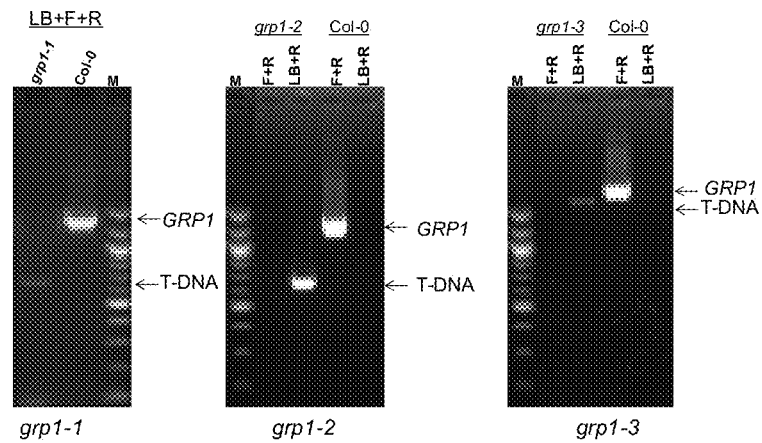
FIGS. 1 (A and B) shows the identification of homozygous T-DNA insertion lines for the GRP1 gene encoding a glycine rich protein. A shows the location of the mutations in the GRP1 gene. The EMS-induced mutation in GRP1, located in exon 2, resulted in an amino acid substitution from Gly to Asp. Three T-DNA insertion mutant lines, CS850460, SALK_148857C and SALK_090245C were termed grp1-1, grp1-2 and grp1-3, respectively. Locations of T-DNA insertions in these three mutants are shown with triangles. T-DNA insertions in grp1-1 and grp1-2 are located in the promoter and in grp1-3 in exon 1. B shows PCR analyses demonstrating that grp1-1, grp1-2 and grp1-3 mutants are in homozygous condition. LB, LB1.3 primer specific to the T-DNA left border. F, forward primer and R, reverse primer that amplify the GRP1 gene fragment from the wild-type ecotype, Col-0. All three primers were simultaneously used in PCR of genomic DNA prepared from grp1-1 and Col-0 (extreme left panel). Note that the GRP1 gene-specific fragment is absent in all three mutants suggesting that the three mutants are homozygous for the T-DNA insertions in the GRP1 gene.

FIG. 1. Identification of homozygous T-DNA insertion lines for the GRP1 gene encoding a glycine rich protein. A) Location of the mutations in the GRP1 gene. The EMS-induced mutation in GRP1, located in exon 2, resulted in an amino acid substitution from Gly to Asp. Three T-DNA insertion mutant lines, CS850460, SALK_148857C and SALK_090245C were termed grp1-1, grp1-2 and grp1-3, respectively. Locations of T-DNA insertions in these three mutants are shown with triangles. T-DNA insertions in grp1-1 and grp1-2 are located in the promoter and in grp1-3 in exon 1. B) PCR analyses showed that grp1-1, grp1-2 and grp1-3 mutants are in homozygous condition. LB, LB1.3 primer specific to the T-DNA left border. F, forward primer and R, reverse primer that amplify the GRP1 gene fragment from the wild-type ecotype, Col-0. All three primers were simultaneously used in PCR of genomic DNA prepared from grp1-1 and Col-0 (extreme left panel). Note that the GRP1 gene-specific fragment is absent in all three mutants suggesting that the three mutants are homozygous for the T-DNA insertions in the GRP1 gene.

Figure 2:
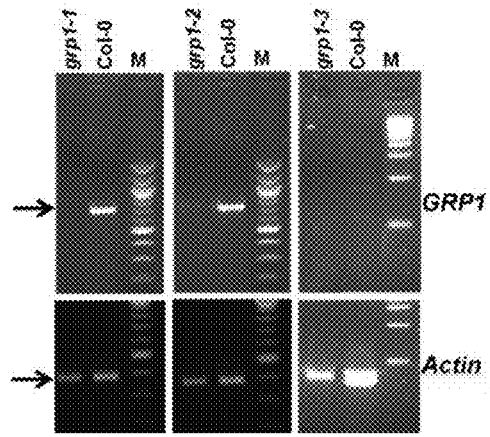
FIG. 2 shows expression analysis of the GRP1 in the homozygous T-DNA insertion lines.

We determined the steady state GRP1 transcript levels in the three grp1 mutants by conducting RT-PCR (FIG. 2). Of the two T-DNA insertion mutations in the promoter region, grp1-1 did not show any GRP1 transcripts and was susceptible to *P. sojae*. grp1-2 with a T-DNA insertion in the promoter, showed leaky expression for GRP1 and was also not always infected by the pathogen (Table 3). The T-DNA insertion mutation in exon 1 (grp1-3), lacking GRP1 transcripts, was infected by the pathogen. These results suggest that GRP1 encoding a glycine rich protein is the candidate Pss1 gene.

GRP1 gene specific primers were used in RT-PCR analysis of the GRP1 transcripts. RNA molecules extracted from leaves of grp1-1, grp1-2 and grp1-3 plants, homozygous for T-DNA insertions, were used in the RT-PCR experiment. GRP1 transcripts were not detected in homozygous grp1-1 and grp1-3 mutants that were infected by *P. sojae* (Table 3). FIG. 2. Steady state GRP1 transcript levels in the three grp1 mutants. RT-PCR was conducted to determine transcript levels of the three selected T-DNA insertion grp1 mutants.

In order to confirm that GRP1 is the Pss1 gene, we have cloned the wild-type GRP1 gene from Col-0 in a binary vector for complementation of the pss1 mutant. Floral dip method (Zhang et al. 2006) was used to transform the pss1 mutant. The bar gene encoding basta resistance was used as a selectable marker to transform the pss1 mutant with the GRP1 gene. PCR was conducted to confirm that basta resistant plants contain the bar gene (FIG. 3).

Figure 3:
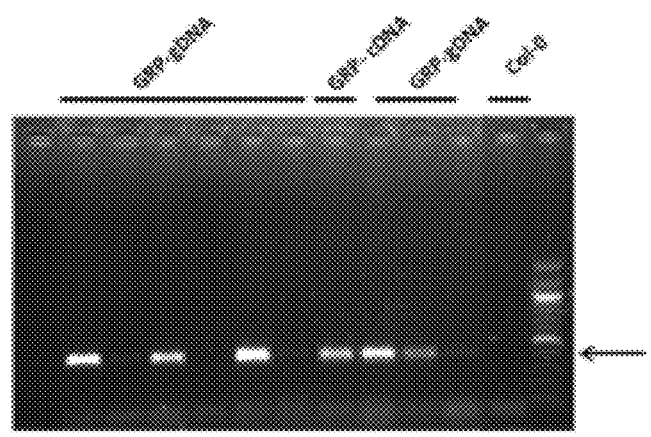
FIG. 3 shows some of the basta resistant *Arabidopsis* transformants by PCR amplification of the bar gene. Progenies of the Agro-infected plants were sprayed multiple times with the basta herbicide and PCR was conducted on some of the basta resistant seedlings using bar gene specific primers. GRP-gDNA, transformants carrying the GRP1 gene; GRP-cDNA, transformants carrying GRP1 cDNA; Col-0, lack of amplification from the non-transgenic ecotype Columbia-0 control plant. Arrow indicates the amplified bar gene.

FIG. 3. Some of the basta resistant *Arabidopsis* transformants showed PCR amplification of the bar gene. Progenies of the Agro-infected plants were sprayed multiple times with the basta herbicide and PCR was conducted on some of the basta resistant seedlings using bar gene specific primers. GRP-gDNA, transformants carrying the GRP1 gene; GRP-cDNA, transformants carrying GRP1 cDNA; Col-0, lack of amplification from the non-transgenic ecotype Columbia-0 control plant. Arrow indicates the amplified bar gene In parallel to cloning Pss1, we have also identified the candidate Pss30 gene. Results are summarized below.

Figure 4:
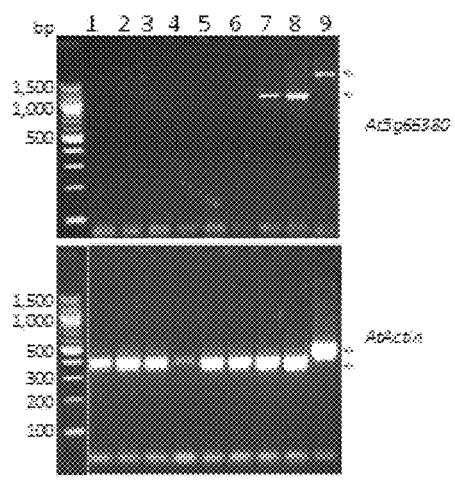
FIG. 4 shows RT-PCR analysis of the At5g66380 gene in the SALK_011184 T-DNA insertion lines that were infected by *P. sojae*. RT-PCR confirmed the absence of At5g66380 expression in the T-DNA-induced mutant lines. Lane 1-6; Individual plants of SALK_011184C line which showed susceptibility to *P. sojae*, 7-8; Col-0 cDNA, 9; Col-0 gDNA samples. Arrows indicate the expected amplicon size from the cDNA (1,024 bp) and gDNA (1,986 bp) templates respectively. Expression of AtActin was used as the internal control.

In order to facilitate cloning of Pss30, we sequenced a bulked DNA sample of five pss30 homozygous families by applying the Solexa sequencing technology at the Iowa State University DNA Facility. By comparing sequences of the Pss30 region in the bulked DNA sample of five susceptible $F_{2:3}$ families homozygous for the pss30 allele with that of the ecotype Col-0 with the aid of the SHORE program (Ossowski et al. 2010), we identified four mutations that are located in three genes of the Pss30 region (Table 4). We sequenced the pen1-1 mutant, in which pss30 was generated for these four mutations and observed that all four mutations are pss30-specific. None of these mutations were originated from the pen1-1 mutant background and therefore the three genes carrying four mutations were considered to be the candidate Pss30 genes. The three genes carrying point mutations are listed in Table 4. We collected the SALK T-DNA insertion lines for the three candidate Pss30 genes (Table 5). Only SALK_011184 carrying T-DNA insertion in the At5g66380 gene was infected by *P. sojae*. The RT-PCR analyses for the At5g66380 gene confirmed the absence of the transcript for this gene in SALK_011184 (FIG. 4).

TABLE 3

Characterization of three grp1 T-DNA insertion mutants

| Mutant allele | T-DNA insertion line | Location of insertion | Homozygosity of insertion | Transcripts | Phenotype |
| --- | --- | --- | --- | --- | --- |
| grp1-1 | CS850460 | Promoter | Yes | Absent | Susceptible |
| grp1-2 | SALK_148857C | Promoter | Yes | Reduced | Segregated |
| grp1-3 | SALK_090245C | Exon-1 | Yes | Absent | Susceptible |

Figure 5:
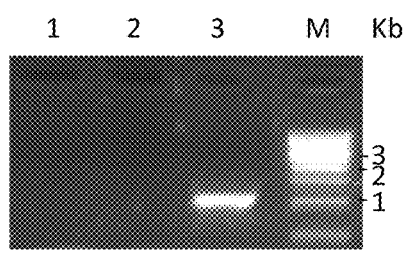
FIG. 5 shows RT-PCR amplification of the three putative Pss30 genes from leaf tissue of Col-0. At5g66380 (Folate transporter 1 in chloroplast envelope) was the only gene that showed expression in Col-0 leaves that express Pss30. Lane 1; At5g64600, Lane 2; At5g65900, Lane 3; At5g66380 specific PCR products and M; 1 Kb marker.

We also investigate all three candidate Pss30 genes for presence of transcripts in leaves of the ecotype Col-0. We observed the RT-PCR products for only the At5g66380 gene (FIG. 5). This result is consistent with the expression levels of these three genes reported in the Genvestigator (https://www.genevestigator.com/gv/plant.jsp) database. Thus, most likely, At5g66380 is the Pss30 gene. It encodes a folate transporter 1 of the chloroplast envelope. Cloning of both cDNA and gDNA sequences of At5g66380 is underway.

TABLE 4

Candidate Pss30 genes carrying mutations in their exonic sequences.

| SNP Location | Base change | Place | Amino acid change | Gene locus | Gene name |
|---|---|---|---|---|---|
| 25827439 | G →A | Exon | Gly/Arg | At5g64600 | O-fucosyltransferase family protein |
| 26358667 | G→A | Exon | Glu/Lys | At5g65900 | DEA(D/H)-box RNA helicase family protein |
| 26514954 | C→T | Exon | Val/Leu | At5g66380 | Folate transporter 1 in chloroplast envelope |
| 26515178 | G→T | Exon | Ala/Asp | At5g66380 | Folate transporter 1 in chloroplast envelope |

TABLE 5

SALK T-DNA insertion lines analyzed for responses to infection by *P. sojae*.

| Gene | SALK T-DNA insertion lines | Phenotype |
|---|---|---|
| At5g64600 | CS849634 | — |
|  | CS859265 | Resistant (2/12) |
|  | SALK_025992 | Resistant (0/16) |
|  | SALK_147742 | Resistant (2/31) |
| At5g65900 | SALK_005280 | Resistant (4/16) |
|  | SALK_059769 | Resistant (0/16) |
|  | SALK_068661 | Resistant (4/11) |
| At5g66380 | SALK_011184C | Susceptible (6/12) |
|  | SALK_125621C | Resistant (0/7) |

FIG. 4. RT-PCR analysis of the At5g66380 gene in the SALK_011184 T-DNA insertion lines that were infected by *P. sojae*. RT-PCR confirmed the absence of At5g66380 expression in the T-DNA-induced mutant lines. Lane 1-6; Individual plants of SALK_011184C line which showed susceptibility to *P. sojae*, 7-8; Col-0 cDNA, 9; Col-0 gDNA samples. Arrows indicate the expected amplicon size from the cDNA (1,024 bp) and gDNA (1,986 bp) templates respectively. Expression of AtActin was used as the internal control.

FIG. 5. RT-PCR amplification of the three putative Pss30 genes from leaf tissue of Col-0. At5g66380 (Folate transporter 1 in chloroplast envelope) was the only gene that showed expression in Col-0 leaves that express Pss30. Lane 1; At5g64600, Lane 2; At5g65900, Lane 3; At5g66380 specific PCR products and M; 1 Kb marker.

REFERENCES

Koch, E. and Slusarenko, A. (1990) *Arabidopsis* is susceptible to infection by a downy mildew fungus. *Plant Cell*, 2, 437-445.

Michelmore, R. W., Paran, I. and Kesseli, R. V. (1991) Identification of markers linked to disease-resistance genes by bulked segregant analysis: a rapid method to detect markers in specific genomic regions by using segregating populations. *Proc. Nat'l Acad. Sci. USA*, 88, 9828-9832.

Ossowski, S., Schneeberger, K., Lucas-Lledó, J. I., Warthmann, N., Clark, R. M., Shaw, R. G., Weigel, D. and Lynch, M. (2010) The rate and molecular spectrum of spontaneous mutations in *Arabidopsis thaliana*. *Science*, 327, 92-94.

Sahu, B. B., Sumit, R., Srivastava S. K. and Bhattacharyya, M. K. (2012) Sequence based polymorphic (SBP) marker technology for targeted genomic regions: its application in generating a molecular map of the *Arabidopsis thaliana* genome. BMC Genomics, 13:20. doi:10.1186/1471-2164-13-20.

Wrather, J. A. and Koenning, S. R. (2006) Estimates of disease effects on soybean yields in the United States 2003-2005. *J. Nematol*, 38, 173-180.

Zhang, X., Henriques, R., Lin, S. S., Niu, Q. W. and Chua, N. H. (2006) *Agrobacterium*-mediated transformation of *Arabidopsis thaliana* using the floral dip method. *Nat Protoc*, 1, 641-646.

Example 2

Figure 10:
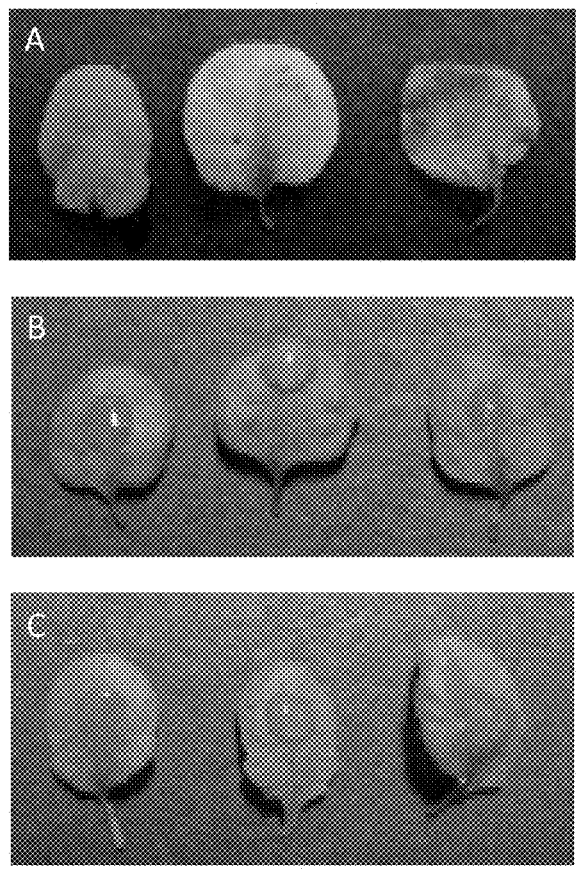
FIG. 10 (A-C) shows *Arabidopsis* glycine rich protein (GRP1) gene complemented the susceptible mutant phenotype in the SALK T-DNA mutant, CS850460 carrying T-DNA insertion in the *Arabidopsis* GRP1 gene. The cDNA fragment of the wild type *Arabidopsis* GRP gene was used to complement the SALK mutant, CS850460. Three leaves of 21-day old *Arabidopsis* seedlings were inoculated with 10 µl *P. sojae* zoospores drop/leaf ($10^5$ zoospores/mL). A shows the SALK mutant, CS850460 lacking a functional *Arabidopsis* GRP1 gene was susceptible to the soybean pathogen, *P. sojae*; B shows the introduction of the cDNA fragment of the wild type GRP1 gene complemented the mutant phenotype and recovered the wild type resistant phenotype in the transgenic SALK CS850460 leaves, which showed resistance comparable to the wild type, Columbia-0 (Col-0) ecotype level. C shows Col-0 leaves showed immunity against *P. sojae*. The images were taken 2 days following inoculation with zoospores of the soybean pathogen, *P. sojae*.

Earlier it was shown by studying T-DNA insertion mutants that GRP1 is the candidate Pss1 gene (Table 3 and FIG. 2). Transformation of a T-DNA insertion grp1 mutant established that the GRP cDNA can complement the lost function of the GRP1 in this mutant (FIG. 10). We subsequently transformed the gene into the soybean cultivar, Williams 82. The progenies of two independent transformations have been evaluated by infecting with multiple *P. sojae* isolates and *F. virguliforme* Mont-1 isolate. The FIGS. 7 and 8 show that incorporation of *Arabidopsis* GRP1 in transgenic soybean resulted in enhanced *Phytophthora* resistance. FIGS. 9 and 10 show that that incorporation of *Arabidopsis* GRP1 in transgenic soybean resulted in enhanced against the SDS pathogen, *F. virguliforme*.

FIG. 10. *Arabidopsis* glycine rich protein (GRP1) gene complemented the susceptible mutant phenotype in the SALK T-DNA mutant, C S850460 carrying T-DNA insertion in the *Arabidopsis* GRP1 gene. The cDNA fragment of the wild type *Arabidopsis* GRP gene was used to complement the SALK mutant, CS850460. Three leaves of 21-day old *Arabidopsis* seedlings were inoculated with 10 μl *P. sojae* zoospores drop/leaf ($10^5$ zoospores/mL). A, the SALK mutant, CS850460 lacking a functional *Arabidopsis* GRP1 gene was susceptible to the soybean pathogen, *P. sojae*; B, the introduction of the cDNA fragment of the wild type GRP1 gene complemented the mutant phenotype and recovered the wild type resistant phenotype in the transgenic SALK CS850460 leaves, which showed resistance comparable to the wild type, Columbia-0 (Col-0) ecotype level. C, Col-0 leaves showed immunity against *P. sojae*. The images were taken 2 days following inoculation with zoospores of the soybean pathogen, *P. sojae*.

Figure 11:
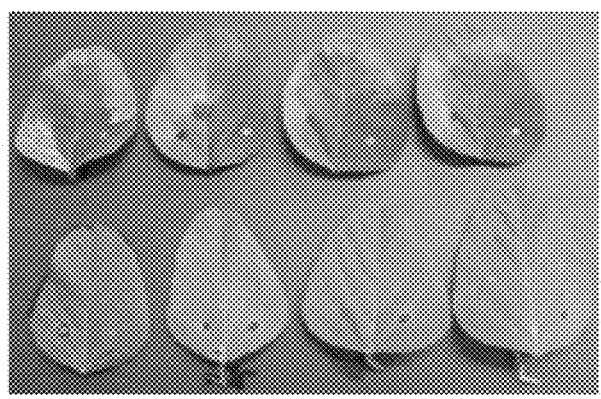
FIG. 11 shows leaves of transgenic soybean Williams 82 plants carrying the *Arabidopsis* GRP1 gene showed resistance to *P. sojae*. Leaves of the nontransgenic soybean cultivar, Williams 82 were susceptible to the pathogen. Two unifoliate leaves of 12 day-old soybean plants were inoculated with *P. sojae* spores (15 µl spore drop/isolate/leaf, $10^5$ spores/mL). Radial growth of disease symptom was recorded at regular interval. Leaves of wild-type soybean cultivar, Williams 82 but not the transgenic soybean line, ST154-13, carrying the *Arabidopsis* GRP1 gene, showed significant spread of disease lesion in inoculated leaves transgenic soybean plants. The results showed that *Arabidopsis* nonhost resistance GRP1 provided nonhost resistance against the oomycete pathogen, *P. sojae* in transgenic soybean plants. This indicates that the *Arabidopsis* nonhost resistance mechanism is functional in soybean plants transformed with the GRP1 gene from *Arabidopsis*. Image shown is representative of inoculated leaves from one of three biological replications.

FIG. 11. Leaves of transgenic soybean Williams 82 plants carrying the *Arabidopsis* GRP1 gene showed resistance to *P. sojae*. Leaves of the nontransgenic soybean cultivar, Williams 82 were susceptible to the pathogen. Two unifoliate leaves of 12 day-old soybean plants were inoculated with *P. sojae* spores (15 μl spore drop/isolate/leaf, $10^5$ spores/mL). Radial growth of disease symptom was recorded at regular interval. Leaves of wild-type soybean cultivar, Williams 82 but not the transgenic soybean line, ST154-13, carrying the *Arabidopsis* GRP1 gene, showed significant spread of disease lesion in inoculated leaves transgenic soybean plants. The results showed that *Arabidopsis* nonhost resistance GRP1 provided nonhost resistance against the oomycete pathogen, *P. sojae* in transgenic soybean plants. This indicates that the *Arabidopsis* nonhost resistance mechanism is functional in soybean plants transformed with the GRP1 gene from *Arabidopsis*. Image shown is representative of inoculated leaves from one of three biological replications.

Figure 12:
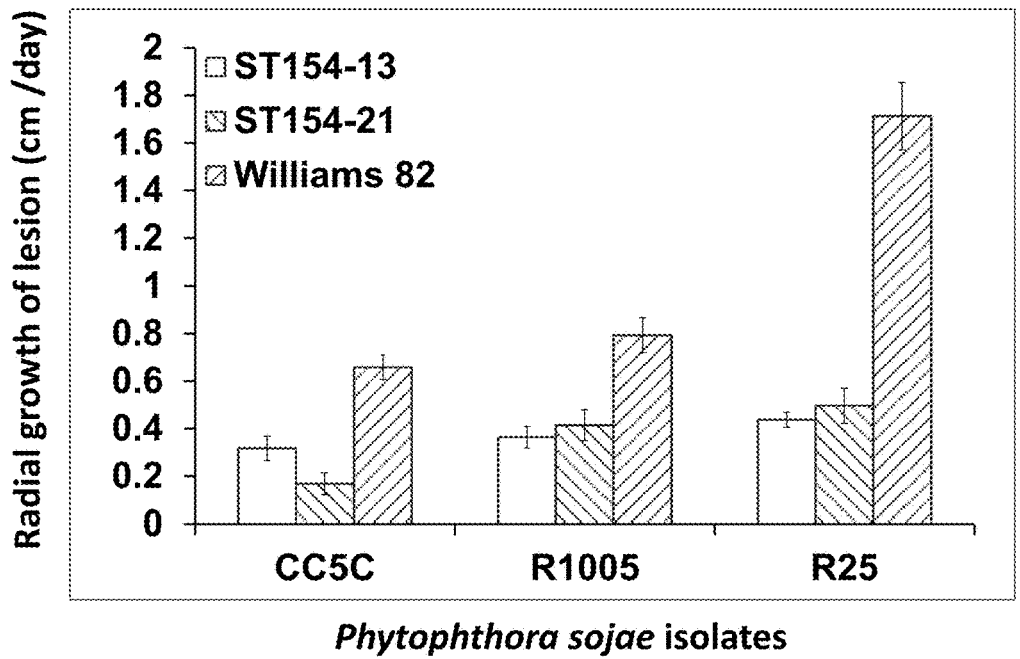
FIG. 12 shows broad-spectrum resistance of transgenic soybeans transformed with *Arabidopsis* GRP1 against *P. sojae*. Radial growth of disease symptom (cm/day) was measured on transgenic soybean plants ($T_2$ generation) carrying the GRP1 cDNA and the wild-type non-transgenic Williams 82 following inoculation with *P. sojae* zoospores.

FIG. 12. Broad-spectrum resistance of transgenic soybeans transformed with *Arabidopsis* GRP1 against *P. sojae*. Radial growth of disease symptom (cm/day) was measured on transgenic soybean plants ($T_2$ generation) carrying the GRP1 cDNA and the wild-type non-transgenic Williams 82 following inoculation with *P. sojae* zoospores. Transgenic plants from two separate transformation events, ST154-13 and ST154-21, were inoculated with *P. sojae* zoospores ($10^5$ spores/mL) from three different *P. sojae* isolates, CC5C, R1005 and R25. Two unifoliate leaves from 12-day old seedlings were inoculated with a 15 μl zoospores drop/isolate/leaf and lesion lengths were recorded 3-day post inoculation (dpi) and 4 dpi. Plants from both transgenic events showed significantly reduced disease lesion against all three *P. sojae* isolates as compared to the wild type, Williams 82 plants. The experiment was conducted two times with similar results. Error bars indicate SE.

FIG. 13. Leaves of transgenic soybean Williams 82 plants carrying the GRP1 gene showed resistance to *F. virguliforme*. The central leaflet of the trifoliate ($3^{rd}$ from top opened leaf) of 26-day old soybean plants were wounded with carborundum powder and then inoculated with the conidial spores of *Fusarium virguliforme* (15 μl from $10^7$ spores/mL) that causes sudden death syndrome in soybean. Bleaching of the leaves was performed by dipping the infected leaf in 80% ethanol at 50° C. for 2 days. A, Leaves of the nontransgenic soybean cultivar, Williams 82 were susceptible to the pathogen. B, Leaves shown in A following bleaching with 80% alcohol. Note that the white area at the advancing region of the lesions was the chlorotic (yellow hallow) caused presumably by pathogen toxins. C, The transgenic soybean leaves carrying the *Arabidopsis* GRP1 gene provides resistance against the pathogen. D, Leaves of C following bleaching with 80% alcohol show necrotic lesions of the resistant response. Images shown are representatives of inoculated leaves from three biological replications.

FIG. 14. *Arabidopsis* GRP1 suppressed the lesion development in *F. virguliforme*-infected leaves of the transgenic soybean lines. The central leaflet of the unifoliate ($3^{rd}$ from top opened leaf) of 26-day old soybean plants were wounded with carborundum powder and infected with the *Fusarium virguliforme* conidial spores (15 μl from $10^7$ spores/mL). Data presented are the average area of the disease spread at the wounded sites. Williams 82, the non-transgenic Williams 82 was used as the negative control. ST154-13, the soybean transgenic line carries *Arabidopsis* GRP1.

Example 3

The following sequence were obtained from World wide web at *Arabidopsis*.org NCBI accession numbers are also given as an alternative sequence source.
Chromosome 5=CP002688.1
Chromosome 3=CP002686.1
At5g64600
Accession number: NM_125856.5

```
O-fucosyltransferase family protein
CDS
                                                        (SEQ ID NO: 1)
   1    ATGGTGAAAC ACAGAAACTC ATCTCGCTCG ATAATCTCAT ATTCTTCTTC

51    AATAGCAAGA TTCTTCTCTA GAAAAGCTAT TTCTCTCTAC TTGATCTTCG

101    TCTTTGCTTT TACCATCTGG GTTCTCGTCT TCAGCTCCAG AAACATTCAA

151    ACCGATGATG ACCACACCAA ACATCAACAA CAACATCATC GGGATCTAAT

201    CGATTCAGAA TCATTTCCGC CACCGTATTT GCCTCCTAGG AAGAATTTGC

251    AGAAACCGTA TGAAAATACT CAACTTTGGA CTCCTCCTTT CAGCTTTGGG

301    TTGCATCCAT GTGTCAAACC TACTCCGAAA TACAAAGAAT TTTCAGAATC

351    AGATCATTAT ATAACAGTGA AAAGTAATGG TGGACTAAAT CAAATGCGTA

401    CTGGTATAGC AGATATAGTG GCTGTTGCGC ACATCATGAA TGCAACTTTA

451    GTCATTCCTG AGCTGGATAA GCGATCGTTT TGGCAAGATT CAAGTGTTTT

501    TTCAGATATT TTTGACGAGG AACAATTCAT TAAATCATTG CGAAGAGATG

551    TCAAGGTTAT TAAAAAGCTC CCAAAGGAAG TGGAATCTCT ACCTAGAGCA

601    AGGAAGCATT TCACTTCTTG GTCTAGTGTT GGATATTATG AAGAAATGAC

651    TCACTTGTGG AAGGAGTACA AGGTCATCCA TGTCGCAAAA TCAGATTCTC

701    GCCTTGCAAA TAATGACCTG CCTATCGACG TTCAAAGACT GAGATGTCGT

751    GTACTATATC GTGGTCTCTG CTTCTCTCCT GCAATTGAAA GCCTTGGACA

801    GAAGCTGGTT GAGAGACTCA AGTCACGTGC TGGGAGATAT ATTGCATTGC
```

```
 851  ACCTGAGATA TGAGAAAGAT ATGTTGGCTT TCACTGGTTG CACCTATGGT
 901  CTCACTGATG CTGAATCCGA AGAACTGAGA GTAATGCGGG AAAGTACAAG
 951  CCATTGGAAG ATCAAAAGTA TAAATTCAAC AGAGCAGAGA GAGGAAGGCC
1001  TTTGTCCATT GACTCCAAAA GAAGTGGGAA TATTTCTGAA AGGTCTCGGA
1051  TATTCTCAGT CAACAGTCAT ATATATTGCA GCAGGGGAAA TCTATGGGGG
1101  TGATGATAGA CTCTCTGAGC TTAAGTCGCG CTTCCCAAAT CTGGTTTTTA
1151  AGGAAACGCT TGCTGGGAAC GAAGAGTTAA AAGGTTTCAC TGGCCATGCG
1201  ACTAAAACGG CTGCTCTTGA TTACATAATT TCTGTTGAGA GTGATGTGTT
1251  TGTTCCTTCA CATTCTGGAA ACATGGCAAG AGCAGTTGAA GGTCACCGCA
1301  GATTTCTAGG GCATCGCAGG ACTATCACTC CCGACAGGAA AGGACTAGTG
1351  AAACTCTTCG TTAAGATGGA GAGAGGACAG CTAAAAGAAG GACCAAAGTT
1401  GTCCAATTTT GTGAATCAAA TGCATAAAGA CAGACAAGGT GCACCGAGGA
1451  GAAGGAAAGG ACCAACGCAG GGGATCAAAG GACGTGCACG GTTTAGAACT
1501  GAAGAAGCCT TTTATGAGAA TCCATATCCA GAGTGTATTT GCAGTTCAAA
1551  GGAGCACAAA GAACCCTAA
```

Genomic (SEQ ID NO: 19)

```
   1  CTTCATCGAA GATGGTGAAA CACAGAAACT CATCTCGCTC GATAATCTCA
  51  TATTCTTCTT CAATAGCAAG ATTCTTCTCT AGAAAAGCTA TTTCTCTCTA
 101  CTTGATCTTC GTCTTTGCTT TTACCATCTG GGTTCTCGTC TTCAGCTCCA
 151  GAAACATTCA AACCGATGAT GACCACACCA ACATCAACA ACAACATCAT
 201  CGGGATCTAA TCGATTCAGA ATCATTTCCG CCACCGTATT TGCCTCCTAG
 251  GAAGGTAAAG TTGTTAATAT TTCATGGGTT GTGGATTTGA ATGAAGAAAT
 301  GAGGTGACTT GATTTGGTTT TTGATCGGAA CAATTGAGAA AGCATAACTT
 351  TATTGAGCTT CAGAATTTGC AGAAACCGTA TGAAAATACT CAACTTTGGA
 401  CTCCTCCTTT CAGCTTTGGG TTGCATCCAT GTGTCAAACC TACTCCGAAA
 451  TACAAAGGTA TGCCAAAGAA GCTCACTTCC AATTTCTGAT GGATCTATCT
 501  TGGGTTTTGT TTATGAATTC AGAACTGTGC TTTTGATTGA TTTCAAGTTC
 551  GTTTCTTGCA GAATTTTCAG AATCAGATCA TTATATAACA GTGAAAAGTA
 601  ATGGTGGACT AAATCAAATG CGTACTGGTG TAAGTAAAAC CATTTAAGTT
 651  GTTGTTTTCA TGATTCTTTT TGTCTTGCTT AGTACCAAAG TGATTCAATA
 701  AGCATGTTAT TGTACAGATA GCAGATATAG TGGCTGTTGC GCACATCATG
 751  AATGCAACTT TAGTCATTCC TGAGCTGGAT AAGCGATCGT TTTGGCAAGA
 801  TTCAAGGTAT TTTGAAACTT CAAACAAACA AAAATGCAG CTTACTTAAT
 851  TAGTGGTTAT GAGATTTATA CTATTTCTAA CTTACATTTT CGCTATGTCT
 901  CAGTGTTTTT TCAGATATTT TTGACGAGGA ACAATTCATT AAATCATTGC
 951  GAAGAGATGT CAAGGTTATT AAAAAGCTCC CAAAGGAAGT GGAATCTCTA
1001  CCTAGAGCAA GGAAGCATTT CACTTCTTGG TCTAGTGTTG ATATTATGA
1051  AGAAATGACT CACTTGTGGA AGGAGTACAA GGTCGGTCTT AAGCAACTTC
1101  TTTTACATTT TGCATTTGCT GTTTCATTCA ACTGCTGATA GAATAATAAC
1151  AATGCAGGTC ATCCATGTCG CAAAATCAGA TTCTCGCCTT GCAAATAATG
```

-continued

```
1201 ACCTGCCTAT CGACGTTCAA AGACTGAGAT GTCGTGTACT ATATCGTGGT
1251 CTCTGCTTCT CTCCTGCAAT TGAAAGCCTT GGACAGGTTG GGACCCTTTT
1301 CCTGTCTTGT ACACAACATA GATAGGCTGT AGTAACATAA AATTCATTTC
1351 ATACACATAA GATTTCAAGT TAATGTTCTC TTTGGGTACC GAATAGCTAT
1401 ATAGAAGTTT CAAAACCATC GTTTGGGTCA ACGAGTTTTC ATTGTCAAAT
1451 GATAGAACTT GCAATAACAT AGTTTATGCA TTTAAGAGGT GTGTAATGAT
1501 AGAATAGGAG AATGGATACA TCTTTTTCTA TCAAACATAG TTTATGCATT
1551 TAAGAGGTGT CCTATGGGGA TTCCTGTAGA CTGTGGGTTC TGAGCAATCA
1601 TGACGGTGAC ACCACAGAAG CTGGTTGAGA GACTCAAGTC ACGTGCTGGG
1651 AGATATATTG CATTGCACCT GAGATATGAG AAAGATATGT TGGCTTTCAC
1701 TGGTTGCACC TATGGTCTCA CTGATGCTGA ATCCGAAGAA CTGAGAGTAA
1751 TGCGGTAATT GATTACTCTC TGCATCTATT CTTAACAAAG CAAACATGCA
1801 AAACGTCTTC ATGGGATAAA ATTACAGTTT CAAGCTCAAT ATGTTATCTG
1851 TTGGTCACAG GGAAAGTACA AGCCATTGGA AGATCAAAAG TATAAATTCA
1901 ACAGAGCAGA GAGAGGAAGG CCTTTGTCCA TTGACTCCAA AGAAGTGGG
1951 AATATTTCTG AAAGGTCTCG GATATTCTCA GTCAACAGTC ATATATATTG
2001 CAGCAGGGGA AATCTATGGG GGTGATGATA GACTCTCTGA GCTTAAGTCG
2051 CGCTTCCCAA ATCTGGTTTT TAAGGTCTGT TCAACCACCT CTAATCTTTC
2101 ATGTTACTGA CAATCTAAAG ATGATAAATG TTTATGTTTC ATGTACTGGA
2151 TTTTGTAGGA AACGCTTGCT GGGAACGAAG AGTTAAAAGG TTTCACTGGC
2201 CATGCGACTA AAACGGCTGC TCTTGATTAC ATAATTTCTG TTGAGAGTGA
2251 TGTGTTTGTT CCTTCACATT CTGGAAACAT GGCAAGAGCA GTTGAAGGTC
2301 ACCGCAGATT TCTAGGGCAT CGCAGGACTA TCACTCCCGA CAGGTTCTAT
2351 CTCCTTCCTT CTGTTACCTT AAAAAAAAGC ATTAATCTTT TAGTCATTTT
2401 GTTATAGGCC ATGACAAGTT TGGTGTTGTA TGCAGGAAAG GACTAGTGAA
2451 ACTCTTCGTT AAGATGGAGA GAGGACAGCT AAAAGAAGGA CCAAAGTTGT
2501 CCAATTTTGT GAATCAAATG CATAAAGACA GGTAGCAAAA GAGTCATACG
2551 TTTGCTTCTT AAACAATAAA CCTATAAAAA AAGCACATC TTTGATGCGA
2601 GAAGAGGATT TGTTTGATCG GTTTTGCAGA CAAGGTGCAC CGAGGAGAAG
2651 GAAAGGACCA ACGCAGGGGA TCAAAGGACG TGCACGGTTT AGAACTGAAG
2701 AAGCCTTTTA TGAGAATCCA TATCCAGAGT GTATTTGCAG TTCAAAGGAG
2751 CACAAAGAAC CCTAACTAAA ATTTTCCAAA CTTTTTTTGT TCTGTATCAT
2801 TACATCTCAT TTATAGTCAT CTTAATTATA GTTTCACAT ATCCCTTGAT
2851 ATCTTTTCTG TTTTTGATAT CCGGAGATCT CTAGCCGAAG TAGAAAGCCA
2901 GAAATTTTTA ACATTTAGTT ATAAAACTTC TCTTTCGGCA TTTTTTCAAA
2951 TATTCCAAAT TTTAACCAAA CTGTTGTCAA TCAGAATGGA ACAAGAATGA
3001 AACACCAAAG TTACTACTG
```

Amino acid
(SEQ ID NO: 2)

```
  1 MVKHRNSSRS IISYSSSIAR FFSRKAISLY LIFVFAFTIW VLVFSSRNIQ
 51 TDDDHTKHQQ QHHRDLIDSE SFPPPYLPPR KNLQKPYENT QLWTPPFSFG
101 LHPCVKPTPK YKEFSESDHY ITVKSNGGLN QMRTGIADIV AVAHIMNATL
```

```
151  VIPELDKRSF WQDSSVFSDI FDEEQFIKSL RRDVKVIKKL PKEVESLPRA

201  RKHFTSWSSV GYYEEMTHLW KEYKVIHVAK SDSRLANNDL PIDVQRLRCR

251  VLYRGLCFSP AIESLGQKLV ERLKSRAGRY IALHLRYEKD MLAFTGCTYG

301  LTDAESEELR VMRESTSHWK IKSINSTEQR EEGLCPLTPK EVGIFLKGLG

351  YSQSTVIYIA AGEIYGGDDR LSELKSRFPN LVFKETLAGN EELKGFTGHA

401  TKTAALDYII SVESDVFVPS HSGNMARAVE GHRRFLGHRR TITPDRKGLV

451  KLFVKMERGQ LKEGPKLSNF VNQMHKDRQG APRRRKGPTQ GIKGRARFRT

501  EEAFYENPYP ECICSSKEHK EP
```

At5g65900
DEA(D/H)-box RNA helicase
Accession number NM_125987.2
CDS

```
                                                               (SEQ ID NO: 3)
   1  ATGGCGAATT TGGATATGGA GCAACATTCA TCCGAAAACG AAGAGATTAA

51  GAAGAAGAAG CATAAGAAAA GAGCGAGAGA CGAAGCTAAG AAACTAAAGC

101  AGCCAGCAAT GGAAGAAGAA CCCGATCATG AAGATGGTGA TGCCAAAGAG

151  AACAATGCGT TAATTGACGA AGAACCGAAG AAGAAGAAGA GAAGAAAAA

201  TAAGAAGCGT GGAGATACTG ATGATGGAGA GGACGAAGCG GTAGCAGAAG

251  AAGAGCCGAA GAAGAAGAAG AAGAAAAATA AAAAGCTACA GCAGCGTGGA

301  GATACTAATG ACGAAGAGGA CGAAGTGATA GCAGAAGAAG AAGAGCCGAA

351  GAAGAAGAAG AAGAAACAGA GGAAGGACAC GGAAGCGAAG TCTGAAGAAG

401  AAGAAGTAGA AGATAAGGAA GAAGAAAAAA AATTGGAAGA AACTAGCATA

451  ATGACTAATA AAACGTTTGA GTCATTGTCA TTATCTGATA ACACTTATAA

501  ATCTATCAAG GAGATGGGTT TTGCACGCAT GACTCAGATA CAAGCTAAAG

551  CAATTCCACC ATTGATGATG GGAGAAGATG TACTTGGAGC TGCCAGGACC

601  GGTTCTGGTA AAACCTTAGC TTTTCTTATT CCTGCTGTTG AGCTTCTTTA

651  CCGTGTTAAG TTTACTCCTC GCAATGGAAC TGGTGTTCTT GTTATTTGCC

701  CAACAAGAGA GCTTGCTATT CAGTCTTATG GAGTGGCAAA AGAACTTCTT

751  AAGTATCATT CACAGACTGT GGGAAAAGTT ATTGGCGGTG AGAAAAGAAA

801  GACAGAAGCT GAGATTCTTG CGAAAGGTGT TAATTTATTA GTAGCTACCC

851  CTGGAAGACT TCTCGACCAC CTTGAAAATA CTAATGGTTT TATTTTCAAG

901  AACTTAAAGT TTCTTGTAAT GGATGAGGCT GATAGGATAT TGGAACAGAA

951  CTTTGAAGAA GACCTCAAGA AGATTTTGAA CCTTCTACCA AAGACTAGAC

1001  AGACGTCACT ATTTTCAGCC ACACAGAGCG CAAAGGTTGA GGATCTTGCT

1051  CGGGTGTCAC TTACCTCACC TGTTTATATT GATGTGGATG AAGGACGAAA

1101  AGAGGTTACA AATGAAGGCT GGAGCAAGG TTATTGCGTT GTGCCAAGTG

1151  CGATGCGGTT ACTTTTTTTA CTTACCTTCT TGAAGAGATT CCAAGGGAAA

1201  AAGAAAATTA TGGTGTTTTT CTCTACATGC AAGTCGACAA AGTTCCACGC

1251  CGAGCTCTTT CGATATATCA AATTCGATTG CCTTGAAATC CGTGGAGGGA

1301  TAGACCAGAA CAAAAGAACT CCAACATTTT TGCAATTCAT AAAGGCGGAA

1351  ACCGGTATTT TGTTGTGTAC TAATGTCGCT GCCCGAGGTC TTGATTTTCC

1401  TCATGTGGAC TGGATTGTGC AGTATGATCC TCCTGATAAC CCAACGGATT

1451  ATATTCATCG AGTTGGTAGA ACAGCTCGTG GTGAAGGAGC AAAAGGAAAG
```

-continued

```
1501  GCTCTGCTTG TCCTAACTCC ACAGGAGTTG AAGTTTATAC AGTATCTCAA

1551  GGCGGCGAAA ATTCCTGTTG AGGAACATGA ATTTGAAGAA AAGAAATTGC

1601  TCGATGTGAA ACCTTTTGTG GAGAATTTGA TATCTGAAAA CTATGCATTG

1651  AAGGAGTCAG CAAAAGAAGC ATACAAGACA TACATTTCAG GATATGATTC

1701  TCACTCTATG AAAGATGTCT TTAATGTTCA CCAACTCAAT CTCACGGAGG

1751  TTGCGACTTC GTTTGGTTTC TCAGATCCTC CCAAAGTTGC TCTGAAGATA

1801  GATCGAGGAG GGTACAGAAG TAAGAGAGAA CCGGTTAATA AGTTTAAGAG

1851  AGGTCGTGGT GGTGGTAGAC CCGGCGGTAA AAGCAAGTTC GAGAGGTACT

1901  AA
```

Genomic (SEQ ID NO: 20)

```
   1  AGAACACTCT CGAATTCGAA GAAAATACGT AGCAAAACCC TTATTTTTGA

51  ATTTCAGACG AATTCCGATT TCTTAATCAA AAATCCGATA AGAGCTTTGG

101  ATTTGGCGGC GAATAAGAAA ACATGGCGAA TTTGGATATG GAGCAACATT

151  CATCCGAAAA CGAAGAGATT AAGAAGAAGA AGCATAAGAA AAGAGCGAGA

201  GACGAAGCTA AGAAACTAAA GCAGCCAGCA ATGGAAGAAG AACCCGATCA

251  TGAAGATGGT GATGCCAAAG AGAACAATGC GTTAATTGAC GAAGAACCGA

301  AGAAGAAGAA GAAGAAGAAA AATAAGAAGC GTGGAGATAC TGATGATGGA

351  GAGGACGAAG CGGTAGCAGA AGAAGAGCCG AAGAAGAAGA GAAGAAAAA

401  TAAAAAGCTA CAGCAGCGTG GAGATACTAA TGACGAAGAG GACGAAGTGA

451  TAGCAGAAGA AGAAGAGCCG AAGAAGAAGA AGAAGAAACA GAGGAAGGAC

501  ACGGAAGCGA AGTCTGAAGA AGAAGAAGTA GAAGATAAGG AAGAAGAAAA

551  AAAATTGGAA GAAACTAGCA TAATGACTAA TAAAACGTTT GAGTCATTGT

601  CATTATCTGA TAACACTTAT AAATCTATCA AGGAGATGGG TTTTGCACGC

651  ATGACTCAGG TAATGTTTTT GGAATTGAAG CTTTATGTTT TTGTATAGCA

701  AAGATTCAAC CTTTTACAGT TTGGAATTTG GTTGGATTTC AACACTTTTG

751  CAGATACAAG CTAAAGCAAT TCCACCATTG ATGATGGGAG AAGATGTACT

801  TGGAGCTGCC AGGACCGGTT CTGGTAAAAC CTTAGCTTTT CTTATTCCTG

851  CTGTTGAGCT TCTTTACCGT GTTAAGTTTA CTCCTCGCAA TGGAACTGGT

901  GTTCTTGTTA TTTGCCCAAC AAGAGAGCTT GCTATTCAGG TTCTAATTCT

951  CTCACAATTT TCTATATAGT CTGTAGAATA TGCTAAAAGT GATACTTACT

1001  ATACATCATT AATGTTTCAG TCTTATGGAG TGGCAAAAGA ACTTCTTAAG

1051  TATCATTCAC AGACTGTGGG AAAAGTTATT GGCGGTGAGA AAGAAAGAC

1101  AGAAGCTGAG ATTCTTGCGA AGGTGTTAA TTTATTAGTA GCTACCCCTG

1151  GAAGACTTCT CGACCACCTT GAAAATACTA ATGGTTTTAT TTTCAAGAAC

1201  TTAAAGGTAA ACACAAATTT CTGATTTCAG TTTTGGGTAT ACTGGTATTG

1251  ATTTAATGCA ACATTTTTTA TTCGTTAATT TGCAGTTTCT TGTAATGGAT

1301  GAGGCTGATA GGATATTGGA ACAGAACTTT GAAGAAGACC TCAAGAAGAT

1351  TTTGAACCTT CTACCAAAGG TATTCTCGTG GCTTGCATAG TGAAGTCACC

1401  TCAACATTCT GAATCATAGA GATGTAAATT TCGTTTCATG TCAATGTGTT

1451  GTTGATAATG GTAAACCGTC TTTTTGTATT GCTGCAGACT AGACAGACGT
```

-continued

```
1501 CACTATTTTC AGCCACACAG AGCGCAAAGG TCTGCTTACC AATCAGTATA

1551 GTTTTCACTT AATTCTTTAT TAGTGTCAGT TTATTAAAAT TACTGGAACT

1601 TGATTAAACC ATCAGGTTGA GGATCTTGCT CGGGTGTCAC TTACCTCACC

1651 TGTTTATATT GATGTGGATG AAGGACGAAA AGAGGTAGCT ATTAACACAA

1701 TTTCTATTAT CTTTTCTCGC AATTTACTTT GTGACCAAAA CAGGCCTTTT

1751 TCAATTATAA GAAAACTGGA AAGTGCAGGT TACAAATGAA GGCTTGGAGC

1801 AAGGTTATTG CGTTGTGCCA AGTGCGATGC GGTTACTTTT TTTACTTACC

1851 TTCTTGAAGA GATTCCAAGG GAAAAGAAA ATTATGGTGT TTTTCTCTAC

1901 ATGCAAGTCG ACAAAGTTCC ACGCCGAGCT CTTTCGATAT ATCAAATTCG

1951 ATTGCCTTGA ATCCGTGGA GGGATAGACC AGAACAAAAG AACTCCAACA

2001 TTTTTGCAAT TCATAAAGGC GGAAACCGGT ATTTTGTTGT GTACTAATGT

2051 CGCTGCCCGA GGTCTTGATT TTCCTCATGT GGTATGCTTT CTTAACAACT

2101 TTAATGTTTT AATAATCTGG ATTGGTTGGT CTTTAATCAA ATTATTGTCT

2151 GCTTGTTTAG GACTGGATTG TGCAGTATGA TCCTCCTGAT AACCCAACGG

2201 TATGTTGCTT ATAATTTAGG GTTTTTATGC AAACACGCGG AAGAATAAGG

2251 GATAAGAAAT CACTCAAATT CTTGAATGTT ACTTTTGATT TAGGATTATA

2301 TTCATCGAGT TGGTAGAACA GCTCGTGGTG AAGGAGCAAA AGGAAAGGCT

2351 CTGCTTGTCC TAACTCCACA GGAGTTGAAG TTTATACAGT ATCTCAAGGT

2401 AAATTATTTT CATTCAATAA AAACTTTGAT AATTTTTCAA ATTATAGAAA

2451 TTTTGATAAA AGAATCTGTT TCCAACTGTA TAATTTGCAG GCGGCGAAAA

2501 TTCCTGTTGA GGAACATGAA TTTGAAGAAA AGAAATTGCT CGATGTGAAA

2551 CCTTTTGTGG TAAAACATTC TTGCTCTTTC AAATAAGTTT TACTACACTG

2601 AAGAAACAAA AGTTGAGAGA TTTATTTAAA ATGTTATTGC AGGAGAATTT

2651 GATATCTGAA AACTATGCAT TGAAGGAGTC AGCAAAAGAA GCATACAAGA

2701 CATACATTTC AGGATATGAT TCTCACTCTA TGAAAGATGT CTTTAATGTT

2751 CACCAACTCA ATCTCACGGT AACCAAATCT GCAGCATACA TATAACAATA

2801 CGAAACGTCA TGAAATCAGG AATACAATTT GTTTTTGTTT TCTGCAATTT

2851 AAACGTTAAC CGAAGGTCTT TGTTTATGTG CAGGAGGTTG CGACTTCGTT

2901 TGGTTTCTCA GATCCTCCCA AGTTGCTCT GAAGATAGAT CGAGGAGGGT

2951 ACAGAAGTAA GAGAGAACCG GTTAATAAGT TTAAGAGAGG TCGTGGTGGT

3001 GGTAGACCCG GCGGTAAAAG CAAGTTCGAG AGGTACTAAA AATACAGTTG

3051 CACAAACAAC GTCATACTTA GTAGTATGGC ACATGCCTTT TAACGAATGT

3101 TGTATCTTAT TTTTGGATTC ATTACGATT GTGTTGTCTT AAGCTGTTTC

3151 CAGAGATATC AGACGAGATA CCAGTTTTGT CCCCGTTACT TAGAAATATT

3201 GATCATTTTG TTTTGCGAAT AAACTTGGTC TTATATAT
```

Aa
```
                                                  (SEQ ID NO: 4)
  1 MANLDMEQHS SENEEIKKKK HKKRARDEAK KLKQPAMEEE PDHEDGDAKE

51 NNALIDEEPK KKKKKKNKKR GDTDDGEDEA VAEEEPKKKK KKNKKLQQRG

101 DTNDEEDEVI AEEEEPKKKK KKQRKDTEAK SEEEEVEDKE EEKKLEETSI

151 MTNKTFESLS LSDNTYKSIK EMGFARMTQI QAKAIPPLMM GEDVLGAART

201 GSGKTLAFLI PAVELLYRVK FTPRNGTGVL VICPTRELAI QSYGVAKELL
```

```
251  KYHSQTVGKV  IGGEKRKTEA  EILAKGVNLL  VATPGRLLDH  LENTNGFIFK

301  NLKFLVMDEA  DRILEQNFEE  DLKKILNLLP  KTRQTSLFSA  TQSAKVEDLA

351  RVSLTSPVYI  DVDEGRKEVT  NEGLEQGYCV  VPSAMRLLFL  LTFLKRFQGK

401  KKIMVFFSTC  KSTKFHAELF  RYIKFDCLEI  RGGIDQNKRT  PTFLQFIKAE

451  TGILLCTNVA  ARGLDFPHVD  WIVQYDPPDN  PTDYIHRVGR  TARGEGAKGK

501  ALLVLTPQEL  KFIQYLKAAK  IPVEEHEFEE  KKLLDVKPFV  ENLISENYAL

551  KESAKEAYKT  YISGYDSHSM  KDVFNVHQLN  LTEVATSFGF  SDPPKVALKI

601  DRGGYRSKRE  PVNKFKRGRG  GGRPGGKSKF  ERY
```

```
At5g66380
ATFOLT1 FOLATE TRANSPORTER 1
FOLT1 FOLATE TRANSPORTER 1
MCBI Accession number: BT010139.1
CDS
                                                        (SEQ ID NO: 5)
  1  ATGGCGGCGT  CGTGGCAGTG  GGAAAATGCC  ACCGCCGGCG  CCGTCGCTGG

51  ATTCGCCACC  GTAGCTGCTA  TGCACTCTCT  TGATGTTGTT  CGTACGAGAT

101  TCCAAGTCAA  CGACGGAAGA  GGGTCAAGTC  TGCCGACGTA  CAAGAACACT

151  GCTCACGCTG  TCTTCACCAT  TGCCCGTCTC  GAGGGTTTGA  GAGGGCTTTA

201  TGCAGGCTTC  TTCCCTGCAG  TTATCGGTTC  TACTGTTTCC  TGGGGCTTAT

251  ACTTCTTTTT  TTATGGAAGA  GCCAAGCAGA  GGTACGCTAG  AGGCAGGGAC

301  GATGAGAAAC  TCAGCCCTGC  TCTCCACCTT  GCTTCTGCTG  CTGAAGCAGG

351  GGCCTTGGTC  TGTTTATGCA  CAAATCCTAT  TTGGCTTGTC  AAAACAAGGT

401  TACAGCTTCA  GACACCTCTT  CATCAAACTC  AACCATACTC  AGGGCTATTA

451  GATGCCTTTA  GAACCATAGT  GAAAGAGGAA  GGACCCAGGG  CGCTCTACAA

501  GGGTATTGTC  CCTGGTCTTG  TACTGGTTTC  TCATGGTGCT  ATTCAGTTCA

551  CAGCTTATGA  GGAACTCCGT  AAAATCATTG  TGGATTTGAA  AGAAAGGAGA

601  AGAAAGTCCG  AATCCACTGA  CAATCTATTG  AACTCAGCAG  ATTATGCTGC

651  ACTTGGTGGC  TCCTCCAAAG  TCGCTGCAGT  TCTTCTTACG  TATCCATTTC

701  AAGTTATACG  AGCACGATTA  CAGCAACGAC  CTAGTACCAA  CGGAATCCCA

751  AGATATATAG  ACAGCTTACA  TGTCATCAGA  GAAACCGCGA  GATATGAAGG

801  TCTCAGGGGT  TTCTACAGGG  GACTAACGGC  TAATCTTTTG  AAAAATGTAC

851  CTGCGTCTTC  CATCACATTC  ATCGTCTATG  AAAACGTTCT  GAAATTGCTA

901  AAACAGCATC  AACAACAAA  AGATTAG
```

```
Genomic
                                                        (SEQ ID NO: 21)
  1  CTTGAACGGA  CGGCAGAACT  CGGAGTCGGA  GATCGTACCG  GAGGACGGCG

51  AATCTTCCAT  CTACTGTCCT  TTCGTTTTTT  ATACGCGTCA  AATGAGTCTT

101  TAACTTCAGA  TTAGCTCTGT  AAACAATCGC  GATTAGTCCG  GATTGCATCT

151  AAGGATTCGT  TGATGGCGGC  GTCGTGGCAG  TGGGAAAATG  CCACCGCCGG

201  CGCCGTCGCT  GGATTCGCCA  CCGTAGCTGC  TATGCACTCT  CTTGATGTTG

251  TTCGTACGAG  ATTCCAAGGT  CTGGTTTTTC  ACTCCTGGAT  TAACTCATCG

301  ATTTTGCTTT  TAAAAAGTTG  CTAACTTGAT  TGAACAACAG  TCAACGACGG

351  AAGAGGGTCA  AGTCTGCCGA  CGTACAAGAA  CACTGCTCAC  GCTGTCTTCA

401  CCATTGCCCG  TCTCGAGGTT  TCCAGATGAA  ACTCTCTTC  TGGCATCTTC
```

-continued

```
 451  CATATTATCT TCTCTATGTT ATGTGGTTGA CTCATTTGGT TTAAATCTTC
 501  TGTAGGGTTT GAGAGGGCTT TATGCAGGCT TCTTCCCTGC AGTTATCGGT
 551  TCTACTGTTT CCTGGGGCTT ATACTTCTTT TTGTGAGTGT TACTTTCGTT
 601  TAGCACATAT CTTCTTTCTT CATGATTTCT ATTCAAACAG TTTTCTGTTA
 651  GTTTTTTTAA TGTTTTTAGC CGTGGATCTT GTTTAAAATG TTCTGGAACA
 701  AATATATTAT CTCTCTGTAG TTATGGAAGA GCCAAGCAGA GGTACGCTAG
 751  AGGCAGGGAC GATGAGAAAC TCAGCCCTGC TCTCCACCTT GCTTCTGCTG
 801  CTGAAGCAGG GGCCTTGGTG AGTCTAACAG GCGCCATAAA CATCTCATTT
 851  CTCCTATGTT TTTTCGATCT CAGTATCAAG GGAATGATGC TTTCAGGTCT
 901  GTTTATGCAC AAATCCTATT TGGCTTGTCA AAACAAGGTT ACAGCTTCAG
 951  ACACCTCTTC ATCAAACTCA ACCATACTCA GGGCTATTAG GTTTGCAATA
1001  TGCTGCACAC ACAAAATTCA GTTTTCATTG TTTCTAGTGT TCATTCTAA
1051  ATGTGTATTT TGTGATCTTA AGATGCCTTT AGAACCATAG TGAAAGAGGA
1101  AGGACCCAGG GCGCTCTACA AGGGTATTGT CCCTGGTCTT GTACTGGTTA
1151  GTAACTATCC TGATCTATCT CTTGTAACGT TCGTTCGTAA AACTACCACA
1201  AGATCCACAG TTTTGGAACT ATAAAGATG ACTATTAGTT GCGAAAGAGG
1251  AGGCCTTACA GATTGAATGG TTTACATTTT GGGTTCAGCA GGTTTCTCAT
1301  GGTGCTATTC AGTTCACAGC TTATGAGGAA CTCCGTAAAA TCATTGTGGA
1351  TTTGAAAGAA AGGAGAAGAA AGTCCGAATC CACTGACAAT CTATTGGTAC
1401  AGAGTAATTC TTCTGAATAG GCTACATTGC GGTTCTTAAG TTATATAGCC
1451  ACATTAATCT TAATTCTACG GCTATTTCCA GCATCACGGA TATATACTAT
1501  TCTAACACAC TCCATTGCAA TTTTTCTTTA GAACTCAGCA GATTATGCTG
1551  CACTTGGTGG CTCCTCCAAA GTCGCTGCAG TTCTTCTTAC GTATCCATTT
1601  CAAGTTATAC GAGCACGATT ACAGGTACCT ATCGACCGTG TCTTCTTCAG
1651  TCTTATTATT GTTAGCTCAA ATCTAAATTC CTTGAGCTTC CTTACTTTCT
1701  ACCTTTGACC TTCTGCAATA TATGAGGATT TCATAAACAT GGTTCTTTTC
1751  TTGTTCAGCA ACGACCTAGT ACCAACGGAA TCCCAAGATA TATAGACAGC
1801  TTACATGTCA TCAGAGAAAC CGCGAGGTCA GGGCATATTC TTGGTCTCGA
1851  TTATGTCTGG AATGATGATC TTTTTGGTTA GTTTCACTGA GTAACACTTT
1901  TGGGTCTCTC TGCAGATATG AAGGTCTCAG GGGTTTCTAC AGGGGACTAA
1951  CGGCTAATCT TTTGAAAAAT GTACCTGCGT CTTCCATCAC ATTCATCGTC
2001  TATGAAAACG TTCTGAAATT GCTAAAACAG CATCCAACAA CAAAAGATTA
2051  GACTCTTCCT CTTCCTTTAC CGTTATTTCT TAGACTCAAC ACGCACGCGG
2101  TTGACTTGTC ACTCCCAATA CTAGAGAATT ATTCTTTGAT ATACATATAT
2151  TTTATGTGCG TTCCATGGTT CT
```

Aa
                                                        (SEQ ID NO: 6)

```
   1  MAASWQWENA TAGAVAGFAT VAAMHSLDVV RTRFQVNDGR GSSLPTYKNT
  51  AHAVFTIARL EGLRGLYAGF FPAVIGSTVS WGLYFFFYGR AKQRYARGRD
 101  DEKLSPALHL ASAAEAGALV CLCTNPIWLV KTRLQLQTPL HQTQPYSGLL
 151  DAFRTIVKEE GPRALYKGIV PGLVLVSHGA IQFTAYEELR KIIVDLKERR
 201  RKSESTDNLL NSADYAALGG SSKVAAVLLT YPFQVIRARL QQRPSTNGIP
```

-continued

```
251  RYIDSLHVIR ETARYEGLRG FYRGLTANLL KNVPASSITF IVYENVLKLL

301  KQHPTTKD
```

At3g59640
gycine-rich protein
NCBI Accesson number NM_001084845.1
CDS (SEQ ID NO: 7)
```
  1  ATGAGCTCTA CGCAGGCTAA TCTATGCAGA CCATCCTTGT TCTGTGCAAG

51  GACAACGCAA ACAAGACATG TCTCTAGTGC ACCTTTTATG TCGTCATTAC

101  GCTTTGATTA TCGACCACTC CCCAAATTAG CTATTCGGGC ATCTGCATCA

151  TCATCGATGT CTTCTCAGTT TTCGCCTCTA CAGAATCATC GCTGCCGGAA

201  TCAGAGGCAA GGTCCTGTTG TGTGTTTACT TGGTGGGAAG GATAAGTCTA

251  ACGGTAGTAA TGAGCTATCA TCAACATGGG AAGCTATTGA GAAAGCAATG

301  GGGAAGAAAT CAGTTGAAGA TATGTTGCGT GAGCAGATAC AAAAGAAAGA

351  CACTGGCGGC ATTCCTCCAC GAGGACGAGG AGGAGGGGGT GGCGGTAGAA

401  ATGGTGGGAA TAATGGGTCT GGAGGCTCAT CAGGGGAAGA TGGTGGTCTT

451  GCTAGTTTTG GGGATGAAAC TCTGCAAGTG GTATTAGCAA CCTTAGGCTT

501  CATCTTTCTG TACTTCTACA TCATCAATGG GGAGGAGTTG TTCCGTCTTG

551  CAAGAGATTA CATTAGGTAC CTTATAGGAA GACCCAAGAG TGTTAGGCTG

601  ACCCGAGTTA TGGAAGGTTG GAGTAGATTC TTCGAGAAGA TGTCGAGGAA

651  AAAAGTGTAT AACGAGTACT GGCTAAAGAT TAAGCGATCA TCAACAAGTC

701  TACCTGGTCT GGTAACCCGG GCAAATACAA ACGCATCTTG A
```

Genomic (SEQ ID NO: 22)
```
  1  ACACAAACAA GAAAACGCAA AACTAATCCT CTCTCGAATT AGGGTTTCGT

51  CAAGGTATTA CATTATTTCA CACCCTTATC ATCATCTTCT GATTTCTGGT

101  AATCTTCTTT TGATTAGATC TTCCTATCGA TTGGTTCAGT CCTTTCTTAT

151  TTTCGAATTC TTGATTGGTT TACCGTGGTT GCTACGATTT AAACCTTTAA

201  CATACCTAAA AGAACGTTTT TGTTTTTGCT TTTTGTTGTT ATTGAAGTTT

251  TTTTTTTTTT TTATTGTTGT TGATGAAGAT CCTGGAGTTG ATGTATTGAG

301  AGAAGCCATT GAGATAAGAG ATGAGCTCTA CGCAGGCTAA TCTATGCAGA

351  CCATCCTTGT TCTGTGCAAG GACAACGCAA ACAAGACATG TCTCTAGTGC

401  ACCTTTTATG TCGTCATTAC GCTTTGATTA TCGACCACTC CCCAAATTAG

451  CTATTCGGGC ATCTGCATCA TCATCGATGT CTTCTCAGTT TTCGCCTCTA

501  CAGAATCATC GCTGCCGGAA TCAGAGGCAA GGTCCTGTTG TGTGTTTACT

551  TGGTGGGAAG GATAAGTCTA ACGGTAGTAA TGAGGTGAGA TGCTTCGTCT

601  TCATTCTAAG ATGTCTTTGC TTATTAGATC ATATAAAGAT GATGCTTAAT

651  CTTTAAATGT TCCAAATTGA TCTTTTTGTG TGTGTGTGCG TGTAAGAAGT

701  TCGGCACAGA GTTGAGTTAT GTTCTGATT ATAAGTAGTA TTGATATGAT

751  TCTTTTCTGT TTTATACTTA CTTGGTCGAA AGGATAAATC TGATAGTAGT

801  TATGAGATCA GATGATTTCT CTTCATTCTA TAGATGTTCT TGCTGAGATT

851  TGAATATTAA ATCTTGCAAA AGTGATCTTT TTGTCTGTGT TTGTAAGTTA

901  AGGCACAGAA CTTTAGTGCG TCTGATATTA ATACGCTCAG TGATGATGTT

951  TTATCATCAG CTATCATCAA CATGGGAAGC TATTGAGAAA GCAATGGGA
```

-continued

```
1001    AGAAATCAGT TGAAGATATG TTGCGTGAGC AGATACAAAA GAAAGACACT
1051    GGCGGCATTC CTCCACGAGG ACGAGGAGGA GGGGGTGGCG GTAGAAATGG
1101    TGGGAATAAT GGGTCTGGAG GCTCATCAGG GGAAGATGGT GGTCTTGCTA
1151    GTTTTGGGGA TGAAACTCTG CAAGTGGTAT TAGCAACCTT AGGCTTCATC
1201    TTTCTGGTAA GGACAAGATC ACAAGCCCGC ACAAGTTATC TTTGAATTAT
1251    AGTATCTTTA GCTTTGATCA TTGTTTCTTT TTTTTGCAGT ACTTCTACAT
1301    CATCAATGGG GAGGAGTTGT TCCGTCTTGC AAGAGATTAC ATTAGGTACC
1351    TTATAGGAAG ACCCAAGAGT GTTAGGCTGA CCCGAGTTAT GGAAGGTTGG
1401    AGTAGATTCT TCGAGAAGAT GTCGAGGAAA AAAGTGTATA ACGAGTACTG
1451    GCTAAAGATT AAGCGATCAT CAACAAGTCT ACCTGGTCTG GTAACCCGGG
1501    CAAATACAAA CGCATCTTGA GATCTTATGT TGATTCAAAT GAAATGAAGA
1551    TAGTGATCGG TTTTCTTACT GGTTTAAGTA GTTTCCCTTA GACCCTTACC
1601    CGTGTTTTTG TTTTTGTTTA AGTTACTTTT GCCAGTAGTA AATATTGATG
1651    CTCATCGTCA CAAGT
```

Amino acid (SEQ ID NO: 8)
```
  1    MSSTQANLCR PSLFCARTTQ TRHVSSAPFM SSLRFDYRPL RKLAIRASAS
 51    SSMSSQFSPL QNHRCRNQRQ GPVVCLLGGK DKSNGSNELS STWEAIEKAM
101    GKKSVEDMLR EQIQKKDTGG IPPRGRGGGG GGRNGGNNGS GGSSGEDGGL
151    ASFGDETLQV VLATLGPIFL YFYIINGEEL FRLARDYIRY LIGRPKSVRL
201    TRVMEGWSRF FEKMSRKKVY NEYWLKIKRS STSLPGLVTR ANTNAS
```

At3G59650
mitochondrial ribosomal protein
L51/S25/CI-B8 family protein
NCBI Accession number NM_001203208.1
Cds (SEQ ID NO: 9)
```
  1    ATGGCGCTTA GAGGAGTTTG GCAGCTCAAG AAACTCGTTG TGAGCTACTG
 51    TAATTGGGGT GGTAGCAGTA GAGGCATCAG AGCCTTTATG GAATCAGAAT
101    TGCCTGCTCT AAAGGAGAAA AACCCGCAGC TCGAAGTAAT TACCGAGCTT
151    TCACGGGGAC AACATCCTTA TTTGAAGGGC ATTTACAGGA ATAGAAATGA
201    AAGGGTAGTG TGTGTGAAGA ACATGGATCC TGAAGAAGTG CTTTTGAATG
251    CAACGAGGCT GAGGAACTCG CTTGGACGGA AAGTGGTTAA ACTGAGGACC
301    AGACATGTCA CCAAACACCC CAGTGTTCAA GGCACCTGGA CAACTGCTGT
351    CAAATTCTGA
```

Genomic (SEQ ID NO: 23)
```
  1    ATCACGTGAT CATCTTCTTT CTTCCTTTTT TCTTGTCATC TGTTACACAT
 51    CGGTTAGGGT TTTAGTTTCT CTTACCGAGA TTCAAATGGC GCTTAGAGGA
101    GTTTGGCAGC TCAAGAAACT CGTTGTGAGC TACTGTAATT GGGGTGGTAG
151    CAGTAGAGGC ATCAGGTAAT TTTGTTTACC TATAATTTGA TTTCGCAATC
201    TATGAGCCGT ATTTTTTCAT TTATCATCGA TCTACCATTT TTCCTGTAAT
251    TCACTTTGGA ACTTGAGACT ATCTATACGA ATCTATGAGT CTGTACTTGG
301    TATTTGTGAA GCAAATTAAC TTTTCATGTC AATGTGGGTT TAGAAATGTG
351    AAGCAAAATG ATTTAGTAAT GAATCGTTAC CATTTCATCC TAGTTTGGTA
```

```
-continued
 401  CTACGCATTT TCTTATGATG TGTTGTTAAA CATACAGAGC CTTTATGGAA
 451  TCAGAATTGC CTGCTCTAAA GGAGAAAAAC CCGCAGCTCG AAGTAATTAC
 501  CGAGCTTTCA CGGGGACAAC ATCCTTATTT GAAGGGCATT TACAGTATGT
 551  ATATTTCTCC TCTATTGAAT ACAATCCTGA TTCAACGGTT GTTGATATTA
 601  GCAATTTCAC TTGCACAATT CATAGGGAAT AGAAATGAAA GGGTAGTGTG
 651  TGTGAAGAAC ATGGATCCTG AAGAAGTGCT TTTGAATGCA ACGAGGCTGA
 701  GGAACTCGCT TGGACGGAAA GTGGTTAAAC TGAGGACCAG AATTCTGAGA
 801  CTTTCCTGCT AAATTGTTTG CAGGTTTTCA TCTTCTAGCT GTTAAATCGA
 851  ATGTTGCAAG TATCAGGATT GGTCGTTTAT CTGTATTGCA ACCCCAAGTT
 901  GTTTGTACCG TCTGTGACTT GGGACAAAGA TGTAGTCTTC AAATGTTTTG
 951  CAGTTTTTGC AATGTTTGAA TTTTGTCTTG TCCTTCTGGT TGAGTCTATA
1001  ATAAGATTAC ACAAGGGTTT AAGGTTA
```

Amino acid
(SEQ ID NO: 10)
```
   1  MALRGVWQLK KLVVSYCNWG GSSRGIRAFM ESELPALKEK NPQLEVITEL
  51  SRGQHPYLKG IYRNRNERVV CVKNMDPEEV LLNATRLRNS LGRKVVKLRT
 101  RHVTKHPSVQ GTWTTAVKF
```

At3g60310
Unknown protein
NCBI Accession number NM_115895.3
CDS
(SEQ ID NO: 11)
```
   1  ATGCCCTCTC CGTCTGCAGT CGCCGATCTC TTGGCCGCTC TTGCTTACAG
  51  GCTTCAGAAC GGAGATGAAT TATTCGAAGA AGAAGAAGAA GCGGAAGAGT
 101  CTACTTCTTC TATGGGACTA GCTATCTCGG AGCTTAACCG ATCTCTGACT
 151  CTGGATATCG GCTGCGAGGA TTCTGGGGTC AGGGTTGTGG ACGCAGCGTT
 201  ATCTATAATG TGCTTCAAGG CACCTCAGGT TTTTGATTCG CAATTGAGT
 251  TTATGGTACG AACAATTGTT TGCGCCTTAT CATCTTCAAG CAATTGTAAG
 301  GTAATTAGGT ATCGAAACGA GGAAACATTA CAGTTTGGGA GCTCCAATTT
 351  ACCTGGCTGC TCTGAAGAAT TGATCGAAAT CTCTAAGGAT ATTATTGAGA
 401  AACTGTGGGG AAATGGAAGA TTGGCTACAT TGTTATTCGA AGCTGTTGTA
 451  AGGTCAGCAG CCTCAACATG TAAGATCAGC AGTTTCAACG CGCATGGAAA
 501  GCTTATGGAT GGAAGAAATA GGGCTGTCTC GAAGCTTCTT GCTTACTTAC
 551  CGGGAGAATC ATCTATAGAG AACCACAAGA TACCTCTGAG GATTCTTTTC
 601  TGGTATCGAG ATCCATTGTC TTTGAAGGTA GATGTTTCCA GAATCTTGAA
 651  AGAGGTGGTG GAAAGGCCTT TCCTTTGTGT AAAAAGGGAG CTTTTCGAGA
 701  GGGGGGAGTG GCGCGATATT GTCATCTGCC TAGCGATATC TCCTACTATG
 751  TTTATCAACA CTAGATCACT CTTACATAAA TGGCTTTTGC TTACGGGACT
 801  TGCTTCTGTT TTTGAAGTAC TTGCTGGTTT GGCCTCTGCA ATAATGGATA
 851  CAATTTCAAG GCCATCGTTG TGGGGTATAC CAATGGAACT AGCTTCCATG
 901  TTGCCATTTT CTGATACATA CTTTCCTTTC CAGTGTCAAT TTCTGAGAAT
 951  CTTGGCGGGT CCTCTCAGTT CCAAGTCCCT CCTAATGTTA GCTCATACTG
1001  TCAGTAAAGC GTCTGCTGTC CCTGGGCAAC AACAACGGGA TACTAATTGT
1051  AAGCCTACTC CAATAAAAGT TCAAGCATTA GATGACAAAA CCGAATGGGC
```

-continued

```
1101 TTTGGCTATT AACTTCCCAG ATTGGTTCTA TTTTGCATCT GCTATGCTCT
1151 TCTCAGAAGG AAAGTCGTTT GAAAATATCC ACCATATATG CGCTTCAAAA
1201 GTGGCTGACT GTAGACAAGT ATGTGATGTA AAGATCTCT CCATTGCTGC
1251 GGCTACATAC ATTTCTTGGA TTCTAAACCC TGGAAGTGGA ACCATTCAAG
1301 AGTCAGTAAG TAAGTCTCTC ATTAGAGTCT CAGAGATATG TATCAGTAAA
1351 AGTTGCGGCT CAGAAGCATA TCGTACTGAG ACTATAACTG CAAGAGAAA
1401 GAAACCAGAT AGGCTCGTTT CTGGCAAAAT AAATGCTTCC AGTATTGTGG
1451 AAGACCTATT GAGAGAATTT GAAACAATA TCACCAATTC AGTTTCTTAT
1501 GATTTGGATT CTCGGAAAAC GCATCCATCT TTCAGCTCTG GCCTCCAAAA
1551 CAATTTGTTG GTAAGAAGAG TTGTGGTTGG CGTTCTGTTT GGTTCTCCAT
1601 ATTCAGTAAC AGATGAGGAG TATGAACTGG TATTACACTA TGCAGCAACT
1651 GGGAAAATTC TTGACTTTAA GAAATCACGG AGTACCGGAT TCAAACAAGG
1701 AAAGAAATTC TCTAGAATAT CTGCTTTACT GTCGAATGAA ATTACCAAGG
1751 AGGAGGCTAC AGAAGGCACA CTTCTTGTTT TCAACTTAAC TGACACTTTG
1801 GAGAGTATGT GTGTATCAAG TTTTGAGGCC AAAGAGGACG CAGAGAAGTT
1851 TATTAACCAT TTTAAGCTGA GATCCAGCAA GTACTTGGTC AAATGCATAG
1901 ATCGCCTGAT ACAACTTCAC TGTACACAAG ATGGAGATCC AATACTAAGT
1951 GACATTAATA TCAGACTGCT GCAATGGACA GTAAAAGGAC TAGAAGATCC
2001 ACATTTTAAC AAAGTTCTTG ATGATATCGC TGCTAAGTTG GCCTGCATAT
2051 TCTCGCGCGT GTAA
```

Genomic
(SEQ ID NO: 24)
```
  1 TCTGAGTGGG CATTACAAAT ATTTGGCTTA ACCGGTTCCG AGCCATTTGT
 51 AATTTCCGAG TATCTACATC GCCGGCGATT GATTCTGCTC ATCTTTTCGA
101 TGCCCTCTCC GTCTGCAGTC GCCGATCTCT TGGCCGCTCT TGCTTACAGG
151 CTTCAGAACG GAGATGAATT ATTCGAAGAA GAAGAAGAAG CGGAAGAGTC
201 TACTTCTTCT ATGGGACTAG CTATCTCGGA GCTTAACCGA TCTCTGACTC
251 TGGATATCGG CTGCGAGGAT TCTGGGGTCA GGGTTGTGGA CGCAGCGTTA
301 TCTATAATGT GCTTCAAGGC ACCTCAGGTT AGTATCATAT CTATCCTGGA
351 CTTGCATTGT TTCTACGTAG CTGAGTTCTT ACTTGTGAGT GATTTTCTTA
401 TTAAAATTCA GGTTTTTGAT TCGGCAATTG AGTTTATGGT ACGAACAATT
451 GTTTGCGCCT TATCATCTTC AAGCAATTGT AAGGTAATTA GGTATCGAAA
501 CGAGGAAACA TTACAGTTTG GGAGCTCCAA TTTACCTGGC TGCTCTGAAG
551 AATTGATCGA AATCTCTAAG GATATTATTG AGAAACTGTG GGGAAATGGT
601 GCGTTTGATT TAGCTTATCC TAGAGTTATC TGAAGATTTT AACTTTTGTT
651 TGTTCTCTCA TATTTTTCTG ACTTGGAAAT GTTCATAGGA AGATTGGCTA
701 CATTGTTATT CGAAGCTGTT GTAAGGTCAG CAGCCTCAAC ATGTAAGATC
751 AGCAGTTTCA ACGCGCATGG AAAGCTTATG GATGGAAGAA ATAGGGCTGT
801 CTCGAAGCTT CTTGCTTACT TACCGGGAGA ATCATCTATA GAGAACCACA
851 AGATACCTCT GAGGTTTGAC CTCTTGTACT GTTTCTGTTC CAAGCTATGT
901 TAGTCTGCAT TTTCCATATT ACTCAAGAAG CCACAGCTTC TGAGATGTTT
951 GCTCTCTTGT TTCAGAAAAA GGTAGACCGG TCTGACACTT TTTGATGATC
```

-continued

```
1001  AGGATTCTTT TCTGGTATCG AGATCCATTG TCTTTGAAGG TAGATGTTTC
1051  CAGAATCTTG AAAGAGGTGG TGGAAAGGCC TTTCCTTTGT GTAAAAAGGG
1101  AGCTTTTCGA GAGGGGGGAG TGGCGCGATA TTGTCATCTG CCTAGCGATA
1151  TCTCCTACTA TGTTTATCAA CACTAGATCA CTCTTACATA AATGGCTTTT
1201  GCTTACGTGA GTTCCTATCC AATTGGTGTC ATGTAAATCT ACAATAATAG
1251  ACATGTGTAA TCTTATGCGT TGTGATCTCT AGTTTTCCAT CTTTCTTGCT
1301  TTCTGATGCA ATTTCTTTCT TTACGCCAGG GGACTTGCTT CTGTTTTTGA
1351  AGTACTTGCT GGTTTGGCCT CTGCAATAAT GGATACAATT TCAAGGCCAT
1401  CGTTGTGGGG TATACCAATG GAACTAGCTT CCATGTTGCC ATTTTCTGAT
1451  ACATACTTTC CTTTCCAGTG TCAATTTCTG AGAATCTTGG CGGGTCCTCT
1501  CAGTTCCAAG TCCCTCCTAA TGTTAGCTCA TACTGTCAGT AAAGCGTCTG
1551  CTGTCCCTGG GCAACAACAA CGGGATACTA ATTGTAAGCC TACTCCAATA
1601  AAAGTTCAAG CATTAGATGA CAAAACCGAA TGGTAACTTT ACATAAAATG
1651  CAAATTGATA CCCTCAGATT TGATCTATTT ATATATACGT GCGTGTGAGT
1701  GGTTTTTGAA TGATGTTGTA TCTTCTGGCA GGGCTTTGGC TATTAACTTC
1751  CCAGATTGGT TCTATTTTGC ATCTGCTATG CTCTTCTCAG AAGGAAAGTC
1801  GTTTGAAAAT ATCCACCATA TATGCGCTTC AAAAGTGGCT GACTGTAGAC
1851  AAGTATGTGA TGTAGAAGAT CTCTCCATTG CTGCGGCTAC ATACATTTCT
1901  TGGATTCTAA ACCCTGGAAG TGGAACCATT CAAGAGTCAG TAAGTAAGTC
1951  TCTCATTAGA GTCTCAGAGA TATGTATCAG TAAAAGTTGC GGCTCAGAAG
2001  CATATCGTAC TGAGACTATA ACTGGCAAGA GAAAGAAACC AGATAGGCTC
2051  GTTTCTGGCA AAATAAATGC TTCCAGTATT GTGGAAGACC TATTGAGAGA
2101  ATTTGAAAAC AATATCACCA ATTCAGTTTC TTATGATTTG GATTCTCGGA
2151  AAACGCATCC ATCTTTCAGC TCTGGCCTCC AAAACAATTT GTTGGTAAGA
2201  AGAGTTGTGG TTGGCGTTCT GTTTGGTTCT CCATATTCAG TAACAGATGA
2251  GGAGTATGAA CTGGTATTAC ACTATGCAGC AACTGGGAAA ATTCTTGACT
2301  TTAAGAAATC ACGGAGTACC GGATTCAAAC AAGGAAAGAA ATTCTCTAGA
2351  ATATCTGCTT TACTGTCGAA TGAAATTACC AAGGAGGAGG CTACAGAAGG
2401  CACACTTCTT GTTTTCAACT TAACTGACAC TTTGGAGAGT ATGTGTGTAT
2451  CAAGTTTTGA GGCCAAAGAG GACGCAGAGA AGTTTATTAA CCATTTTAAG
2501  CTGAGATCCA GCAAGTACTT GGTCAAATGC ATAGATCGCC TGATACAACT
2551  TCACTGTACA CAAGATGGAG ATCCAATACT AAGTGACATT AATATCAGAC
2601  TGCTGCAATG GACAGTAAAA GGACTAGAAG ATCCACATTT TAACAAAGTT
2651  CTTGATGATA TCGCTGCTAA GTTGGCCTGC ATATTCTCGC GCGTGTAACT
2701  GTCACCATAT AGCCTGACTT GTGTCATATT TGGTGGTACA CTAATTTTTG
2751  GGAAAATGGT GATCAAATGT GAACTGTTCA AGCACTCGC ACGACTGGTA
2801  TGAGGATATA ACTGGTGTAC AGGTAATTGT AATTGATTGG TCTAATTTCT
2851  AATACAGTAA CACAATCATA AGTGATAAGC CGGTTTAGTC GTCAAAGTAG
2901  CAACATTCTT GGCTAAATTT GAGTTGGATG TCTGAATGTC TTTGGTATCA
2951  GTGTAATGGT TATCTATAAT ATGTTGCCAC CGCTAAATAT GATCTAGTAC
```

```
3001  ACTAGTTTGT TTAGAGCCTA AAGTTTTTTA TGTTGGTGGC TATCATATGT
3051  TATCATCAAG GGAGCTTTAT GTTTAATATA TTACTCTACA TGGGTGATGA
3101  GACATTTGAC CTGCATTTTT TTTTCATAAT ACTGTTAAAT TTTTTGTGAT
3151  CATAATAACA TATTACCTTC ATCCTTTCTA TTTCAGCTCC ACAACTGAAA
3201  TTATTTGATC TGCCTGGACT GGACCAGAGA ATTGTGGACA ATTCAATGGT
3251  GAGCCTTGAA AGCACTTGAT GCCTTATTCA ATGGTGAGCC TTGGAACCAC
3301  TTGATGCCTT TGCCATGCTC TCTTAATTCC ACTTGATAAC CACAAAACAA
3351  TAACCGGATT TCCTGCTGAA AAGGGTAATG TAGATTCATT ATCATGATTT
3401  GCTCTCTATG TTCAAATAGT CATTTGTTTC TTAGATCTCT TGGCTAATTA
3451  TGCGCAAAAA CACAATTAGC CAGGGCATCT GAGTTTCGTC ATCCCAAGCC
3501  CCTGAGAGTT GCAAAAGGAG TATGATCCAG AGAAGTGAGT TATTGTGAGT
3551  ACATGTACTT GGGTTTTGCC TTTTAGGCTT TTAATCATGT TGTTAAATAT
3601  TTCTTATTGA ATCAGTTGGT TTCAGAC
```

Amino acid
(SEQ ID NO: 12)
```
  1  MPSPSAVADL LAALAYRLQN GDELFEEEEE AEESTSSMGL AISELNRSLT
 51  LDIGCEDSGV RVVDAALSIM CFKAPQVFDS AIEFMVRTIV CALSSSSNCK
101  VIRYRNEETL QFGSSNLPGC SEELIEISKD IIEKLWGNGR LATLLLFEAVV
151  RSAASTCKIS SFNAHGKLMD GRNRAVSKLL AYLPGESSIE NHKIPLRILF
201  WYRDPLSLKV DVSRILKEVV ERPFLCVKRE LFERGEWRDI VICLAISPTM
251  FINTRSLLHK WLLLTGLASV FEVLAGLASA IMDTISRPSL WGIPMELASM
301  LPFSDTYFPF QCQFLRILAG PLSSKSLLML AHTVSKASAV PGQQQRDTNC
351  KPTPIKVQAL DDKTEWALAI NFPDWFYFAS AMLFSEGKSF ENIHHICASK
401  VADCRQVCDV EDLSIAAATY ISWILNPGSG TIQESVSKSL IRVSEICISK
451  SCGSEAYRTE TITGKRKKPD RLVSGKINAS SIVEDLLREF ENNITNSVSY
501  DLDSRKTHPS FSSGLQNNLL VRRVVVGVLF GSPYSVTDEE YELVLHYAAT
551  GKILDFKKSR STGFKQGKKF SRISALLSNE ITKEEATEGT LLVFNLTDTL
601  ESMCVSSFEA KEDAEKFINH FKLRSSKYLV KCIDRLIQLH CTQDGDPILS
651  DINIRLLQWT VKGLEDPHFN KVLDDIAAKL ACIFSRV
```

At3G60840
MAP65-4 MICROTUBULE-ASSOCIATED PROTEIN 65-4
NCBI Accession number NM_115948.1
Cds
(SEQ ID NO: 13)
```
  1  ATGGGAGAGA CTGAGGATGA AAAAGATGCT TCTTTGGCTG ATATCGAGAA
 51  GGAGTGTCTC TCGGTTTATA AGCAAAAGGT CGAGGAGGCT AGTCGGGGTA
101  AAGCGAATTT GCTGAAAGAA ATCGCTGTTG CAGAGCAGA AATTGCAGCT
151  ATTGGCTCTT CTATGGGTGG ACAAGAGATT CATTCTAACA GCAGGTTAGG
201  AGAAAACTTG AAAGAGGAGC TTGAGAATGT TAATGTGCAA TTGGATGGAC
251  TGCGCAAAAG GAAAGCTGAG AGAATGATTC GGTTTAATGA AGTTATCGAT
301  CAGTTACTGA AGTTGTCACT GCAACTTGGA AATCCAACAG ATTATCTGAA
351  GAAGTTTGCT GCTGAAGAGA CCGATCTTTC GCTTCAGAGG TTGGAGGAAT
401  TGCGTAGCCA GTTGGGTGAG CTCCAAAATG AAAAGAGCAA AGATTGGAA
451  GAGGTAGAGT GTTTGCTGAA AACGCTTAAC TCGTTGTGCT CGGTTCTTGG
```

```
 501  TGAAGATTTC AAAGGCATGA TAAGAGGGAT ACATTCATCT CTGGTTGATT
 551  CCAACACTAG GGATGTGAGC AGAAGTACTC TTGATAAGTT GGATATGATG
 601  ATTGTGAATT TACGAGAGGC CAAGTTACAG CGAATGCAGA AGGTTCAAGA
 651  TCTTGCAGTG TCCTTGTTGG AGCTCTGGAA TCTGCTGGAC ACGCCTGCGG
 701  AAGAGCAAAA GATATTTCAC AATGTCACAT GTAGCATCGC TTTGACTGAG
 751  TCTGAAATAA CTGAGGCCAA CATACTTTCT GTTGCTTCCA TTAAACGCGT
 801  TGAGGATGAA GTCATTAGGC TTAGCAAGAT CAAATAACT AAGATCAAAG
 851  AGGTGATACT GAGGAAGAGG CTTGAGCTTG AGGAAATATC AAGGAAGATG
 901  CACATGGCCA CCGAAGTTCT TAAATCAGAA AACTTTTCAG TTGAAGCTAT
 951  AGAATCTGGT GTCAAGGATC CTGAGCAGTT GTTAGAGCAA ATTGATTCCG
1001  AGATTGCAAA GGTCAAAGAG GAAGCTTCAA GCAGGAAGGA GATTCTTGAA
1051  AAAGTGGAGA AATGGATGTC AGCTTGTGAA GAAGAGTCTT GGCTGGAAGA
1101  GTACAATCGG GATGATAACC GGTACAACGC TGGAAGAGGA GCTCATCTTA
1151  CATTGAAGCG TGCAGAAAAA GCCCGTTTAC TTGTCAATAA ACTTCCTGGG
1201  ATGGTGGAAG CTTTGACCGC CAAAGTCACT GCTTGGGAGA ATGAAGAGG
1251  AAATGAATTC TTATATGATG GGGTCCGAGT CTTATCGATG CTTGGTCAGT
1301  ACAAGACTGT ATGGGAAGAG AAAGAGCATG AAAAACAGAG ACAGAGAGAT
1351  ATGAAGAAAC TTCATGGACA ACTCATAACA GAGCAAGAAG CTCTTTATGG
1401  GTCTAAACCA AGCCCAAATA AAAGCGGAAA GAAACCACTG AGAACACCAG
1451  TAAATGCTGC CATGAACAGA AAACTCTCCC TTGGTGGTGC CATGCTTCAT
1501  CAAAGCTTAA AGCATGAGAA GGCAACACTC AATAGCAAAA GGACGAAGTA
1551  CTATGACCAG AACGCTACTA GTAGAAGAGA TTCAGCTCTT CCAACTCTTT
1601  CAGGGAGGAG AAACTCAGAG CTTCCTGGTC GTATCAGATC AAAGAACGTT
1651  CCGGTTGCAG GAAAAGCTGC GAGATCTCCA ATGCTTAGGA AGCCTCTTTC
1701  ACCTGTCACT TCCAATATCT TGAATTCCCC AGAAGATCAT CACAAGGATG
1751  CTTACACAAC AAAGGAGAGA ATCTTGACAC CTAAAACCAA CGAAGAAAAG
1801  AAAAGAGCTG TTCCAACAAC TCCTGCAGCT TCAGTCGCTA TGACAGAGGC
1851  AACAACGCCG TTCACTCCTG CTGTGGAGAA GAGAATGGAT GAGGAAGACG
1901  TTATTGTTGA GTATTCGTTT GAAGAGGTTA GGGCCGGTTT TTGCTAA
```

Genomic (SEQ ID NO: 25)

```
  1  ATGGGAGAGA CTGAGGATGA AAAAGATGCT TCTTTGGCTG ATATCGAGAA
 51  GGAGTGTCTC TCGGTTTATA AGCGAAAGGT CGAGGAGGCT AGTCGGGGTA
101  AAGCGAATTT GCTGAAAGAA ATCGCTGTTG GCAGAGCAGA AATTGCAGCT
151  ATTGGCTCTT CTATGGGTGG ACAAGAGATT CATGTAAGTG TATTCAAGAC
201  TTCAGTTTTG ATATATTTGG TTTTTGTCTG CTGGAGTTAT GGCAAGTAAT
251  GGTGCATTTT CTTCTTACAG TCTAACAGCA GGTTAGGAGA AAACTTGAAA
301  GAGGAGCTTG AGAATGTTAA TGTGCAATTG GATGGACTGC GCAAAAGGAA
351  AGCTGAGAGA ATGATTCGGT TTAATGAAGT TATCGATCAG TTACTGAAGT
401  TGTCACTGCA ACTTGGAAAT CCAACAGATT ATCTGAAGAA GTTTGCTGCT
451  GAAGAGACCG ATCTTTCGCT TCAGAGGTTG GAGGAATTGC GTAGCCAGTT
```

-continued

```
 501 GGGTGAGCTC CAAAATGAAA AGGTTGGTTT TGCTGTTAGA TCTCATGATA
 551 TGGGACTTAT ATTACAAGAG CATGTGCACC TGTTTTCCTT ATGTTAACTT
 601 TGAATTCTTT TCAAATGTA GAGCAAAAGA TTGGAAGAGG TAGAGTGTTT
 651 GCTGAAAACG CTTAACTCGT TGTGCTCGGT TCTTGGTGAA GATTTCAAAG
 701 GCATGATAAG AGGGATACAT TCATCTCTGG TTGATTCCAA CACTAGGGAT
 751 GTGAGCAGAA GTACTCTTGA TAAGTTGGAT ATGATGATTG TGAATTTACG
 801 AGAGGCCAAG TTACAGCGAA TGCAGAAGGT TACAAGTCTG AGCTCTTCTT
 851 TGTAATGTAG TGCAAGTTTT TCTGCGTGAT TATGGTTTCT GACTCTCATC
 901 ACTTTGTTTT TCTAGGTTCA AGATCTTGCA GTGTCCTTGT TGGAGCTCTG
 951 GAATCTGCTG GACACGCCTG CGGAAGAGCA AAAGATATTT CACAATGTCA
1001 CATGTAGCAT CGCTTTGACT GAGTCTGAAA TAACTGAGGC CAACATACTT
1051 TCTGTTGCTT CCATTAAACG CGTGAGTGCA CAGGACCAAA CCTTTCTGTG
1101 TTTTCTCCCT GTATTGTTTA GTCTATCCGT TTATAATAGT ATAGGAACAA
1151 TCTTTTTTAT AATGTGAGTT TGTTTTACAG GTTGAGGATG AAGTCATTAG
1201 GCTTAGCAAG ATCAAAATAA CTAAGATCAA AGAGGTGATA CTGAGGAAGA
1251 GGCTTGAGCT TGAGGAAATA TCAAGGAAGA TGCACATGGC CACCGAAGTT
1301 CTTAAATCAG AAAACTTTTC AGTTGAAGCT ATAGAATCTG GTAAACCATT
1351 ATTAGGAACA GCTTATTCTT TACATAATAT GATGTGCACA AACTCCAGAA
1401 ATGTTATGCT CATTATACTG GTAGATAACA TGAACATGCT AATAATAACA
1451 TGTTTCCACT CATCTTTTAG GTGTCAAGGA TCCTGAGCAG TTGTTAGAGC
1501 AAAATTGATTC CGAGATTGCA AAGGTCAAAG AGGAAGCTTC AAGCAGGAAG
1551 GAGATTCTTG AAAAAGTGGA GAAATGGATG TCAGCTTGTG AAGAAGAGTC
1601 TTGGCTGGAA GAGTACAATC GGGTTAGACA TTTAAATCTA AATCTATTCC
1651 TTTGCCTCAA TCTTTTTTTT GTTTTGTTCT CACATCGTTG GCTTCGCAGG
1701 ATGATAACCG GTACAACGCT GGAAGAGGAG CTCATCTTAC ATTGAAGCGT
1751 GCAGAAAAAG CCCGTTTACT TGTCAATAAA CTTCCTGGTA ACATTCTTGC
1801 TCTTTAGATT ATATTACAAA AACCTACAAA CTCATAACTT ATGATCTTTT
1851 TTGTCTATTG CTTTCTGCTG CTATTGATGC AGGGATGGTG GAAGCTTTGA
1901 CCGCCAAAGT CACTGCTTGG GAGAATGAAA GAGGAAATGA ATTCTTATAT
1951 GATGGGGTAA GTGGTTTTTT ACTGATCAAT GATCTGTTCT ACACAATTAT
2001 CAAATCAGCA TCTTTACACA AAAGCACGTA ATATTTCAG GTCCGAGTCT
2051 TATCGATGCT TGGTCAGTAC AAGACTGTAT GGGAAGAGAA AGAGCATGAA
2101 AAACAGAGAC AGAGAGTAAG GAAAACTGTT TTTTACTAGG AACCAAGGTC
2151 ACTATGAGCC AAAAGCATCA TTGGCAATTT GACATTGTTA CTTTCATCTC
2201 AGGATATGAA GAAACTTCAT GGACAACTCA TAACAGAGCA AGAAGCTCTT
2251 TATGGGTCTA AACCAAGCCC AAATAAAAGC GGAAAGAAAC CACTGAGAAC
2301 ACCAGTAAAT GCTGCCATGA ACAGAAAACT CTCCCTTGGT GGTGCCATGC
2351 TTCATCAAAG CTTAAAGCAT GAGAAGGCAA CACTCAATAG CAAAAGGACG
2401 AAGTACTATG ACCAGAACGC TACTAGTAGA AGAGATTCAG CTCTTCCAAC
2451 TCTTTCAGGT ACATAATAAT AACACAAGAT TTGGTTTAC ACTTAACAGA
2501 GACCAAGAGA GAGATTTGTG TTAAGAGAAT TATGTCAATA TGTGTAGGGA
```

```
2551  GGAGAAACTC AGAGCTTCCT GGTCGTATCA GATCAAAGAA CGTTCCGGTT

2601  GCAGGAAAAG CTGCGAGATC TCCAATGCTT AGGAAGCCTC TTTCACCTGT

2651  CACTTCCAAT ATCTTGAATT CCCCAGAAGA TCATCACAAG GATGCTTACA

2701  CAACAAAGGA GAGAATCTTG ACACCTAAAA CCAACGAAGA AAAGAAAAGA

2751  GCTGTTCCAA CAACTCCTGC AGCTTCAGTC GCTATGACAG AGGCAACAAC

2801  GCCGTTCACT CCTGCTGTGG AGAAGAGAAT GGATGAGGAA GACGTTATTG

2851  TTGAGTATTC GTTTGAAGAG GTTAGGGCCG GTTTTTGCTA A
```

```
   1  MGETEDEKDA SLADIEKECL SVYKRKVEEA SRGKANLLKE IAVGRAEIAA
  51  IGSSMGGQEI HSNSRLGENL KEELENVNVQ LDGLRKRKAE RMIRFNEVID
 101  QLLKLSLQLG NPTDYLKKFA AEETDLSLQR LEELRSQLGE LQNEKSKRLE
 151  EVECLLKTLN SLCSVLGEDF KGMIRGIHSS LVDSNTRDVS RSTLDKLDMM
 201  IVNLREAKLQ RMQKVQDLAV SLLELWNLLD TPAEEQKIFH NVTCSIALTE
 251  SEITEANILS VASIKRVEDE VIRLSKIKIT KIKEVILRKR LELEEISRKM
 301  HMATEVLKSE NFSVEAIESG VKDPEQLLEQ IDSEIAKVKE EASSRKEILE
 351  KVEKWMSACE EESWLEEYNR DDNRYNAGRG AHLTLKRAEK ARLLVNKLPG
 401  MVEALTAKVT AWENERGNEF LYDGVRVLSM LGQYKTVWEE KEHEKQRQRD
 451  MKKLHGQLIT EQEALYGSKP SPNKSGKKPL RTPVNAAMNR KLSLGGAMLH
 501  QSLKHEKATL NSKPTKYYDQ NATSRRDSAL PTLSGRRNSE LPGRIRSKNV
 551  PVAGKAARSP MLRKPLSPVT SNILNSPEDH HKDAYTTKER ILTPKTNEEK
 601  KRAVPTTPAA SVAMTEATTP FTPAVEKRMD EEDVIVEYSF EEVRAGFC
```

At3g60920
CONTAINS InterPro DOMAIN/s: Beige/BEACH
(InterPro:IPR000409); BEST *Arabidopsis
thaliana* protein match is: WD-40 repeat
family protein/beige-related
(TAIR:AT2G45540.1); NCBI Accession
number NM_115956.3
Genomic (SEQ ID NO: 26)
```
   1  ATGAATGGAA AGGAATCAAG AGGACCTGCG TGTAGCTTTG AGTTTGTTGG
  51  TGAAAGCTCA GGTTTACTTG GTCCAGGAGA AAGTCGCTGG CCTTTTACCA
 101  ATGGCTATGC ATTTGCGACT TGGATTTATA TTGAATCATT TGCTGACACA
 151  TTAGATGCTT CAACCGCGGC AGCTGCAATT GCTGCTGCTT CAGCGGCAAA
 201  ATCAGGAAAA ATATCTAATG CAGCGCCTGC GAATGTACAC ACTGGTGAGG
 251  GTACTGCTCA TATGCCTCGT CTGTTCAGCT TTTTGACCCC TGATAATCAG
 301  GGAATTGAAG CTTATTTCTA TGCACAATTT TTGGTGGTTG AGAGTGGCAG
 351  TGGGAAAGGA AGTAAAACTT CACTTCATTT CACTCATGCA TTTAAGCCTC
 401  AGTGTTGGTA CTTTATTGGC CTTGAGCATA CCTGCAATCA GGGACTTTTA
 451  GGGAATTCAG ATAGTGAATT ACGGCTATAT ATTGACGGGT CGTTGTATGA
 501  AACTCGACCA TTTGACTATC CTCGGATATC CAAACCGCTT TCTTTCTGTT
 551  GCATTGGGTC AAATCCTCCT TCTACAACTG CTGGTCTACA ACGTCGTCGA
 601  CGTCAGTGTG CTTTGTTTGC TGAGATGGGA CCAGTTTATA TATTTAAAGA
 651  ACCGATTGGT CCTGAAAGAA TGACACGATT GGCAACTAGA GGTGGGGATG
 701  TTTTGCCTTG TTTTGGCAAT GGGGCAGGTC TTCCATGGTT AGCTACAAAT
```

```
 751   GACCATGTCC GTAATGTGGC AGAGGAAAGT AGTCTTTCGG ATGCAGAGCT
 801   TGGAGGATAC ATTCACCTAC TTTACCACCC ATGTCTACTA AGTGGGCGGT
 851   TCTGTCCAGA TGCTTCTCTT TCTGGAGCAG CAGGTGCTTA TATTATACTC
 901   TTGATTTTTA ATATATCTGA GAAGGCTCTA CAAGTCTGAA AAATATTCCC
 951   TAGTATGATG TGTTTTATTA GTACTTGTTT TCAGATGCTC ATTTGGTTGA
1001   GTTTGTTGTA TACTTTTATC TGTTCTTGTG CTATCTATAT CGCTTTCACT
1051   CGGTCTCACT ATTCTCCATT TTCATATGAA CTTTGTTTTT ATTTATCTTG
1101   TGTCTTAGGA GATGAGAAAA CACCATATTC TTTTTCTGCT GTAGTTTTCG
1151   CACTTTGTTA TTTGGTTTTC CCTTACTTTG GAAGTTCGTT ATTTTTTCTT
1201   GATTAAGGCA CTCAAAGACG ACCAGCTGAG GTAATTGGAC AAGTCCATGT
1251   TGCAACGAGA ATGAAGTCTG GAGTCCTTCT GGGCCTTAGC TTATGGAGGA
1301   CCCATGTCTT TGCTTCCTCT AACCGTAAGC AGTGTGCACA AAGATAATCT
1351   AGAGCCATGT TCTAGAAATG TTCCATCTTC TTTGACAACA TATTCTCTGG
1401   CTGCACCTAT TTTTAGAATG ATCTCATTTG CTATTAAACA TCCTGGGAAC
1451   AATGAAGAGT TATCTCGTAC TAGGGGGCCT GAAATTCTGG CCACAGTTCT
1501   CGGTTACCTT CTTCATTCAC TTGCATCCTT TGATATCAAG CACGATAGAG
1551   TAGGAGATGA GGAGCTAGTT GCTGCTATTG TTTCTCTTTG CCAATCTCAA
1601   AAGATCAATC ATGCTCTTAA AGTGCAGCTC TTCTGTACAC TATTGTTGGA
1651   TCTGAAGATA TGGAGTGTGT GCAGTTACAG ACTCCAAAAG AAGCTGTTGT
1701   CATCTCTTCA AGATATGGTT TTCACCGAAG CAACAGCTAT GAGGAATGCT
1751   GATGCCATTC AGGTACTTCT GGATGGATGT CGAAGATATT TCTGGACAAT
1801   TCAAGAGAAA GACTCCGTGA ACACGTTTTC TCTAGATGGG GATGCACGTC
1851   AAGTGGGGGA AGTTAATGCA TTGGTTGATG AACTTTTGGT GATTATTGAA
1901   CTTCTAATGG GAGCAGCATC TCCTTCGTTT GCTGCTGATG ACCTCCATCG
1951   ATTACTTGGC TTTATAATTG AGAGTCCACA ACCAAATCAG GTAACACGTT
2001   TCTTAGTGAT ATTTCATAAT TGTTAAACAT GTGTCATTTC TCAGATCTTT
2051   TAATATTTTT TCTCTGACAT CATTCAGTTG TTACCTCTAT TTAGGTTGCA
2101   AGGGTATTGC ATCTCATGTT TAGGTTGGTT GTACAGCCAA ATGCTGCAAA
2151   GGCTCAGACA TTTGCAGAGG CATTTATCAC ATCTGGTGGG ATAGAAACAC
2201   TTCTTGTTCT CATAGCAAAC AGAGTCAACA CAATGGGCCT GGTTTGTTAA
2251   AGTTGGATTC AGTTCCACAA GATAATGAGG GTGACCCTCA TGCTCATGAT
2301   GATAATGTAG GATCTTTGAA GGAAACAGAG TCATTTCAAC AAGTAAAAGT
2351   GCATGGATCC GAAACTGTCA TTTGTGAGAC TGGCTCAGTT ACCCTCTCCA
2401   GTTCCGTGAA TGCTGACAGA ATATCCTCTG TTTCTGAAAC TCCATTCAAT
2451   AATAATGCAA GAAACAATGT TGACGATAGA GATCGTGTCA TGGTTGGGAT
2501   CATCAGATTG ATTGGTGCGT TGATTTCAAA AGGGCACTTA AAATTTTCCG
2551   TTGGTGCCAA ATCTGATGTA ATGAGTAACC TCATGGGTAG TGAGTTTCGT
2601   GAAAATGGTG GAACAATGTT TGATTATAAA GTCGCATTGC TTCTATTTGC
2651   TCTGCTGAAA GCATTTCAAG CAGCTCCAAA CAGATTGATG ACCGACAATG
2701   TCTACACAAC TTTGCTTGGG GCTTCGGTAT GACATGTCTT AATATATCTT
2751   TCATTTGTTT GATCTATCTT TAAGCGTAGC TGGTTTAATG TCAAGAATTT
```

```
2801  GGTGGAAAAA GAGAGTCTCT GAGGTGCAAC TTTTTTTTAG TAAGATTTAT
2851  ATGTATACCT GGTTTAATGT CAAGGATCTT TCTTGCAGGT TAATGCTTCA
2901  TCAACTGAGG ATGGCCTGAA CTTTTGTGAT TTAGGTCATC GATTTGAACA
2951  TCCTCAACTT CTGTTAATCC TCCTGCGTTC TCTACCATTT GCATCTAAGG
3001  CACTACAAAA TCGAGCACTT CAGGTATAAA TGTCATAGTT AAAGACACTT
3051  TTGTGCACCA AATGCACTTG TGAAAGTGCT CTACAAACTT CTACTTGTCC
3101  GGTCTCTACA ATGTCTCCTT CTGAACTCAC TTTTTCTACG TCAGGATATT
3151  CTATTTTTGG CTTGTACCCA TCCAGAAAAA AGGAGTAGTC TGACCAAAAT
3201  GGAAGAGTGG CCTGAGTGGA TCTTGGAGAT TTTAATCTCT AACTACGAGG
3251  TATAACTCAA ACGTTAAAAA TTTTAAAGTT CGCCTCCATG ATTATTGTAT
3301  CAGTAATGAG CCAAGTTGGC TATATTTACA CTAGTGTGAT AAGGCGAGTT
3351  ACATTTTTTA TCTGGCAAGT CTCTTAAGCA TGTACCATAA AACTTTAAAA
3401  ATGCTGACTA TTCTGCGTAC ACACAGAAAG ATGCAGGGAA ACAATCTGCT
3451  TCACCCGGTT CTGCTGAAGA GGAGGATCTG ATTCATAACT TCTTGATCAT
3501  AATGTTGGAA CATTCAATGC GCCAGAAGGA TGGCTGGAAG GTAAATTTGT
3551  TTGTTTCAGC GGTCTACCAG ATTAATTCCC TTTCACGTTT TTTCCAAGCT
3601  CATTTGTGTT TATTTATATT TTTCGCTACA TCTGATTCCT TTTACAGGAT
3651  ATTGAGGCTA CAATTCATTG TGCAGAGTGG CTTACTTTTG TTGGTGGGTC
3701  TAGCACTGGG GAGAAACGAA TTAGGTATTT TCATGCACTA CTGCGCCACA
3751  TTTTACGCGT GCCTTTTGGG ATGCCAATAA CATTTTGAGT GTCATCTGTT
3801  TTTCTTGTCA CATTGTTAGT TTGTGAAGGT ATCTTTTGGA TCATATTGTT
3851  GTTGCACTGT AGTGCTTCTT CCATGTATTT TGAGATAAGC ATGTTTCTGT
3901  TCAATTATAT TTACACTTTT TTCCTAATAC TTTTTTCAAA GGCGTGAGGA
3951  ATCACTGCCA ATTTTCAAAC GAAGACTTTT AGGTGGATTG CTAGACTTTG
4001  CTGCCAGTGA ACTGCAAGCT CAGGTATAGC TCCTGTTTTA TCTTTGACTT
4051  ATATGGTTAG TTATACAATT CCTTGCTAGA GAAACACGAA GTTCGTCTTA
4101  CACATGCATT GTATAGTTGA CATTGGTCGT ACTCTCACAA GAAAATATTG
4151  TCAGATCTTT TTTTATTTGC TCTATATTAG CTATAATATT GTTAAAGACA
4201  GTAAGCTTTC AAGCCTTGTT CTGTTATGTT GGTCGACTGC TATAATTTAA
4251  CCTACACATT AAACTTTCCC CAAACAGACT CAAGTTATAG CTGCAGCATC
4301  TGCTGGTTTC GCGGCAGAGA GTCTAACACC AAAAGATGCA AAAGCGGGAG
4351  TAGAAAATGC TGCACTGCTT TCAGTGTTTC TAGTGGAAAA TACAGTTGTG
4401  ATTTTGATGC TTGTCGAAGA TCATTTGCGA CTACAAAGCA AGCAAAATTG
4451  TGCTGCAAGC GCAGTTGATG TCTCTCCATC TCCTCTTTCA CTTGTTTATC
4501  CTCCCAACTA CCGTTCACAC ACATTGCCAA CGGTCGGAGA ATCATCAGAG
4551  GTTTCTAGTA GCTGTGCTTC AGTGTCCAGT GATTCAGGAG GGTCCATTT
4601  AGATGTAAGT GGAAATTACT CTCAATTTCT TTCTTCCGGA TCAATATCTC
4651  CCCTTATTTA TTGGCTTTTT TCCTTTTTGT TTTTATAACA TCATTTAAGA
4701  AAGATAGTTC TGATCATCTG ATTAACTTTC TGCTATTTTC CTGCTTTTAC
4751  TTTTTCTTCA GATACTTGCT TCAATGGCCG ATGCAAGTGG CCAGATATCT
```

```
4801  ACAGCCGTAA TGGAGCGTCT TGCTGCTGCT GCTGCAGCTG AGCCCTATGA
4851  ATCTGTTTCT TGCGCTTTTG TTTCATATGG AAGTTGTACC AGGGATTTGG
4901  CTGATGCTTG GAAGTACAGA AGTCGATTGT GGTACGGTGT TGGACTACCT
4951  TCTAAAACTA GTTGTTTTGG TGGTGGTGGA AGTGGTTGGG ACTCTTGGAA
5001  GCATGCTCTA CAAAAGATG  CTCAGGGTAA CTGGATCGAA CTTCCTTTGG
5051  TTAAAAAATC AGTATCCATG CTTCAAGCCT TGCTGCTAGA TGAGTCTGGA
5101  CTTGGAGGTG GCCTAGGAAT TGGTGGAGGA TCTGGTACCG GGATGGGAGG
5151  GATGTCAGGC CTCTACCAGT TGCTAGATAG TGATCAGCCT TTCTTATGCA
5201  TGCTTCGAAT GGTACTCTTG TCTTTGAGGG AAGAAGACCA TGGTGAAGAT
5251  AGTCTGTTGA TGAAAATTT  AAGTTCTGAA GATGGTATAA CTGGTGGACT
5301  CCAGTGCCCC TTAGGAAATT CTGCCTCAGT AGATATCAGT TCTCAGTTGT
5351  CTATGCGACA GTCACCATCA GCTTTATTGT GGAGGTAAAG TAATAACATG
5401  TTTTTTCTTA CTTCCCTATG TGACTTTGCG AATTATAAAC CCATCTGCAT
5451  TGATACGATT TTGTCCAAAG TATGTTGTCG CTCACTCAAG ATTATGACCA
5501  CATGCCTTAA GCATTTTTAG ACTAGACTTT GTCACAAAAT TAGAATACAA
5551  GGGCATATTT GGCATCTTTT GGACGCCTGA CTTGACGTTG CATGCCTTCT
5601  AAATGGTTGT TTGCTCATAG AGAATTTAAT GTGACTGTTT TTTTTTATCT
5651  CCAGTGTGCT CTCTCCCGTT CTAAACATGC CAATCTCTGA TTCTAAGAGG
5701  CAGAGGGTAT TGGTTACTAC ATGTGTTCTA TATTCTGAGG TTAGTTCTCC
5751  CCTAATTAAG GTTCCATACT TCAATTAATT ATGGTCTGGT CTCACATTTT
5801  CATGTTGAGT TTTTGGAGAA CGATAATGGA AATTGCTCCC CTAGTCTTCT
5851  TTGTGAACTT AATAATGCTC ACTTTGTTTT ATTTTATGGT TTTTCGATTT
5901  TTTGATTCAA AATCTGTTGC AGGTATGGAA TGCTGTTAGC AAAGATAAAA
5951  GACCACTACG TAAGCAGTAT CTAGAGGCTA TTTTACCACC ATTTGTTGCA
6001  ATTCTCCGAA GATGGAGGCC TCTTTTGGCT GGTATTCATG AACTTTCCAC
6051  TGGTGATGGT GTGAATCCCC TTGTCGTTGA TACTCGTGCT TTGGCTGCTG
6101  ATGCACTTCC CATTGAGGTT CCACAAATCT GTTCACATAC CCTGTAGTTT
6151  CTATCACATA TATTTATAGC TTCTGACAGT GCTGCTTCAT CCCTTAGCCT
6201  AAGGTATTAA ACTGTTACTT TTTATTCTAG GCGGCTCTCT CTATGATTTC
6251  TCCGGAGTGG GCAGCTGCTT TTGCATCGCC TCCTTCTGCA ATGGCACTGG
6301  CAATGATAGC TGCAGGGGCA GCTGGTTGGG AAGCGCCGGC ACATCCAGCA
6351  CCTCCAGCGC CTCCACCTCT TAGGCGAGAC AGTTCATTAC TTGAGCGTAA
6401  GAGTACCAAA CTTCAGACCT TTTCAAGCTT CCAGAAACCC TTGGAGGCTC
6451  CAAATGATGA TACACCAGGT CGAGCAAGAG ATAAGGCTGC TGCAAATATT
6501  GATTCACATT TATTGATTCA ACCGCTCACC AGATTGACAG GCGTATGCAA
6551  AATGATAAAA TAGTGAAAAA TCGCTTATGC ATGGGAATCC GTGGTTGGCG
6601  CAAACTCGTT CGTTACTTGG TGGACATGAG ATGCTTCTTT GGACCCTTCG
6651  GAGACCATTT ATGCAGTCCC AAACACGTAA GCTACGTTGT TCTGGGGTAA
6701  ATTTAAAACA TGTTGAGAAC ATTTCCAGTG ATGTAACATC ATCACATATG
6751  CAGGTTTTCT GGAAACTGGA TTCTATGGAA AGTTCTTCGA GGATGAGACA
6801  ATGTTTAAGG AGGAATTATT CTGGCACTGG TCATCTTGAG ACAACAAGAA
```

-continued

```
6851  ACTATGGGGA TCAGACATAC TTGATGAATA ATCACGACTC ACCTGTTCTT
6901  GCTGTTGAAG CAATATCAAA GGAAATAATG TATGAAGATG ATGAACATGG
6951  AGATGCCGAT GATCTTGAAA TAGAGGGTAA TGTTGGAGAA CGCAAAGGGG
7001  AAAACGAAGA GAGAAGGTCT GGCTCACTTG AGGATGCAAT AACACTGTCA
7051  ACTGGAATCA ACGATCATCG ACCTTTGAGT GAACAGAATA TGGTTCAAAA
7101  TTCTACAGAA GTAAAAGATC TCAGTGAACT TAAAGAAAGG ATTGTTCTTG
7151  AAATTTCCTC TACTATGGTC CGACCACTAG GGGTTGTGAA AGGAACCTTT
7201  CAAGTATGCT CTCACTAACA CTACCTATTT ATCTTTTGAA CAAATAGCTG
7251  ACACAAATGA GTATTCCATT GATGACCAAG AAATAAAACA GAGCATAAGT
7301  GACCAGATTT TGTAATGTTT GTTTTCTGTC TTTCTCAGAT CACAACACGG
7351  AGAATAAATT TTATTGTTGA CATCAGAGAA GACCAACATT TGGATGAAAA
7401  GTCAGACGGT TCAAAATCAA GAGACGAAGA AAGAGATCGA AGTTGGCTGA
7451  TGTCTTCTCT TCATCAGATT TATAGCCGAC GGTAAAGTTC ATCATTAATG
7501  TTGTCTCTAG CTCACTATTT CCTCCGCATT ATCATGTAAA TAGATGGAGA
7551  CCTATATCTT TGTTAATATT TTTCTTTCAC AGATATCTAC TGAAGAAGAG
7601  TGCTCTTGAA CTATTTATGG TGGATCGCTC AAACTTCTTC TTTGATTTTG
7651  GGGTATCTAA AAAACTCTCT CTGTTACATT ACATTATTTG ATCTCTTTCG
7701  TTGGAAATTT CAAGTTTCTA GCTCCTCTCA CTATATGATG TTTGATGAAA
7751  ACTATAGAAC ACCGAGGGAC GAAGAAATGC TTGTCGGGCT ATTGTTCAAG
7801  CAAGGCCTCC TCATTTGAAA AATATTTACT CGGCAACTCA GGTTTTTTTT
7851  TTTCCCTCCG TTTGCCCATT CTTTAGTGCA TGGTGGACAA AGCTAGGAAT
7901  CAAGCTGAGT AAATTTTTCT CAATGCTGCA AAACTTACAT AAAACGTTTC
7951  CTTTTTAGAA GCCAGAACAA GTTTCGAGAA GAACACAGTT AATGGAGCGT
8001  TGGGCTAGAT GGGAGGTAAC CAGAGAATAT CCTTTATCTC CATCATGCAA
8051  TTTCATTTTG TTCCCTTGAA TAACATCTGG CAGTAACTCT CGCTGGATAC
8101  TTTGCATCTT TTCTGCAGAT CAGCAATTTT GAGTACTTAA TGCAGCTCAA
8151  CACATTGGCT GGGCGTAGTT ATAATGACAT CACTCAGGTA AATCTCGTGC
8201  TAGTTAAAAT GTTTTTTCTT ATAATCTTTG ATATCATTTT CTCTTTGGTT
8251  ATCTTGATCT ATTTTTCATA TCTTTGCAGT ATCCTATTTT CCCATGGATT
8301  TTATGCGACT ATGTATCAGA AATTTTGGAC CTATCAAATC CATCTAATTA
8351  CAGGGATCTT TCCAAGGTGG TATTATTAGT AATTTATTAT TAGTAGTTTT
8401  TCGCTTTATG CTTGCCTATA GTTATCCATA AACCTATAAA ACTGGTTGTA
8451  ATGTGGATCC GTATATGTTC AGCCAATTGG TGCACTGAAC CCGGAGCGGC
8501  TGAAAAAGTT TCAAGAAAAA CACTCTAGCT TTGAAGATCC AGTCATCCCC
8551  AAATTTCATT ATGGTTCACA TTACTCAAGT GCTGGAGCAG TAAGTTATCT
8601  TCTCTATGAT ATCTGCCATA GTTTTATCA TTTCTTCTCT TACATTTTCT
8651  TCGTTTTAAA ACTCTGTTCC TCCTATCACC AAAGAAAGAC AATAATTAGT
8701  ATTTTGATTT GCAAGAGGAT AGAGTTTTCA CTAAATACTA ATGATGGTCT
8751  AATAATTTGT TATTTCTTGT GTGTAGGTGT TGCATTATCT AGCTAGAGTC
8801  GAACCTTTTA CAACCCTTTC GATTCAACTG CAAGGTAGAA AGTTTGATCG
```

-continued

```
8851  TGCAGACCAA ATATTTTCAG ACATTGCAGC CACTTGGAAA GGAGTTCTCC
8901  AAGATATGAA TAATGTGAAG GAGTTGGTAA GACTTGGTTC CTCCCAAAAA
8951  CATTCAAACG AGTATCCATA ATCGCCGTCC TTTGCTTTGC AAGTGAAGAG
9001  CCTAGCCATA TTTATTTTGC TTCCTCATTT TCGTATATTA TACGACCATC
9051  TATCTTTAGG GTTTATGAAC TTACGGACAA ACCCGGAATT GTTCAAAAGT
9101  TTCAGGAAAA TTTATTGCAA ATGGTAAATT CAGTTTGTCT TTGGCGTTTT
9151  AGTTACATTC GTTTTTCATG GTATCAACAT TAATGTGATT TTTTTTATTT
9201  ACAGAACACA ACTGATCCAA ACACTCACAT GGTCTCAAGC TTTTCAAACC
9251  CAACTACCAG CGAGGTTTGC TACTGAATAA GCATTAGATA GACAACAAAT
9301  TTCATTTAGG GATAAGTAAT TATTTTGGTG ATATCTTTTT TAGACTGAAC
9351  CTGATTCAGA CATGAACATT GTCTCTACCC CTTCAAATGC AACTACAAAT
9401  CAGGTAATAA CTCTAACGTT CCATTACATT TAATTTTCAA GTGCTTATGT
9451  ATTTTAAAAT TTTGAATTTT ATTTTTGTTT AGATTGACAC TGAATCTTCC
9501  GAGGCGGCTA ACTATGAAAA CAGCAACTCG TCTATCAAGA CTTCTAAGAA
9551  CACTTCAAAG ATCACTAAAT TGACCCCGAC GTCAAAACGA TCACTAACTT
9601  CATCGAAAGA TAATGCAGCT CAAAAGTCAT CTACAAAGCC TAAATTGTTG
9651  TCCAAGGCTG AGATAATAAA GGTTGATGTT TATTCGTATA TTATGAGTTT
9701  ATAG
```

Cds (SEQ ID NO: 15)
```
   1  ATGAATGGAA AGGAATCAAG AGGACCTGCG TGTAGCTTTG AGTTTGTTGG
  51  TGAAAGCTCA GGTTTACTTG GTCCAGGAGA AAGTCGCTGG CCTTTTACCA
 101  ATGGCTATGC ATTTGCGACT TGGATTTATA TTGAATCATT TGCTGACACA
 151  TTAGATGCTT CAACCGCGGC AGCTGCAATT GCTGCTGCTT CAGCGGCAAA
 201  ATCAGGAAAA ATATCTAATG CAGCGCCTGC GAATGTACAC ACTGGTGAGG
 251  GTACTGCTCA TATGCCTCGT CTGTTCAGCT TTTTGACCCC TGATAATCAG
 301  GGAATTGAAG CTTATTTCTA TGCACAATTT TTGGTGGTTG AGAGTGGCAG
 351  TGGGAAAGGA AGTAAAACTT CACTTCATTT CACTCATGCA TTTAAGCCTC
 401  AGTGTTGGTA CTTTATTGGC CTTGAGCATA CCTGCAATCA GGGACTTTTA
 451  GGGAATTCAG ATAGTGAATT ACGGCTATAT ATTGACGGGT CGTTGTATGA
 501  AACTCGACCA TTTGACTATC CTCGGATATC CAAACCGCTT TCTTTCTGTT
 551  GCATTGGGTC AAATCCTCCT TCTACAACTG CTGGTCTACA ACGTCGTCGA
 601  CGTCAGTGTG CTTTGTTTGC TGAGATGGGA CCAGTTTATA TATTTAAAGA
 651  ACCGATTGGT CCTGAAAGAA TGCACGATT GGCAACTAGA GGTGGGGATG
 701  TTTTGCCTTG TTTTGGCAAT GGGGCAGGTC TTCCATGGTT AGCTACAAAT
 751  GACCATGTCC GTAATGTGGC AGAGGAAAGT AGTCTTTCGG ATGCAGAGCT
 801  TGGAGGATAC ATTCACCTAC TTTACCACCC ATGTCTACTA AGTGGGCGGT
 851  TCTGTCCAGA TGCTTCTCTT TCTGGAGCAG CAGGAGATGA GAAAACACCA
 901  TATTCTTTTT CTGCTGTAGT TTTCGCACTT TGTTATTTGG TTTTCCCTTA
 951  CTTTGGAAGA CCCATGTCTT TGCTTCCTCT AACCGTAAGC AGTGTGCACA
1001  AAGATAATCT AGAGCCATGT TCTAGAAATG TTCCATCTTC TTTGACAACA
1051  TATTCTCTGG CTGCACCTAT TTTTAGAATG ATCTCATTTG CTATTAAACA
```

-continued

```
1101  TCCTGGGAAC AATGAAGAGT TATCTCGTAC TAGGGGGCCT GAAATTCTGG

1151  CCACAGTTCT CGGTTACCTT CTTCATTCAC TTGCATCCTT TGATATCAAG
1201  CACGATAGAG TAGGAGATGA GGAGCTAGTT GCTGCTATTG TTTCTCTTTG

1251  CCAATCTCAA AAGATCAATC ATGCTCTTAA AGTGCAGCTC TTCTGTACAC

1301  TATTGTTGGA TCTGAAGATA TGGAGTGTGT GCAGTTACAG ACTCCAAAAG

1351  AAGCTGTTGT CATCTCTTCA AGATATGGTT TTCACCGAAG CAACAGCTAT

1401  GAGGAATGCT GATGCCATTC AGGTACTTCT GGATGGATGT CGAAGATATT

1451  TCTGGACAAT TCAAGAGAAA GACTCCGTGA ACACGTTTTC TCTAGATGGG

1501  GATGCACGTC AAGTGGGGGA AGTTAATGCA TTGGTTGATG AACTTTTGGT

1551  GATTATTGAA CTTCTAATGG GAGCAGCATC TCCTTCGTTT GCTGCTGATG

1601  ACCTCCATCG ATTACTTGGC TTTATAATTG AGAGTCCACA ACCAAATCAG

1651  GTTGCAAGGG TATTGCATCT CATGTTTAGG TTGGTTGTAC AGCCAAATGC

1701  TGCAAAGGCT CAGACATTTG CAGAGGCATT TATCACATCT GGTGGGATAG

1751  AAACACTTCT TGTTCTCATA GCAAACAGAG TCAACACAAT GGGCCTGGAA

1801  ACAGAGTCAT TCAACAAGT AAAAGTGCAT GGATCCGAAA CTGTCATTTG

1851  TGAGACTGGC TCAGTTACCC TCTCCAGTTC CGTGAATGCT GACAGAATAT

1901  CCTCTGTTTC TGAAACTCCA TTCAATAATA ATGCAAGAAA CAATGTTGAC

1951  GATAGAGATC GTGTCATGGT TGGGATCATC AGATTGATTG GTGCGTTGAT

2001  TTCAAAAGGG CACTTAAAAT TTTCCGTTGG TGCCAAATCT GATGTAATGA

2051  GTAACCTCAT GGGTAGTGAG TTTCGTGAAA ATGGTGGAAC AATGTTTGAT

2101  TATAAAGTCG CATTGCTTCT ATTTGCTCTG CTGAAAGCAT TCAAGCAGC

2151  TCCAAACAGA TTGATGACCG ACAATGTCTA CACAACTTTG CTTGGGGCTT

2201  CGGTTAATGC TTCATCAACT GAGGATGGCC TGAACTTTTG TGATTTAGGT

2251  CATCGATTTG AACATCCTCA ACTTCTGTTA ATCCTCCTGC GTTCTCTACC

2301  ATTTGCATCT AAGGCACTAC AAAATCGAGC ACTTCAGGAT ATTCTATTTT

2351  TGGCTTGTAC CCATCCAGAA AAAAGGAGTA GTCTGACCAA AATGGAAGAG

2401  TGGCCTGAGT GGATCTTGGA GATTTTAATC TCTAACTACG AGAAAGATGC

2451  AGGGAAACAA TCTGCTTCAC CCGGTTCTGC TGAAGAGGAG GATCTGATTC

2501  ATAACTTCTT GATCATAATG TTGGAACATT CAATGCGCCA GAAGGATGGC

2551  TGGAAGGATA TTGAGGCTAC AATTCATTGT GCAGAGTGGC TTACTTTTGT

2601  TGGTGGGTCT AGCACTGGGG AGAAACGAAT TAGGCGTGAG GAATCACTGC

2651  CAATTTTCAA ACGAAGACTT TTAGGTGGAT TGCTAGACTT TGCTGCCAGT

2701  GAACTGCAAG CTCAGACTCA AGTTATAGCT GCAGCATCTG CTGGTTTCGC

2751  GGCAGAGAGT CTAACACCAA AGATGCAAA AGCGGGAGTA GAAAATGCTG

2801  CACTGCTTTC AGTGTTTCTA GTGGAAAATA CAGTTGTGAT TTTGATGCTT

2851  GTCGAAGATC ATTTGCGACT ACAAAGCAAG CAAAATTGTG CTGCAAGCGC

2901  AGTTGATGTC TCTCCATCTC CTCTTTCACT TGTTTATCCT CCCAACTACC

2951  GTTCACACAC ATTGCCAACG GTCGGAGAAT CATCAGAGGT TTCTAGTAGC

3001  TGTGCTTCAG TGTCCAGTGA TTCAGGAGGG GTCCATTTAG ATATACTTGC

3051  TTCAATGGCC GATGCAAGTG GCCAGATATC TACAGCCGTA ATGGAGCGTC

3101  TTGCTGCTGC TGCTGCAGCT GAGCCCTATG AATCTGTTTC TTGCGCTTTT
```

```
3151  GTTTCATATG GAAGTTGTAC CAGGGATTTG GCTGATGCTT GGAAGTACAG

3201  AAGTCGATTG TGGTACGGTG TTGGACTACC TTCTAAAACT AGTTGTTTTG

3251  GTGGTGGTGG AAGTGGTTGG GACTCTTGGA AGCATGCTCT ACAAAAAGAT

3301  GCTCAGGGTA ACTGGATCGA ACTTCCTTTG GTTAAAAAAT CAGTATCCAT

3351  GCTTCAAGCC TTGCTGCTAG ATGAGTCTGG ACTTGGAGGT GGCCTAGGAA

3401  TTGGTGGAGG ATCTGGTACC GGGATGGGAG GGATGTCAGG CCTCTACCAG

3451  TTGCTAGATA GTGATCAGCC TTTCTTATGC ATGCTTCGAA TGGTACTCTT

3501  GTCTTTGAGG GAAGAAGACC ATGGTGAAGA TAGTCTGTTG ATGAAAAATT

3551  TAAGTTCTGA AGATGGTATA ACTGGTGGAC TCCAGTGCCC CTTAGGAAAT

3601  TCTGCCTCAG TAGATATCAG TTCTCAGTTG TCTATGCGAC AGTCACCATC

3651  AGCTTTATTG TGGAGTGTGC TCTCTCCCGT TCTAAACATG CCAATCTCTG

3701  ATTCTAAGAG GCAGAGGGTA TTGGTTACTA CATGTGTTCT ATATTCTGAG

3751  GTATGGAATG CTGTTAGCAA AGATAAAAGA CCACTACGTA AGCAGTATCT

3801  AGAGGCTATT TTACCACCAT TTGTTGCAAT TCTCCGAAGA TGGAGGCCTC

3851  TTTTGGCTGG TATTCATGAA CTTTCCACTG GTGATGGTGT GAATCCCCTT

3901  GTCGTTGATA CTCGTGCTTT GGCTGCTGAT GCACTTCCCA TTGAGGCGGC

3951  TCTCTCTATG ATTTCTCCGG AGTGGGCAGC TGCTTTTGCA TCGCCTCCTT

4001  CTGCAATGGC ACTGGCAATG ATAGCTGCAG GGGCAGCTGG TTGGGAAGCG

4051  CCGGCACATC CAGCACCTCC AGCGCCTCCA CCTCTTAGGC GAGACAGTTC

4101  ATTACTTGAG CGTAAGAGTA CCAAACTTCA GACCTTTTCA AGCTTCCAGA

4151  AACCCTTGGA GGCTCCAAAT GATGATACAC CAGGTCGAGC AAGAGATAAG

4201  GCTGCTGCAA ATATTGATTC ACATTTATTG ATTCAACCGC TCACCAGATT

4251  GACAGGCGTT TTCTGGAAAC TGGATTCTAT GGAAAGTTCT TCGAGGATGA

4301  GACAATGTTT AAGGAGGAAT TATTCTGGCA CTGGTCATCT TGAGACAACA

4351  AGAAACTATG GGATCAGAC ATACTTGATG AATAATCACG ACTCACCTGT

4401  TCTTGCTGTT GAAGCAATAT CAAAGGAAAT AATGTATGAA GATGATGAAC

4451  ATGGAGATGC CGATGATCTT GAAATAGAGG GTAATGTTGG AGAACGCAAA

4501  GGGGAAAACG AAGAGAGAAG GTCTGGCTCA CTTGAGGATG CAATAACACT

4551  GTCAACTGGA ATCAACGATC ATCGACCTTT GAGTGAACAG AATATGGTTC

4601  AAAATTCTAC AGAAGTAAAA GATCTCAGTG AACTTAAAGA AAGGATTGTT

4651  CTTGAAATTT CCTCTACTAT GGTCCGACCA CTAGGGGTTG TGAAAGGAAC

4701  CTTTCAAATC ACAACACGGA GAATAAATTT TATTGTTGAC ATCAGAGAAG

4751  ACCAACATTT GGATGAAAAG TCAGACGGTT CAAAATCAAG AGACGAAGAA

4801  AGAGATCGAA GTTGGCTGAT GTCTTCTCTT CATCAGATTT ATAGCCGACG

4851  ATATCTACTG AAGAAGAGTG CTCTTGAACT ATTTATGGTG GATCGCTCAA

4901  ACTTCTTCTT TGATTTTGGG AACACCGAGG GACGAAGAAA TGCTTGTCGG

4951  GCTATTGTTC AAGCAAGGCC TCCTCATTTG AAAAATATTT ACTCGGCAAC

5001  TCAGCCAGAA CAAGTTTCGA GAAGAACACA GTTAATGGAG CGTTGGGCTA

5051  GATGGGAGAT CAGCAATTTT GAGTACTTAA TGCAGCTCAA CACATTGGCT

5101  GGGCGTAGTT ATAATGACAT CACTCAGTAT CCTATTTTCC CATGGATTTT
```

```
-continued
5151  ATGCGACTAT GTATCAGAAA TTTTGGACCT ATCAAATCCA TCTAATTACA

5201  GGGATCTTTC CAAGGTGCCA ATTGGTGCAC TGAACCCGGA GCGGCTGAAA

5251  AAGTTTCAAG AAAAACACTC TAGCTTTGAA GATCCAGTCA TCCCCAAATT

5301  TCATTATGGT TCACATTACT CAAGTGCTGG AGCAGTGTTG CATTATCTAG

5351  CTAGAGTCGA ACCTTTTACA ACCCTTTCGA TTCAACTGCA AGGTAGAAAG

5401  TTTGATCGTG CAGACCAAAT ATTTTCAGAC ATTGCAGCCA CTTGGAAAGG

5451  AGTTCTCCAA GATATGAATA ATGTGAAGGA GTTGAACACA ACTGATCCAA

5501  ACACTCACAT GGTCTCAAGC TTTTCAAACC CAACTACCAG CGAGACTGAA

5551  CCTGATTCAG ACATGAACAT TGTCTCTACC CCTTCAAATG CAACTACAAA

5601  TCAGATTGAC ACTGAATCTT CCGAGGCGGC TAACTATGAA ACAGCAACT

5651  CGTCTATCAA GACTTCTAAG AACACTTCAA AGATCACTAA ATTGACCCCG

5701  ACGTCAAAAC GATCACTAAC TTCATCGAAA GATAATGCAG CTCAAAAGTC

5751  ATCTACAAAG CCTAAATTGT TGTCCAAGGC TGAGATAATA AAGGTTGATG

5801  TTTATTCGTA TATTATGAGT TTATAG
```

Amino acid
(SEQ ID NO: 16)
```
   1  MNGKESRGPA CSFEFVGESS GLLGPGESRW PFTNGYAFAT WIYIESFADT

51  LDASTAAAAI AAASAAKSGK ISNAAPANVH TGEGTAHMPR LFSFLTPDNQ

101  GIEAYFYAQF LVVESGSGKG SKTSLHFTHA FKPQCWYFIG LEHTCNQGLL

151  GNSDSELRLY IDGSLYETRP FDYPRISKPL SFCCIGSNPP STTAGLQRRR

201  RQCALFAEMG PVYIFKEPIG PERMTRLATR GGDVLPCFGN GAGLPWLATN

251  DHVRNVAEES SLSDAELGGY IHLLYHPCLL SGRFCPDASL SGAAGDEKTP

301  YSFSAVVFAL CYLVFPYFGR PMSLLPLTVS SVHKDNLEPC SRNVPSSLTT

351  YSLAAPIFRM ISFAIKHPGN NEELSRTRGP EILATVLGYL LHSLASFDIK

401  HDRVGDEELV AAIVSLCQSQ KINHALKVQL FCTLLLDLKI WSVCSYRLQK

451  KLLSSLQDMV FTEATAMRNA DAIQVLLDGC RRYFWTIQEK DSVNTFSLDG

501  DARQVGEVNA LVDELLVIIE LLMGAASPSF AADDLHRLLG FIIESPQPNQ

551  VARVLHLMFR LVVQPNAAKA QTFAEAFITS GGIETLLVLI ANRVNTMGLE

601  TESFQQVKVH GSETVICETG SVTLSSSVNA DRISSVSETP FNNNARNNVD

651  DRDRVMVGII RLIGALISKG HLKFSVGAKS DVMSNLMGSE FRENGGTMFD

701  YKVALLLFAL LKAFQAAPNR LMTDNVYTTL LGASVNASST EDGLNFCDLG

751  HRFEHPQLLL ILLRSLPFAS KALQNRALQD ILFLACTHPE KRSSLTKMEE

801  WPEWILEILI SNYEKDAGKQ SASPGSAEEE DLIHNFLIIM LEHSMRQKDG

851  WKDIEATIHC AEWLTFVGGS STGEKRIRRE ESLPIFKRRL LGGLLDFAAS

901  ELQAQTQVIA AASAGFAAES LTPKDAKAGV ENAALLSVFL VENTVVILML

951  VEDHLRLQSK QNCAASAVDV SPSPLSLVYP PNYRSHTLPT VGESSEVSSS

1001  CASVSSDSGG VHLDILASMA DASGQISTAV MERLAAAAAA EPYESVSCAF

1051  VSYGSCTRDL ADAWKYRSRL WYGVGLPSKT SCFGGGGSGW DSWKHALQKD

1101  AQGNWIELPL VKKSVSMLQA LLLDESGLGG GLGIGGGSGT GMGGMSGLYQ

1151  LLDSDQPFLC MLRMVLLSLR EEDHGEDSLL MKNLSSEDGI TGGLQCPLGN

1201  SASVDISSQL SMRQSPSALL WSVLSPVLNM PISDSKRQRV LVTTCVLYSE

1251  VWNAVSKDKR PLRKQYLEAI LPPFVAILRR WRPLLAGIHE LSTGDGVNPL
```

-continued

```
1301   VVDTRALAAD ALPIEAALSM ISPEWAAAFA SPPSAMALAM IAAGAAGWEA

1351   PAHPAPPAPP PLRRDSSLLE RKSTKLQTFS SFQKPLEAPN DDTPGRARDK

1401   AAANIDSHLL IQPLTRLTGV FWKLDSMESS SRMRQCLRRN YSGTGHLETT

1451   RNYGDQTYLM NNHDSPVLAV EAISKEIMYE DDEHGDADDL EIEGNVGERK

1501   GENEERRSGS LEDAITLSTG INDHRPLSEQ NMVQNSTEVK DLSELKERIV

1551   LEISSTMVRP LGVVKGTFQI TTRRINFIVD IREDQHLDEK SDGSKSRDEE

1601   RDRSWLMSSL HQIYSRRYLL KKSALELFMV DRSNFFFDFG NTEGRRNACR

1651   AIVQARPPHL KNIYSATQPE QVSRRTQLME RWARWEISNF EYLMQLNTLA

1701   GRSYNDITQY PIFPWILCDY VSEILDLSNP SNYRDLSKVP IGALNPERLK

1751   KFQEKHSSFE DPVIPKFHYG SHYSSAGAVL HYLARVEPFT TLSIQLQGRK

1801   FDRADQIFSD IAATWKGVLQ DMNNVKELNT TDPNTHMVSS FSNPTTSETE

1851   PDSDMNIVST PSNATTNQID TESSEAANYE NSNSSIKTSK NTSKITKLTP

1901   TSKRSLTSSK DNAAQKSSTK PKLLSKAEII KVDVYSYIMS L
```

At3g61580
SLD1 SPHINGOID LCB DESATURASE 1
ATSLD1
NCBI Accession number NM_115922.2
CDS (SEQ ID NO: 17)
```
   1   ATGGCGGAAG AGACGGAGAA AAAGTACATT ACGAACGAAG ATCTTAAAAA

51   ACACAACAAA TCTGGAGATC TATGGATCGC GATTCAAGGC AAGGTCTACA

101   ACGTCTCCGA TTGGATTAAA ACTCATCCCG GAGGCGACAC GGTGATTCTC

151   AATCTCGTTG GTCAAGACGT CACCGATGCT TTCATCGCAT TCATCCCGG

201   AACCGCTTGG CACCATCTCG ACCATCTCTT CACCGGTTAC ACATCAGAG

251   ATTTCCAAGT CTCCGAAGTC TCACGCGATT ACCGTCGTAT GGCTGCCGAG

301   TTTCGTAAAC TCGGTCTCTT CGAAAACAAA GGTCACGTTA CTCTCTACAC

351   TCTAGCCTTC GTCGCCGCCA TGTTCCTCGG AGTTCTCTAC GGTGTTTTGG

401   CTTGTACCTC CGTCTTCGCT CACCAAATCG CCGCCGCGCT TCTCGGTCTC

451   CTCTGGATCC AGAGCGCTTA CATAGGTCAC GATTCTGGTC ATTACGTTAT

501   CATGTCGAAC AAATCTTATA ACAGATTCGC TCAGCTTCTC TCCGGTAACT

551   GTCTCACCGG AATCTCAATC GCGTGGTGGA AATGGACTCA CAATGCTCAT

601   CATCTAGCTT GTAACAGCCT CGATTACGAT CCAGATCTAC AACACATCCC

651   TGTCTTCGCC GTCTCCACCA AATTCTTCTC CTCATTGACC TCGAGATTCT

701   ACGATCGGAA ACTCACGTTT GATCCAGTCG CGAGATTCTT AGTCAGCTAT

751   CAACACTTTA CTTATTATCC AGTTATGTGC TTTGGAAGAA TCAATCTCTT

801   CATTCAAACG TTTCTCTTGC TCTTCTCCAA ACGTGAAGTA CCAGATCGTG

851   CTTTAAACTT CGCCGGAATC TTAGTCTTCT GGACTTGGTT CCCACTCTTA

901   GTCTCATGTC TACCAAACTG GCCTGAGAGA TTCTTCTTCG TCTTCACAAG

951   CTTCACCGTC ACGGCGCTTC AACACATTCA ATTCACGCTT AACCATTTCG

1001   CTGCTGATGT CTACGTTGGT CCACCCACCG GTAGCGACTG GTTCGAGAAG

1051   CAAGCGGCGG AACAATCGA TATCTCTTGT AGATCATACA TGGATTGGTT

1101   CTTTGGTGGA TTACAGTTTC AGCTTGAGCA TCATTTGTTC CCTCGCTTAC

1151   CTCGTTGCCA TCTCCGGAAA GTTCTCCGG TGGTTCAAGA GCTTTGCAAG
```

-continued

```
1201 AAGCATAATC TTCCGTATAG GAGTATGTCG TGGTTTGAAG CAAATGTTT
1251 GACCATTAAC ACTTTGAAGA CAGCAGCTTA TCAAGCTAGA GACGTGGCTA
1301 ATCCGGTGGT TAAGAACTTG GTTTGGGAAG CTTTGAATAC TCATGGCTAA
```

Genomic
(SEQ ID NO: 27)

```
   1 AAGGAAGGAG TCGAAGATAA GCGGAGAGAG AGAGAGAGAC AGAGAGAGAT
  51 TCAAAAATCC GATTCCAGAT CCATTCCTGG GCAAACAAAG GTTGGTGTTT
 101 CTCTAATCTC AAAGCTTTTT TCAAATTCGG AAAAAGCAAA TCGTGGGAAG
 151 AGATTCATCT TCTCTCTGTG CGTTCATCGG ATCTCGGAGC TTTTGGTTCG
 201 TCGTCAATGG CGGAAGAGAC GGAGAAAAAG TACATTACGA ACGAAGATCT
 251 TAAAAAACAC AACAAATCTG GAGATCTATG GATCGCGATT CAAGGCAAGG
 301 TCTACAACGT CTCCGATTGG ATTAAAACTC ATCCCGGAGG CGACACGGTG
 351 ATTCTCAATC TCGTTGGTCA AGACGTCACC GATGCTTTCA TCGCATTTCA
 401 TCCCGGAACC GCTTGGCACC ATCTCGACCA TCTCTTCACC GGTTACCACA
 451 TCAGAGATTT CCAAGTCTCC GAAGTCTCAC GCGATTACCG TCGTATGGCT
 501 GCCGAGTTTC GTAAACTCGG TCTCTTCGAA AACAAAGGTC ACGTTACTCT
 551 CTACACTCTA GCCTTCGTCG CCGCCATGTT CCTCGGAGTT CTCTACGGTG
 601 TTTTGGCTTG TACCTCCGTC TTCGCTCACC AAATCGCCGC CGCGCTTCTC
 651 GGTCTCCTCT GGATCCAGAG CGCTTACATA GGTCACGATT CTGGTCATTA
 701 CGTTATCATG TCGAACAAAT CTTATAACAG ATTCGCTCAG CTTCTCTCCG
 751 GTAACTGTCT CACCGGAATC TCAATCGCGT GGTGGAAATG GACTCACAAT
 801 GCTCATCATC TAGCTTGTAA CAGCCTCGAT TACGATCCAG ATCTACAACA
 851 CATCCCTGTC TTCGCCGTCT CCACCAAATT CTTCTCCTCA TTGACCTCGA
 901 GATTCTACGA TCGGAAACTC ACGTTTGATC CAGTCGCGAG ATTCTTAGTC
 951 AGCTATCAAC ACTTTACTTA TTATCCAGTT ATGTGCTTTG GAAGAATCAA
1001 TCTCTTCATT CAAACGTTTC TCTTGCTCTT CTCCAAACGT GAAGTACCAG
1051 ATCGTGCTTT AAACTTCGCC GGAATCTTAG TCTTCTGGAC TTGGTTCCCA
1101 CTCTTAGTCT CATGTCTACC AAACTGGCCT GAGAGATTCT TCTTCGTCTT
1151 CACAAGCTTC ACCGTCACGG CGCTTCAACA CATTCAATTC ACGCTTAACC
1201 ATTTCGCTGC TGATGTCTAC GTTGGTCCAC CCACCGGTAG CGACTGGTTC
1251 GAGAAGCAAG CGGCGGGAAC AATCGATATC TCTTGTAGAT CATACATGGA
1301 TTGGTTCTTT GGTGGATTAC AGTTTCAGCT TGAGCATCAT TTGTTCCCTC
1351 GCTTACCTCG TTGCCATCTC CGGAAAGTTT CTCCGGTGGT TCAAGAGCTT
1401 TGCAAGAAGC ATAATCTTCC GTATAGGAGT ATGTCGTGGT TTGAAGCAAA
1451 TGTGTTGACC ATTAACACTT TGAAGACAGC AGCTTATCAA GCTAGAGACG
1501 TGGCTAATCC GGTGGTTAAG AACTTGGTTT GGGAAGCTTT GAATACTCAT
1551 GGCTAAATGA TTTTAATCAA AACAAAATAT GCTTTTGTTT GGGTTAAATT
1601 TGATGTGTTG TTTTTATGCT TTATTGAATC TTTGAATTTC GTTTTGTTAC
1651 TTACTTACAT GGAAGAGATG TTTTAGATCG AAATTGAATC GAGATTTGAT
1701 TTTTTTATTA GACAACTCTT CGTATCGTAA TGATTTATTA ATAATATTAT
1751 TTTGAATTTA ATTTGTTTTT TTATATAAGT TTTTGTTTCA CATGGCTCTT
1801 TTTTGTTGCC TGTGACTTAC TTTGTGGTTT TGCGGCTTTT GGCCTTTTCA
```

-continued

```
1851   ATGTTTTGTC GTGTTACATT AAAATACGTG TGTGGATGCT ATTTGAGATC

1901   CTCTATATGT AAGGTTTTAA CAGATC
```

Amino acid (SEQ ID NO: 18)

```
  1   MAEETEKKYI TNEDLKKHNK SGDLWIAIQG KVYNVSDWIK THPGGDTVIL

51   NLVGQDVTDA FIAFHPGTAW HHLDHLFTGY HIRDFQVSEV SRDYRRMAAE

101   FRKLGLFENK GHVTLYTLAF VAAMFLGVLY GVLACTSVFA HQIAAALLGL

151   LWIQSAYIGH DSGHYVIMSN KSYNRFAQLL SGNCLTGISI AWWKWTHNAH

201   HLACNSLDYD PDLQHIPVFA VSTKFFSSLT SRFYDRKLTF DPVARFLVSY

251   QHFTYYPVMC FGRINLFIQT FLLLFSKREV PDRALNFAGI LVFWTWFPLL

301   VSCLPNWPER FFFVFTSFTV TALQHIQFTL NHFAADVYVG PPTGSDWFEK

351   QAAGTIDISC RSYMDWFFGG LQFQLEHHLF PRLPRCHLRK VSPVVQELCK

401   KHNLPYRSMS WFEANVLTIN TLKTAAYQAR DVANPVVKNL VWEALNTHG
```

---

What is claimed is:

1. A transgenic plant with improved plant pathogen resistance; said transgenic plant having a heterologous nucleotide sequence stably integrated within said plants genome which includes a non-host resistance nucleic acid sequence from *Arabidopsis*, said non-host resistance nucleic acid sequence encoding a At3g59640 protein as set forth in SEQ ID NO:8, wherein said transgenic plant has greater *Phytophthora* and *Fusarium* tolerance compared to the *Phytophthora* and *Fusarium* tolerance of a corresponding plant with no such modification, wherein said transgenic plant is one of maize, soybean, sunflower, sorghum, canola, wheat, alfalfa, cotton, rice, barley, and millet.

2. The plant of claim 1 wherein said non-host resistance nucleic acid is At3g59640 as set forth in SEQ ID NO:7 or 22.

3. The plant of claim 1 wherein said non-host resistance nucleic acid is one or more of the following: SEQ ID NOS: 7, 22.

4. A method for conferring or improving *Phytophthora* resistance in a plant, said method comprising:
   transforming said plant with a nucleic acid molecule comprising a heterologous sequence operably linked to a promoter that induces transcription of said heterologous sequence in a plant cell; and
   regenerating stably transformed plants, wherein said heterologous sequence comprises a nucleic acid molecule that encodes At3g59640 *Arabidopsis* non-host resistance protein as set forth in SEQ ID NO:8
   wherein said transformed plant has greater *Phytophthora* and *Fusarium* tolerance compared to the *Phytophthora* and *Fusarium* tolerance of a corresponding plant that has not been transformed.

5. The method of claim 4 wherein said nucleic acid sequence includes:
   a nucleotide sequence comprising the sequence set forth in SEQ ID NO: 7 or 22.

6. The method of 4, wherein said plant is a dicot.

7. The method of 4, wherein said dicot is soybean.

8. A nucleotide construct comprising:
   a nucleic acid molecule wherein said nucleic acid sequence includes:
   (a) a nucleotide sequence comprising the sequence set forth in SEQ ID NO: 7 or 22; or
   (b) a nucleotide sequence that encodes the protein sequence of SEQ ID NO: 8;
   wherein said nucleic acid molecule is operably linked to a heterologous promoter that drives expression in a plant host cell.

9. A method for conferring or improving *Phytophthora* resistance of a plant, said method comprising:
   stably introducing into the genome of a plant, at least one nucleotide construct comprising a non-host resistance nucleic acid molecule operably linked to a heterologous promoter that drives expression in a plant cell, wherein said nucleic acid molecule encodes a At3g59640 polypeptide as set forth in SEQ ID NO:8,
   wherein said plant into which said nucleotide construct has been introduced has greater *Phytophthora* and *Fusarium* tolerance compared to the *Phytophthora* and *Fusarium* tolerance of a corresponding plant that has not been transformed.

* * * * *